US011180567B2

(12) United States Patent
Nadler et al.

(10) Patent No.: US 11,180,567 B2
(45) Date of Patent: *Nov. 23, 2021

(54) ANTIBODY POLYPEPTIDES THAT ANTAGONIZE CD40L

(71) Applicants: Bristol-Myers Squibb Company, Princeton, NJ (US); Domantis Limited, Middlesex (GB)

(72) Inventors: Steven G. Nadler, Princeton, NJ (US); James K. Tamura, Yardley, PA (US); Laura Price, Langhorne, PA (US); Robert P. Rehfuss, North Wales, PA (US); Suzanne J. Suchard, Portland, OR (US); Anish Suri, Ekeren (BE); James William Bryson, Langhorne, PA (US); Aaron Yamniuk, Lawrenceville, NJ (US); Steven Grant, Swaffham Prior (GB); Olga Ignatovich, Cambridge (GB); Philip Drew, Histon (GB)

(73) Assignees: Bristol-Myers Squibb Company, Princeton, NJ (US); Domantis Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/218,077

(22) Filed: Dec. 12, 2018

(65) Prior Publication Data
US 2019/0100595 A1    Apr. 4, 2019

Related U.S. Application Data

(63) Continuation of application No. 15/668,305, filed on Aug. 3, 2017, now Pat. No. 10,196,451, which is a continuation of application No. 14/950,949, filed on Nov. 24, 2015, now Pat. No. 9,765,150, which is a continuation of application No. 14/510,474, filed on Oct. 9, 2014, now Pat. No. 9,228,018, which is a continuation of application No. 13/650,493, filed on Oct. 12, 2012, now Pat. No. 8,895,010.

(60) Provisional application No. 61/546,800, filed on Oct. 13, 2011, provisional application No. 61/655,110, filed on Jun. 4, 2012.

(51) Int. Cl.
| A61K 39/395 | (2006.01) |
| C07K 16/28 | (2006.01) |
| A61K 45/06 | (2006.01) |
| C07K 16/46 | (2006.01) |
| C07K 16/18 | (2006.01) |
| A61K 39/00 | (2006.01) |
| A61K 38/00 | (2006.01) |

(52) U.S. Cl.
CPC ...... *C07K 16/2878* (2013.01); *A61K 39/3955* (2013.01); *A61K 45/06* (2013.01); *C07K 16/18* (2013.01); *C07K 16/283* (2013.01); *C07K 16/2833* (2013.01); *C07K 16/2875* (2013.01); *C07K 16/2896* (2013.01); *C07K 16/46* (2013.01); *C07K 16/468* (2013.01); *A61K 38/00* (2013.01); *A61K 2039/505* (2013.01); *A61K 2039/545* (2013.01); *C07K 2317/21* (2013.01); *C07K 2317/31* (2013.01); *C07K 2317/34* (2013.01); *C07K 2317/52* (2013.01); *C07K 2317/565* (2013.01); *C07K 2317/567* (2013.01); *C07K 2317/569* (2013.01); *C07K 2317/71* (2013.01); *C07K 2317/76* (2013.01); *C07K 2317/92* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| 5,876,950 A | 3/1999 | Siadak et al. |
| 6,001,358 A | 12/1999 | Black et al. |
| 7,094,874 B2 | 8/2006 | Peach et al. |

(Continued)

FOREIGN PATENT DOCUMENTS

| CL | 19900284 | 9/1999 |
| CL | 200100584 | 12/2001 |

(Continued)

OTHER PUBLICATIONS

Aruffo, et al., "The CD40 Ligand, gp39, Is Defective in Activated T Cells from Patients with X-Linked Hyper-Igm Syndrome," *Cell* (1993) 72:291-300.

(Continued)

*Primary Examiner* — Phillip Gambel
(74) *Attorney, Agent, or Firm* — Faegre Drinker Biddle & Reath LLP

(57) ABSTRACT

Antibody polypeptides that specifically bind human CD40L are provided. The antibody polypeptides do not activate platelets. The antibody polypeptides are useful in the treatment of diseases involving CD40L activation, such as graft-related diseases and autoimmune diseases. The antibody polypeptides may be domain antibodies (dAbs) comprising a single $V_H$ or $V_K$ domain. The half-life of the antibody polypeptides may be increased by modifying the antibody polypeptides to be dual specific reagents that can also bind human serum albumin (HSA) or another antigen.

20 Claims, 26 Drawing Sheets
(20 of 26 Drawing Sheet(s) Filed in Color)
Specification includes a Sequence Listing.

(56) References Cited

U.S. PATENT DOCUMENTS

| | | | |
|---|---|---|---|
| 7,482,327 | B2 | 1/2009 | Hagerty et al. |
| 8,895,010 | B2 | 11/2014 | Nadler et al. |
| 8,981,072 | B2 | 3/2015 | Nadler et al. |
| 9,228,018 | B2 | 1/2016 | Nadler et al. |
| 9,765,150 | B2 | 9/2017 | Nadler et al. |
| 10,196,451 | B2 * | 2/2019 | Nadler ............... A61P 21/04 |
| 2009/0297524 | A1 | 12/2009 | Grant et al. |
| 2010/0166774 | A1 | 7/2010 | Dali et al. |
| 2017/0051059 | A1 | 2/2017 | Suri et al. |

FOREIGN PATENT DOCUMENTS

| | | |
|---|---|---|
| CL | 200700768 | 11/2007 |
| CL | 2007001335 | 1/2008 |
| CL | 201202737 | 2/2013 |
| CL | 201303043 | 6/2014 |
| CL | 201301124 | 7/2014 |
| TW | 200911825 A | 3/2009 |
| WO | WO-9942075 A2 | 8/1999 |
| WO | WO-0168860 A1 | 9/2001 |
| WO | WO-2005003175 A2 | 1/2005 |
| WO | WO-2005035572 A2 | 4/2005 |
| WO | WO-2006030220 A1 | 3/2006 |
| WO | WO-2007129895 A2 | 11/2007 |
| WO | WO-2008118356 A2 | 10/2008 |
| WO | WO-2010023482 A2 | 3/2010 |
| WO | WO-2011123489 A2 | 10/2011 |
| WO | WO-2012065950 A1 | 5/2012 |
| WO | WO-2012115241 A1 | 8/2012 |
| WO | WO-2012145673 A1 | 10/2012 |
| WO | WO-2013118858 A1 | 8/2013 |

OTHER PUBLICATIONS

Ashokkumar, et al., "Allospecific CD154+ T Cells Associate with Rejection Risk After Pediatric Liver Transplantation," *Amer. J. Transplantation* (2009) 9: 179-191.

Ashokkumar, et al., Allospecific CD154+ T cells identify rejection-prone recipients after pediatric small-bowel transplantation, *Surgery* (2009) 146: 166-173.

Bartlett, et al., "Analysis of Intragraft Gene and Protein Expression of Costimulatory Molecules, CD80, CD86 and CD154, and Orthotopic Liver Transplant Recipients," *Amer. J. Transplantation* (2003) 3: 1363-1368.

Baumgart, et al., "Exaggerated inflammatory response of primary human myeloid dendritic cells to lipopolysaccharide in patients with inflammatory bowel disease," *Clinical and Experimental Immunology* (2009) 157: 423-436.

Biaconne, et al., "Expression of inducible lymphocyte costimulatory molecules in human renal allograft," *Nephrol. Diall. Transplant.* (1998) 13: 716-722.

Boumpas, et al., "A Short Course of BG9588 (Anti-CD40 Ligand Antibody) Improves Serologic Activity and Decreases Hematuria in Patients With Proliferative Lupus Glomerulonephritis," *Arthritis & Rheumatism* (2003), 48: 719-727.

Danese, et al., "Activated platelets are the source of elevated levels of soluble CD40 ligand and the circulation of inflammatory bowel disease patients," *Gut* (2003) 52: 1435-1441.

Grammer, et al., Abnormal germinal center reactions in systemic lupus erythematosus demonstrated by blockade of CD154-CD40 interactions *J. Clin. Invest.* (2003) 112: 1506-1520.

Kasran, et al., "Safety and tolerability of antagonist anti-human CD40 Mab ch5D12 in patients with moderate to severe Crohn's disease," *Aliment. Pharmacol. Ther.* (2005) 22: 111-122.

Kawai, et al., "CD154 Blockade for Induction of Mixed Chimerism and Prolonged Renal Allograft Survival in Nonhuman Primates," *Amer. J. Transplantation* (2004) 4: 1391-1398.

Kenyon, et al., "Long-term survival and function of intrahepatic islet allografts in rhesus monkeys treated with humanized anti-CD154," *Proc. Natl. Acad. Sci. USA* (1999) 96: 8132-8137.

Kimura, et al., "Study of Plasma Levels of Soluble CD40 Ligand in Systemic Lupus Erythematosus Patients Who Have Undergone Plasmapheresis," *Therapeutic Apheresis and Dialysis* (2005) 9: 64-68.

Kirk, et al., "CTLA4-Ig and anti-CD40 ligand prevent renal allograft rejection in primates," *Proc. Natl. Acad. Sci. USA* (1997) 94: 8789-8794.

Komura, et al., "Elevated Circulating CD40 Concentrations in Patients with Systemic Sclerosis," *J. Reumatol.* (2004) 31: 514-519.

Ludwiczek, et al., "Plasma levels of soluble CD40 ligand are elevated in inflammatory bowel diseases," *Int. J. Colorectal Dis.* (2003) 18: 142-147.

Mach, et al., "Reduction of Atherosclerosis in mice by inhibition of CD40 signalling," *Nature* (1998) 394: 200-203.

Menchén, et al., "Matrix metalloproteinase 9 is involved in Crohn's disease associated platelet hyperactivation through th release of soluble CD40 ligand," *Gut* 58: (2009) 920-928.

Mirabet, et al., Platelet pro-aggregatory effects of CD40 monoclonal antibody, *Mol. Immunol.* (2008) 45: 937-44.

Montgomery, et al., "Combination Induction Therapy With Monoclonal Antibodies Specific for CD80, CD86, and CD154 in Nonhuman Primate Renal Transplantation," *Transplantation* (2002) 74: 1365-1369.

Orozco, et al., "Association of CD40 with rheumatoid arthritis confirmed in a large UK case-control study," *Ann. Rheum. Dis.* (2010) 69: 813-816.

Patel, et al., "The effect of anti-CD40 ligand in immune thrombocytopenic purpura," *British J. Haematology* (2008) 141: 545-548.

Prahalad, et al., "Elevated serum levels of soluble CF154 in children with juvenile idiopathic arthritis," *Pediatric Rheumatology* (2008) 6: 1-8.

Preston, et al., "IDEC-131 (Anti-CD154), Sirolimus and Donor Specific Transfusion Facilitate Operational Tolerance in Non-Human Primates," *Amer. J. Transplantation* (2005) 5: 1032-1041.

Raychaudhuri, et al., "Common variants at CD40 and other loci confer risk of rheumatoid arthritis", *Nature Genetics* (2008) 40: 1216-1223.

Robles-Carrillo, et al., "Anti-CD40L Immune Complexes Potently Activate Platelets In Vitro and Cause Thrombosis in FCGRA2A Transgenic Mice," *The Journal of Immunology* (2010) 185: 1577-1583.

Schönbeck, et al., "Inhibition of CD40 signaling limits evolution of established atherosclerosis in mice," *Proc. Natl. Acad. Sci.* (2000) 97: 7458-7463.

Schuler, et al., "Efficacy and Safety of AB1793, A Novel Human Anti-Human CD154 Monoclonal Antibody, In Cynomolgus Monkey Renal Allotransplantation," *Transplantation* (2004) 77: 717-726.

Vakkalanka, et al., "Elevated Levels and Functional Capacity of Soluble CD40 Ligand in Systemic Lupus Erythematosus Sera,", *Arthritis & Rheumatism* (1999) 42: 871-881.

Xu, et al., "Effects of Dose and Duration of Anti-CD154 Antibody Therapy in Preventing Renal Allograft Rejection in a Nonhuman Primate Model," *Transplantation Proceedings* (2001) 33: 223-224.

Adams, et al., "Development of a Chimeric Anti-CD40 Monoclonal Antibody That Synergizes with LEA29Y to Prolong Islet Allograft Survival" (2005) J. Immunol. 174: 542-550.

Daoussis, et al., "Increased expression of CD154 (CD40L) on stimulated T-cells from patients with psoriatic arthritis", *Rheumatology* (2007) 46: 227-231.

Chapman, et al., "PEGylated antibodies and antibody fragments for improved therapy: a review", *Adv. Drug Deliv. Rev.* (2002) 54(4):531-545.

De Kruif, et al., "Rapid selection of cell subpopulation-specific human monoclonal antibodies from a synthetic phage antibody library", *Proc. Natl. Acad. Sci. USA* (1995) 92: 3938-3942.

Duffau, et al., "Platelet CD154 Potentiates Interferon-α Secretion by Plasmacytoid Dendritic Cells in Systemic Lupus Erythematosus", *Sci. Transl. Med.* (2010) 2: 47: 1-10 (2010).

Durie, et al., "Antibody to the Ligand of CD40, GP39, Blocks the Occurrence of the Acute and Chronic Forms of Graft-vs-Host Disease", *J. Clin. Invest.* (1994) 94: 1333-1338.

(56) References Cited

OTHER PUBLICATIONS

Ferroni, et al., "Contribution of Platelet-Derived CD40 Ligand to Inflammation, Thrombosis and Neoangiogenesis", *Curr. Med. Chem.* (2007) 14: 2170-2180.

Garcia, et al., "Monocytic suppressive cells mediate cardiovascular transplantation tolerance in mice", *J. Clin. Inv.* (2010) 120: 2486-2496.

Gilson, et al., "Anti-CD40 Monoclonal Antibody Synergizes with CTLA4-Ig in Promoting Long-Term Graft Survival in Murine Models of Transplantation", *J. Immunol.* (2009) 183: 1625-1635.

Harrison, et al., "Screening of Phage Antibody Libraries", *Meth. Enzymol.* (1996) 267: 83-109.

Hoogenboom, et al., "Multi-subunit proteins on the surface of filamentous phage: methodologies for displaying antibody (Fab) heavy and light chains", *Nucleic Acids Res.* (1991) 19:4133-4137.

Huang, et al., "The Effect of Anti-CD40 Ligand Antibody on B Cells in Human Systemic Lupus Erythematosus", Arthritis & Rheumatism (2002) 46: 1554-1562.

Im, et al., "Blockade of CD40 Ligand Suppresses Chronic Experimental Myasthenia Gravis by Down-Regulation of Th1 Differentiation and Up-Regulation of CTLA-4", *J. Immunol.* (2001) 166: 6893-6898.

Kanmaz, et al., "Monotherapy With the Novel Human Anti-CD-154 Monoclonal Antibody AB1793 in Rhesus Monkey Renal Transplantation Model", *Transplantation* (2004) 77: 914-920.

Koyama, et al., "Thrombophilia Associated With Anti-CD154 Monoclonal Antibody Treatment and Its Prophylaxis in Nonhuman Primates", *Transplantation* (2004) 77: 460-461.

Kuwana, et al., "T and B Cell Collaboration Is Essential for the Autoantibody Response to DNA Topoisomerase I in Systemic Sclerosis", *J. Immunol.* (1995) 155: 2703-2714.

Larsen, et al., "Rational Development of LEA29Y (belatacept), a High-Affinity Variant of CTLA4-Ig with Potent Immunosuppressive Properties", *Amer. J. Transplant.* (2005) 5: 443-453.

Lederer, et al., "Reduced CD4L Expression on ex vivo Activated CD4+ T-Lymphocytes from Patients with Excellent Renal Allograft Function Measured with a Rapid Whole Blood Flow Cytometry Procedure", *Int. Arch. Allergy Immunol.* (2004) 133: 276-284.

Marks, et al., "Human Antibody Fragments Specific for Human Blood Group Antigens from a Phage Display Library", *BioTechnology* (1993) 11: 1145-1149.

Oosterwegel, et al., "CTLA-4 and T cell activation", *Curr. Opin. Immunol.* (1999) 11: 294-300.

Reilly, et al., "Genetic Diversity in Human Fc Receptor II for Immunoglobulin G: Fcγ Receptor IIA Ligand-Binding Polymorphism", *Clin. Diagn. Lab. Immunol.* (1994) 1: 640-644.

Shi, et al., "Differential requirements for CD28 and CD40 ligand in the induction of experimental autoimmune myasthenia gravis", *Eur. J. Immunol.* (1998) 28: 3587-3593.

Tomiyama, et al., "Response of Human Platelets to Activating Monoclonal Antibodies: Importance of FcγRII (CD32) Phenotype and Level of Expression", *Blood* (1992) 80: 2261-2268.

Daley et al., "Fc-Disabled Anti-Mouse CD40L Antibodies Retain Efficacy in Promoting Transplantation Tolerance," American Journal of Transplantation, Nov. 1, 2008, vol. 8, No. 11, pp. 2265-2271.

Ge et al., "Functional expression of chimeric Fab of an anti-CD40L mAb: Vector design an culture condition optimization", Biomedicine & Pharmacotherapy, Sep. 17, 2010, vol. 65, No. 1, pp. 52-59.

Holt, et al., "Domain antibodies: proteins for therapy", Trends in Biotechnology, Nov. 1, 2003, vol. 21, No. 11, pp. 484-490.

Suri, et al., "Investigative Studies Demonstrate Reduced Risk for Thromboembolism (TE) by BMS-986004, an Anti-CD40L Domain antibody," Session 71: Novel Approaches to Treatment & Monitoring of Allograft Injury, Jun. 6, 2012, Publication p. No. 518, XP002690660, Abstract.

International Search Report dated Mar. 12, 2013, issued in PCT Application No. PCT/US2012/059977 filed Oct. 12, 2012.

International Preliminary Report on Patentability and Written Opinion of the International Search Authority dated Apr. 24, 2014 in PCT Application No. PCT/US2012/059977.

Borcherding et al., "The CD40-CD40L pathway contributes to the proinflammatory function of intestinal epithelial cells in inflammatory bowel disease," Am J Pathol. (2010) 176(4):1816-27. {doi:10.2353/ajpath.2010.090461. Epub Feb. 4, 2010.).

Gen Bank Accession No. CAJ90635.1 (2006).

Office Action dated Feb. 20, 2017 in Canadian Patent Application No. 2,851,814.

Rudikoff et al., "Single amino acid substitution altering antigen-binding specificity," PNAS Immunology, vol. 79, pp. 1979-1983, Mar. 1982.

\* cited by examiner

FIG. 1A

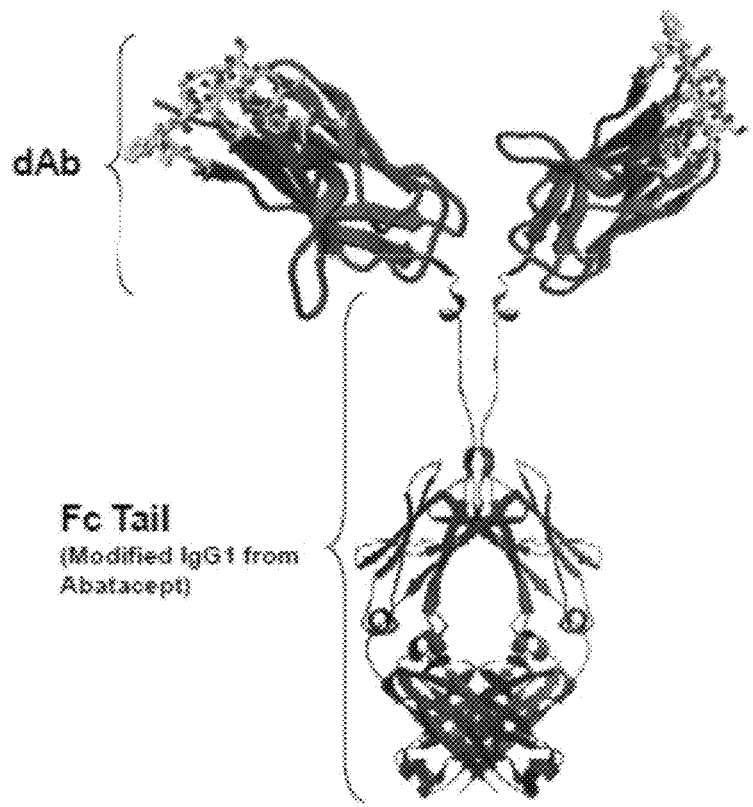

FIG. 1B

EVQLLESGGGLVQPGGSLRLSCAASGFTFNWELMGWARQAPGKGLEWVSQIESPGDYTYYADSVKGRFTISRDNSKNTLYLQMNSLRAEDTAVYY
CVKVGKDAKSDYRGQGTLVTVSSASTEPKSSDKTHTSPPSPAPELLGGSSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK
(MW=77,384 daltons)

dAb
Linker
Modified IgG1 Fc from Abatacept (Cys→Ser; Pro→Ser)

Domain antibody-[AS]-THTCPPCP...

CT-long

Domain antibody-[AST]-EPKSSDKTHTSPPSP ...

CT-short

Domain antibody-[AS]-THTSPPSP...

N297Qlong Fc

Domain antibody-[AST]-EPKSSDKTHTSPPSP...

N297Qshort Fc

Domain antibody-[AS]-THTSPPSP...

Osteonectin signal peptide sequence:

MRAWIFFLLCLAGRALA ^ EVQLLES...(start of Domain antibody)

FIG. 4

BMS2h-572-633-CT-L2

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSSASTEPKSSDKTHTSPPSPAPELLGGSSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-CT-S1

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSSASTHTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

BMS2h-572-633-N297Q long Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSSASTEPKSSDKTHTCPPCPAPELLGGPSVFLFPPKPKDTLMISRTPEVTCVVVDVSH
EDPEVKFNWYVDGVEVHNAKTKPREEQYQSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-N297Q short Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSSASTHTCPPCPAPELLGGPSVFLFPPKPKDTLMISRTPEVTCVVVDVSHEDPEVKFN
WYVDGVEVHNAKTKPREEQYQSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

FIG. 14
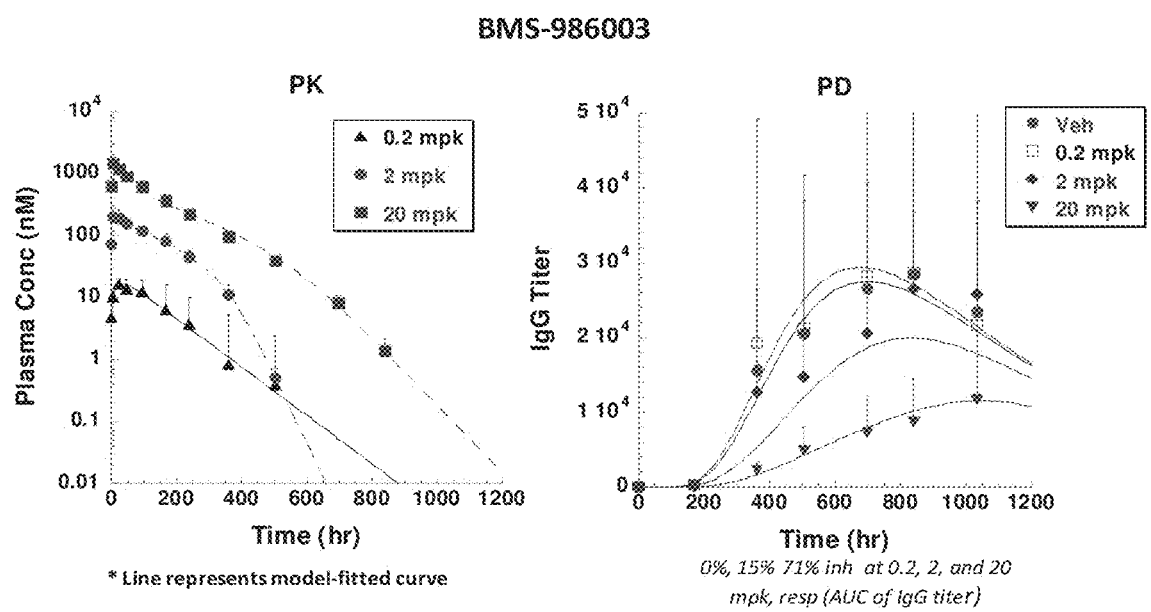
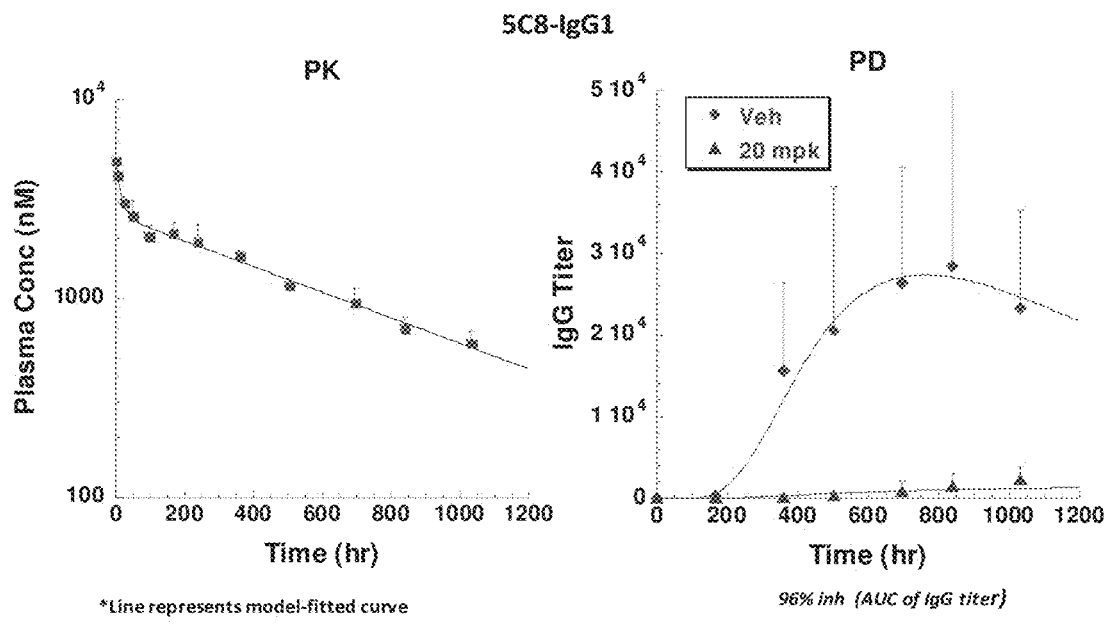

FIG. 21

|  |  | CDR1 | CDR2 |  |
|---|---|---|---|---|
| BMS2h-572-6 | EVQLLESGGGLVQPGGSLRLSCAASGFTFNWQLMGWVRQAPGKGLEWVSGIEGPGDVTYY | 60 |
| BMS2h-572-608 | EVQLLESGGGLVQPGGSLRLSCAASGFTFNWELMGWARQAPGKGLEWVSGIEGPGDVTYY | 60 |
| BMS2h-572-614 | EVQLLESGGGLVQPGGSLRLSCAASGFTFNWELMGWVRQAPGKGLEWVSGIEGPGDVTYY | 60 |
| BMS2h-572-619 | EVQLLESGGGLVQPGGSLRLSCAASGFTFNWQLMGWVRQAPGKGLEWVSGIEGPGDVTYY | 60 |
| BMS2h-572-633 | EVQLLESGGGLVQPGGSLRLSCAASGFTFNWELMGWARQAPGKGLEWVSGIEGPGDVTYY | 60 |
| BMS2h-572-634 | EVQLLESGGGLVQPGGSLRLSCAASGFTFNWELMGWARQAPGKGLEWVSGIEGPGDVTYY | 60 |
| BMS2h-572-635 | EVQLLESGGGLVQPGGSLRLSCAASGFTFNWELMGWARQAPGKGLEWVSGIEGPGDVTYY | 60 |
|  | ************************************************************ |

|  | CDR2 | CDR3 |  |
|---|---|---|---|
| BMS2h-572-6 | ADSVKGRFTISRDNSKNTLYLQMNSLRAEDTAVYYCVKVGKESNSDYRGQGTLVTVSS | 118 |
| BMS2h-572-608 | ADSVKGRFTISRDNSKNTLYLQMNSLRAEDTAVYYCVKVGKESNSDYRGQGTLVTVSS | 118 |
| BMS2h-572-614 | ADSVKGRFTISRDNSKNTLYLQMNSLRAEDTAVYYCVKVGKDAKSDYRGQGTLVTVSS | 118 |
| BMS2h-572-619 | ADSVKGRFTISRDNSKNTLYLQMNSLRAEDTAVYYCVKVGNDSRSDYRGQGTLVTVSS | 118 |
| BMS2h-572-633 | ADSVKGRFTISRDNSKNTLYLQMNSLRAEDTAVYYCVKVGKDAKSDYRGQGTLVTVSS | 118 |
| BMS2h-572-634 | ADSVKGRFTISRDNSKNTLYLQMNSLRAEDTAVYYCVKVGNDSRSDYRGQGTLVTVSS | 118 |
| BMS2h-572-635 | ADSVKGRFTISRDNSKNTLYLQMNSLRAEDTAVYYCVKVGKDSKSDYRGQGTLVTVSS | 118 |
|  | ********************************************************** |

FIG. 22

|  | CDR1 | CDR2 |  |
|---|---|---|---|
BMS2h-719-2    EVQLLESGGGLVQPGGSLRLSCAASGFTFKRYEMMWVRQAPGKGLEWVSSISSDGSFTYY 60
BMS2h-719-202  EVQLLESGGGLVQPGGSLRLSCAASGFTFKKYEMMWVRQAPGKGLEWVSSISSDGSFTYY 60
BMS2h-719-203  EVQLLESGGGLVQPGGSLRLSCAASGFTFNSYEMMWVRQAPGKGLEWVSSISSDGSFTYY 60
BMS2h-719-213  EVQLLESGGGLVQPGGSLRLSCAASGFTFKRYEMMWVRQAPGKGLEWVSSISSDGSFTYY 60
BMS2h-719-214  EVQLLESGGGLVQPGGSLRLSCAASGFTFKRYEMMWVRQAPGKGLEWVSSISSDGSFTYY 60
BMS2h-719-215  EVQLLESGGGLVQPGGSLRLSCAASGFTFKRYEMMWVRQAPGKGLEWVSSISSDGSFTYY 60
BMS2h-719-218  EVQLLESGGGLVQPGGSLRLSCAASGFTFKRYEMMWVRQAPGKGLEWVSSISSDGSFTYY 60
BMS2h-719-225  EVQLLESGGGLVQPGGSLRLSCAASGFTFNTYEMQWVRQAPGKGLEWVSSISSDGSFTYY 60
               ************************  *********************

CDR2                                              CDR3

BMS2h-719-2    ADSVKGRFTISRDNSKNTLYLQMNSLRAEDTAVYYCAEPFTEFDYWGHGTLVTVSS 116
BMS2h-719-202  ADSVKGRFTISRDNSKNTLYLQMNSLRAEDTAVYYCAEPFTEFDYWGHGTLVTVSS 116
BMS2h-719-203  ADSVKGRFTISRDNSKNTLYLQMNSLRAEDTAVYYCAEPFTEFDYWGHGTLVTVSS 116
BMS2h-719-213  ADSVKGRFTISRDNSKNTLYLQMNSLRAEDTAVYYCADPFTEMDYWGHGTLVTVSS 116
BMS2h-719-214  ADSVKGRFTISRDNSKNTLYLQMNSLRAEDTAVYYCADPFTEFDYWGHGTLVTVSS 116
BMS2h-719-215  ADSVKGRFTISRDNSKNTLYLQMNSLRAEDTAVYYCAEPFTELDYWGHGTLVTVSS 116
BMS2h-719-218  AESVKGRFTISRDNSKNTLYLQMNSLRAEDTAVYYCAEPFTEFDYWGHGTLVTVSS 116
BMS2h-719-225  ADSVKGRFTISRDNSKNTLYLQMNSLRAEDTAVYYCAEPFTEFDYWGHGTLVTVSS 116
               * *******************************  ************

FIG. 23

```
BMS2h-503-1    DIQMTQSPSSLSASVGDRVTITCRASHHIQRYLSWYQQKPGKAPKLLILWGSQLQSGVPS  60
BMS2h-503-2    DIQMTQSPSSLSASVGDRVTITCRASHDIQRYLSWYQQKPGKAPKLLIWGSQLQSGVPS  60
               *******************************:****************************

BMS2h-503-1    RFSGSGSGTDFTLTISSLQPEDFATYYCGQWAPPQTFGQGTKVEIKR  103
BMS2h-503-2    RFSGSGSGTDFTLTISSLQPEDFATYYCGQWAPPQTFGQGTKVEIKR  108
               ***********************************************
```

FIG. 24

```
BMS2h-116-1312   DIQMTQSPSSLSASVGDRVTITCRASQPIGPDLLWYQQKPGKAPKLLIYQTSILRSGVPS  60
BMS2h-116-1313   DIQMTQSPSSLSASVGDRVTITCRASQPIGPDLLWYQQKPGKAPKLLIYQTSILRSGVPS  60
BMS2h-116-1320   DIQMTQSPSSLSAYVGDRVTITCRASQPIGPDLLWYQQKPGKAPKLLIYQTSILRSGVPS  60
                 ************ ***********************************************

BMS2h-116-1312   RFSGSGSETDFTLTISNLQPEDLATYYCQQYWAFPVTFGKGTKVVIKR  108
BMS2h-116-1313   RFSGSGSETDFTLTISNLQPEDFATYYCQQYWAFPVTFGRGTKVVIKR  108
BMS2h-116-1320   RFSGSGSETDFTLTISNLQPEDFAKYYCQQYWAFPVTFGQGTKVVIKR  108
                 *********************  * *************  *******
```

US 11,180,567 B2

ANTIBODY POLYPEPTIDES THAT ANTAGONIZE CD40L

REFERENCE TO RELATED APPLICATIONS

This application is a continuation of U.S. application Ser. No. 15/668,305, filed Aug. 3, 2017, now U.S. Pat. No. 10,196,451, issued Feb. 15, 2019, which is a continuation of U.S. application Ser. No. 14/950,949, filed Nov. 24, 2015, now U.S. Pat. No. 9,765,150, issued Sep. 19, 2017, which is a continuation of U.S. application Ser. No. 14/510,474, filed Oct. 9, 2014, now U.S. Pat. No. 9,228,018, issued Jan. 5, 2016, which is a continuation of U.S. application Ser. No. 13/650,493, filed Oct. 12, 2012, now U.S. Pat. No. 8,895,010, issued Nov. 25, 2014, which claims the benefit of U.S. Provisional Application No. 61/655,110, filed Jun. 4, 2012, and U.S. Provisional Application No. 61/546,800, filed Oct. 13, 2011, which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Dec. 11, 2018, is named 200896_0005_05_US_584438.txt and is 1,222,324 bytes in size.

TECHNICAL FIELD

Antibodies and fragments thereof that target CD40L, compositions comprising the same, and methods of using the same for treatment of diseases involving CD40L activity are provided.

BACKGROUND

CD40 ligand (CD40L), also known as CD154, gp39, TNF-related activation protein (TRAP), 5c8 antigen, or T-BAM, is a trimeric transmembrane protein of the tumor necrosis factor (TNF) superfamily of molecules. CD40L is primarily expressed on activated T cells, as well as on activated leukocytes, eosinophils, basophils, natural killer cells, mast cells, and non-immune cells such as platelets and activated endothelial cells. CD40L also exists in soluble form (sCD40L) that is produced by microsomal stimulus-dependent cleavage of the membrane-bound CD40L. Most of sCD40L in circulation (>90%) is platelet-derived.

CD40L binds CD40, a type I transmembrane glycoprotein belonging to the TNF receptor (TNFR) family. Although all monomeric, dimeric, and trimeric forms of sCD40L can bind to CD40, the trimeric form of sCD40L has the most potent biological activity through oligomerization of cell surface CD40, a common feature of TNFR family. The highest expression of CD40 has been observed on antigen presenting cells (APCs), such as B cells, macrophages, and dendritic cells, while lower expression of this receptor is noted on a variety of other cell types, including stromal cells and thymic epithelium. The CD40-CD40L interaction is essential for normal T-B cell interactions, including increased co-stimulation, T-cell priming, cytokine production, antibody-class switching and affinity maturation, and antibody and autoantibody production.

The crucial role of CD40-CD40L interactions in immune and inflammatory responses has made them a promising target for treatment of pathological immuno-inflammatory processes. Blockade of CD40-CD40L interactions by means of specific CD40L monoclonal antibodies (mAbs) successfully prevents allograft rejection in primates and treats autoimmune diseases and atherosclerosis in animal models. Montgomery et al., *Transplantation* 74: 1365-1369 (2002).

In humans, two different anti-CD40L mAb clones have been used in clinical trials for treatment of different autoimmune diseases. Maribel et al., *Mol. Immunol.* 45: 937-44 (2008). Monoclonal antibodies, however, can display unusually high incidence of thromboembolic (TE) complications, such as atherothrombotic central nervous system events, myocardial infarction, pulmonary embolism, and deep vein thrombosis. For example, the usefulness of the anti-CD40L mAb clone hu5c8 (anti-CD40L mAb, Biogen) is limited by an unusually high incidence of TE complications. TE by these antibodies is thought to result from the formation of higher-order immune complexes (IC) of the mAbs with membrane-bound CD40L on platelets, or sCD40L shed from platelets, that can ligate and thereby aggregate neighboring platelets via their FcgRIIa receptors, resulting in thrombi formation. The risk of thromboembolism has led to a halt in all ongoing clinical trials. Boumpas et al., *Arthritis & Rheumatism* 48: 719-727 (2003).

SUMMARY

Anti-CD40L antibody antagonists that are less likely to cause platelet aggregation and thus cause thromboembolism are still needed in a clinical setting. Novel antibody polypeptides that specifically bind human CD40L are provided. The antibody polypeptides advantageously do not cause platelet aggregation. The antibody polypeptides are useful in the treatment of diseases involving CD40L activation, including autoimmune diseases, transplant rejection, and allergic responses. The antibody polypeptides comprise a variable domain. Exemplary antibody polypeptides are in the form of a domain antibody (dAb) that contains a single variable domain. Alternatively, the dAbs can be bi-specific reagents that comprise a second variable domain that can bind another antigen, such as human serum albumin (HSA), for example.

An antibody polypeptide is provided comprising a first variable domain that specifically binds human CD40L, wherein the first variable domain comprises the amino acid sequence of one of the variable domains selected from the BMS2h lineage. Further provided is an isolated antibody polypeptide comprising a first variable domain that specifically binds human CD40L, wherein CD40L comprises the amino acid sequence of SEQ ID NO: 1, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, (c) a CDR3 region which differs from the CDR3 region of BMS2h-572-633 by up to three amino acids, (d) a FR1 region which differs from the FR1 region of BMS2h-572-633 by up to three amino acids, (e) a FR2 region which differs from the FR2 region of BMS2h-572-633 by up to three amino acids, (f) a FR3 region which differs from the FR3 region of BMS2h-572-633 by up to three amino acids, and (g) a FR4 region which differs from the FR4 region of BMS2h-572-633 by up to three amino acids; and wherein the antibody polypeptide inhibits binding of CD40L to CD40 with an EC50 of 100 pM to 100 nM. Also provided is an antibody polypeptide, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, and (c) a CDR3 region which differs from the CDR3 region of BMS2h-572-633 by up to three amino acids. Alternatively, the amino acid sequence of the first variable domain can differ from the amino acid sequence of BMS2h-572-633 by up to and including 10 amino acids. Furthermore, the amino acid sequence of the first variable domain can differ from the amino acid sequence of BMS2h-572-633 by up to and including 5 amino acids. The amino acid sequence of the first variable domain can also differ from the amino acid sequence of BMS2h-572-633 by up to and including 2 amino acids. Alternatively, the first variable domain differs from the amino acid sequence of BMS2h-572-633 by 1 amino acid.

Also provided is an antibody polypeptide selected from the lineage group of BMS2h-572, wherein the amino acid sequence of the first variable domain further comprises: (a) a CDR1 region having a sequence Trp-$X_1$-Leu-Met-Gly (SEQ ID NO: 2), wherein $X_1$ is Glu or Gln; (b) a CDR2 region having a sequence Gly-Ile-Glu-Gly-Pro-Gly-Asp-Val-Thr-Tyr-Tyr-Ala-Asp-Ser-Val-Lys-Gly (SEQ ID NO: 3); and (c) a CDR3 region having a sequence Lys-$X_2$-$Y_2$-$Z_2$-Ser-Asp-Tyr (SEQ ID NO: 4), wherein $X_2$ is Asp or Glu, $Y_2$ is Ala or Ser, and $Z_2$ is Lys, Asn, or Arg. Also provided is the antibody polypeptide, wherein the amino acid sequence of the first variable domain further comprises: (a) a FR1 region having a sequence Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Asn (SEQ ID NO: 5); (b) a FR2 region having a sequence Trp-$X_1$-Arg-Gln-Ala-Pro-Gly-Lys-Gly-Leu-Glu-Trp-Val-Ser (SEQ ID NO: 6), wherein $X_1$ is Ala or Val; (c) a FR3 region having a sequence Arg-Thr-Phe-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Val-Lys-Val-Gly (SEQ ID NO: 7); and (d) a FR4 region having a sequence Arg-Gly-Gln-Gly-Thr-Leu-Val-Thr-Val-Ser-Ser (SEQ ID NO: 8).

Alternatively, the first variable domain of the antibody polypeptide can comprise the amino acid sequence of BMS2h-572-633.

Also provided is an antibody polypeptide selected from the lineage group of BMS2h-719, comprising a first variable domain with the following consensus sequence: Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-$X_1$-$Y_1$-Tyr-Glu-Met-$Z_1$-Trp-Val-Arg-Gln-Ala-Pro-Gly-Lys-Gly-Leu-Glu-Trp-Val-Ser-Ser-Ile-Ser-Ser-Asp-Gly-Ser-Phe-Thr-Tyr-Tyr-Ala-$A_1$-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-$B_1$-Pro-Phe-Thr-Glu-$C_1$-Asp-Tyr-Trp-Gly-His-Gly-Thr-Leu-Val-Thr-Val-Ser-Ser (SEQ ID NO: 9), wherein $X_1$ is Lys or Asn; $Y_1$ is Arg, Lys, Ser, or Thr; $Z_1$ is Met or Gln; $A_1$ is Asp or Glu; $B_1$ is Asp or Glu; and $C_1$ is Phe, Met, or Leu.

Also provided is an antibody polypeptide selected from the lineage group of BMS2h-503, comprising a first variable domain with the following consensus sequence: Asp-Ile-Gln-Met-Thr-Gln-Ser-Pro-Ser-Ser-Leu-Ser-Ala-Ser-Val-Gly-Asp-Arg-Val-Thr-Ile-Thr-Cys-Arg-Ala-Ser-His-$X_1$-Ile-Gln-Arg-Tyr-Leu-Ser-Trp-Tyr-Gln-Gln-Lys-Pro-Gly-Lys-Ala-Pro-Lys-Leu-Leu-Ile-Leu-Trp-Gly-Ser-Gln-Leu-Gln-Ser-Gly-Val-Pro-Ser-Arg-Phe-Ser-Gly-Ser-Gly-Ser-Gly-Thr-Asp-Phe-Thr-Leu-Thr-Ile-Ser-Ser-Leu-Gln-Pro-Glu-Asp-Phe-Ala- Thr-Tyr-Tyr-Cys-Gly-Gln-Trp-Trp-Ala-Pro-Pro-Gln-Thr-Phe-Gly-Gln-Gly-Thr-Lys-Val-Glu-Ile-Lys-Arg (SEQ ID NO: 10), wherein $X_1$ is His or Asp.

Also provided is an antibody polypeptide selected from the lineage group of BMS2h-116, comprising a first variable domain with the following consensus sequence: Asp-Ile-Gln-Met-Thr-Gln-Ser-Pro-Ser-Ser-Leu-Ser-Ala-$X_1$-Val-Gly-Asp-Arg-Val-Thr-Ile-Thr-Cys-Arg-Ala-Ser-Gln-Pro-Ile-Gly-Pro-Asp-Leu-Leu-Trp-Tyr-Gln-Gln-Lys-Pro-Gly-Lys-Ala-Pro-Lys-Leu-Leu-Ile-Tyr-Gln-Thr-Ser-Ile-Leu-Arg-Ser-Gly-Val-Pro-Ser-Arg-Phe-Ser-Gly-Ser-Gly-Ser-Glu-Thr-Asp- Phe-Thr-Leu-Thr-Ile-Ser-Asn-Leu-Gln-Pro-Glu-Asp-$Y_1$-Ala-$Z_1$-Tyr-Tyr-Cys-Gln-Gln-Tyr-Trp-Ala-Phe-Pro-Val-Thr-Phe-Gly-$A_1$-Gly-Thr-Lys-Val-Val-Ile-Lys-Arg (SEQ ID NO: 11), wherein $X_1$ is Ser or Tyr; $Y_1$ is Leu or Phe; $Z_1$ is Thr or Lys; and $A_1$ is Lys, Arg, or Gln.

Also provided is an antibody polypeptide comprising a first variable domain that specifically binds human CD40L, wherein the antibody polypeptide is a domain antibody (dAb). The antibody polypeptide can be a fusion polypeptide comprising the first variable domain and an Fc domain. Alternatively, the fusion polypeptide can comprise an IgG4 Fc domain. The fusion polypeptide also can comprise an IgG1 Fc domain. The fusion polypeptide can also comprise an IgG1 Fc domain. Alternatively, the fusion polypeptide can comprise a CT-Long domain. The fusion polypeptide can also comprise a CT-short domain. Alternatively, the fusion polypeptide can comprise a N297Q Long Fc domain. The fusion polypeptide can alternatively comprise a N297Q Short Fc domain.

Also provided is an antibody polypeptide comprising a first variable domain that specifically binds human CD40L, wherein the antibody polypeptide further comprises a second variable domain that specifically binds a second antigen, wherein the second antigen is an antigen other than human CD40L. The second antigen can be a cluster of differentiation (CD) molecule or a Major Histocompatibility Complex (MHC) Class II molecule. Alternatively, the second antigen can be serum albumin (SA).

Also provided is a nucleic acid encoding any of the antibody polypeptides provided herein. Further contemplated is a vector comprising the nucleic acid. An isolated host cell can comprise such vector.

A pharmaceutical composition is provided comprising a therapeutically-effective amount of the presently provided antibody polypeptide and a pharmaceutically acceptable carrier. The pharmaceutical composition can further comprise an immunosuppressive/immunomodulatory and/or anti-inflammatory agent.

A method of treating an immune disease in a patient in need of such treatment is provided comprising administering to the patient a therapeutically effective amount of the pharmaceutical composition described herein. An exemplary method administers the pharmaceutical composition in combination with an immunosuppressive/immunomodulatory and/or anti-inflammatory agent. The immune disease can be an autoimmune disease or a graft-related disease. Alternatively, the immune disease is a graft-related disease. Furthermore, the graft-related disease can comprise solid organ, tissue and/or cell transplant rejection. Alternatively, the graft-related disease is graft versus host disease (GVHD). The graft-related disease can further be an acute transplant rejection. Alternatively, the graft-related disease can be a chronic transplant rejection.

Also provided is the method of treating a graft-related disease, wherein the pharmaceutical composition is co-administered with a CTLA4 mutant molecule. The CTLA4 mutant molecule can be L104EA29Y-Ig (belatacept).

A method of treating an immune disease in a patient in need of such treatment is also provided comprising administering to the patient a therapeutically effective amount of the pharmaceutical composition provided herein, wherein the immune disease is selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, alcohol addiction, and drug addiction. Alternatively, the immune disease can be myasthenia gravis, idiopathic thrombocytopenic purpura, or systemic sclerosis.

Also provided is a use of an isolated antibody polypeptide disclosed herein for the preparation of a medicament for the treatment of a patient, wherein the patient has or is at risk of having an immune disease. Further provided is a use of an isolated antibody polypeptide disclosed herein for preparation of a medicament for alleviating at least one symptom of an immune disease in a patient in need thereof.

Further provided herein is an isolated antibody polypeptide comprising a first variable domain, wherein said antibody polypeptide specifically binds human CD40L, wherein CD40L comprises the amino acid sequence of SEQ ID NO: 1, wherein the antibody polypeptide competes with the binding of BMS2h-572-633, and wherein the antibody polypeptide inhibits binding of CD40L to CD40 with an EC50 of 100 pM to 100 nM. In one aspect, the first variable domain comprises the amino acid sequence of one of the antibody polypeptides selected from the lineage group consisting of BMS2h-572, BMS2h-719, BMS2h-503, and BMS2h-116. In another aspect, the first variable domain comprises an amino acid sequence at least 95% identical to BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320. In yet another aspect, the first variable domain comprises the amino acid sequence of BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A depicts the domain antibody that comprises a $V_H$ variable domain BMS2h-572-633 fused to a modified Fc tail from Abatacept IgG1.

FIG. 1B shows the amino acid sequence (SEQ ID NO: 1355) of the variable domain BMS2h-572-633 (in blue). The Fc fusion protein is a dimer of molecular weight 77,984 Daltons, with each polypeptide chain consisting of 354 amino acids. The variable domain is fused by a linker (green) to the mutated Fc construct of human IgG1, wherein three cysteine residues (shown in purple) are substituted with serine, and one proline (shown in red) is substituted with a serine residue.

FIG. 3 provides sequences (SEQ ID NOS 1356-1361, respectively, in order of appearance) of various Fc domains. Linker regions are shown in boxes.

FIG. 4 shows examples of various Fc-formatted domain antibodies (SEQ ID NOS 1362-1365, respectively, in order of appearance). Linker regions are indicated by boxes.

FIG. 14 demonstrates PK/PD modeling of BMS-986003 and 5c8-IgG1 plasma exposures and anti-KLH antibody response (IgG Titers).

FIGS. 21, 22, 23, and 24 show is ClustalW2 alignments of representative domain antibody polypeptides from lineages BMS2h-572, BMS2h-719, BMS2h-503, and BMS2h-116, respectively. FIG. 21 discloses SEQ ID NOS 243, 251, 257, 262 and 274-276, respectively, in order of appearance, FIG. 22 discloses SEQ ID NOS 352, 354-355 and 357-361, respectively, in order of appearance, FIG. 23 discloses SEQ ID NOS 1087-1088, respectively, in order of appearance, and FIG. 24 discloses SEQ ID NOS 970-971 and 974, respectively, in order of appearance.

DETAILED DESCRIPTION

Figure 2:
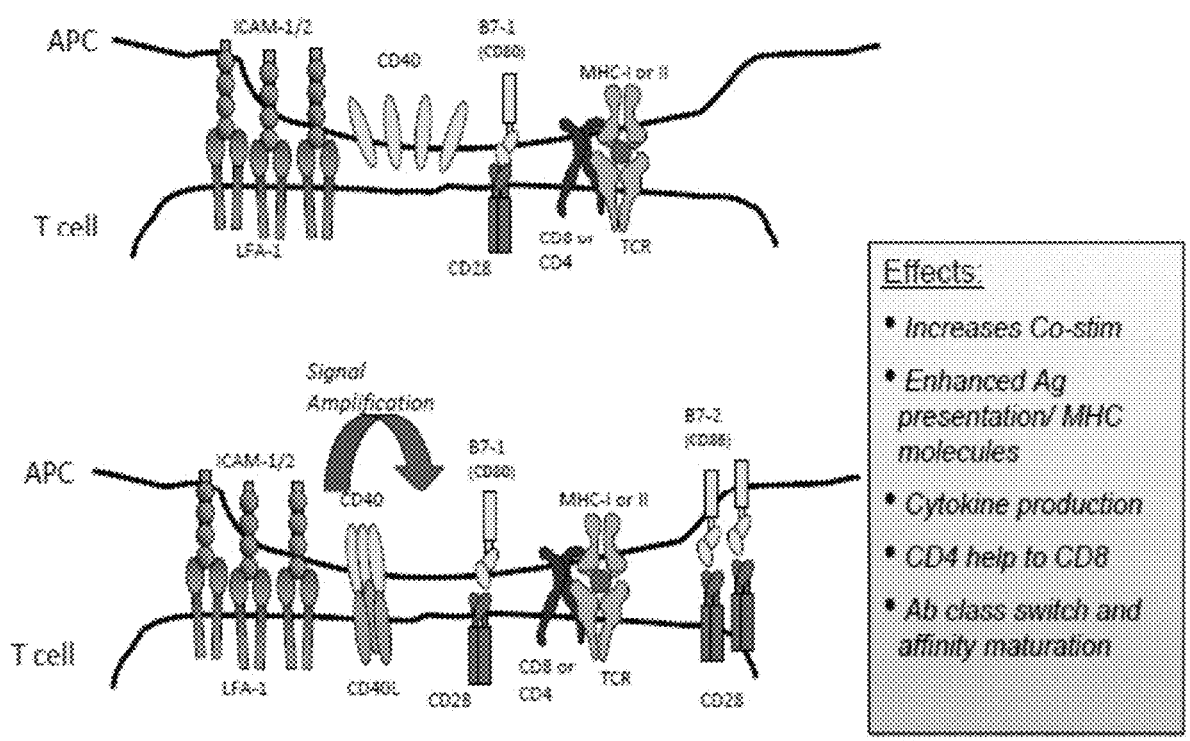
FIG. 2 depicts a working model for the CD40-40L pathway. The top panel demonstrates initial stages of an encounter between a T cell and an APC. The initial encounter driven by T cell receptor (TCR) engagement of pMHC complex (signal 1) coupled with an early CD28-CD80 interaction (signal 2) is sufficient for the cell surface expression of trimeric CD40L (bottom panel). Engagement of CD40 by CD40L results in numerous biological responses outlined in the grey box.

Antibody polypeptides that specifically bind to human CD40L are provided. The antibody polypeptides do not activate platelets, and the antibody polypeptides are useful in the treatment of diseases involving CD40L activation, such as graft-related diseases and autoimmune diseases. The antibody polypeptides may be selected using a primary screen that utilizes cell binding assays, followed by one or more rounds of error-prone or degenerate oligonucleotide-directed affinity maturation. As a result, a genus of antibody polypeptides that specifically bind CD40L are provided.

A "lineage" is a set of related antibody polypeptides that were prepared from a common precursor by error-prone or degenerate oligonucleotide-directed affinity maturation, as disclosed in the examples below, and that are expected to bind CD40L. The nomenclature of the antibody polypeptides is used to designate the various lineages. The nomenclature "BMS2h-572," for example, refers to antibody polypeptides of lineage 572, which were raised against human CD40L. "Lineage BMS2h-572" antibody polypeptides include BMS2h-572-1 through BMS2h-572-19, BMS2h-572-21 through BMS2h-572-24, BMS2h-572-601 through BMS2h-572-627, and BMS2h-572-630 through BMS2h-572-635.

Accordingly, in one aspect, an antibody polypeptide comprises a variable domain that specifically binds human CD40L, where the antibody polypeptide competes with the binding of any one of the domain antibodies (dAbs) listed in TABLE 1 or TABLE 3. For example, the antibody polypeptide may compete with a dAb selected from the 2h lineage. The dAb also may be selected from a lineage selected from the group consisting of BMS2h-116, BMS2h-503, BMS2h-572, and BMS2h-719, such as the dAb BMS2h-572-633, BMS2h-572-608, or BMS2h-572-614, for instance. In another aspect, an antibody polypeptide specifically binds human CD40L as any one of the dAbs listed in TABLE 1 and TABLE 3. For example, the antibody polypeptide may comprise a variable domain that specifically binds human CD40L as the dAb BMS2h-572-633, BMS2h-572-608, or BMS2h-572-614, for instance.

The antibody polypeptides may be a domain antibody containing a single variable domain. The antibody polypeptides also may comprise additional domains, such as an Fc domain. For instance, the antibody polypeptide may comprise a second variable domain that specifically binds human serum albumin (HSA). Such dual specific antibody polypeptides may have an increased half-life, for example.

As used herein, "specific binding" refers to the binding of an antigen by an antibody polypeptide with a dissociation constant ($K_d$) of about 1 μM or lower as measured, for example, by surface plasmon resonance (SPR). Suitable assay systems include the BIAcore™ surface plasmon resonance system and BIAcore™ kinetic evaluation software (e.g., version 2.1). The affinity or $K_d$ for a specific binding interaction may be about 1 μM or lower, about 500 nM or lower or about 300 nM or lower.

The term "about" will be understood by persons of ordinary skill in the art and will vary to some extent on the context in which it is used. Generally, about encompasses a range of values that are plus/minus 10% of a referenced value.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

1. CD40L and CD40L Activities

Antibody polypeptides are provided that bind human CD40L. CD40L is also known as CD154, gp39, TNF-related activation protein (TRAP), 5c8 antigen, or T-BAM. Relevant structural information for human CD40L can be found, for example, at UniProt Accession Number P29965. "Human CD40L" refers to the CD40L comprising the following amino acid sequence:

```
                                          (SEQ ID NO: 1)
         10          20         30          40
MIETYNQTSP RSAATGLPIS MKIFMYLLTV FLITQMIGSA 50          60         70          80
LFAVYLHRRL DKIEDERNLH EDFVFMKTIQ RCNTGERSLS 90         100        110         120
LLNCEEIKSQ FEGFVKDIML NKEETKKENS FEMQKGDQNP 130         140        150         160
QIAAHVISEA SSKTTSVLQW AEKGYYTMSN NLVTLENGKQ
```

```
            170        180        190        200
LTVKRQGLYY IYAQVTFCSN REASSQAPFI ASLCLKSPGR 210        220        230        240
FERILLRAAN THSSAKPCGQ QSIHLGGVFE LQPGASVFVN 250        260
VTDPSQVSHG TGFTSFGLLK L
```

CD40L has also been sequenced in *Sus scrofa, Mus musculus, Canis familiaris, Bos ffini, Macaca mulatta, Aotus tivirgatus, Callithrix jacchus, Cercocebus torquatus atys, Macaca nemestrina, Rattus norvegicus, Gallus gallus, Felis catus,* and *Sus scrofa.*

Binding of the present antibody polypeptides to CD40L antagonizes CD40L activity. "CD40L activities" include, but are not limited to, costimulation and activation an APC in association with T cell receptor stimulation by MHC molecules on the APC, secretion of all immunoglobulin isotypes in the presence of cytokines, stimulation of B cell proliferation, cytokine production, antibody class switching and affinity maturation. For example, patients with X-linked hyper-IgM syndrome express functional CD40 on their B cells, but their activated T cells have a defective CD40L protein, resulting in its inability to activate B cells and induce immunoglobulin isotype switching. Aruffo et al., *Cell* 72:291-300 (1993).

CD40L activities can be mediated by interaction with other molecules. "CD40 activities" include the functional interaction between CD40L and the following molecules: CD40 (CD40L receptor), α5β1 integrin, and αIIbβ3. For example, CD40L binds its receptor, CD40, which is expressed on a variety of APCs, such as B cells, macrophages, and dendritic cells, as well as on stromal cells, vascular endothelial cells, and platelets.

As used herein, the terms "activate," "activates," and "activated" refer to an increase in a given measurable CD40L activity by at least 10% relative to a reference, for example, at least 10%, 25%, 50%, 75%, or even 100%, or more. A CD40L activity is "antagonized" if the activity is reduced by at least 10%, and in an exemplary embodiment, at least 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40L activity. In one embodiment, the antibody polypeptide does not activate B cell proliferation. In another embodiment, the antibody polypeptide does not activate cytokine secretion by T cells or dendritic cells (DCs), where the cytokine is at least one cytokine selected from the group consisting of IL-2, IL-6, IL-10, IL-12, IL-13, IL-17, IL-23, TNF-α, and IFN-γ.

2. Antibody Polypeptides

The antibody polypeptides comprise a variable domain. In one embodiment, the antibody polypeptides are in the form of a dAb that contains a single variable domain. Antibody polypeptides may be full-length anti-CD40L immunoglobulin molecules comprising two heavy (H) chains and two light (L) chains interconnected by disulfide bonds. In this embodiment, the amino terminal portion of each chain includes a variable domain ($V_L$ or $V_H$) of about 100-120 amino acids. The complementarity determining regions (CDRs) contained therein are primarily responsible for antigen recognition, although framework residues can play a role in epitope binding. The carboxy-terminal "half" of each heavy chain defines a constant region (Fc) primarily responsible for effector function.

Antibody polypeptides also may be "fragments" comprising a portion of the full-length anti-CD40L immunoglobulin molecule that comprises a variable domain that specifically binds CD40L. Thus, the term "antibody polypeptides" includes an antigen-binding heavy chain, light chain, heavy chain-light chain dimer, Fab fragment, F(ab')$_2$ fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or ε, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40L antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, and FR4. The three CDRs of the light chain are referred to as "LCDR1, LCDR2, and LCDR3" and the three CDRs of the heavy chain are referred to as "HCDR1, HCDR2, and HCDR3."

As used herein, the term "Fc domain" refers to the constant region antibody sequences comprising CH2 and CH3 constant domains as delimited according to Kabat et al., *Sequences of Immunological Interest*, 5$^{th}$ ed., U.S. Dept. Health & Human Services, Washington, D.C. (1991). The Fc domain may be derived from an IgG1 or an IgG4 Fc region, for example.

A variable domain may be fused to an Fc domain. Examples of various Fc-formatted domain antibodies and their potency are provided in TABLE 6. FIG. 3 provides sequences of various Fc domains provided herein. Linker regions are shown in boxes. As used in TABLE 6, "Fc" indicates that the dAb is fused to a human IgG1 short Fc. "CT Long Fc," also called CT-L2, refers to the Fc from CTLA4. The underlined S are cysteine-to-serine point mutations made to eliminate the disulfides in the Fc hinge. "CT Short," also called CT-S1, is shorter than CT Long by 7 amino acids. "N297Q Long Fc," also referred to as N297Q-L4, is the Fc domain of human IgG1 with a N297Q mutation made to eliminate the N-linked carbohydrate in the Fc. "N297Q Short Fc," also called N297Q-S3, is short than N297Q Long Fc by 7 amino acids, and is a human IgG1 with a N297Q point mutation made to eliminate the N-linked carbohydrate in the Fc domain. "CT-Fc SP5" is the CT Long Fc, where SP5 refers to the octeonectin signal peptide used for secretion from the mammalian expression host. Cleavage site is indicated by "A". FIG. 4 further provides examples of various Fc domain formats.

When a variable domain is fused to an Fc domain, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen.

In one embodiment, the variable domain of an antibody polypeptide comprises CDR1, CDR2, and CDR3 regions that have the same amino acid sequence as the CDR1, CDR2, and CDR3 regions of one of the dAbs listed in TABLE 1 or TABLE 3 or that each differ from the CDR1, CDR2, and CDR3 regions by one, two, or three amino acids. For example, the antibody polypeptide may comprise CDR1, CDR2, and CDR3 regions that have the same amino acid sequence as the CDR1, CDR2, and CDR3 regions of BMS2h-572-633, BMS2h-572-608, or BMS2h-572-614, for example.

A "domain antibody" (dAb) comprises a single variable ($V_L$ or $V_H$) domain that is capable of specifically and monovalently binding an antigen, such as CD40L. For example, a dAb may have a $V_{HH}$ structure, characteristic of a camelid dAb. A "$V_H$ domain" as used herein is meant to include a $V_{HH}$ structure. In another embodiment, the $V_H$ domains (including all features and combination of features presented as embodiments herein) are other than $V_{HH}$ domains. dAbs may form homo- or heterodimers in solution. While not limited by any particular theory, it is believed that the dAbs disclosed herein do not cause platelet aggregation, because the antibodies containing mutated Fc constructs do not bind FcγRIIa (also known as CD32a) on the platelet surface and do not activate platelets.

As used herein, the term "variable domain" refers to immunoglobulin variable domains defined by Kabat et al., *Sequences of Immunological Interest*, 5$^{th}$ ed., U.S. Dept. Health & Human Services, Washington, D.C. (1991). The numbering and positioning of CDR amino acid residues within the variable domains is in accordance with the well-known Kabat numbering convention.

The term "human," when applied to antibody polypeptides, means that the antibody polypeptide has a sequence, e.g., framework regions and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more FR with the same amino acid sequence as a corresponding framework region encoded by a human germline antibody gene segment. For example, a domain antibody may comprise the $V_H$ germline gene segments DP47, DP45, or DP38, the $V_\kappa$ germline gene segment DPK9, the $J_H$ segment JH4b, or the $J_\kappa$ segment $J_\kappa 1$.

Changes may be made to antibody polypeptide sequences while retaining the ability to bind CD40L specifically. Specifically, the antibody polypeptides (e.g., a dAb) may comprise a variant variable domain that retains the function of specifically binding CD40L as the dAb BMS2h-572-633. In one embodiment, the variant variable domain may compete with BMS2h-572-633 for specific binding to CD40L. Error-prone affinity maturation, as disclosed in the examples below, provides one exemplary method for making and identifying antibody polypeptides with variant sequences that specifically bind CD40L.

For example, a variant variable domain may differ from one of the variable domains listed in TABLE 1 and TABLE 3 by up to 10 amino acids or any integral value between, where the variant variable domain specifically binds CD40L. Alternatively, the variant variable domain may have at least 90% sequence identity (e.g., at least 91%, 92%, 93%, 94%, 95%, 96%, 97%, 98%, or 99% sequence identity) relative to a sequence listed in the present Sequence Listing. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST.

In one embodiment, amino acid substitutions may be made to individual FR regions, such that a FR comprises 1, 2, 3, 4, or 5 amino acid differences relative to the amino acid sequence of the corresponding FR encoded by a human germline antibody gene segment. In another embodiment, the variant variable domain may contain one or two amino acid substitutions in a CDR. In other embodiments, amino acid substitutions to FR and CDR regions may be combined. Representative variable domains that specifically bind CD40L are listed in TABLE 1 and TABLE 3.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40L. The amplified variable domain may be inserted into a suitable expression vector, e.g., pHEN-1 (Hoogenboom et al. (1991) *Nucleic Acids Res.* 19:4133-4137) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NSO, and the like, followed by purification using one or a combination of methods, including protein A affinity chromatography, ion exchange, reverse phase techniques, or the like.

In one aspect, the antibody polypeptide is a "dual specific" antibody polypeptide comprising a first variable domain that specifically binds human CD40L. Dual specific antibody polypeptides comprise a second variable domain that specifically binds a second antigen that is other than human CD40L.

In another embodiment, the second antigen may be a cell surface molecule of an immune effector cell or a soluble molecule such as a cytokine, for example. Binding of the dual specificity antibody polypeptide could be used to antagonize CD40L and antagonize a biological activity of the second antigen. Cell surface molecules of immune effector cells include the cluster of differentiation (CD) molecules. Representative CD markers are listed on the Internet at hypertext transfer protocol http://en.wikipedia.org/wiki/List_of_human_clusters_of_differentiation (last modified on Aug. 8, 2012). Cell surface molecules of immune effector cells also include Major Histocompatibility Complex (MHC) Class II molecules. Antibodies against these cell surface molecules are known in the art and can be used a source of a variable domain to construct a dual specific antibody polypeptide.

In one embodiment, antibody polypeptides of a dual specific ligand may be linked by an "amino acid linker" or "linker." For example, a dAb may be fused to the N-terminus of an amino acid linker, and another dAb may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include $(GGGGS)_n$ (SEQ ID NO: 12), where n may be any integer between 1 and 5. Other suitable linker sequences may be selected from the group consisting of AS, AST, TVAAPS (SEQ ID NO: 13), TVA, and ASTSGPS (SEQ ID NO: 14).

The binding of the second antigen can increase the in vivo half-life of the antibody polypeptide. For example, the second variable domain of the dual specific antibody polypeptide may specifically bind serum albumin (SA), e.g., human serum albumin (HSA). The antibody polypeptide formatted to bind I can have an increased in vivo t-α ("alpha half-life") or t-β ("beta half-life") half-life relative to the same unformatted antibody polypeptide. The t-α and t-β half-lives measure how quickly a substance is distributed in and eliminated from the body. The linkage to I may be accomplished by fusion of the antibody polypeptide with a second variable domain capable of specifically binding I, for example. Anti-human serum albumin antibodies are well-known in the art. See, e.g., Abcam®, Human Serum Albumin antibodies ab10241, ab2406, and ab8940, available on the Internet at hypertext transfer protocol www.abcam.com/index.html, or GenWay, ALB antibody, available on the Internet at hypertext transfer protocol www.genwaybio.com. Variable domains that specifically bind I can be obtained from any of these antibodies, and then fused to an antibody polypeptide of the disclosure using recombinant techniques that are well known in the art.

Alternatively, the linking of the antibody polypeptide to I can be accomplished by directly fusing the antibody polypeptide sequence to an I coding sequence using techniques well known to the skilled artisan. The I coding sequences can be obtained by PCR using primers derived from the cDNA sequence available at GenBank Accession No. NM000477, for example.

In one embodiment, the tα-half-life of the I-linked domain antibody composition is increased by 10% or more. In another embodiment, the tα-half-life of the I-linked domain antibody composition is in the range of 0.25 hours to 6 hours. In another embodiment, the tβ-half-life of the I-linked domain antibody composition is increased by 10% or more. In another embodiment, the tβ-half-life of the I-linked domain antibody composition is in the range of 12 to 48 hours.

In another embodiment, an antibody polypeptide may be formatted to increase its in vivo half-life by PEGylation. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxylsuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman, et al., "PEGylated antibodies and antibody fragments for improved therapy: a review," *Adv. Drug Deliv. Rev.* 54(4):531-45 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

3. Pharmaceutical Compositions and Methods of Treatment

A pharmaceutical composition comprises a therapeutically-effective amount of one or more antibody polypeptides and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, THE SCIENCE AND PRACTICE OF PHARMACY, A. Gennaro, et al., eds., 21$^{st}$ ed., Mack Publishing Co. (2005).

The pharmaceutical composition further may comprise an immunosuppressive/immunomodulatory and/or anti-inflammatory agent. A method of treating an immune disease in a patient in need of such treatment may comprise administering to the patient a therapeutically effective amount of the pharmaceutical composition. Antagonizing CD40L-mediated T cell activation could inhibit undesired T cell responses occurring during autoimmunity, transplant rejection, or allergic responses, for example. Inhibiting CD40L-mediated T cell activation could moderate the progression and/or severity of these diseases.

As used herein, a "patient" means an animal, e.g. mammal, including humans. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to graft-related disease, inflammation, allergy, and autoimmune disease. The autoimmune disease may be selected from the group consisting of systemic lupus erythematosus, multiple sclerosis, rheumatoid arthritis, diabetes, psoriasis, scleroderma, atherosclerosis, inflammatory bowel disease, and ulcerative colitis.

Diseases that can be treated by administering the pharmaceutical composition may be selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus' phenomenon, anaphylaxis, alcohol addiction, and drug addiction.

Preferred indications for administration of the present pharmaceutical compositions are, for example, immune thrombocytopenic purpura, systemic sclerosis, myasthenia gravis, allograft rejection, and graft-versus-host disease.

The pharmaceutical composition may be administered alone or in combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

For example, the disclosed pharmaceutical composition may be co-administered, concomitantly or sequentially, with a cytotoxic T-lymphocyte antigen 4 (CTLA4) mutant molecule, such as L104EA29Y-Ig (belatacept). CTLA4 binds to CD80 (B7-1) and CD86 (B7-2) with higher avidity than CD28, and it is transiently expressed on T cells following their activation, where it interrupts the interaction between CD28 and CD80/86. Oosterwegel et al., *Curr. Opin. Immunol.* 11: 294-300 (1999). This creates a negative feedback signal for T cell activation.

CTLA4 mutant molecules, including L104EA29Y-Ig, have increased binding avidity to CD80/86 compared to wild-type CTLA4. Intervention of the CD28-CD80/86 pathway by L104EA29Y-Ig has been successfully pursued, for example, to treat graft-related diseases in non-human primate transplant models, alone or in combination with other immunosuppressive agents. Larsen et al., *Amer. J. Transplant.* 5: 443 (2005). U.S. Patent Application number 2010/ 0166774 describes the structure of L104EA29Y-Ig, methods of producing it, and a formulation comprising a CTLA4 molecule; and the application is herein incorporated by reference. U.S. Pat. Nos. 7,094,874 and 7,482,327 further disclose administration (including co-administration with one or more other drugs) and dosage schedule of L104EA29Y-Ig, and the disclosures of these patents are herein incorporated by reference.

Any suitable method or route can be used to administer the antibody polypeptide or the pharmaceutical composition. Routes of administration include, for example, oral, intravenous, intraperitoneal, subcutaneous, or intramuscular administration. A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of a domain antibody is 0.1-20 mg/kg, and in an aspect, 1-10 mg/kg, relative to the body weight of the patient. The dose of antibody polypeptide(s) can be further guided by the amount of antibody polypeptide(s) required for CD40 antagonism in in vitro and/or in vivo models of disease states. Representative models are described below and in the examples.

4. In Vitro and In Vivo Models

The ability of antibody polypeptides of the disclosure to antagonize CD40L can be tested in one of several available in vitro or in vivo model systems. Appropriate human, animal, and cell model systems are described below. Further cell assay systems are described in the examples.

4.1. Immune Thrombocytopenic Purpura (ITP) In Vivo Model:

The potential role of CD40-CD40L in the pathogenesis of ITP is reported by Patel et al., *British J. Haematology* 141: 545-548 (2008). Antiplatelet autoantibodies in patients with ITP bind to circulating platelets and accelerate their destruction. The primary mechanism by which anti-CD40L antibodies are thought to increase the platelet count in ITP is by blocking T-cell based activation of autoreactive B cells that produce anti-platelet antibodies. Anti-CD40L antibodies may also block expression of CD40L on platelets, thus preventing autopresentation of platelet glycoprotein antigens to macrophages. Furthermore, anti-CD40L mAbs inhibit direct interactions between platelet CD40L and other cells, such as plasmacytoid dendritic cells (DCs), which have recently been implicated in driving the type 1 interferon (IFN) response in human lupus patients. Duffau et al., *Sci. Transl. Med.* 2: 47 (2010).

Patel et al. demonstrated efficacy of two humanized anti-CD40L monoclonal antibodies, hu5c8 and IDEC-131, in 46 human patients with chronic ITP refractory to conventional therapies. The patients had an overall 24% response rate, characterized by increased platelet counts. This demonstrated the potential role of CD40-CD40L in the pathogenesis of ITP.

4.2. Lupus In Vivo and In Vitro Models:

Glomerular and tubular CD40 expression is markedly upregulated in proliferative nephritis. Several studies have reported hyperexpression of CD40L by T cells and elevated soluble sCD40L concentrations in human lupus. Kimura et al., *Therapeutic Apheriss and Dialysis* 9: 64-68 (2005); Vakkalanka et al., *Arthritis & Rheumatism* 42: 871-881 (1999).

Systemic lupus erythematosus (SLE) is a chronic autoimmune disease characterized by the production of multiple autoantibodies and by B cell hyperactivity. Grammer et al., *J. Clin. Invest.* 112: 1506-1520 (2003) reports the results of treatment of patients with SLE with humanized anti-CD40L mAb 5c8 (BG9588). See also Huang et al., *Arthritis & Reumatism* 46: 1554-1562 (2002). Grammer et al. report that CD19+ peripheral B cells were examined before and after treatment with the anti-CD40L mAb. Before treatment, SLE patients manifested activated B cells that expressed CD40L, CD69, CD38, CD5, and CD27. The activated B cells disappeared from the periphery during and post-treatment. Before treatment, active SLE patients had circulating $CD38^{bright}$ Ig-secreting cells that were not found in normal individuals. Disappearance of these plasma cells during treatment was associated with decreases in anti-double stranded DNA (anti-dsDNA) Ab levels, proteinuria, and SLE disease activity index. Consistent with this finding, peripheral B cells cultured in vitro spontaneously proliferated and secreted Ig in a manner that was inhibited by anti-CD40L mAb. The CD38+/++IgD+, CD38+++, and CD38+IgD-B cell subsets present in the peripheral blood of SLE patients also disappeared following treatment with the anti-CD40L mAb. Together, these results suggest that spontaneous CD40L-CD40 interactions in active SLE patients drive B cell activation, proliferation, and differentiation to autoantibody-secreting plasma cells that mediate proteinuria and disease activity.

Proliferative lupus glomerulonephritis is a protracted autoimmune disease with a waxing and waning course, characterized by increased level of anti-dsDNA antibodies, decreased serum C3 concentrations, and hematuria. Boumpas et al, *Arthritis & Reumatism* 48: 719-727 (2003) report results of a phase II, multicenter, open-label study evaluating the toxicity and efficacy of BG9688, a humanized anti-CD40L monoclonal antibody, in patients with proliferative lupus glomerulonephritis. Although the study had to be terminated prematurely because of thromboembolic events occurring in patients in several BG9588 protocols, a short course of the anti-CD40L antibody treatment in patients with proliferative lupus nephritis reduced anti-dsDNA antibodies, increased C3 concentrations, and decreased hematuria, suggesting that the drug has immunomodulatory function.

4.3. Inflammatory Bowel Disease (IBD) In Vivo Models:

Crohn's disease (CD) and ulcerative colitis (UC) are IBDs that are characterized by leukocytic infiltrates in inflamed intestinal mucosa, which consists primarily of activated CD25+ cells, B cells, and macrophages. Ludwiczek et al., *Int. J. Colorectal Dis.* 18: 142-147 (2003) report that in CD patients, plasma levels of sCD40L were significantly higher than in healthy individuals. Moreover, CD patients with fistulas and/or abscesses had significantly higher levels of sCD40L than patients with uncomplicated CD. It has also been reported that the CD40-CD40L pathway contributes to the proinflammatory function of intestinal epithelial cells in IBD. Borcherding et al., *Am. J. Pathol.* 176: 1816-1827 (2010). Patients with CD also have an increased risk of systemic thromboembolism, and the hyperactive state of platelets from such patients likely results from the enhanced release of sCD40L as a consequence of their higher endogenous content of CD40L. Menchen et al., *Gut* 58: 920-928 (2009); see also Danese et al., *Gut* 52: 1435-1441 (2003).

Kasran et al., *Aliment. Pharmacol. Ther.* 22: 111-122 (2005) investigated the use of a chimeric anti-human CD40 mAb ch5D12 to treat Crohn's disease. The mAb was administered to 18 patients with moderate to severe CD in a single dose, open-label dose escalation phase I/IIa study. Of the 18 patients, 13 (or 72%) experienced a favorable response to the antibody infusion, and 4 patients (or 22%) experienced a remission. Treatment with the anti-CD40 mAb reduced microscopic disease activity and intensity of the lamina propria cell infiltrate, and the mAb was well tolerated.

4.4. Rheumatoid Arthritis (RA), Juvenile Idiopathic Arthritis (JIA), and Psoriatic Arthritis (PsA) In Vivo Models:

Rheumatoid arthritis is a systemic autoimmune disease with intra-articular inflammation as a dominant feature that affects up to 1% of the population. The disease can be subdivided clinically by the presence or absence of autoantibodies (antibodies to cyclic citrullinated peptide (CCP) or rheumatoid factor (RF), both of which are highly correlated to each other. Raychaudhuri et al., *Nature Genetics* 40: 1216-1223 (2008) reported that they conducted a meta-analysis of two published genome-wide association (GWA) studies totaling 3,393 cases and 12,462 controls, in order to identify RA risk loci in European populations. They genotyped 31 top-ranked short nucleotide polymorphisms (SNPs) not previously associated with RA in an independent replication of 3,929 autoantibody-positive RA cases and 5,807 matched controls from eight separate collections. They identified a common variant at the CD40 gene locus, which implied a central role for the CD40 signaling pathway in RA pathogenesis. The strong association of the CD40 gene with susceptibility to RA was robustly replicated in another study in a large UK cohort of 3,962 patients with RA. Orozso et al., *Ann. Rheum. Dis.* 69: 813-816 (2010).

A major role of CD40L has also been found in the pathogenesis of juvenile idiopathic arthritis (JIA). Prahalad et al., *Pediatric Rheumatology* 6: 1-8 (2008). JIA is a heterogeneous group of arthropathies of unknown etiology. It was found that sCD40L was significantly elevated in the serum of children with JIA, along with some cytokines. Logistic regression analysis suggested that sCD40L, as well as IL-6 and TNFα, were positively associated with JIA. sCD40L was elevated in all JIA subtypes, with highest levels among more severe subtypes. These results implicated sCD40L as a potential biomarker for treatment and monitoring of patients with JIA.

It has also been demonstrated that activated T cells from patients with psoriatic arthritis (PsA), and particularly those with active disease, have a significantly increased expression of CD40L. Daoussis et al., *Rheumatology* 46: 227-231 (2007). These results indicate a role of the CD40-CD40L pathway in the pathogenesis of PsA and that a therapy selectively targeting CD40L could benefit PsA patients.

4.5. Systemic Sclerosis In Vivo Models:

Systemic sclerosis (SSc) is an autoimmune connective tissue disorder characterized by fibrous and vascular changes in the skin and internal visceral organs. In a study involving 52 Japanese patients with SSc, serum sCD40L levels were elevated when compared with healthy controls. Komura et al., *J. Reumatol.* 31: 514-519 (2004). Moreover, levels of sCD40L in patients with SSc were higher than in patients with systemic lupus erythematosus (SLE) who had elevated sCD40L levels compared to controls, and sCD40L levels correlated positively with C reactive peptide levels in SSc patients. It has also been reported that blockade of CD40L with anti-CD40L antibody in cultured T and B cells from SSc patients inhibited anti-topoisomerase I antibody production. Kuwana et al., *J. Immunol.* 155: 2703-2714 (1995). These results suggest that inhibition of CD40-CD40L interactions may be potential therapeutic targets in therapy of SSc as well as SLE.

4.6. Atherosclerosis In Vivo Models:

Several studies have suggested a role of CD40-CD40L signaling pathway during atherogenesis. Mach et al. demonstrated that in mice, treatment with monoclonal anti-CD40L antibody limited atherosclerosis in mice lacking receptor for low-density lipoprotein that had been fed a high-cholesterol diet for 12 weeks. Nature 394: 200-203 (1998). The antibody reduced the size of aortic atherosclerotic lesions by 59% and their lipid content by 79%. Additionally, atheroma of mice treated with anti-CD40L antibody contained significantly fewer macrophages and T lymphocytes, and exhibited decreased expression of vascular cell adhesion molecule-1.

Anti-CD40L antibody treatment of low-density lipoprotein receptor-deficient mice during the second half of a 26-week regimen of a high-cholesterol diet did not regress, but did significantly reduce further progression of established atherosclerotic lesions within the aortic arch and particularly the thoracic and abdominal aorta, as compared to control treatment. Schonbeck et al., *Proc. Natl. Acad. Sci.* 97: 7458-7463 (2000). Furthermore, anti-CD40L treatment changed the composition of atheroma in manners thought to favor plaque stability, e.g., reduced relative content of macrophages and lipid, as well as increased relative content of smooth muscle cells and collagen. These studies lend support to the importance of the CD40-CD40L signaling pathway in atherosclerosis and its complications, such as coronary artery disease.

4.7. Allograft Rejection In Vivo Models:

Targeting the CD40-CD40L pathway has long been of much interest for prevention of rejection of solid organ transplants (SOT), particularly in light of the promising data from numerous published transplant studies in non-human primates. It has been demonstrated that reduced CD40L expression on ex vivo activated CD4+T lymphocytes correlates with excellent renal allograft function. Lederer et al., *Int. Arch. Allergy Immunol.* 133: 276-284 (2004). Furthermore, several studies have demonstrated that anti-CD40L mAbs can both prevent and reverse acute allograft rejection in primates. For example, Kirk et al., *Proc. Natl. Acad. Sci. USA* 94: 8789-8794 (1997) reported that, in rhesus monkeys transplanted with renal allografts, anti-CD40L mAb 5C8 alone or in combination with CTLA4-Ig significantly prolonged rejection-free survival. The CD40L-specific mAb hu5c8 alone also allowed for allogeneic islet engraftment and long-term insulin independence in rhesus monkeys that were transplanted an adequate number of viable pancreatic islets. Kenyon et al., *Proc. Natl. Acad. Sci. USA* 96: 8132-8137 (1999). Preston et al., *Amer. J. Transplantation* 5: 1032-1041 (2005) performed renal transplants in MHC-mismatched rhesus monkeys and treated the recipients with combinations of CD40L-specific mAb IDEC-131, and/or sirolimus, and/or pre-transplant donor-specific transfusion. IDEC-131 was highly effective in preventing renal allograft rejection in primates. In cynomolgus monkeys that underwent renal allotransplantation, treatment with anti-CD40L mAb ABI793 effectively prevented graft rejection. Schuler et al., *Transplantation* 77: 717-726 (2004). In addition to preventing allograft rejection, CD40L-specific mAbs induced donor specific tolerance in primate transplant models. Preston et al., *Amer. J. Transplantation* 5: 1032-1041 (2005); Kenyon et al., *Proc. Natl. Acad. Sci. USA* 96: 8132-8137 (1999).

In pediatric human patients that were undergoing acute graft rejection after liver or small-bowel transplantation, a correlation was observed between the expression of CD40L on CD8+ T cells and the risk of transplant rejection. Ashokkumar et al., *Amer. J. Transplantation* 9: 179-191 (2009) and Ashokkumar et al., *Surgery* 146: 166-173 (2009). Similarly, in adult patients that were undergoing allograft rejection following liver or renal transplantation, histological analysis demonstrated an association between CD40L expression and acute or chronic rejection. Bartlett et al., *Amer. J. Transplantation* 3: 1363-1368 (2003) and Biancone et al., *Nephrol. Diall. Translpant.* 13: 716-722 (1998).

Several studies support targeting CD40L over CD40 to achieve better efficacy in transplantation. For example, graft survival is longer and more durable when CD40L is selectively blocked, compared to CD40. Gilson et al., *J. Immunol.* 183: 1625-35 (2009). Furthermore, recent data suggest that CD40L blockade may enhance induction of Tregs and/or suppressor cells to promote graft survival. Garcia et al., *J. Clin. Inv.* 120: 2486-96 (2010). Also, blockade of CD40L, but not CD40, has demonstrated induction of long-lived immunological tolerance resulting in indefinite graft survival, particularly when combined with blockade of the B7 pathway. Kenyon et al., *Proc. Natl. Acad. Sci. USA* 96: 8132-8137 (1999); Kawai et al., *Amer. J. Transplantation* 4: 1391-1398 (2004); Preston et al., *Amer. J. Transplantation* 5: 1032-1041 (2005); Adams et al., *J. Immunol.* 174: 542-50 (2005). The synergy of blocking CD40-40L and B7-CD28 pathways in enhancing graft survival is especially important, because it presents the presently disclosed domain antibodies as a natural choice for combination with belatacept (CTLA4-Ig) for SOT.

4.8. Graft-Versus-Host Disease In Vivo Model:

Chronic and acute graft-versus-host disease (cGVHD and aGVHD) are complications that can occur after a stem cell or bone marrow transplant in which the transplanted donor cells attack the transplant recipient's body. Acute GVHD in humans takes place withing about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies.

CD40L-CD40 interactions appear to be critical in the development of both cGVHD and aGVHD. Durie et al., *J. Clin. Invest.* 94: 1333-1338 (1994). In a mouse in vivo model, anti-CD40L antibodies blocked the following cGVHD-associated phenomena: splenomegaly, in vitro polyclonal Ig production, elevated levels of serum IgE and serum anti-DNA autoantibodies, and the generation of anti-host cytotoxic T cells. Antibody production remained inhibited for extended periods of time after the end of anti-CD40L antibody administration. In mice with aGVHD, which is associated with the induction of a profound antiallogenic cytotoxic T cell (CTL) response, treatment with anti-CD40L prevented the generation of H-2b-derived CTL. The results of the study suggest that CD40L-CD40 interactions are critical in GVHD and that CD40L may be a valuable ligand for targeting immunotherapeutic agents to control GVHD.

4.9. Myasthenia Gravis In Vivo Model:

Myasthenia gravis (MG) and its animal model, experimental autoimmune MG (EAMG), are T-cell dependent autoimmune disorders caused by autoantibodies against the nicotinic acetylcholine receptors (AChR) at the neuromuscular junction of skeletal muscle. The role of CD40-CD40L in EAMG was shown in CD40L (CD40L−/−) knockout mice. Shi et al, *Eur. J. Immunol.* 28: 3587-3593 (1998). The CD40L knockout mice were completely resistant to EAMG induction and had diminished Th1 and Th2 responses as well as severely impaired T-cell dependent AChR-reactive B cell responses.

It has also been demonstrated that blockade of CD40L-CD40 signaling by anti-CD40L antibodies is capable of suppressing EAMG. Im et al., *J. Immunol.* 166: 6893-6898

(2001). Antibodies given to rats at the chronic stage of EAMG suppress the clinical progression of the autoimmune response and lead to a decrease in the AChR-specific humoral response and delayed-type hypersensitivity. The effect of anti-CD40L treatment during the chronic phase of EAMG is of particular relevance to human MG, which is a chronic disease. It suggests that antagonizing CD40L can be used for immunotherapy of MG and other antibody-mediated autoimmune diseases.

5. Thromboembolism

CD40-CD40L interactions on T and antigen presenting cells are important for adaptive immune responses, such as B-cell proliferation, immunoglobulin (Ig) production, upregulation of co-stimulatory activity (CD80, CD86), cytokine production, and Ig class-switching. The receptor and ligand are also expressed on platelets (off-target cell population), where CD40 is constitutively found on platelets, while CD40L is expressed on activated platelets and cleaved to sCD40L (>90% of circulating sCD40L is derived from platelets). Feroni et al., *Curr. Med. Chem.* 14: 2170-2180 (2007). At least three anti-CD40L monoclonal antibodies (mAb) caused TE in the clinic and/or nonclinical studies conducted in non-human primates (NHP). hu5c8 (BG9588) caused TE in multiple clinical trials (lupus and renal transplantation). Boumpas et al., *Arthritis & Rheumatism* 48: 719-727 (2003). IDEC131 caused TE in one patient in a Crohn's disease trial, leading to termination of ongoing trials at the time. Sidiropoulus & Boumpas, *Lupus* 13: 391-397 (2004). Both hu5c8 and ABI1793 (which binds CD40 at a different epitope from 5c8) caused TE/thrombosis in renal transplantation studies in cynomolgus or rhesus monkeys. Schuler et al., *Transplantation* 77: 717-726 (2004); Kanmaz et al., *Transplantation* 77: 914-920 (2004); Koyama et al., *Transplantation* 77: 460-461 (2004). In a non-published disclosure, Biogen reported a thrombosis incidence of 1/4 and 6/12 in rhesus monkeys given 5 and 20 mg/kg weekly, respectively, for 6-months, but not in cynomolgus monkeys given 50 mg/kg at the same frequency and duration. The basis for the species difference is not clear.

Figure 10:
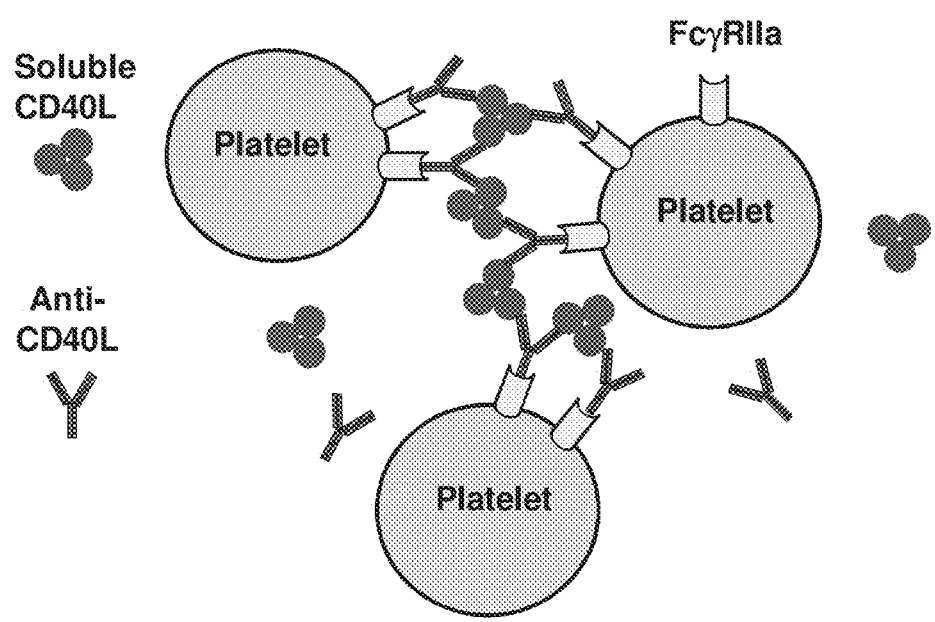
FIG. 10 provides a hypothetic model for anti-CD40 monoclonal antibody-mediated platelet aggregation.

One of the hypotheses is that the TE associated with administration of these antibodies is mediated by anti-CD40Lmab-CD40L immune complex (IC)-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. Approaches and methods developed to evaluate the risk for TE/thrombosis are described in Examples below.

EXAMPLES

TABLE 1 lists representative anti-human CD40L VH domain amino acid sequences useful for the disclosed antibody polypeptides. TABLE 2 discloses representative nucleic acids that encode the VH domain sequences listed in TABLE 1. TABLE 3 lists representative anti-human CD40L VK domain amino acid sequences useful for the antibody polypeptides of the present disclosure. TABLE 4 in turn discloses representative nucleic acids that encode the VK domain sequences listed in TABLE 3. As well known in the art, multiple codons can encode the same amino acid. Nucleic acids encoding a protein sequence thus include nucleic acids having codon degeneracy. The antibody polypeptides disclosed in TABLE 1 and TABLE 3 specifically bind CD40L. They were made using the reiterative initial/primary screening and affinity methodologies described in the examples that follow.

TABLE 1

Anti-human CD40L VH Domain Amino Acid Sequences

BMS2h-10 (SEQ ID NO: 15)
EVQLLESGGG LVQPGGSLRL SCAASGFTFI AYDMSWVRQA PGKGLEWVSW IDEWGLQTYY
ADSVKGRFTI SRDNSKNTLY LQMNSLRAED TAVYYCAKKT PEE------- FDYWGQGTLV TVSS

BMS2h-11 (SEQ ID NO: 16)
EVQLLESGGG LVQPGGSLRL SCAASGFTFG DYEMSWVRQA PGKGLEWVSG IDGEGSDTYY
ADSVKGRFTI SRDNSKNTLY LQMNSLRAED TAVYYCAKPG RS-------- FDYWGQGTLV TVSS

BMS2h-111 (SEQ ID NO: 17)
EVQLLESGGG LVQPGGSLRL SCAASGFTFE RYPMTWVRQA PGKGLEWVST IHGSGSATYY
ADSVKGRFTI SRDNSKNTLY LQMNSLRAED TAVYYCAKGP YTSRHNSLGH FDYWGQGTLV TVSS

BMS2h-112 (SEQ ID NO: 18)
EVQLLESGGG LVQPGGSLRL SCAASGFTFM DYPMGWVRQA PGKGLEWVSS IGPVGMSTYY
ADSVKGRFTI SRDNSKNTLY LQMNSLRAED TAVYYCAKYG GTSGRHNTK- FDYWGQGTLV TVSS

BMS2h-113 (SEQ ID NO: 19)
EVQLLESGGG LVQPGGSLRL SCAASGFTFT EYPMSWVRQA PGKGLEWVSV ISPLGFTTYY
ADSVKGRFTI SRDNSKNTLY LQMNSLRAED TAVYYCAKWT GGSGILNSS- FDYWGQGTLV TVSS

BMS2h-114 (SEQ ID NO: 20)
EVQLLESGGG LVQPGGSLRL SCAASGFRVS NYDLTWVRQA PGKGLEWVST ISATNGSTYY
ADSVKGRFTI SRDNSKNTLY LQMNSLRAED TAVYYCAAVT WWLLRHNDN- LGFWGQGTLV TVSS

BMS2h-115 (SEQ ID NO: 21)
EVQLLESGGG LVQPGGSLRL SCAASGFSIS YKNMAWVRQA PGKGLEWVSA IKAANGSTYY
ADSVKGRFTI SRDNSKNTLY LQMNSLRAED TAVYYCATGS QKKRTYT--- FDFWGQGTLV TVSS

BMS2h-12 (SEQ ID NO: 22)
EVQLLESGGG LVQPGGSLRL SCAASGFTFR LYEMAWVRQA PGKGLEWVSG IDILGSRTYY
ADSVKGRFTI SRDNSKNTLY LQMNSLRAED TAVYYCAKDL SWQG------ FDYWGQGTLV TVSS

BMS2h-120 (SEQ ID NO: 23)
EVQLLESGGG LVQPGGSLRL SCAASGFTFR SYTMGWVRQA PGKGLEWVSS INPMGYQTYY
ADSVKGRFTI SRDNSKNTLY LQMNSLRAED TAVYYCAKHG VGKGTKPHN FDYWGQGTLV TVSS

TABLE 1-continued

Anti-human CD40L VH Domain Amino Acid Sequences

BMS2h-121 (SEQ ID NO: 24)
EVQLLESGGG LVQPGGSLRL SCAASGFTFE LYRMSWVRQA PGKGLEWVSE ISGSGFPTYY
ADSVKGRFTI SRDNSKNTLY LQMNSLRAED TAVYYCAKSL HDKTQHHQE FDYWGQGTLV TVSS

BMS2h-123 (SEQ ID NO: 25)
EVQLLESGGG LVQPGGSLRL SCAASGFTFI EYPMRWVRQA PGKGLEWVSL ISPSGVFTYY
ADSVKGRFTI SRDNSKNTLY LQMNSLRAED TAVYYCAKGD ESST FDYWGQGTLV TVSS

BMS2h-124 (SEQ ID NO: 26)
EVQLLESGGG LVQPGGSLRL SCAASGFTFK RYDMDWVRQA PGKGLEWVST IGSSGYPTYY
ADSVKGRFTI SRDNSKNTLY LQMNSLRAED TAVYYCAERM PGYFPGFARQ FDYWGQGTLV TVSS

BMS2h-125 (SEQ ID NO: 27)
EVQLLESGGG LVQPGGSLRL SCAASGFTFW RYAMGWVRQA PGKGLEWVST INDEGRETYY
ADSVKGRFTI SRDNSKNTLY LQMNSLRAED TAVYYCAKKR VSSSVNAPYE FDYWGQGTLV TVSS

BMS2h-126 (SEQ ID NO: 28)
EVQLLESGGG LVQPGGSLRL SCAASGFTFA NYSMSWVRQA PGKGLEWVSS IDRLGTHTYY
ADSVKGRFTI SRDNSKNTLY LQMNSLRAED TAVYYCAKVL ADLIAGHAE FDYWGQGTLV TVSS

BMS2h-127 (SEQ ID NO: 29)
EVQLLESGGG LVQPGGSLRL SCAASGFTFP SYDMAWVRQA PGKGLEWVSG ISRSGSMTYY
ADSVKGRFTI SRDNSKNTLY LQMNSLRAED TAVYYCAKGV DAHVYYMEPF FDYWGQGTLV TVSS

BMS2h-128 (SEQ ID NO: 30)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG TV FDYWGQGTLV TVSS

BMS2h-129 (SEQ ID NO: 31)
EVQLLESGGG LVQPGGSLRL SCAASGFTFP KYEMAWVRQA PGKGLEWVSS IDGDGKSTYY
ADSVKGRFTI SRDNSKNTLY LQMNSLRAED TAVYYCAKPD QF FDYWGQGTLV TVSS

BMS2h-13 (SEQ ID NO: 32)
EVQLLESGGG LVQPGGSLRL SCAASGFTFS YYSMYWVRQA PGKGLEWVSS ISPFGWGTYY
ADSVKGRFTI SRDNSKDTLY LQMNSLRAED TAVYYCAKYG ETSGPISEN FDYWGQGTLV TVSS

BMS2h-130 (SEQ ID NO: 33)
EVQLLESGGG LVQPGGSLRL SCTASGFTFA GYQMSWVRQA PGKGLEWVSS ITNEGVSTYY
ADSVKGRFTI SRDNSKNTLY LQMNSLRAED TAVYYCAKPG KY FDYWGQGTLV TVSS

BMS2h-131 (SEQ ID NO: 34)
EVQLLESGGG LVQPGGSLRL SCAASGFTFG EYEMVWVRQA PGKGLEWVSS ITSDGLSTYY
ADSVKGRFTI SRDNSKNTLY LQMNSLRAED TAVYYCAKPG IRFDYWGQGTLV TVSS

BMS2h-132 (SEQ ID NO: 35)
EVQLLESGGG LVQPGGSLRL SCAASGFTFA DYDMAWVRQA PGKGLEWVSG IVDDGLMTYY
ADSVKGRFTI SRDNSKNTLY LQMNSLRAED TAVYYCAKPD VAFDYWGQGTLVTVSN

BMS2h-133 (SEQ ID NO: 36)
EVQLLESGGG LVQPGGSLRL SCAASGFTFI GYAMAWVRQA PGKGLEWVSS IGPLGATTYY
ADSVKGRFTI SRDNSKNTLY LQMNSLRAED TAVYYCAKLP AGTSSHSVDFDYWGQGTLV TVSS

BMS2h-134 (SEQ ID NO: 37)
EVQLLESGGG LVQPGGSLRL SCAASGFTFA DYEMTWVRQA PGKGLEWVSS ITSDGVSTYY
ADSVKGRFTI SRDNSKNTLY LQMNSLRAED TAVYYCAKPS VQ FDYWGQGTLV TVSS

BMS2h-135 (SEQ ID NO: 38)
EVQLLESGGG LVQPGGSLRL SCAASGFTFR RYVMGWVRQA PGKGLEWVSW IEADGRTTYY
ADSVKGRFTI SRDNSKNTLY LQMNSLRAED TAVYYCAKGL TDQHVIE FDYWGQGTLV TVSS

BMS2h-136 (SEQ ID NO: 39)
EVQLLESGGG LVQPGGSLRL SCAASGFTFD GYRMGWVRQA PGKGLEWVSS IAPDGNYTYY
ADSVKGRFTI SRDNSKNTLY LQMNSLRAED TAVYYCAKFW GMQFDYWGQGTLV TVSS

BMS2h-137 (SEQ ID NO: 40)
EVQLLESGGG LVQPGGSLRL SCAASGFTFA SYPMGWVRQA PGKGLEWVSS IGPIGFTTYY
ADSVKGRFTI SRDNSKNTLY LQMNSLRAED TAVYYCAEMK SPYKPQ---- FDYWGQGTLV TVSS

BMS2h-138 (SEQ ID NO: 41)
EVQLLESGGG LVQPGGSLRL SCAASGFTFL AYWMVWVRQA PGKGLEWVSS ISPSGTHTYY
ADSVKGRFTI SRDNSKNTLY LQMNSLRVED TAVYYCAKYT EPGLGS---- FDYWGQGTLV TVSS

BMS2h-139 (SEQ ID NO: 42)
EVQLLESGGG LVQPGGSLRL SCAASGFTFS NYEMGWVRQA PGKGLEWVSV ISEVGSLTYY
ADSVKGRFTI SRDNSKNTLY LQMNSLRAED TAVYYCAKPH DSSIG----- FDYWGQGTLV TVSS

TABLE 1-continued

Anti-human CD40L VH Domain Amino Acid Sequences

BMS2h-14 (SEQ ID NO: 43)
EVQLLESGGG LVQPGGSLRL SCAASGFTFW SYDMTWVRQA PGKGLEWVSS IMASGDDTYY
ADSVKGRFTI SRDNSKNTLY LQMNSLRAED TAVYYCAKWD RD-------- FDYWGQGTLV TVSS

BMS2h-15 (SEQ ID NO: 44)
EVQLLESGGG LVQPGGSLRL SCAASGFTFE EYVMSWVRQA PGKGLEWVST ISPIGLTTYY
ADSVKGRFTI SRDNSKNTLY LQMNSLRAED TAVYYCAEFP LIILPD---- FDYWGQGTLV TVSS

BMS2h-16 (SEQ ID NO: 45)
EVQLLESGGG LVQPGGSLRL SCAASGFTFM EYAMIWVRQA PGKGLEWVSI ISPLGLSTYY
ADSVKGRFTI SRDNSKNTLY LQMNSLRAED TAVYYCAKYQ DSSDSQYTN- FDYWGQGTLV TVSS

BMS2h-17 (SEQ ID NO: 46)
EVQLLESGGG LVQPGGSLRL SCAASGFTFE DYGMGWARQA PGKGLEWVSS IGPLGLWTYY
ADSAKGRFTI SRDNSKNTLY LQMNSLRAED TAVYYCAKSP LEGLITN--- FDYWGQGTLV TVSS

BMS2h-176 (SEQ ID NO: 47)
EVQLLESGGG LVQPGGSLRL SCAASGFTFD AYEMGWVRQA PGKGLEWVSI IDWDGNSTYY
ADSVKGRFTI SRDNSKNTLY LQMNSLRAED TAVYYCAKPG DNVGI----- FDYWGQGTLV TVSS

BMS2h-177 (SEQ ID NO: 48)
EVQLLESGGG LVQPGGSLRL SCAASGFTFS NYYMVWVRQA PGKGLEWVSA IDEWGFATYY
ADSVKGRFTI SRDNSKNTLY LQMNSLRAED TAVYYCAKHW EFTSDTSR- FDYWGQGTLV TVSS

BMS2h-178 (SEQ ID NO: 49)
EVQLLESGGG LVQPGGSLRL SCAASGFTFE DFDMAWVRQA PGKGLEWVSS INDQGSLTYY
ADSVKGRFTI SRDNSKNTLY LQMNSLRAED TAVYYCAKPD QF-------- FDYWGQGTLV TVSS

BMS2h-179 (SEQ ID NO: 50)
EVQLLESGGG LVQPGGSLRL SCAASGFTFS AYDMMWVRQA PGKGLEWVSR ISPQGQRTYY
ADSVKGRFTI SRDNSKNTLY LQMNSLRAED TAVYYCAKIR GQSRIPMR- FDYWGQGTLV TVSS

BMS2h-18 (SEQ ID NO: 51)
EVQLLESGGG LVQPGGSLRL SCAASGFTFP EYDMTWVRQA PGKGLEWVSY ISSDGYSTYY
ADSVKGRFTI SRDNSKNTLY LQMNSLRAED TAVYYCAKPH GSPRE----- FDYWGQGTLV TVSS

BMS2h-180 (SEQ ID NO: 52)
EVQLLESGGG LVQPGGSLRL SCAASGFTFT DYEMGWVRQA PGKGLEWVST ITSLGESTYY
ADSVKGRFTI SRDNSKNTLY LQMNSLRAED TAVYYCAKPG RI-------- FDYWGQGTLV TVSS

BMS2h-181 (SEQ ID NO: 53)
EVQLLESGGG LVQPGGSLRL SCAASGFTFA FYPMMWVRQA PGKGLEWVSW IDATGTRTYY
ADSVKGRFTI SRDNSKNTLY LQMNSLRAED TAVYYCAEGN YGSSYTMGV- FDYWGQGTLV TVSS

BMS2h-182 (SEQ ID NO: 54)
EVQLLESGGG LVQPGGSLRL SCAASGFTFD EYPMYWVRQA PGKGLEWVSS IGPSGPNTYY
ADSVKGRFTI SRDNSKNTLY LQMNSLRAED TAVYYCAKSP YFDVIPSY- FDYWGQGTLV TVSS

BMS2h-183 (SEQ ID NO: 55)
EVQLLESGGG LVQPGGSLRL SCAASGFTFA DYGMGWVRQA PGKGLEWVSS IQSSGLRTYY
ADSVKGRFTI SRDNSKNTLY LQMNSLRAED TAVYYCAKRA NSRRG----- FDYWGQGTLV TVSS

BMS2h-184 (SEQ ID NO: 56)
EVQLLESGGG LVQPGGSLRL SCAASGFTFS DYEMMWVRQA PGKGLEWVSS ITSHGGSTYY
ADSVKGRFTI SRDNSKNTLY LQMNSLRAED TAVYYCAKPD KD-------- FDYWGQGTLV TVSS

BMS2h-185 (SEQ ID NO: 57)
EVQLLESGGG LVQPGGSLRL SCAASGFTFA HYPMSWVRQA PGKGLEWVSS IGRLGNRTYY
ADSVKGRFTI SRDNSKNTLY LQMNSLRAED TAVYYCAKRA TPVPIKGL- FDYWGQGTLV TVSS

BMS2h-186 (SEQ ID NO: 58)
EVQLLESGGG LVQPGGSLRL SCAASGLTFG RYEMAWVRQA PGKGLEWVSS IDSDGWVTYY
ADSVKGRFTI SRDNSKNTLY LQMNSLRAED TAVYYCAQPD SL-------- FDYWGQGTLV TVSS

BMS2h-187 (SEQ ID NO: 59)
EVQLLESGGG LVQPGGSLRL SCAASGFTFS SYSMVWVRQA PGKGLEWVSG INRGGTRTYY
ADSVKGRFTI SRDNSKNTLY LQMNSLRAED TAVYYCAKGW RRG------- FDYWGQGTLV TVSS

BMS2h-188 (SEQ ID NO: 60)
EVQLLESGGG LVQPGGSLRL SCAASGFTFT RYRMSWVRQA PGKGLEWVSG ISRDGYRTYY
ADSVKGRFTI SRDNSKNTLY LQMNSLRAED TAVYYCAKGM TAS------- FDYWGQGTLV TVSS

BMS2h-189 (SEQ ID NO: 61)
EVQLLESGGG LVQPGGSLRL SCAASGFTFQ MYPMGWVRQA PGKGLEWVSM IEPAGDLTYY
ADSVKGRFTI SRDNSKNTLY LQMNSLRAED TAVYYCAKYQ EQPW------ FDYWGQGTLV TVSS

TABLE 1-continued

Anti-human CD40L VH Domain Amino Acid Sequences

BMS2h-19 (SEQ ID NO: 62)
EVQLLESGGG LVQPGGSLRL SCAASGFPFP QYQMAWVRQA PGKGLEWVSM ITSDGLDTYY
ADSVKGRFTI SRDNSKNTLY LQMNSLRAED TAVYYCAKPE PL-------- FDYWGQGTLV TVSS

BMS2h-190 (SEQ ID NO: 63)
EVQLLESGGG LVQPGGSLRL SCAASGFTFS MYDMHWVRQA PGKGLEWVST ILSDGTDTYY
ADSVKGRFTI SRDNSKNTLY LQMNSLRAED TAVYYCAKYG AM-------- FDYWGQGTLV TVSS

BMS2h-191 (SEQ ID NO: 64)
EVQLLESGGG LVQPGGSLRL SCAASGFTFK LYPMTWVRQA PGKGLEWVSS IDAGGHETYY
ADSVKGRFTI SRDNSKNTLY LQMNSLRAED TAVYYCAKDW WDYL------ FDYWGQGTLV TVSS

BMS2h-192 (SEQ ID NO: 65)
EVQLLESGGG LVQPGGSLRL SCAASGFTFS RYPMSWVRQA PGKGLEWVSS INRSGMRTYY
ADSVKGRFTI SRDNSKNTLY LQMNSLRAED TAVYYCAEGH QAP------- FDYWGQGTLV TVSS

BMS2h-193 (SEQ ID NO: 66)
EVQLLESGGG LVQPGGSLRL SCAASGFTFT GYAMSWVRQA PGKGLEWVST INANGIRTYY
ADSVKGRFTI SRDNSKNTLY LQMNGLRAED TAVYYCAKGG VWRWGTGHK- FDYWGQGTLV TVSS

BMS2h-194 (SEQ ID NO: 67)
EVQLLESGGG LVQPGGSLRL SCAASGFTFK QYDMRWVRQA PGKGLEWVST ISQNGTKTYY
ADSVKGRFTI SRDNSKNTLY LQMNSLRAED TAVYYCAKSR TGRY------ FDYWGQGTLV TVSS

BMS2h-195 (SEQ ID NO: 68)
EVQLLESGGG LVQPGGSLRL SCAASGFTFG TYDMGWVRQA PGKGLEWVSR INWQGDRTYY
ADSVKGRFTI SRDNSKNTLY LQMNSLRAED TAVYYCAKAG FGHYVDGLG- FDYWGQGTLV TVSS

BMS2h-196 (SEQ ID NO: 69)
EVQLLESGGG LVQPGGSLRL SCAASGFTFS GYEMAWVRQA PGKGLEWVSS ITDMGDSTYY
ADSVKGRFTI SRDNSKNTLY LQMNSLRAED TAVYYCAKPG TA-------- FDYWGPGTLV TVSS

BMS2h-197 (SEQ ID NO: 70)
EVQLLESGGG LVQPGGSLRL SCAASGFTFA KYKMWWVRQA PGKGLEWVSS ITPKGHSTYY
ADSVKGRFTI SRDNSKNTLY LQMNSLRAED TAVYYCAKRP MTP------- FDYWGQGTLV TVSS

BMS2h-198 (SEQ ID NO: 71)
EVQLLESGGG LVQPGGSLRL SCAASGFTFE RYNMSWVRQA PGKGLEWVSS IRPRGGKTYY
ADSVKGRFTI SRDNSKNTLY LQMNSLRAED TAVYYCAKWR REGYTGSK- FDYWGQGTLV TVSS

BMS2h-199 (SEQ ID NO: 72)
EVQLLESGGG LVQPGGSLRL SCAASGFTFE RYGMTWVRQA PGKGLEWVSS IWPRGQKTYY
ADSVKGRFTI SRDNSKNTLY LQMNSLRAED TAVYYCAKGN SRYV------ FDYWGQGTLV TVSS

BMS2h-2 (SEQ ID NO: 73)
EVQLLESGGG LVQPGGSLRL SCAASGFTFS DYEMMWVRQA PGKGLEWVST ITSDGISTYY
ADSVKGRFTI FRDNSKNTLY LQMNSLRAED TAVYYCAKSG RF-------- FDYWGQGTLV TVSS

BMS2h-20 (SEQ ID NO: 74)
EVQLLESGGG LVQPGGSLRL SCAASGFTFS GYQMAWVRQA PGKGLEWVSG ISSEGLTTYY
ADSVKGRFTI SRDNSKNTLY LQMNSLRAED TAVYYCAKLG RR-------- FDYWGQGTLV TVSS

BMS2h-200 (SEQ ID NO: 75)
EVQLLESGGG LVQPGGSLRL SCAASGFTFT NYSMGWVRQA PGKGLEWVST IRPNGTKTYY
ADSVKGRFTI SRDNSKNTLY LQMNSLRAED TAVYYCAKRS SAHLQR---- FDYWGQGTLV TVSS

BMS2h-201 (SEQ ID NO: 76)
EVQLLESGGG LVQPGGSLRL SCAASGFTFG NYSMGWVRQA PGKGLEWVSS IGRHGGRTYY
ADSVKGRFTI SRDNSKNTLY LQMNSLRAED TAVYYCAKKG STYPR----- FDYWGQGTLV TVSS

BMS2h-202 (SEQ ID NO: 77)
EVQLLESGGG LVQPGGSLRL SCTASGFTFS HYEMGWVRQA PGKGLEWVSS IEPFGGGTYY
ADSVKGRFTI SRDNSKNTLY LQMNSLRAED TAVYYCAKVY PQGS------ FDYWGQGTLV TVSS

BMS2h-203 (SEQ ID NO: 78)
EVQLLESGGG LVQPGGSLRL SCAASGFTFS NYTMGWVRQA PGKGLEWVSS IRPDGKITYY
ADSVKGRFTI SRDNSKNTLY LQMNSLRAED TAVYYCAEVY SSCAMCTPLL FDYWGQGTLV TVSS

BMS2h-204 (SEQ ID NO: 79)
EVQLLESGGG LVQPGGSLRL SCAASGFTFK RYSMAWVRQA PGKGLEWVSD IGPRGFSTYY
ADSVKGRFTI SRDNSKNTLY LQMNSLRAED TAVYYCAKVG RGQRDTSQP- FDYWGQGTLV TVSS

BMS2h-205 (SEQ ID NO: 80)
EVQLLESGGG LVQPGGSLRL SCAASGFTFA SYQMAWVRQA PGKGLEWVSG ITSGGLSTYY
ADSVKGRFTI SRDNSKNTLY LQMNSLRAED TAVYYCAKPG RG-------- FDYWGQGTLV TVSS

TABLE 1-continued

Anti-human CD40L VH Domain Amino Acid Sequences

BMS2h-206 (SEQ ID NO: 81)
EVQLLESGGG LVQPGGSLRL SCAASGFTFA SYEMTWVRQA PGKGLEWVSG ISSDGLSTYY
ADSVKGRFTI SRDNSKNTLY LQMNSLRAED TAVYYCAKPG VL-------- FDYWGQGTLV TVSS

BMS2h-207 (SEQ ID NO: 82)
EVQLLESGGG LVQPGGSLRL SCAASGFTFD KYLMSWVRQA PGKGLEWVSG IEPLGDVTYY
ADSVKGRFTI SRDNSKNTLY LQMNSLRAED TAVYYCAKEA SGD------- FDYWGQGTLV TVSS

BMS2h-208 (SEQ ID NO: 83)
EVQLLESGGG LVQPGGSLRL SCAASGFTFT EYEMSWVRQA PGKGLEWVSS IDNVGSSTYY
ADSVKGRFTI SRDNSKNTLY LQMNSLRAED TAVYYCAKPG KL-------- FDYWGQGTLV TVSS

BMS2h-209 (SEQ ID NO: 84)
EVQLLESGGG LVQPGGSLRL SCAASGFTFA DYEMWWVRQA PGKGLEWVSA ISRQGFATYY
ADSVKGRFTI SRDNSKNTLY LQMNSLRAED TAVYYCAKDL ERDD------ FDYWGQGTLV TVSS

BMS2h-21 (SEQ ID NO: 85)
EVQLLESGGG LVQPGGSLRL SCAASGFTFA NYEMGWARQA PGKGLEWVSV ISEWGYSTYY
ADSAKGRFTI SRDNSKNTLY LQMNSLRAED TAVYYCAKLV GGTQYE---- FDYWGQGTLV TVSS

BMS2h-22 (SEQ ID NO: 86)
EVQLLESGGG LVQPGGSLRL SCAASGFTFH NYEMSWVRQA PGKGLEWVSS ISSGGSSTYY
ADSVKGRFTI SRDNSKNTLY LQMNSLRAED TAVYYCAKPG VK-------- FDYWGQGTLV TVSS

BMS2h-23 (SEQ ID NO: 87)
EVQLLESGGG LVQPGGSLRL SCAASGFTFG LYEMTWVRQA PGKGLEWVSS ITGDGISTYY
ADSVKGRFTI SRDNSRNTLY LQMNSLRAED TAVYYCAKAG RK-------- FDYWGQGTLV TVSS

BMS2h-24 (SEQ ID NO: 88)
EVQLLESGGG LVQPGGSLRL SCAASGFTFS NYQMAWVRQA PGKGLEWVSS ITSEGGSTYY
ADSVKGRFTI SRDNSKNTLY LQMNSLRAED TAVYYCAKPG KN-------- FDYWGQGTLV TVSS

BMS2h-24-1 (SEQ ID NO: 89)
EVQLLESGGG LVQPGGSLRL SCAASGFTFS DYQMAWVRQA PGKGLEWVSS ITSEGGSTYY
ADSVKGRFTI SRDNSKNTVY LQMNSLRAED TAVYYCAKPG KN-------- FDYWGQGTLV TVSS

BMS2h-25 (SEQ ID NO: 90)
EVQLLESGGG LVQPGGSLRL SCAASGFTFD NYEMTWVRQA PGKGLEWVST ITSQGTSTYY
ADSVKGRFTI SRDNSKNTLY LQMNSLRAED TAVYYCAKPD RS-------- FDYWGQGTLV TVSS

BMS2h-26 (SEQ ID NO: 91)
EVQLLESGGG LVQPGGSLRL SCAASGFTFR SYEMTWVRQA PGKGLEWVSS ITSDGGTTYY
ADSVKGRFTI SRDNSKNTLY LQMNSLRAED TAVYYCAKPD KT-------- FDYWGQGTLV TVSS

BMS2h-27 (SEQ ID NO: 92)
EVQLLESGGG LVQPGGSLRL SCAASGFTFN LYEMTWVRQA PGKGLEWVSS ITSDGVSTYY
ADSVKGRFTI SRDNSKNTLY LQMNSLRAED TAVYYCAKPD SP-------- FDYWGQGTLV TVSS

BMS2h-28 (SEQ ID NO: 93)
EVQLLESGGG LVQPGGSLRL SCAASGFTFG HYDMAWVRQA PGKGLEWVST ISDNGNGTYY
ADSVKGRFTI SRDNSKNTLY LQMNSLRAED TAVYYCAKPG RD-------- FDYWGQGTLV TVSS

BMS2h-29 (SEQ ID NO: 94)
EVQLLESGGG LVQPGGSLRL SCAASGFTFG RYQMAWVRQA PGKGLEWVSS ISSDGGGTYY
ADSVKGRFTI SRDNSKNTLY LQMNSLRAED TAVYYCAKPG RA-------- FDYWGQGTLV TVSS

BMS2h-30 (SEQ ID NO: 95)
EVQLLESGGG LVQPGGSLRL SCAASGFTFA RYQMAWVRQA PGKGLEWVST ISDDGDSTYY
ADSVKGRFTI SRDNSKNTLY LQMNSLRAED TAVYYCAKLD KL-------- FDYWGQGTLV TVSS

BMS2h-300 (SEQ ID NO: 96)
EVQLLESGGG LVQPGGSLRL SCAASGFTFD NDEMTWVRQA PGKGLEWVSA IDTTGGQTYY
ADSVKGRFTI SRDNSKNTLY LQMNSLRAED TAVYYCAKPG KE-------- FDYWGQGTLV TVSS

BMS2h-301 (SEQ ID NO: 97)
EVQLLESGGG LVQPGGSLRL SCAASGFTFG ESEMSWVRQA PGKGLEWVSS ILDEGSGTYY
ADSVKGRFTI SRDNSKNTLY LQMNSLRAED TAVYYCAKPD KD-------- FDYWGQGTLV TVSS

BMS2h-302 (SEQ ID NO: 98)
EVQLLESGGG LVQPGGSLRL SCAASGFTFG EEEMSWVRQA PGKGLEWVSA ITDDGDDTYY
ADSVKGRFTI SRDNSKNTLY LQMNSLRAED TAVYYCAKPN AGA------- FDYWGQGTLV TVSS

BMS2h-303 (SEQ ID NO: 99)
EVQLLESGGG LVQPGGSLRL SCAASGFTFE VYDMAWVRQA PGKGLEWVSG IVNDGSSTYY
ADSVKGRFTI SRDNSKNTLY LQMNSLRAED TAVYYCAKPD KD-------- FDYWGQGTLV TVSS

TABLE 1-continued

Anti-human CD40L VH Domain Amino Acid Sequences

BMS2h-304 (SEQ ID NO: 100)
EVQLLESGGG LVQPGGSLRL SCAASGFTFG NTEMTWVRQA PGKGLEWVSS IADDGSSTYY
ADSVKGRFTI SRDNSKNTLY LQMNSLRAED TAVYYCAKPG QA-------- FDYWGQGTLV TVSS

BMS2h-31 (SEQ ID NO: 101)
EVQLLESGGG LVQPGGSLRL SCAASGFTFE EYQMAWVRQA PGKGLEWVST ISDDGSSTYY
ADSVKGRFTI SRDNSKNTLY LQMNSLRAED TAVYYCAKPD LY-------- FDYWGQGTLV TVSS

BMS2h-32 (SEQ ID NO: 102)
EVQLLESGGG LVQPGGSLRL SCAASGFTFE VYQMGWVRQA PGKGLEWVSF IVPGGDLTYY
ADSVKGRFTI SRDNSKNTLY LQMNSLRAED TAVYYCAETW PE-------- FDYWGQGTLV TVSS

BMS2h-4 (SEQ ID NO: 103)
EVQLLESGGG LVQPGGSLRL SCAASGFTFD NYEMTWVRQA PGKGLEWVSS ITSDGTSTYY
ADSVKGRFTI SRDNSKNTLY LQMNSLRAED TAVYYCAKPN PP-------- FDYWGQGTLV TVSS

BMS2h-40 (SEQ ID NO: 104)
EVQLLESGGG LVQPGGSLRL SCAASGFTFK AYDMGWVRQA PGKGLEWVSQ IGRDGSFTYY
ADSVKGRFTI SRDNSKNTLY LQMNSLRAED TAVYYCAKPR RYAIF----- TFDRGQGTLV TVSS

BMS2h-400 (SEQ ID NO: 105)
EVQLLESGGG LVQPGGSLRL SCAASGFTFK QYPMVWVRQA PGKGLEWVST ISTNGVRTYY
ADSVKGRFTI SRDNSKNTLY LQMNSLRAED TAVYYCAKWT DIISSSE--- FDYWGQGTLV TVSS

BMS2h-401 (SEQ ID NO: 106)
EVQLLESGGG LVQPGGSLRL SCAASGFTFF NYDMSWVRQA PGKGLEWVSA ISGSGGSTYY
ADSVKGRFTI SRDNSKNTLY LQMNSLRAED TAVYYCAKVF VWSADIDFD- FDYWGQGTLV TVSS

BMS2h-402 (SEQ ID NO: 107)
EVQLLESGGG LVQPGGSLRL SCAASGFTFS WYDMSWVRQA PGKGLEWVSH IASWGGKTYY
ADSVKGRFTI SRDNSKNTLY LQMNSLRAED TAVYYCAKVT VKDGGYLMD- FDYWGQGTLV TVSS

BMS2h-403 (SEQ ID NO: 108)
EVQLLESGGG LVQPGGSLRL SCAASGFTFA EYAMAWVRQA PGKGLEWVSS IGRDGAVTYY
ADSVKGRFTI SRDNSKNTLY LQMNSLRAED TAVYYCAKWK AAKERGSW-FDYWGQGTLV TVSS

BMS2h-404 (SEQ ID NO: 109)
EVQLLESGGG LVQPGGSLRL SCAASGFTFQ AYQMWVRQA PGKGLEWVST ISPNGLFTYY
ADSVKGRFTI SRDNSKNTLY LQMNSLRAED TAVYYCAKWL SS-------- FDYWGQGTLV TVSS

BMS2h-407 (SEQ ID NO: 110)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-408 (SEQ ID NO: 111)
EVQLLESGGG LVQPGGSLRL SCAASGFTFP TYMMSWVRQA PGKGLEWVST INTNGRDTYY
ADSVKGRFTI SRDNSKNTLY LQMNSLRAED TAVYYCAKGD SNMSF----- FDYWGQGTLV TVSS

BMS2h-409 (SEQ ID NO: 112)
EVQLLESGGG LVQPGGSLRL SCAASGFTFE GYSMTWVRQA PGKGLEWVSS INASGTLTYY
ADSVKGRFTI SRDNSKNTLY LQMNSLRAED TAVYYCAKDG NRSEVF---- FDYWGQGTLV TVSS

BMS2h-41 (SEQ ID NO: 113)
EVQLLESGGG LVQPGGSLRL SCAASGFTFF EYEMTWVRQA PGKGLEWVSS IANDGSTTYY
ADSVKGRFTI SRDNSKNTLY LQMNSLRAED TAVYYCAKPD RQ-------- FDYWGQGTLV TVSS

BMS2h-410 (SEQ ID NO: 114)
EVQLLESGGG LVQPGGSLRL SCAASGFTFQ DYLMAWVRQA PGKGLEWVSE INQDGTVTYY
ADSVKGRFTI SRDNSKNTLY LQMNSLRAED TAVYYCAESS PY-------- FDYWGQGTLV TVSS

BMS2h-411 (SEQ ID NO: 115)
EVQLLESGGG LVQPGGSLRL SCAASGFTFD NYAMSWVRQA PGKGLEWVSS ISRDGHVTYY
ADSVKGRFTI SRDNSKNTLY LQMNSLRAED TAVYYCAKLS SKGGTFASS- FDYWGQGTLV TVSS

BMS2h-412 (SEQ ID NO: 116)
EVQLLESGGG LVQPGGSLRL SCAASGFTFS AVPMTWVRQA PGKGLEWVSA ITDDGLRTYY
ADSVKGRFTI SRDNSKNTLY LQMNSLRAED TAVYYCAKGH IYGDY----- FDYWGQGTLV TVSS

BMS2h-413 (SEQ ID NO: 117)
EVQLLESGGG LVQPGGSLRL SCAASGFTFE LYRMMWVRQA PGKGLEWVSA ISSDGDTTYY
ADSVKGRFTI SRDNSKNTLY LQMNSLRAED TAVYYCAEHW LGTTLSLRD- FDYWGQGTLV TVSS

BMS2h-414 (SEQ ID NO: 118)
EVQLLESGGG LVQPGGSLRL SCAASGFTFY RYTMAWVRQA PGKGLEWVSQ ISPRGNITYY
ADSVKGRFTI SRDNSKNTLY LQMNSLRAED TAVYYCAKSG VAGAESPEY- FDYWGQGTLV TVSS

TABLE 1-continued

Anti-human CD40L VH Domain Amino Acid Sequences

BMS2h-415 (SEQ ID NO: 119)
EVQLLESGGG LVQPGGSLRL SCAASGFTFL GYYMSWIRQA PGKGLEWVST IGPIGGGTYY
ADSVKGRFTI SRDNSKNTLY LQMNSLRAED TAVYYCAKSQ NIYGP----- FDYWGQGTLV TVSS

BMS2h-416 (SEQ ID NO: 120)
EVQLLESGGG LVQPGGSLRL SCAASGFTFE QYDMAWVRQA PGKGLEWVSE ISRDGGRTYY
ADSVKGRFTI SRDNSKNTLY LQMNSLRAED TAVYYCAEEY PY-------- FDYWGQGTLV TVSS

BMS2h-417 (SEQ ID NO: 121)
EVQLLESGGG LVQPGGSLRL SCAASGFTFP QYSMVWVRQA PGKGLEWVST ISPLGSSTYY
ADSVKGRFTI SRDNSKNTLY LQMNSLRAED TAVYYCAKMS KLLLSRE--- FDYWGQGTLV TVSS

BMS2h-418 (SEQ ID NO: 122)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-419 (SEQ ID NO: 123)
EVQLLESGGG LVQPGGSLRL SCAASGFTFT RHGMAWVRQA PGKGLEWVST ITPTGNTTYY
ADSVKGRFTI SRDNSKNTLY LQMNSLRAED TAVYYCAKDA HDEGY----- FDYWGQGTLV TVSS

BMS2h-42 (SEQ ID NO: 124)
EVQLLESGGG LVQPGGSLRL SCAASGFTFG PYEMTWVRQA PGKGLEWVSS IVGDGLDTYY
ADSVKGRFTI SRDNSKNTLY LQMNSLRAED TAVYYCAKPD RV-------- FDYWGQGTLV TVSS

BMS2h-420 (SEQ ID NO: 125)
EVQLLESGGG LVQPGGSLRL SCAASGFTFG STPMMWVRQA PGKGLEWVSE IRDTGLATYY
ADSVKGRFTI SRDNSKNTLY LQMNSLRAED TAVYYCASVS ---------- FDYWGQGTLV TVSS

BMS2h-421 (SEQ ID NO: 126)
EVQLLESGGG LVQPGGSLRL SCAASGFTFH LGDMHWVRQA PGKGLEWVSS ISGTGHTTYY
ADSVKGRFTI SRDNSKNTLY LQMNSLRAED TAVYYCAKPM NDQG------ FDYWGQGTLV TVSS

BMS2h-422 (SEQ ID NO: 127)
EVQLLESGGG LVQPGGSLRL SCAASGFTFM DEDMLWVRQA PGKGLEWVSR INSLGTHTYY
ADSVKGRFTI SRDNSKNTLY LQMNSLRAED TAVYYCAKSF MM-------- FDYWGQGTLV TVSS

BMS2h-423 (SEQ ID NO: 128)
EVQLLESGGG LVQPGGSLRL SCAASGFTFR NYQMHWVRQA PGKGLEWVSG IDATGRATYY
ADSVKGRFTI SRDNSKNTLY LQMNSLRAED TAVYYCARST RS-------- FDYWGQGTLV TVSS

BMS2h-424 (SEQ ID NO: 129)
EVQLLESGGG LVQPGGSLRL SCAASGFTFT NADMVWVRQA PGKGLEWVSS ISGSGGSTYY
ADSVKGRFTI SRDNSKNTLY LQMNSLRAED TAVYYCAKGY LTSH------ FDYWGQGTLV TVSS

BMS2h-425 (SEQ ID NO: 130)
EVQLLESGGG LVQPGGSLRL SCAASGFTFR DYSMAWVRQA PGKGLEWVST ITPSGLTTYY
ADSVKGRFTI SRDNSKNTLY LQMNSLRAED TAVYYCAEWS QAVTRS---- FDYWGQGTLV TVSS

BMS2h-426 (SEQ ID NO: 131)
EVQLLESGGD LVQPGGSLRL SCAASGFTFS DEGMMWVRQA PGKGLEWVSE INQQGSATYY
ADSVKGRFTI SRDNSKNTLY LQMNSLRAED TAVYYCAKTI GM-------- FDYWGQGTLV TVSS

BMS2h-427 (SEQ ID NO: 132)
EVQLLESGGG LVQPGGSLRL SCAASGFTFT DQPMVWVRQA PGKGLEWVSS IGARGGPTYY
ADSVKGRFTV SRDNSKNTLY LQMNSLRAED TAVYYCAKWF DIIAWDPFS- FDYWGQGTLV TVSS

BMS2h-428 (SEQ ID NO: 133)
EVQLLESGGG LVQPGGSLRL SCAASGFTFN QYPMMWVRQA PGKGLEWVSS ITPSGFLTYY
ADSVKGRFTI SRDNSKNTLY LQMNSLRAED TAVYYCAEWN PFITT----- FDYWGQGTLV TVSS

BMS2h-429 (SEQ ID NO: 134)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-43 (SEQ ID NO: 135)
EVQLLESGGG LVQPGGSLRL SCAASGFTFA SYEMAWVRQA PGKGLEWVSS IGSDGGPTYY
ADSVKGRFTI SRDNSKNTLY LQMNSLRAED SAVYYCAKPD RA-------- FDYWGQGTLV TVSS

BMS2h-430 (SEQ ID NO: 136)
EVQLLESGGG LVQPGGSLRL SCAASGFTFS AEQMTWARQA PGKGLEWVST ITPHGDSTYY
ADSVKGRFTI SRDNSKNTLY LQMNSLRAED TAVYYCAKWR TLVDWPTSES FDYWGQGTLV TVSS

BMS2h-44 (SEQ ID NO: 137)
EVQLLESGGG LVQPGGSLRL SCAASGFTFT SYEMGWVRQA PGKGLEWVSS IEPTGITTYY
ADSVKGRFTI SRDNSKNTLY LQMNSLRAED TAVYYCAKPH FTELG----- FDYWGQGTLV TVSS

TABLE 1-continued

Anti-human CD40L VH Domain Amino Acid Sequences

BMS2h-449 (SEQ ID NO: 138)
EVQLLESGGG LVQPGGSLRL SCAASGFTFE GEQMAWVRQA PGKGLEWVST ITLPGPYTFY
ADSVKGRFTI SRDNSKNTLY LQMNSLRAED TAVYYCAKGN GTF------- FDYWGQGTLV TVSS

BMS2h-45 (SEQ ID NO: 139)
EVQLLESGGG LVQPGGSLRL SCAASGFTFG NYAMAWVRQA PGKGLEWVSK IGAQGLHTYY
AGSVKGRFTI SRDNSKNTLY LQMNSLRAED TAVYYCAKQT TMDYER---- FDYWGQGTLV TVSS

BMS2h-450 (SEQ ID NO: 140)
EVQLLESGGG LVQPGGSLRL SCAASGFTFD EVDMSWVRQA PGKGLEWVSA IGNNGLKTYY
ADSVKGRFTI SRDNSKNTLY LQMNSLRAED TAVYYCAKSA LSYRPPV--- FDYWGQGTLV TVSS

BMS2h-451 (SEQ ID NO: 141)
EVQLLESGGG LVQPGGSLRL SCAASGFTFQ DDTMSWVRQA PGKGLEWVST ITLKGPSTYY
ADSVKGRFTI SRDNSKNTLY LQMNSLRAED TAVYYCAKSR DGLY------ FDYWGQGTLV TVSS

BMS2h-452 (SEQ ID NO: 142)
EVQLLESGGG LVQPGGSLRL SCAASGFTFA SSPMAWVRQA PGKGLEWVSS IGRDGSTTYY
ADSVKGRFTI SRDNSKNTLY LQMNSLRAED TAVYYCAKPS PYRR------ FDYWGQGTLV TVSS

BMS2h-453 (SEQ ID NO: 143)
EVQLLESGGG LVQPGGSLRL SCAASGFTFT DYSMVWVRQA PGKGLEWVST IVSHGGTTYY
ADSVKGRFTI SRDNSKNTLY LQMNSLRAED TAVYYCAKGK GYNAQY---- FDYWGQGTLV TVSS

BMS2h-454 (SEQ ID NO: 144)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-455 (SEQ ID NO: 145)
EVQLLESGGG LVQPGGSLRL SCAASGFTFN DYDMIWVRQA PGKGLEWVST ISSHGDSTYY
ADSVKGRFTI SRDNSKNTLY LQMNSLRAED TAVYYCAKGD VF-------- FDYWGQGTLV TVSS

BMS2h-456 (SEQ ID NO: 146)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAEWS DS-------- FDYRGQGTLV TVSS

BMS2h-457 (SEQ ID NO: 147)
EVQLLESGGG LVQPGGSLRL SCAASGFTFA DYEMAWVRQA PGKGLEWVSG IQSNGNITYY
ADSVKGRFTI SRDNSKNTLY LQMNSLRAED TAVYYCAKAN SQVEY----- FDYWGQGTLV TVSS

BMS2h-458 (SEQ ID NO: 148)
EVQLLESGGG LVQPGGSLRL SCAASGFTFG VEPMSWVRQA PGKGLEWVSN IGRDGSMTYY
ADSVKGRFTI SRDNSKNTLY LQMNSLRAED TAVYYCAKLG KHGT------ FDYWGQGTLV TVSS

BMS2h-459 (SEQ ID NO: 149)
EVQLLESGGG LVQPGGSLRL SCAASGFTFP EYRMMWVRQA PGKGLEWVSW IDERGSLTYY
ADSVKGRFTI SRDNSKNTLY LQMNSLRAED TAVYYCAKRR KGTKQ----- FDYWGQGTLV TVSS

BMS2h-46 (SEQ ID NO: 150)
EVQLLESGGG LVQPGGSLRL SCAASGFTFE LYAMAWVRQA PGKGLEWVSG IGAVGETTYY
ADSVKGRFTI SRDNSKNTLY LQMNSLRAED TAVYYCAKEA NNLSDNLV-FDYWGQGTLV TVSS

BMS2h-460 (SEQ ID NO: 151)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKWS VEW------- FDYWGQGTLV TVSS

BMS2h-461 (SEQ ID NO: 152)
EVQLLESGGG LVQPGGSLRL SCAASGFTFN SYTMNWVRQA PGKGLEWVSS INPWGSRTYY
ADSVKGRFTI SRDNSKNTLY LQMNSLRAED TAVYYCAKGL VL-------- FDYWGQGTLV TVSS

BMS2h-462 (SEQ ID NO: 153)
EVQLLESGGG LVQPGGSLRL SCAASGFTFD GDMMSWVRQA PGKGLEWVSS ITQLGSRTYY
ADSVKGRFTI SRDNSKNTLY LQMNSLRAED TAVYYCAKQN WRTLT----- FDYWGQGTLV TVSS

BMS2h-463 (SEQ ID NO: 154)
EVQLLESGGG LVQPGGSLRL SCAASGFTFN AYGMMWVRQA PGKGLEWVSS ILSDGVITYY
ADSVKGRFTI SRDNSKNTLY LQMNSLRAED TAVYYCAKSA RGANF----- FDYWGQGTLV TVSS

BMS2h-464 (SEQ ID NO: 155)
EVQLLESGGG LVQPGGSLRL SCAASGFTFG HYMMVWVRQA PGKGLEWVSS ITPHGTSTYY
ADSVKGRFTI SRDNSKNTLY LQMNSLRAED TAVYYCAEFN AIFSEA---- FDYWGQGTLV TVSS

BMS2h-465 (SEQ ID NO: 156)
EVQLLESGGG LVQPGGSLRL SCAASGFTFR DYSMAWVRQA PGKGLEWVST ITPSGLTTYY
ADSVKGRFTI SRDNSKNTLY LQMNSLRAED TAVYYCAEWS QAVTRS---- FDYWGQGTLV TVSS

TABLE 1-continued

Anti-human CD40L VH Domain Amino Acid Sequences

BMS2h-466 (SEQ ID NO: 157)
EVQLLESGGG LVQPGGSLRL SCAASGFTFD LYAMAWVRQA PGKGLEWVSM IGRDGRFTYY
ADSVKGRFTI SRDNSKNTLY LQMNSLRAED TAVYYCAKLA GSLRGR---- FDYWGQGTLV TVSS

BMS2h-467 (SEQ ID NO: 158)
EVQLLESGGG LVQPGGSLRL SCAASGFTFN KASMGWVRQA PGKGLEWVST ITPHGSSTYY
ADSVKGRFTI SRDNSKNTLY LQMNSLRAED TAVYYCAKQR WGVE------ FDYWGQGTLV TVSS

BMS2h-468 (SEQ ID NO: 159)
EVQLLESGGG LVQPGGSLRL SCAASGFTFQ GYSMGWVRQA PGKGLEWVSS IAGRGGVTYY
ADSVKGRFTI SRDNSKNTLY LQMNSLRAED TAVYYCAKGL YIYHSL---- FDYWGQGTLV TVSS

BMS2h-469 (SEQ ID NO: 160)
EVQLLESGGG LVQPGGSLRL SCAASGFTFP GMEMSWVRQA PGKGLEWVSA ITGTGSTTYY
ADSVKGRFTI SRDNSKNTLY LQMNSLRAED TAVYYCAKGY HP-------- FDYWGQGTLV TVSS

BMS2h-470 (SEQ ID NO: 161)
EVQLLESGGG LVQPGGSLRL SCAASGFTFP MVAMSWVRQA PGKGLEWVSS IARDGNVTYY
ADSVKGRFTI SRDNSKNTLY LQMNSLRAED AAVYYCAKVS PTG------- FDYWGQGTLV TVSS

BMS2h-471 (SEQ ID NO: 162)
EVQLLESGGG LVQPGGSLRL SCAASGFTFG HQDMSWVRQA PGKGLEWVSG ITDDGESTYY
ADSVKGRFTI SRDNSKNTLY LQMNSLRAED TAVYYCAKGD YD-------- FDYWGQGTLV
TVSS

BMS2h-472 (SEQ ID NO: 163)
EVQLLESGGG LVQPGGSLRL SCAASGFTFG EYNMMWVRQA PGKGLEWVSQ ITRDGSRTYY
ADSVRGRFTI SRDNSRNTLY LQMNSLRAED SAVYYCAKLS NIG------- FDYWGQGTLV TVSS

BMS2h-473 (SEQ ID NO: 164)
EVQLLESGGG LVQPGGSLRL SCAASGFTFS DYSMIWARQA PGKGLEWVSS ITPYGSYTYY
ADSVKGRFTI SRDNSKNTLY LQMNSLRAED TAVYYCAKTD YL-------- FDYWGQGTLV TVSS

BMS2h-474 (SEQ ID NO: 165)
EVQLLESGGG LVQPGGSLRL SCAASGFTFD TYSMMWVRQA PGKGLEWVST ITPYGSSTYY
ADSVKGRFTI SRDNSKNTLY LQMNSLRAED TAVYYCAKWG LV-------- FDYWGQGTLV TVSS

BMS2h-475 (SEQ ID NO: 166)
EVQLLESGGG LVQPGGSLRL SCAASGFTFT TGPMMWVRQA PGKGLEWVSA IGIGGDTTYY
ADSVKGRFTI SRDNSKNTLY LQMNSLRAED TAVYYCAKLT PSNQ------ FDYWGQGTLV TVSS

BMS2h-476 (SEQ ID NO: 167)
EVQLLESGGG LVQPGGSLRL SCAASGFTFK QYQMMWVRQA PGKGLEWVSS ITPSGFLTYY
ADSVKGRFTI SRDNSKNTLY LQMNSLRAED TAVYYCAEWN PFIST----- FDYWGQGTLV TVSS

BMS2h-477 (SEQ ID NO: 168)
EVQLLESGGG LVQPGGSLRL SCAASGFTFP NYDMVWVRQA PGKGLEWVSS ISALGNVTYY
ADSVKGRFTI SRDNSKNTLY LQTNSLRAED TAVYYCAKWR SAITGN----
FDYWGQGTLV TVSS

BMS2h-478 (SEQ ID NO: 169)
EVQLLESGGG LVQPGGSLRL SCAASGFTFK EYQMSWVRQA PGKGLEWVST ISPSGMNTYY
ADSVKGRFTI SRDNSKNTLY LQMNSLRAED TAVYYCAEWR SVVRPWPGV- FDYWGQGTLV TVSS

BMS2h-479 (SEQ ID NO: 170)
EVQLLESGGG LVQPGGSLRL SCAASGFTFD DESMAWVRQA PGKGLEWVSS ITPHGTFTYY
ADSVKGRFTI SRDNSKNTLY LQMNSLRAED TAVYYCAKLH LKLYESH--- FDYWGQGTLV TVSS

BMS2h-480 (SEQ ID NO: 171)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG ST-------- FDYWGQGTLV TVSS

BMS2h-481 (SEQ ID NO: 172)
EVQLLESGGG LVQPGGSLRL SCAASGFTFD FMPMAWVRQA PGKGLEWVSS IGRDGAYTYY
ADSVKGRFTI SRDNSKNTLY LQMNSLRAED TAVYYCAKLA SPAQ------ FDYWGQGTLV TVSS

BMS2h-482 (SEQ ID NO: 173)
EVQLLESGGG LVQPGGSLRL SCAASGFTFG DEPMLWVRQA PGKGLEWVSS IGGTGTTTYY
ADSVKGRFTI SRDNSKNTLY LQMNSLRAED TAVYYCAKGN QGDFINR--- FHYWGQGTLV TVSS

BMS2h-483 (SEQ ID NO: 174)
EVQLLESGGG LVQPGGSLRL SCAASGFTFH AYNMAWVRQA PGKGLEWVST ISPRGSYTYY
ADSVKGRFTI SRDNSKNTLY LQMNSLRAED TAVYYCAKWP PPSSH----- FDYWGQGTLV TVSS

BMS2h-5 (SEQ ID NO: 175)
EVQLLESGGG LVQPGGSLRL SCAASGFTFD GYEMAWVRQA PGKGLEWVSS ITSDGTSTYY
ADSVKGRFTI SRDNSKNTLY LQMNSLRAED TAVYYCAKPG LR-------- FDYWGQGTLV TVSS

TABLE 1-continued

Anti-human CD40L VH Domain Amino Acid Sequences

BMS2h-505 (SEQ ID NO: 176)
EVQLLESGGG LVQPGGSLRL SCAASGFTFE GYMMYWVHQA PGKGLEWVSS ISPQGHFTYY
ADSVKGRFTI SRDNSKNTLY LQMNSLRAED TAVYYCAELR ELPRL----- FDYWGQGTLV TVSS

BMS2h-506 (SEQ ID NO: 177)
EVQLLESGGG LVQPGGSLRL SCAASGFTFS SYAMGWVRQA PGKGLEWVSS IDASGGPTYY
ADSVKGRFTI SRDNSKNTLY LQMNSLRAED TAVYYCAKAN GKKFPFTKY- FDYWGQGTLV TVSS

BMS2h-507 (SEQ ID NO: 178)
EVQLLESGGG LVQPGGSLRL SCAASGFTFP SVHMAWVRQA PGKGLEWVSG INLTGVDTYY
ADSVKGRFTI SRDNSKNTLY LQMNSLRAED TAVYYCAKSA TTRQAHPLY- FDYWGQGTLV TVSS

BMS2h-515 (SEQ ID NO: 179)
EVQLLESGGG LVQPGGSLRL SCAASGFTFK EGEMYWVRQA PGKGLEWVST ISTNGLTTYY
ADSVKGRFTI SRDNSKNTLY LQMNSLRAED TAVYYCAKST RDLG------ FAYWGQGTLV TVSS

BMS2h-516 (SEQ ID NO: 180)
EVQLLESGGG LVQPGGSLRL SCAASGFTFE EYEMAWARQA PGKGLEWVSF ISPRGHFTYY
ADSVKGRFTI SRDNSKNTLY LQMNSLRAED TAVYYCAKPA KT-------- FDYWGQGTLV TVSS

BMS2h-517 (SEQ ID NO: 181)
EVQLLESGGG LVQPGGSLRL SCAASGFTFD TYEMLWVRQA PGKGLEWVSR ISVDGSITYY
ADSVKGRFTI SRDNSKNTLY LQMNSLRAED TAVYYCAKTR MR-------- FDYWGQGTLV TVSS

BMS2h-518 (SEQ ID NO: 182)
EVQLLESGGG LVQPGGSLRL SCAASGFTFS SYAMSWVRQA PGKGLEWVSN ISRDGSKTYY
ADSVKGRFTI SRDNSKNTLY LQMNSLRAED TAVYYCAEAQ SGGLRSGLTT FDYWGQGTLV TVSS

BMS2h-519 (SEQ ID NO: 183)
EVQLLESGGG LVQPGGSLRL SCADSGFTFS SYAMSWVRQA PGKGLEWVSS IGRDGAYTYY
ADSVKGRFTI SRDNSKNTLY LQMNSLRAED TAVYYCAKAG PKGIA----- FDYWGQGTLV TVSS

BMS2h-520 (SEQ ID NO: 184)
EVQLLESGGG LVQPGGSLRL SCAASGFTFS PHAMAWVRQA PGKGLEWVSG IDGGGSMTYY
ADSVKGRFTI SRDNSKNTLY LQMNSLRAED TAVYYCAKSD PP-------- FDYWGQGTLV TVSS

BMS2h-521 (SEQ ID NO: 185)
EVQLLESGGG LVQPGGSLRL SCAASGFTFH AGEMHWVRQA PGKGLEWVSS ITLPGDMTYY
ADSVKGRFTI SRDNSKNTLY LQMNSLRAED TAVYYCAKPN TGYT------ FDYWGQGTLV TVSS

BMS2h-522 (SEQ ID NO: 186)
EVQLLESGGG LVQPGGSLRL SCAASGFTFG NYGMSWVRQA PGKGLEWVSS ISWDGSLTYY
ADSVKGRFTI SRDNSKNTLY LQMNSLRAED TAVYYCAQNT RL-------- FDYWGQGTLV TVSS

BMS2h-523 (SEQ ID NO: 187)
EVQLLESGGG LVQPGGSLRL SCAASGFTFH DADMLWVRQA PGKGLEWVSG ILSPGEDTYY
ADSVKGRFTI SRDNSKNTLY LQMNSLRAED TAVYYCAKFG LP-------- FDYWGQGTLV TVSS

BMS2h-524 (SEQ ID NO: 188)
EVQLLESGGG LVQPGGSLRL SCAASGFTFR TDQMNWVRQA PGKGLEWVSS ISPSGAYTYY
ADSVKGRFTI SRDNSKNTLY LQMNSLRAED TAVYYCAKGL GA-------- FDYWGQGTLV TVSS

BMS2h-525 (SEQ ID NO: 189)
EVQLLESGGG LVQPGGSLRL SCAASGFIFE QYQMVWVRQA PGKGLEWVSW ISPDGTHTYY
ADSVKGRFTI SRDNSKNTLY LQMNSLRAED TAVYYCAKFS LRKMEK---- FDYWGQGTLV TVSS

BMS2h-526 (SEQ ID NO: 190)
EVQLLESGGG LVQPGGSLRL SCAASGFTFQ DEQMAWVRQA PGKGLEWVSS IASDGMSTYY
ADSVKGRFTI SRDNSKNTLY LQMNSLRAED TAVYYCAQPG KN-------- FDHWGQGTLV TVSS

BMS2h-527 (SEQ ID NO: 191)
EVQLLESGGG LVQPGGSLRL SCAASGFTFS DYAMSWVRQA PGKGLEWVSS ITTGGERTYY
ADSVKGRFTI SRDNSKNTLY LQMNSLRAED TAVYYCAKRW NLYTES---- FDYWGQGTLV TVSS

BMS2h-528 (SEQ ID NO: 192)
EVQLLESGGG LVQPGGSLRL SCAASGFTFG GQPMDWVRQA PGKGLEWVSS IAPDGIHTYY
ADSVKGRFTI SRDNSKNTLY LQMNSLRAED TAVYYCAKNL GQG------- FDYWGQGTLV TVSS

BMS2h-529 (SEQ ID NO: 193)
EVQLLESGGG LVQPGGSLRL SCAASGFTFE RYQMTWVRQA PGKGLEWVSS ISPSGTFTYY
ADSVKGRFTI SRDNSKNTLY LQMNSLRAED TAVYYCAEWK AL-------- FDYWGQGTLV TVSS

BMS2h-530 (SEQ ID NO: 194)
EVQLLESGGG LVQPGGSLRL SCAASGFTFP HSTMYWVRQA PGKGLEWVSL ILPSGSRTYY
ADSVKGRFTI SRDNSKNTLY LQMNSLRAED TAVYYCAKFS DER------- FDYWGQGTLV TVSS

TABLE 1-continued

Anti-human CD40L VH Domain Amino Acid Sequences

BMS2h-531 (SEQ ID NO: 195)
EVQLSESGGG LVQPGGSLRL SCAASGFTFG DGNMDWVRQA PGKGLEWVSG ISSDGVTTYY
ADSVKGRFTI SRDNSKNTLY LQMNSLRAED TAVYYCAKDR GQG------- FDYWGQGTLV TVSS

BMS2h-532 (SEQ ID NO: 196)
EVQLLESGGG LVQPGGSLRL SCAASGFTFD DYMMWVRQA PGKGLEWVSS ISPHGVYTYY
ADSVKGRFTI SRDNSKNTLY LQMNSLRAED TAVYYCAKWL HT-------- FDYWGQGTLV TVSS

BMS2h-533 (SEQ ID NO: 197)
EVQLLESGGG LVQPGGSLRL SCAASGFTFS NYTMAWGRQA PGKGLEWVSF IAGPGNYTYY
ADSVKGRFTI SRDNSKNTLY LQMNSLRAED TAVYYCAKPG STATYNNGQ- FDYWGQGTLV TVSS

BMS2h-534 (SEQ ID NO: 198)
EVQLLESGGG LVQPGGSLRL SCAASGFTFT EYSMVWVRQA PGKGLEWVSS ISGSGRVTYY
ADSVKGRFTI SRDNSKNTLY LQMNSLRAED TAVYYCAKWL KLVRAPNP-FDYWGQGTLV TVSS

BMS2h-535 (SEQ ID NO: 199)
EVQLLESGGG LVQPGGSLRL SCAASGFTFS NYQMAWVRQA PGKGLEWVSG ISKTGHSTYY
ADSVKGRFTI SRDNSRNTLY LQMNSLRAED TAVYYCAKAS HSLGPL---- FDYWGQGTLV TVSS

BMS2h-54 (SEQ ID NO: 200)
EVQLLESGGG LVQPGGSLRL SCAASGFTFT AYRMAWVRQA PGKGLEWVSW ISPSGSGTYY
ADSVKGRFTI SRDNSKNTLY LQMNSLRAED TAVYYCAKTL TDSPSGHYE- FDYWGQGTLV TVSS

BMS2h-55 (SEQ ID NO: 201)
EVQLLESGGG LVQPGGSLRL SCAASGFTFA RYEMGWVRQA PGKGLEWVSR ITAQGLGTYY
ADSVKGRFTI SRDNSKNTLY LQMNSLRAED TAVYYCAKYL TDFSSGHQE- FDYWGQGTLV TVSS

BMS2h-553 (SEQ ID NO: 202)
EVQLLESGGG LVQPGGSLRL SCAASGFTFD DYGMSWVRQV PGKGLEWVSG ISHNGMLTYY
ADSVKGRFTI SRDNSKNTLY LQMNSLRAED TAVYYCAKYW PSTSWETD-FDYWGQGTLV TVSS

BMS2h-554 (SEQ ID NO: 203)
EVQLLESGGG SVQPGGSLRL SCAASGFTFG NEPMAWVRQA PGKGLEWVSS IEMQGKNTYY
ADSVKGRFTI SRDNSKNTLY LQMNSLRAED TAVYYCAKDR GQG------- FDYWGQGTLV TVSS

BMS2h-555 (SEQ ID NO: 204)
EVQLLESGGG LVQPGGSLRL SCAASGFTFG EEEMSWVRQA PGKGLEWVSC IDNLGSPTYY
ADSVKGRFTI SRDNSKNTLY LQMNSLRAED AAVYYCAKTI SHQYDR---- FDYWGQGTLV TVSS

BMS2h-556 (SEQ ID NO: 205)
EVQLLESGGG LVQPGGSLRL SCAASGFTFG EEEMSWVRQA PGKGLEWVSS IDEGGRWTYY
ADSVKGRFTI SRDNSKNTLY LQMNSLRAED TAVYYCAKWT PHKQLS---- FDYWGQGTLV TVSS

BMS2h-557 (SEQ ID NO: 206)
EVQLLESGGG LVQPGGSLRL SCAASGFSFA DEYMVWARQA PGKGLEWVSE IDPLGTGTYY
ADSVKGRFTI SRDNSKNTLY LQMNSLRAED TAVYYCAKYG TA-------- FDYWGQGTLV TVSS

BMS2h-558 (SEQ ID NO: 207)
EVQLLESGGG LVQPGGSLRL SCAASGFTFS THDMMWVRQA PGKGLEWVSS ISDDGISTYY
ADSVKGRFTI SRDNSKNTLY LQMNSLRAED TAVYYCAKPD MSLIE----- FDYWGQGTLV TVSS

BMS2h-559 (SEQ ID NO: 208)
EVQLLESGGG LVQPGGSLRL SCAASGFTFD GTPMVWVRQA PGKGLEWVSG ISGDGRNTYY
ADSVKGRFTI SRDNSKNTLY LQMNSLRAED TAVYYCAEPY ALTSSKP--- FDYWGQGTLV TVSS

BMS2h-56 (SEQ ID NO: 209)
EVQLLESGGG LVQPGGSLRL SCAASGFTFN DYTMGWVRQA PGKGLEWVSW IHGTGGQTYY
ADSVKGRFTI SRDNSKNTLY LQMNSLRAED TAVYYCAKAL ADRSGGVVE- FDYWGQGTLV TVSS

BMS2h-560 (SEQ ID NO: 210)
EVQLLESGGG LVQPGGSLRL SCAASGFTFE AETMAWVRQA PGKGLEWVSC ISNDGNTTYY
ADSVKGRFTI SRDNSKNTLY LQMNSLRAED TAVYYCAKES LISPGL---- FDYWGQGTLV TVSS

BMS2h-561 (SEQ ID NO: 211)
EVQLLESGGG LVQPGGSLRL SCAASGFTFT GEYMNWVRQA PGKGLEWVST INETGYMTYY
ADSVKGRFTI SRDNSKNTLY LQMNSLRAED TAVYYCAKLS TRGVP----- FDYWGQGTLV TVSS

BMS2h-562 (SEQ ID NO: 212)
EVQLLESGGG LVQPGGSLRL SCAASGFTFR SYDMGWVRQA PGKGLEWVST ISPMGVFTYY
ADSVKGRFTI SRDNSKNTLY LQMNSLRAED TAVYYCAKSN QHADP----- FDYWGQGTLV TVSS

BMS2h-563 (SEQ ID NO: 213)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKAA LTEPM----- FDYWGQGTLV TVSS

TABLE 1-continued

Anti-human CD40L VH Domain Amino Acid Sequences

BMS2h-564 (SEQ ID NO: 214)
EVQLLESGGG LVQPGGSLRL SCAASGFTFR DYDMGWVRQA PGKGLEWVST ISPLGHFTYY
ADSVKGRSTI SRDNSKNTLY LQMNSLRAED TAVYYCAKAE EA-------- FDYWGQGTLV TVSS

BMS2h-565 (SEQ ID NO: 215)
EVQLLESGGG LVQPGGSLRL SCAASGFAFP RYGMTWVRQA PGKGLEWVSN IDQFGMKTYY
ADSVKGRFTI SRDNSKNTLY LQMNSLRAED TAVYYCAEEY AS-------- FDYWGQGTLV TVSS

BMS2h-566 (SEQ ID NO: 216)
EVQLLESGGG LVQPGGSLRL SCAASGFTFD KYDMGWVRQA PGKGLEWVST ISPMGVFTYY
ADSVKGRFTI SRDNSKNTLY LQMNSLRAED TAVYYCAKGR GNTSD----- FDYWGQGTLV TVSS

BMS2h-567 (SEQ ID NO: 217)
EVQLLESGGG LVQPGGSLRL SCAASGFTFS NYDMAWVRQA PGKGLEWVST ISGAGHFTYY
ADSVKGRFTI SRDNSKNTLY LQMNSLRAED TAVYYCAKSF PRDE------ FDYWGQGTLV TVSS

BMS2h-568 (SEQ ID NO: 218)
EVQLLESGGG LVQPGGSLRL SCAASGFTFP KYEMRWVRQA PGKGLEWVSE IGLDGSPTYY
ADSVKGRFTI SRDNSKNTLY LQMNSLRAED TAVYYCAKLG DPNG------ FDYWGQGTLV TVSS

BMS2h-569 (SEQ ID NO: 219)
EVQLLESGGG LVQPGGSLRL SCAASGFTFP TSEMDWVRQA PGKGLEWVSG IGPDGLTTYY
ADSVKGRFTI SRDNSKNTLY LQMNSLRAED TAVYYCAKHA DW-------- FDYWGQGTLV TVSS

BMS2h-57 (SEQ ID NO: 220)
EVQLLESGGG LVQPGGSLRL SCAASGFTFS EYDMYWVRQA PGKGLEWVSW IDTDGGDTYY
ADSVKGRFTI SRDNSKNTLY LQMNSLRAED TAVYYCAKPG LK-------- FDYWGQGTLV TVSS

BMS2h-570 (SEQ ID NO: 221)
EVQLLESGGG LVQPGGSLRL SCTASGFTFE NASMQWVRQA PGKGLEWVSS IEGQGNATYY
ADSVKGRFTI SRDNSKNTLY LQMNSLRAED TAVYYCAKSS SWS------- FDYWGQGTLV TVSS

BMS2h-571 (SEQ ID NO: 222)
EVQLLESGGG LVQPGGSLRL SCAASGFTFT RNEMGWVRQA PGKGLEWVST ITPTGTFTYY
ADSVKGRFTI SRDNSKNTLY LQMNSLRAED TAVYYCAKTD PGNRY----- FDYWGQGTLV TVSS

BMS2h-572 (SEQ ID NO: 223)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-1 (SEQ ID NO: 224)
EVQLLESGGG LVQPGGSLRL SCAASGFTFN WQLMGWFRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-10 (SEQ ID NO: 225)
EVQLLESGGG LVQPGGSLRL SCAASGFTFN WQLMGWVRQA PGKGLEWVSG IEGPGDVTYY
ADSVKGRFTV SRDNSKNTLY LQMNSLRAED TAVYYCAKVG KESN------ SDYRGQGTLV TVSS

BMS2h-572-11 (SEQ ID NO: 226)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESN------ SDYRGQGTQV TVSS

BMS2h-572-12 (SEQ ID NO: 227)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-13 (SEQ ID NO: 228)
EVQLLESGGG LVQPGGSLRL SCAASGFTFN WQLMGWARQA PGKGLEWVSG IEGPGDVTYY
ADSVKDRFTI SRDNSKNTLY LLMNSLRAED TAVYYCAKVG KESN------ FDYWGQGTLV TVSS

BMS2h-572-14 (SEQ ID NO: 229)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCVKVG KESN------ SDYRGQGTLV TVSS

BMS2h-572-15 (SEQ ID NO: 230)
EVRLLESGGG LVQPGGSLRL SCAASGFNFN WQLMGWIRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-16 (SEQ ID NO: 231)
EVQLLESGGG LVRPGGSLRL SCVASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-17 (SEQ ID NO: 232)
EVQLLESGGG LVQTGGSLRL SCAASGFTYN WQLMGWVRQA PGKGLEWVSG IEGPGDVTYY
ADSVKGRFTI SRDNSKNTLY LQMNSLRADD TAVYYCVKVG KESN------ FDYRGHGTLV TVSS

TABLE 1-continued

Anti-human CD40L VH Domain Amino Acid Sequences

BMS2h-572-18 (SEQ ID NO: 233)
EVQLLESGGG LVQPGGSLRL SCAASGFTFN WQLMGWVRKA PGKGLEWVSG IEGPGDVTYY
ADSVKGRFTI SRDNSKNTLY LQMNSLRAED TAVYYCAKVG KESN------ FDYRGQGTLV TVSS

BMS2h-572-19 (SEQ ID NO: 234)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCAKVG KESN------ FDYRGQGTLV TVSS

BMS2h-572-2 (SEQ ID NO: 235)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESK------ FDYLGQGTLV TVSS

BMS2h-572-21 (SEQ ID NO: 236)
EVQLLESGGG LVQPGGSLRL SCAASGFTFN WQLMGWVRQA PGKGLEWVSG IEGPGDVTYY
AESVKGRFTI SRDNSKNTLY LQMNSLRAED TAVYYCAKVG KESN------ LDYRGQGTLV TVSS

BMS2h-572-22 (SEQ ID NO: 237)
EVQLFESGGG SVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-23 (SEQ ID NO: 238)
EVQLLESGGG LVQPGGSLRL TCAASGFTFN WQLMGWVRQA PGKGLEWVSG IEGPGDVTYY
ADSVKGRFII SRDNSKNTLY LQMNSLRAED TAVYYCAKVG KESN------ SDYRGQGTLV TVSS

BMS2h-572-24 (SEQ ID NO: 239)
EVQLLESGGG LVQPGGSLRL SCAASGFTFN WQLMGWVRQA PGKGLEWVSG IEGPGDVTYY
ADSVKGRFTI SRDNSTNTLY LQMNSLRAED TAVYYCAKVG KESE------ FDYRGQGTLV TVSS

BMS2h-572-3 (SEQ ID NO: 240)
EVRLLESGGG LVQPGGSLRL SCAASGFTFN WQLMGWVRQA PGKGLEWVSG IEGPGDVTYY
ADSVKGRFTI TRDNSKNTLY LQMNSLRAED TAVYYCVKVG KESN------ LDYRGQGTLV TVSS

BMS2h-572-4 (SEQ ID NO: 241)
EVQLLVSGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-5 (SEQ ID NO: 242)
EVQLLVSGGG LVQPGGSLRL SCAASGFTFN WQLMGWVRQA PGKGLEWVSG IEGPGDVTYY
ADSVKGRFTI SRDNSKNMLY LQMNGLRAED TAVYYCAKVG KESN------ FDYRGQGTLV TVSS

BMS2h-572-6 (SEQ ID NO: 243)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-601 (SEQ ID NO: 244)
EVQLLESGGG LVQPGGSLRL SCAASGFTFK WQLMGWARQA PGKGLEWVSG IEGPGDVTYY
ADPVKGRFTI SRDNSKNTLY LQMNSLRAED TAVYYCVKVG KESN------ SDYRGQGTLV TVSS

BMS2h-572-602 (SEQ ID NO: 245)
EVQLLESGGG LVQPGGSLRL SCAASGFTFK WHLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-603 (SEQ ID NO: 246)
EVQLLESGGG LVQPGGSLRL SCAASGFTFN WHLMAWARQA PGKGLEWVSG IEGPGDVTYY
ADSVKGRFTI SRDNSKNTLY LQMNSLRAED TAVYYCVKVG KESN------ SDYRGQGTLV
TVSS

BMS2h-572-604 (SEQ ID NO: 247)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-605 (SEQ ID NO: 248)
EVQLLESGGG LVQPGGSLRL SCAASGFTFK WQLMAWARQA PGKGLEWVSG IEGPGDITYY
ADSVKGRFTI SRDNSKNTLY LQMNSLRAED TAVYYCVKVG KESN------ SDYRGQGTLV TVSS

BMS2h-572-606 (SEQ ID NO: 249)
EVQLLESGGG LVQPGGSLRL SCAASGFTFN WHLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-607 (SEQ ID NO: 250)
EVQLLESGGG LVQPGGSLRL SCAASGFTFK WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-608 (SEQ ID NO: 251)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KESN------ SDYRGQGTLV TVSS

TABLE 1-continued

Anti-human CD40L VH Domain Amino Acid Sequences

BMS2h-572-609 (SEQ ID NO: 252)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-610 (SEQ ID NO: 253)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-611 (SEQ ID NO: 254)
EVQLLESGGG LVQPGGSLRL SCAASGFTFN WQLMGWVRRA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-612 (SEQ ID NO: 255)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSN------ SDYRGQGTLV TVSS

BMS2h-572-613 (SEQ ID NO: 256)
EVQLLESGGG LAQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-614 (SEQ ID NO: 257)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-615 (SEQ ID NO: 258)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDKN------ SDYRGQGTLV TVSS

BMS2h-572-616 (SEQ ID NO: 259)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESK------ SDYRGQGTLV TVSS

BMS2h-572-617 (SEQ ID NO: 260)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG RDSK------ SDYRGQGTLV TVSS

BMS2h-572-618 (SEQ ID NO: 261)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KYSN------ SDYRGQGTLV TVSS

BMS2h-572-619 (SEQ ID NO: 262)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-620 (SEQ ID NO: 263)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDDS------ SDYRGQGTLV TVSS

BMS2h-572-621 (SEQ ID NO: 264)
EVQLLEFGGG LVQPGGSLRF SCAASGFTFN WQLMGWFRQA PGKGLEWVSG IEGPGDVTYY
ADSVKGRFTI SRDNSKNTLY LQMNSLRAED TAVYYCVKVG RDSN------ SDYRGQGTLV TVSS

BMS2h-572-622 (SEQ ID NO: 265)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDST------ SDYRGQGTLV TVSS

BMS2h-572-623 (SEQ ID NO: 266)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-624 (SEQ ID NO: 267)
EVQLLESGGG LVQPGGSLRL SCAASGFTFN WQLMGWVRQA PGKGLEWVSG IEGPGDVTYY
ADSVKGRFTI FRDNSKNTLY LQMNSLRAED TAVYYCVKVG KDSA------ SDYRGQGTLV TVSS

BMS2h-572-625 (SEQ ID NO: 268)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG NDSY------ SDYRGQGTLV TVSS

BMS2h-572-626 (SEQ ID NO: 269)
EVQLLESGGG LVQPGGSLRL SCAASGFTFN WQLMGWVRQA PGKGLEWVSG IEGPGDVTYY
ADSVKGRFTI SRDNSKNTLY LQMNGLRAED TAVYYCVKVG KDSS------ SDYRGQGTLV TVSS

BMS2h-572-627 (SEQ ID NO: 270)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAIYYCVKVG KDSA------ SDYRGQGTLV TVSS

TABLE 1-continued

Anti-human CD40L VH Domain Amino Acid Sequences

BMS2h-572-630 (SEQ ID NO: 271)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-631 (SEQ ID NO: 272)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-632 (SEQ ID NO: 273)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-633 (SEQ ID NO: 274)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-634 (SEQ ID NO: 275)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-635 (SEQ ID NO: 276)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-7 (SEQ ID NO: 277)
EVQLLESGGG LVQPGGSLRL SCAASGFTFN WQLMGWARQA PGKGLEWVSG IEGPGDVTYY
ADSVKGRFTI SRDNSKNTLY LQMNSLRAED SAVYYCAKVG KESN------ FDYLGQGTLV TVSS

BMS2h-572-8 (SEQ ID NO: 278)
EVQLLESGGG LVQPGGSLRL SCVASGFTFN WQLMGWARQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-9 (SEQ ID NO: 279)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCAKVG KESN------ SDYRGQGTLV TVSS

BMS2h-573 (SEQ ID NO: 280)
EVQLLESGGG LVQPGGSLRL SCAASGFTFS GWEMGWVRQA PGKGLEWVSS IDESGLNTYY
ADSVKGRFTI SRDNSKNTLY LQMNSLRAED TAVYYCAEGA PQYQIT---- FDYWGQGTLV TVSS

BMS2h-574 (SEQ ID NO: 281)
EVQLLESGGG LVQPGGSLRL SCAASGFTFP NYGMYWVRQA PGKGLEWVSY ISRRGLLTYY
ADSVKGRFTI SRDNSKNTLY LQMNSLRAED TAVYYCAKTS HYMNNG---- FDYWGQGTLV TVSS

BMS2h-575 (SEQ ID NO: 282)
EVQLLESGGG LVQPGGSLRL SCAASGFTFV DYTMAWVRQA PGKGLEWVSS ISPIGTFTYY
ADSVKGRFTI SRDNSKNTLY LQMNSLRAED TAVYYCAKDP YGMEDGLTW- FDYWGQGTLV TVSS

BMS2h-576 (SEQ ID NO: 283)
EVQLLESGGG LVQPGGSLRL SCAASGFTFD AYDMQWVRQA PGKGLEWVST ITSEGLSTYY
ADSVKGRFTI SRDNSKNTLY LQMNSLRAED TAVYYCAKPS DL-------- FDYWGQGTLV TVSS

BMS2h-577 (SEQ ID NO: 284)
EVQLLESGGG LVQPGGSLRL SCAASGFTFD GYDMGWVRQA PGKGLEWVST ISRGGWFTYY
ADSVKGRFTI SRDNSKNTLY LQMNSLRAED TAVYYCAKGT SQSSTGS--- FDYWGQGTLV TVSS

BMS2h-578 (SEQ ID NO: 285)
EVQLLESGGG LVQPGGSLRL SCAASGFTFR RYDMLWARQA PGKGLEWVSE ISPTGALTYY
ADSVKGRFTI SRDNSKNTLY LQMNSLRAED TAVYYCAKLG ST-------- FDYWGQGTLV TVSS

BMS2h-579 (SEQ ID NO: 286)
EVQLLESGGG LVQPGGSLRL SCAASGFTFF PYYMSWVRQA PGKGLEWVSS ISGTGGLTYY
ADSVKGRFTI SRDNSKNTLY LQMNSLRAED TAVYYCAKTT QNATL----- FDYWGQGTLV TVSS

BMS2h-58 (SEQ ID NO: 287)
EVQLLESGGG LVQPGGSLRL SCAASGFTFE VYTMAWVRQA PGKGLEWVST IDESGRDTYY
ADSVKGRFTI SRDNSKNTLY LQMNSLRAED TAVYYCAKPG VW-------- FDYWGQGTLV TVSS

BMS2h-580 (SEQ ID NO: 288)
EVQLLESGGG LVQPGGSLRL SCAASGFTFA FYKMGWVRQA PGKGLEWVST ITPKGHHTYY
ADSVKGRFTI SRDNSKNTLY LQMNSLRAED TAVYYCAKVF KGKGWTRPSG FDYWGQGTLV TVSS

BMS2h-581 (SEQ ID NO: 289)
EVQLLESGGG LVQPGGSLRL SCAASGFTFN EYSMMWVRQA PGKGLEWVSS IGRRGWLTYY
ADSVKGRFTI SRDNSKNTLY LQMNSLRAED TAVYYCAKAV LLDSTK---- FDYWGQGTLV TVSS

TABLE 1-continued

Anti-human CD40L VH Domain Amino Acid Sequences

BMS2h-582 (SEQ ID NO: 290)
EVQLLESGGG LVQPGGSLRL SCAASGFTFD EYPMTWVRQA PGKGLEWVST ISARGPFTYY
ADSVKGRFTI SRDNSKNTLY LQMNSLRAED TAVYYCAKGR HWLRNGR--- FDYWGQGTLV TVSS

BMS2h-583 (SEQ ID NO: 291)
EVQLLESGGG LVQPGGSLRL SCAASGFTFG MQSMQWVRQA PGKGLEWVSS ITDDGTSTYY
ADSVKGRFTI SRDNSKNTLY LQMNSLRAED TAVYYCAKPD RV-------- FDYWGQGTLV TVSS

BMS2h-584 (SEQ ID NO: 292)
EVQLLESGGG LVQPGGSLRL SCAASGFTFG AADMQWVRQA PGKGLEWVSL ITNDGISTYY
ADSVKGRFTI SRDNSKNTLY LQMNSLRAED TAVYYCAKAG DR-------- FDYWGQGTLV TVSS

BMS2h-586 (SEQ ID NO: 293)
EVQLLESGGG LVQPGGSLRL SCAASGFTFN KYRMQWVRQA PGKGLEWVSS IDSSGELTYY
ADSVKGRFTI SRDNSKNTLY LQMNSLRAED TAVYYCAEEV PMGNQTF--- FDYWGQGTLV TVSS

BMS2h-587 (SEQ ID NO: 294)
EVQLLESGGG LVQPGGSLRL SCAASGFTFT DYTMGWVRQA PGKGLEWVSS ITSQGAFTYY
ADSVKGRFTI SRDNSKNTLY LQMNSLRAED TAVYYCAKAT GTDSS----- FDYWGQGTLV TVSS

BMS2h-588 (SEQ ID NO: 295)
EVQLLESGGG LVQPGGSLRL SCAASGFTFE DYEMSWVRQA PGKGLEWVSC IGPGGKPTYY
ADSVKGRFTI SRDNSKNTLY LQMNSLRAED TAVYYCAKVD GH-------- FDYWGQGTLV TVSS

BMS2h-589 (SEQ ID NO: 296)
EVQLLESGGG LVQPGGSLRL SCAASGFTFS QYDMGWVRQA PGKGLEWVST ISSRGWLTYY
ADSVKGRFTI SRDNSKNTLY LQMNSLRAED TAVYYCAKGP GGRRR----- FDYWGQGTLV TVSS

BMS2h-59 (SEQ ID NO: 297)
EVQLLESGGG LVQPGGSLRL SCAASGFTFL DYAMGWVRQA PGKGLEWVST ISPMGMGTYY
ADSVKGRFTI SRDNSKNTLY LQMNSLRAED TAVYYCAKSS AISFTSDISN FDYWGQGTLV TVSS

BMS2h-590 (SEQ ID NO: 298)
EVQLLESGGG LVQPGGSLRL SCAASGFTFS DYPMSWVRQA PGKGLEWVSS ISWSGFQTYY
ADSVKGRFTI SRDNSKNTLY LQMNSLRAED TAVYYCAKPG VARMPTGIA- FDYWGQGTLV TVSS

BMS2h-591 (SEQ ID NO: 299)
EVQLLESGGG LVQPGGSLRL SCAASGFTFS AYEMQWVRQA PGKGLEWVSS IDSAGTFTYY
ADSVKGRFTI SRDNSKNTLY LQMNSLRAED TAVYYCAEPF GM-------- FDYWGQGTLV TVSS

BMS2h-592 (SEQ ID NO: 300)
EVQLLESGGG LVQPGGSLRL SCAASGFTFS EYPMKWVRQA PGKGLEWVST IDRQGDRTYY
ADSVKGRFTI SRDNSKNTLY LQMNSLRAED TAVYYCAKTV RRGLPRPSRY FDYWGQGTLV TVSS

BMS2h-593 (SEQ ID NO: 301)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKGL SVYSGLD--- FDYWGQGTLV TVSS

BMS2h-594 (SEQ ID NO: 302)
EVQLLESGGG LVQPGGSLRL SCAASGFTFS HYDMGWVRQA PGKGLEWVSD IDYIGKTTYY
ADSVKGRFTI SRDNSKNTLY LQMNSLRAED TAVYYCAKAS DEVGVNTSK- FDYWGQGTLV TVSS

BMS2h-595 (SEQ ID NO: 303)
EVQLLESGGG LVQPGGSLRL SCAASGFTFA RYDMGWVRQA PGKGLEWVST ISPTGVLTYY
ADSVKGRFTI SRDNSKNTLY LQMNSLRAED TAVYYCAKGF ED-------- FDYWGQGTLV TVSS

BMS2h-596 (SEQ ID NO: 304)
EVQLLESGGG LVQPGGSLRL SCAASGFTFE AYPMSWVRQA PGKGLEWVSL ISHTGHATYY
ADSVKGRFTI SRDNSKNTLY LQMNSLRAED TAVYYCAKGH WP-------- FDYRGQGTLI TVSS

BMS2h-597 (SEQ ID NO: 305)
EVQLLESGGG LVQPGGSLRL SCAASGFTFE DEWMSWVRQA PGKGLEWVSD ISPGGWTTYY
ADSVKGRFTI SRDNSKNTLY LQMNSLRAED TAVYYCAKGY RPFDE----- FDYWGQGTLV TVSS

BMS2h-598 (SEQ ID NO: 306)
EVQLLESGGG LVQPGGSLRL SCAASGVTFD AIEMSWVRQA PGKGLEWVSS ISRHGEYTYY
ADSVKGRFTI SRDNSKNTLY LQMNSLRAED TAVYYCAEDA WSRH------ FDYWGQGTLV TVSS

BMS2h-599 (SEQ ID NO: 307)
EVQLLESGGG LVQPGGSLRL SCAASGFTFD STDMSWVRQA PGKGLEWVSG ILDNGSNTYY
ADSVKGRFTI SRDNSKNMLY LQMNSLRAED TAVYYCAKGA RD-------- FDYWGQGTLV TVSS

BMS2h-600 (SEQ ID NO: 308)
EVQLLESGGG LVQPGGSLRL SCAASGFTFG RQSMQWVRQA PGKGLEWVSS IDDDGFSTYY
ADSVKGRFTI SRDNSKNTLY LQMNSLRAED TAVYYCAKGD PWG------- FDYWGQGTLV TVSS

TABLE 1-continued

Anti-human CD40L VH Domain Amino Acid Sequences

BMS2h-601 (SEQ ID NO: 309)
EVQLLESGGG LVQPGGSLRL SCTASGFTFS DTQMAWVRQA PGKGLEWVSG IDDGGVSTYY
ADSVKGRFTI SRDNSKNTLY LQMNSLRAED TAVYYCAKPD RH-------- FDYWGQGTLV TVSS

BMS2h-602 (SEQ ID NO: 310)
EVQLLESGGG LVQPGGSLRL SCAASGFTFG STTMGWVRQA PGKGLEWVSV ISDDGGFTYY
ADSVKGRFTI SRDNSRNTLY LQMNSLRAED TAVYYCAKVD GYGV------ FDYWGQGTLV TVSS

BMS2h-603 (SEQ ID NO: 311)
EVQLLESGGG LVQPGGSLRL SCAASGFTFR SGDMNWVRQA PGKGLEWVST ITNDGTSTYY
ADSVKGRFTI SRDNSKNTLY LQMNSLRAED TAVYYCAKSD SD-------- FDYWGQGTLV TVSS

BMS2h-61 (SEQ ID NO: 312)
EVQLLESGGG LVQPGGSLRL SCAASGFTFA AYAMTWVRQA PGKGLEWVSY ISPNGTATYY
ADSVKGRFTI SRDNSKNTLY LQMNSLRAED TAVYYCAEYV GMRWNS---- FDYWGQGTLV TVSS

BMS2h-62 (SEQ ID NO: 313)
EVQLLESGGG LVQPGGSLRL SCAASGFTFS SYEMAWVRQA PGKGLEWVSS ITSLGTSTYY
ADSVKGRFTI SRDNSKNTLY LQMNSLRAED TAVYYCAKPG RK-------- FDYWGQGTLV TVSS

BMS2h-65 (SEQ ID NO: 314)
EVQLLESGGG LVQPGGSLRL SCAASGFTFN EYEMTWVRQA PGKGLEWVST ITSEGSGTYY
ADSVKGRFTI SRDNSKNTLY LQMNSLRAED TAVYYCAKPN GK-------- FDYWGQGTLV TVSS

BMS2h-66 (SEQ ID NO: 315)
EVQLLESGGG LVQPGGSLRL SCAASGFTFS DYEMLWVRQA PGKGLEWVST ITSEGHSTYY
ADSVKGRFTI SRDNSKNTLY LQMNSLRAED TAVYYCAKPG TS-------- FDYWGQGTLV TVSS

BMS2h-67 (SEQ ID NO: 316)
EVQLLESGGG LVQPGGSLRL SCAASGFTFS DYEMSWVRQA PGKGLEWVST IDSDGSFTYY
ADSVKGRFTI SRDNSKNTLY LQMNSLRAED TAVYYCAKPG VK-------- FDYWGQGTLV TVSS

BMS2h-68 (SEQ ID NO: 317)
EVQLLESGGG LVQPGGSLRL SCAASGFTFK DYEMTWVRQA PGKGLEWVSS ISSTGQSTYY
ADSVKGRFTI SRDNSKNTLY LQMNSLRAED TAVYYCAKPG NK-------- FDYWGQGTLV TVSS

BMS2h-69 (SEQ ID NO: 318)
EVQLLESGGG LVQPGGSLRL SCAASGFTFL DYGMAWVRQA PGKGLEWVSA ISPLGLSTYY
ADSVKSRFTI SRDNSKNTLY LQMNSLRAED TAVYYCAKEV RVGRGVHPPK FDYWGQGTLV TVSS

BMS2h-7 (SEQ ID NO: 319)
EVQLLESGGG LVQPGGSLRL SCAASGFTFN LYEMTWVRQA PGKGLEWVSS ITSDGVSTYY
ADSVKGRFTI SRDNSKNTLY LQMNSLRAED TAVYYCAKAG VI-------- FDYWGQGTLV TVSS

BMS2h-70 (SEQ ID NO: 320)
EVQLLESGGG LVQPGGSLRL SCAASGFTFE NYAMSWVRQA PGKGLEWVST IAPLGVPTYY
ADSVKGRFTI SRDNSKNTLY LQMNSLRAED TAVYYCAKKK VGAWLQSRS- FDYWGQGTLV TVSS

BMS2h-701 (SEQ ID NO: 321)
EVQLLESGGG LVQPGGSLRL SCAASGFTFM DYEMHWVRQA PGKGLEWVST IGASGHYTYY
ADSVKGRFTI SRDNSKNTLY LQMNSLRAED TAVYYCAKYL DMLLFG---- FDYWGQGTLV TVSS

BMS2h-702 (SEQ ID NO: 322)
EVQLLESGGG LVQPGGSLRL SCAASGFTFA EYEMMWARQA PGKGLEWVSR IAGNGSRTYY
ADSVKGRFTI SRDNSKNTLY LQMNSLRAED TAVYYCAIML SH-------- FDYWGQGTLV TVSS

BMS2h-703 (SEQ ID NO: 323)
EVQLLESGGG LVQPGGSLRL SCAASGFTFY NYDMSWVRQA PGKGLEWVSG IDSMGLVTYY
ADSVKGRFTI SRDNSKNTLY LQMNSLRAED TAVYYCAKGS NASDWVV--- FDYWGQGTLV TVSS

BMS2h-704 (SEQ ID NO: 324)
EVQLLESGGG LVQPGGSLRL SCAASGFTFA SYHMTWVRQA PGKGLEWVSS IADTGDRTYY
ADSVKGRFTI SRDNSKNTLY LQMNSLRAED TAVYYCAKLR GMARVWG--- FDYWGQGTLV TVSS

BMS2h-705 (SEQ ID NO: 325)
EVQLLESGGG LVQPGGSLRL SCAASGFTFS YYDMMWVRQA PGKGLEWISS ISDRGLQTYY
ADSVKGRFTI SRDNSKNTLY LQMNSLRAED TAVYYCAKFT EIPLDWLEV- FDYWGQGTLV TVSS

BMS2h-706 (SEQ ID NO: 326)
EVQLLESGGG LVQPGGSLRL SCAASGFTFG SYKMLWVRQA PGKGLEWVSS ITNSGTETYY
ADSVKGRFTI SRDNSKNTLY LQMNSLRAED TAVYYCAKSM YPDLEIVH-FDYWGQGTLV TVSS

BMS2h-707 (SEQ ID NO: 327)
EVQLLESGGG LVQPGGSLRL SCAASGFTFE TYRMSWVRQA PGKGLEWVSA IDQEGSATYY
ADSVKGRFTI SRDNSKNTLY LQMNSLRAED TAVYYCAKNS GTRPGLR--- FDYWGQGTLV TVSS

TABLE 1-continued

Anti-human CD40L VH Domain Amino Acid Sequences

BMS2h-708 (SEQ ID NO: 328)
EVQLLESGGG LVQPGGSLRL SCAASGFTFS SYDMLWVRQA PGKGLEWVSR IDASGYFTYY
ADSVKGRFTI SRDNSKNTLY LQMNSLRAED TAVYYCAQLL KLSLNPN--- FDYWGQGTLV TVSS

BMS2h-709 (SEQ ID NO: 329)
EVQLLESGGG LVQPGGSLRL SCAASGFTFS SYAMSWVRQA PGKGLEWVSS IHNTGLSTYY
ADSVKGRFTI SRDNSKNTLY LQMNSLRAED TAVYYCAKGT QHRFVV---- FDYWGQGTLV TVSS

BMS2h-71 (SEQ ID NO: 330)
EVQLLESGGG LVQPGGSLRL SCAASGFTFE GYPMSWVRQA PGKGLEWVST ISPLGPDTYY
ADSVKGRFTI SRDNSKNTLY LQMNSLRAED TAVYYCAKLL MGEYLNSRT- FDYWGQGTLV TVSS

BMS2h-710 (SEQ ID NO: 331)
EVQLLESGGG LVQPGGSLRL SCAASGFTFN TYSMSWVRQA PGKGLEWVSW IDADGWVTYY
ADSVKGRFTI SRDNSKNTLY LQMNSLRAED TAVYYCAQTG HT-------- FDYWGQGTLV TVSS

BMS2h-711 (SEQ ID NO: 332)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-712 (SEQ ID NO: 333)
EVQLLESGGG LVQPGGSLRL SCAASGFTFP EYEMKWVRQA PGKGLEWVST ITPSGGHTYY
ADSVKGRFTI SRDNSKNTLY LQMNSLRAED AAVYYCAIPL SS-------- FDYWGRGTLV TVSS

BMS2h-713 (SEQ ID NO: 334)
EVQLLESGGG LVQPGGSLRL SCAASGFTFS NYVMIWVRQA PGKGLEWVSL INGAGDMTYY
ADSVKGRFTI SRDNSKNTLY LQMNSLRAED TAVYYCAEGG ARSFGVPPN- FDYWGQGTLV TVSS

BMS2h-714 (SEQ ID NO: 335)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-715 (SEQ ID NO: 336)
EVQLLESGGG LVQPGGSLRL SCVASGFTFT LYNMSWVRQA PGKGLEWVSV ISSKGDSTYY
ADSVKGRFTI SRDNSKNTLY LQMNSLRAED TAVYYCAQTS SV-------- FDYWGQGTLV TVSS

BMS2h-716 (SEQ ID NO: 337)
EVQLLESGGG LVQPGGSLRL SCAASGFTFE AYYMSWVRQA PGKGLEWVSG IVNNGLLTYY
ADSVKGRFTI SRDNSKNMLY LQMNSLRAED TAVYYCAKSA VHPSYRAEL- FDYWGQGTLV TVSS

BMS2h-717 (SEQ ID NO: 338)
EVQLLESGGG LVQPGGSLRL SCAASGFTFS SYEMAWVRQA PGKGLEWVSR IEPDGSNTYY
ADSVKGRFTI SRDNSKNTLY LQMNSLRAED TAVYYCAKGP DNFTM----- FDYWGQGTLV TVSS

BMS2h-718 (SEQ ID NO: 339)
EVQLLESGGG LVQPGGSLRL SCAASGFTFN KYMMGWVRQA PGKGLEWVSS IDSLGHYTYY
ADSVKGRFTI SRDNSKNTLY LQMNSLRAED TAVYYCAEAE FP-------- FDYWGQGTLV TVSS

BMS2h-719 (SEQ ID NO: 340)
EVQLLESGGG LVQPGGSLRL SCAASGFTFK RYEMTWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-1 (SEQ ID NO: 341)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-10 (SEQ ID NO: 342)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-11 (SEQ ID NO: 343)
EVQLLESGGG LVQPGGSLRL SCAASGFTFK RYEMMWVRKA PGKGLEWVSS ISSDGSFTYY
ADSVKGRFTI SRDNSENTLY LQMNSLRAED TAVYYCADPF TE-------- FDYWGQGTLV TVSS

BMS2h-719-12 (SEQ ID NO: 344)
EVQLLESGGG LVQPGGSLRL SCAASGFTFK RYEMMWVRQA PGKGLEWVSS ISSDGSFTYY
ADSVKGRFTV SRDNSKNTLY LQMNSLRAED TAVYYCADPF TE-------- FDYWGQGTLV TVSS

BMS2h-719-13 (SEQ ID NO: 345)
EVQLLESGGG LVQPGGSLRL SCAASGFTFK RYEMMWVRQA PGKGLEWVSS ISSDGSFTYY
ADSVKGRFTI SRDNTKNTLY LQMNSLRAED TAVYYCADPF TE-------- LDYWGHGTLV TVSS

BMS2h-719-14 (SEQ ID NO: 346)
EVQLLESGGG LVRPGGSLRL SCAASGFTFK RYEMMWVRQA PGKGLEWVSS ISSDGSFTYY
ADSVKGRFTI SRDNSKNTLY LQMNSLRAED TAVYFCADPF TE-------- FDYWGQGTLV TVSS

TABLE 1-continued

Anti-human CD40L VH Domain Amino Acid Sequences

```
BMS2h-719-15 (SEQ ID NO: 347)
EVQLLESGGG LVQPGGSLRL SCAASGFAFK RYEMTWVRQA PGKGLEWVSS ISSDGSFTYY
ADSVKGRFTI SRDNSKNTLY LHMNSLRAED TAVYYCADPF TE-------- IDYWGQGTLV TVSS

BMS2h-719-16 (SEQ ID NO: 348)
EVQLLESGGG LVQPGGSLRL SCAASGFPFK RYEMTWVRQA PGKGLEWVSS ISSDGSFTYY
ADSVKGRFTI SRDNSKNTLY LQMNSLRAED TAVYYCAEPF TE-------- FDYRAQGTLV TVSS

BMS2h-719-17 (SEQ ID NO: 349)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCADPF TE-------- IDYWGQGTQV TVSS

BMS2h-719-18 (SEQ ID NO: 350)
EVQLLESGGG LVHPGGSLRL SCAASGFTFK RYEMMWVRQA PGKGLEWVSS ISSDGSFTYY
ADSVKGRFTI SRDNSKNTLY LQMNSLRDED TAVYYCAEPF TE-------- FDYGGQGTLV TVSS

BMS2h-719-19 (SEQ ID NO: 351)
EVQLLESGGG WVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-2 (SEQ ID NO: 352)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-20 (SEQ ID NO: 353)
EVQLLESGGG LVQPGGSLRL SCAASGFTFK RYEMTWVRQA PGKGLEWVSS ISSDGSFTYY
ADSVKGRFTI SRDNSKNTLY LQMNSLRAED TAVYYCAEPF TE-------- IDYRGQGTLV TVSS

BMS2h-719-202 (SEQ ID NO: 354)
EVQLLESGGG LVQPGGSLRL SCAASGFTFK KYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-203 (SEQ ID NO: 355)
EVQLLESGGG LVQPGGSLRL SCAASGFTFN SYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-21 (SEQ ID NO: 356)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-213 (SEQ ID NO: 357)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- MDYWGHGTLV TVSS

BMS2h-719-214 (SEQ ID NO: 358)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGHGTLV TVSS

BMS2h-719-215 (SEQ ID NO: 359)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- LDYWGHGTLV TVSS

BMS2h-719-218 (SEQ ID NO: 360)
EVQLLESGGG LVQPGGSLRL SCAASGFTFK RYEMMWVRQA PGKGLEWVSS ISSDGSFTYY
AESVKGRFTI SRDNSKNTLY LQMNSLRAED TAVYYCAEPF TE-------- FDYWGHGTLV TVSS

BMS2h-719-225 (SEQ ID NO: 361)
EVQLLESGGG LVQPGGSLRL SCAASGFTFN TYEMQWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-226 (SEQ ID NO: 362)
EVQLLESGGG LVQPGGSLRL SCAASGFTFN KYEMMWARQA PGKGLEWVSS ISSDGSFTYY
ADSVKGRFTI SRDNSRNTLY LQMNSLRAED TAVYYCAEPF TE-------- FDYWGHGTLV TVSS

BMS2h-719-3 (SEQ ID NO: 363)
EVQLSESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-4 (SEQ ID NO: 364)
EVQLLESGGG LVQPGGSLRL SCAASGFTFK RYEMMWVRQT PGKGLEWVSS ISSDGSFTYY
ADSVKGRFTI SRDNSKNTLY LQMNSLRAED TAVYYCAEPF TE-------- FDYWGQGTLV TVSS

BMS2h-719-5 (SEQ ID NO: 365)
EVQLLESGGG LVQPGGSLRL SCAASGFTFK RYEMMWVRQA PGKGLEWVSS ISSDGSFTYY
ADSVKGRFTI SRDNSKNTLY LEMNSMRAED TAVYYCAEPF TE-------- FDNWGQGTLV TVSS
```

TABLE 1-continued

Anti-human CD40L VH Domain Amino Acid Sequences

BMS2h-719-6 (SEQ ID NO: 366)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-7 (SEQ ID NO: 367)
EVQLLESGGG LVQPGGSLRL SCAASGFNFK RYEMTWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-8 (SEQ ID NO: 368)
EVQLLESGGD LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYRGQGTLV TVSS

BMS2h-719-9 (SEQ ID NO: 369)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCAEPF TE-------- FDYWGRGTLV TVSS

BMS2h-72 (SEQ ID NO: 370)
EVQLLESGGG LVQPGGSLRL SCAASGFTFE AYPMSWVRQA PGKGLEWVSS ISPLGLWTYY
ADSVKGRFTI SRDNSKNTLY LQMNSLRAED TAVYYCAKLS AGAETHVYRL FDYWGQGTLV TVSS

BMS2h-720 (SEQ ID NO: 371)
EVQLLESGGG LVQPGGSLRL SCAASGFTFG NYEMMWVRQA PGKGLEWVSS IGVLGHTTYY
ADSVKGRFTI SRDNSKNTLY LQMNSLRAED TAVYYCAKLM SLRTFENL- FDYWGQGTLV TVSS

BMS2h-722 (SEQ ID NO: 372)
EVQLLESGGG LVQPGGSLRL SCAASGFTFT KYPMAWVRQA PGKGLEWVSG IDANGNRTYY
ADSVKGRFTI SRDNSKNTLY LQMNSLRAED TAVYYCAEGT WRRHFAI--- FDYWGQGTLV TVSS

BMS2h-723 (SEQ ID NO: 373)
EVQLLESGGG LVQPGGSLRL SCAASGFTFD LYDMMWVRQA PGKGLEWVSS ISDLGTLTYY
ADSVKGRFTI SRDNSKNTLY LQMNSLRAED TAVYYCAKNG FRVTSNDRR- FDYWGQGTLV TVSS

BMS2h-724 (SEQ ID NO: 374)
EVQLLESGGG LVQPGGSLRL SCAASGFTFT GGDMWVRQA PGKGLEWVSM IEGGGVTTYY
ADSVKGRFTI SRDNSKNTLY LQMNSLRAED TAVYYCAELD LRTGQ----- FDYWGQGTLV TVSS

BMS2h-725 (SEQ ID NO: 375)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FDYWGQGTLV TVSS

BMS2h-725-1 (SEQ ID NO: 376)
EVQLLESGGG LVQPGGSLHL SCAASGFTFS AYTMGWVRQA PGKGLEWVSL IGDRGSWTYY
ADSVKGRFTI SRDNSKNTLY LQMNSLRAED TAVYFCADPS DPTK------ FDYWGQGTLV TVSS

BMS2h-725-10 (SEQ ID NO: 377)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FDYWGQGTLV TVSS

BMS2h-725-11 (SEQ ID NO: 378)
EVQLLESGGG LVQPGGSLRL SCAASGFTFS AYTMGWVRQA PGKGLEWVSL IGDRGSWTYY
ADSVKGRFTI SRDNSKNTLY LQMSSLRAED TAVYYCADPS DPTK------ FDYWGQGTLV TVSS

BMS2h-725-12 (SEQ ID NO: 379)
EVQLLESGGG LVQPGGSLRL SCAASGFTFP AYTMGWVRQA PGKGLEWVSL IGDRGSWTYY
ADSVKGRFTI SRDDSKNTLY LQMNSLRVED TAVYYCAEPS DPTM------ FVYWGQGTLV TVSS

BMS2h-725-13 (SEQ ID NO: 380)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTM------ FVYWGQGTLV TVSS

BMS2h-725-14 (SEQ ID NO: 381)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTM------ FDYWGQGTLV TVSS

BMS2h-725-15 (SEQ ID NO: 382)
EVQLLESGGG MVQPGGSLRL SCAASGFTFS AYTMGWVRQA PGKGLEWVSL IGDRGSWTYY
ADSVKGRFTI SRDNSKNTLY LQMNSMRAED TAVYYCADPS DPTK------ FDYWGQGTLV TVSS

BMS2h-725-16 (SEQ ID NO: 383)
EVQLLESGGG LVQPGGSLRL SCAASGFTFS AYTMGWVRQA PGKGLEWVTL IGDRGSWTYY
ADSVKGRFTI SRDNSKNTLY LQMNSLRAED TAVYYCAEPS DPTM------ FDYWGQGTLV TVSS

BMS2h-725-17 (SEQ ID NO: 384)
EVQLLESGGG LVQPGGSLRL SCAASGFTFT AYTMGWVRQA PGKGLEWVSL IGDRGSWTYY
ADSVKGRFTI SRDNSKNTLY LQMNSLRAED TAVYYCAEPS DPTK------ LDYWGQGTLV TVSS

TABLE 1-continued

Anti-human CD40L VH Domain Amino Acid Sequences

```
BMS2h-725-18 (SEQ ID NO: 385)
EVQLSESGGG LVQPGGSLRL TCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

BMS2h-725-19 (SEQ ID NO: 386)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

BMS2h-725-2 (SEQ ID NO: 387)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FVYWGQGTPV TVSS

BMS2h-725-3 (SEQ ID NO: 388)
VQLLESGGG LVQPGGSLRL SCAASGFTFS AYTMGWVRQA PGKGLEWVSL IGDRGSWTYY
ADSVKGRFTI SRDNSRNMLY LQMKSLRAED TAVYYCADPS DPTK------ FVYWGQGTQV TVSS

BMS2h-725-4 (SEQ ID NO: 389)
EVQLLESGGG LVQPGGSLRL SCAASGFTFS AYTMGWVRQA PGKGLEWVSL IGDRGSWTYY
ADSVKGRFTI FRDNSKNTLY LQMNSLRAED TAVYYCADPS DPTK------ FVYWGQGTLV TVSS

BMS2h-725-5 (SEQ ID NO: 390)
EVQLLESGGG LLQPGGSLRL SCAASGFTFS DYTMGWVRQA PGKGLEWVSL IGDRGSWTYY
ADSVKGRFTI SRDNSKNTLY LQMNSLRAED TAVYYCAEPS DPTK------ FDYWGRGTLV TVSS

BMS2h-725-6 (SEQ ID NO: 391)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FVYWGQGTLV TVSS

BMS2h-725-7 (SEQ ID NO: 392)
EVQLLESGGG LVQPGGSLRL SCAASGFTFS AYTMGWVRQA PGKGLEWVSL IGDRGTWTYY
ADPVKGRFTI SRDNSKNTLY LQMNSLRAED TAVYYCADPS DPTK------ FDYWGQGTLV TVSS

BMS2h-725-8 (SEQ ID NO: 393)
EVQLLESGGG LVQPGGSLRL SCAASGFTFS AYTMGWVRQA PGKGLEWVSL IGDRGSWTYY
ADSVKGRFTV SRDNSKNTLY LQMNSLRAED TAVYYCAEPS DPTK------ FDYWGQGTLV TVSS

BMS2h-725-9 (SEQ ID NO: 394)
EVQLLESGGG LVQPGGSLRL SCAASGFTFS AYTMGWVRQA PGMGLEWVSL IGDRGSWTYY
ADSVKGRFTI SRDNSKNTLY LQMNSLRAED TAVYYCAEPS DPTK------ FDYWGQGTLV TVSS

BMS2h-726 (SEQ ID NO: 395)
EVQLLESGGG LVQPGGSLRL SCAASGFTFD NYKMYWVRQA PGKGLEWVSS ISEIGNLTYY
ADSVKGRFTI SRDNSKNTLY LQMNSLRAED TAVYYCAIAL TR-------- FDYWGQGTLV TVSS

BMS2h-727 (SEQ ID NO: 396)
EVQLLESGGG LVQPGGSLRL SCAASGFTFA SYRMYWVRQA PGKGLEWVSY IDPPGSRTYY
ADSVKGRFTI SRDNSKNTLY LQMNSLRAED TAVYYCAKSL NLSFPYIN-FDYWGQGTLV TVSS

BMS2h-728 (SEQ ID NO: 397)
EVQLLESGGG LVQPGGSLRL SCAASGFTFE RYEMLWVRQA PGKGLEWVSR ISHSGRTTYY
ADSVKGRFTI SRDNSKNTLY LQMNSLRAED TAVYYCAQLD GP-------- FDYWGQGTLV TVSS

BMS2h-729 (SEQ ID NO: 398)
EVQLLESGGG LVQPGGSLRL SCAASGFTFK RYYMDWVRQA PGKGLEWVSR INHNGSVTYY
ADSVKGRFTI SRDNSKNTLY LQMNSLRAED TAVYYCAKMP QGTSDWYY-FDYWGQGTLV TVSS

BMS2h-73 (SEQ ID NO: 399)
EVQLLESGGG LVQPGGSLRL SCAASGFTFS KYDMSWVRQA PGKGLEWVST ILEDGLTTYY
ADSVKGRFTI SRDNSKNTLY LQMNSLRAED TAVYYCAKPG RL-------- FDYWGQGTLV TVSS

BMS2h-74 (SEQ ID NO: 400)
EVQLLESGGG LVQPGGSLRL SCAASGFTFS DYPMTWVRQA PGKGLEWVST ILSPGTETYY
ADSVKGRFTI SRDNSKNTLY LQMNSLRAED TAVYYCAKAE KD-------- FDYWGQGTLV TVSS

BMS2h-741 (SEQ ID NO: 401)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG EV-------- FDYWGQGTLV TVSS

BMS2h-742 (SEQ ID NO: 402)
EVQLLESGGG LVQPGGSLRL SCAASGFTFR EYHMKWARQA PGKGLEWVSG ISRDGMNTYY
ADSVKGRFTI SRDNSKNTLY LQMNSLRAED TAVYYCAIQL AL-------- FDYWGQGTLV TVSS

BMS2h-743 (SEQ ID NO: 403)
EVQLLESGGG LVQPGGSLRL SCAASGFTFR DYEMLWARQA PGKGLEWVSG ILPSGGATYY
ADSVKGRFTI SRDNSKNTLY LQMNSLRAED TAVYYCAKAG SGNGPIL--- FDYWGQGTLV TVSS
```

TABLE 1-continued

Anti-human CD40L VH Domain Amino Acid Sequences

BMS2h-744 (SEQ ID NO: 404)
EVQLLESGGG LVQPGGSLRL SCAASGFTFK EHDMFWVRQA PGKGLEWVSG IGAEGVWTYY
ADSVKGRFTI SRDNSKNTLY LQMNSLRAED TAVYYCAEPT MSNGSQSR- FDYWGQGTLV TVSS

BMS2h-745 (SEQ ID NO: 405)
EVQLLESGGG LVQPGGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-1 (SEQ ID NO: 406)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-10 (SEQ ID NO: 407)
EVQLLESGGG LVQPGGSLRL SCAASGFTFD NTEMAWVRQA PGKGLEWVSG ITEDGNRTYY
ADSVKGRFTI SRDNSKNTLY LQMNNLRAED TAVYYCAKIR NLHWDVGRQ- FDYWGQGTLV TVSS

BMS2h-745-11 (SEQ ID NO: 408)
EVQLLESGGG LVQPGGSLRL SCAASGFTFD NTEMAWIRQA PGKGLEWVSG ITEDGNRTYY
ADSVKGRFTI SRDNFKNTLY LQMNSLRAED TAVYYCAKIR NLHWDVGRQ- FDYWGQGTLV TVSS

BMS2h-745-12 (SEQ ID NO: 409)
EVQLLESGGG LVQPGGSLRL SCAASGFTFD NTEMAWVRQA PGKGLEWVSG ITEDGNRTYY
ADSVKGRFTI SRDNSMNTLY LQMNSLRAED TAVYYCAKIR NLHWDVGRQ- FVYWGQGTLV TVSS

BMS2h-745-13 (SEQ ID NO: 410)
EVQLLESGGG LVQPGGSLRL SCAASGFTFD NTEMAWIRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-14 (SEQ ID NO: 411)
EVQLLESGGG LVQPGGSLRL SCAASGFTFD NTEMAWIRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-15 (SEQ ID NO: 412)
EVQLLESGGG LVQPGGSLRL SCAASGFTFD NTEMAWIRQA PGKGLEWVSG ITEDGNRTYY
ADSVKGRFTI SRDNSKNALY LQMNSLRAED TAVYYCAKIR NLHWDVGRQ- FDYWGLGTLV TVSS

BMS2h-745-16 (SEQ ID NO: 413)
EVQLLESGGG LVQPGGSLRL SCAASGFTFD NTEMAWVRQA PGKGLEWVSG ITEDGNRTYY
ADSVKGRFTI SRDNTKNTLY LQMNSLRAED TAVYYCAKIR NLHWDVGRQ- FVYWGQGTLV TVSS

BMS2h-745-17 (SEQ ID NO: 414)
EVQLLESGGG LVQPGGSLRL SCAASGFTFD NTEMAWIRQA PGKGLEWVSG IIEDGNRTYY
ADSVKGRFTI SRDNSKNRLY LQMNSLRAED TAVYYCAKIR NLHWDVGRQ- FDYWGQGTLV TVSS

BMS2h-745-18 (SEQ ID NO: 415)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYHCAKIR NLHWDVGRQ- FDYWGQGTLV TVSS

BMS2h-745-19 (SEQ ID NO: 416)
EVQLLESGGG LVQPEGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-2 (SEQ ID NO: 417)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED SAVYYCAKIR NLHWDVGRQ- FVYWGQGTLV TVSS

BMS2h-745-3 (SEQ ID NO: 418)
EVQLLESGGG LVEPGGSLRL SCAASGFTFD NTEMAWVRQA PGKGLEWVSG ITEDGNRTYY
ADSVKGRFTI SRDNSKNTLY LQMSSLRAED TAVYYCAKIR NLHWDVGRQ- FDYWGQGTLV TVSS

BMS2h-745-4 (SEQ ID NO: 419)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED TAVYHCAKIR NLHWDVGRQ- FDYWGQGTLV TVSS

BMS2h-745-5 (SEQ ID NO: 420)
EVQLLESGGG LVQPGGSLRL SCAASGFTFD NTEMAWVRQA PGKGLEWVSG ITEDGNRTYY
ADSVKGRFII SRDNSKNTLN LQMNSLRAED TAVYYCAKIR NLHWDVGRQ- FDYWGQGTLV TVSS

BMS2h-745-6 (SEQ ID NO: 421)
EVQLLESGGG LVQPGGSLRL SCAASGFTFD NTEMAWIRQA PGRGLEWVSG VTEDGNRTYY
ADSVKGRFTI SRDNSKNTLY LQMNSLRAED TAVYYCAKIR NLHWDVGRQ- FDYWGQGTLV TVSS

BMS2h-745-7 (SEQ ID NO: 422)
EVQLLESGGG LVQPGGSLRL SCEASGFTFD NTEMAWIRQA PGKGLEWVSG IIEDGNRTYY
ADSVKGRFTI SRDNTKNTLY LQMNSLRAED TAVYYCAKIR NLHWDVGRQ- FDYWGQGTLV TVSS

TABLE 1-continued

Anti-human CD40L VH Domain Amino Acid Sequences

```
BMS2h-745-8 (SEQ ID NO: 423)
EVQLLESGGG LVQPGGSLRL SCAASGFTFD NTEMAWIRQA PGKGLEWVSG ITEDGDRTYY
ADSVKGRFTI SRDNSKSSLY LQMNSLRAED TAVYYCAKIR NLHWDVGRQ- FDYWGQGTLV TVSS

BMS2h-745-9 (SEQ ID NO: 424)
EVQLLESGGG SVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FVYWGQGTLV TVSS

BMS2h-746 (SEQ ID NO: 425)
EVQLLESGGG LVQPGGSLRL SCAASGFTFG SAEMGWVRQA PGKGLEWVSG ISRPGQVTYY
ADSVKGRFTI SRDNSKNTLY LQMNSLRAED TAVYYCAKIR NLHWDVGRQ- FDYWGQGTLV TVSS

BMS2h-747 (SEQ ID NO: 426)
EVQLLESGGG LVQPGGSLRL SCAASGFTFD DGTMGWARQA PGKGLEWVSL ILPSGSRTYY
ADSVKGRFTI SRDNSKNTLY LQMNSLRAED TAVYYCAKHS LTNRP----- FDYWGQGTLV TVSS

BMS2h-748 (SEQ ID NO: 427)
EVQLLESGGG LVQPGGSLRL SCAASGFTFS KYDMRWARQA PGKGLEWVSD IDAVGTRTYY
ADSVKGRFTI SRDNSKNTLY LQMNSLRAED TAVYYCAIPG GT-------- FDYWGQGTLV TVSS

BMS2h-749 (SEQ ID NO: 428)
EVQLLESGGG LVQPGGSLRL SCAASGFTFE MYGMMWARQA PGKGLEWVSS IEGAGHATYY
ADSVKGRFTI SRDNSKNTLY LQMNSLRAED TAVYYCAIVL GM-------- FDYWGQGTLV TVSS

BMS2h-75 (SEQ ID NO: 429)
EVQLLESGGG LVQPGGSLRL SCAASGFTFL QYPMGWVRQA PGKGLEWVST ISPVGLTTYY
ADSVKGRFTI SRDNSKNTLY LQMNSLRAED TAVYYCAKLF EGSRIQRDVG FDYWGQGTLV TVSS

BMS2h-750 (SEQ ID NO: 430)
EVQLLESGGG LVQPGGSLRL SCAASGFTFE KYQMGWARQA PGKGLEWVSS IRGSGLVTYY
ADSVKGRFTI SRDNSKNTLY LQMNSLRAED TAVYYCAKVH TTLHTEVIG- FDYWGQGTLV TVSS

BMS2h-751 (SEQ ID NO: 431)
EVQLLESGGG LVQPGGSLRL SCAASGFTFS QYTMYWARQA PGKGLEWVSE ISHSGSNTYY
ADSVKGRFTI SRDNSKNTLY LQMNSLRAED TAVYYCAISG LH-------- FDYWGQGTLV TVSS

BMS2h-752 (SEQ ID NO: 432)
EVQLLESGGG LVQPGGSLRL SCAASGFTFS DYAMAWVRQA PGKGLEWVSR IGVEGGDTYY
ADSVKGRFTI SRDNSKNTLY LQMNSLRAED TAVYYCAKLL RLYRLG---- FDYWGQGTLV TVSS

BMS2h-753 (SEQ ID NO: 433)
EVQLLESGGG LVQPGGSLRL SCAASGFTFA KYDMTWVRQA PGKGLEWVSK INSDGGLTYY
ADSVKGRFTI SRDNSKNTLY LQMNSLRAED TAVYYCAKGL HGRGFVI--- FDYWGQGTLV TVSS

BMS2h-754 (SEQ ID NO: 434)
EVQLLESGGG LVQPGGSLRL SCAASGFTFS RYDMVWVRQA PGKGLEWVSR INSMGLATYY
ADSVKGRFTI SRDNSKNTLY LQMNSLRAED TAVYYCAKDY SVAPHGYPLG FDYWGQGTLV TVSS

BMS2h-755 (SEQ ID NO: 435)
EVQLLESGGG LVQPGGSLRL SCAASGFTFK DYSMMWVRQA PGKGLEWVST ITDNGTSTYY
ADSVKGRFTI SRDNSKNTLY LQMNSLRAED TAVYYCAKHM SLATYLQF-FDYWGQGTLV TVSS

BMS2h-756 (SEQ ID NO: 436)
EVQLLESGGG LVQPGGSLRL SCAASGFTFM EYDMLWVRQA PGKALEWVSR ISSDGLWTYY
ADSVKGRFTI SRDNSKNTLY LQMNSLRAED TAVYYCAKGV SALAPFDIG- FDYWGQGTLV TVSS

BMS2h-757 (SEQ ID NO: 437)
EVQLLESGGG LVQPGGSLRL SCAASGFTFK EYNMAWVRQA PGKGLEWVSS INFAGRTTYY
ADSVKGRFTI SRDNSKNTLY LQMNSLRAED TAVYYCAKLS LPLDIFS--- FDYWGQGTLV TVSS

BMS2h-758 (SEQ ID NO: 438)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FDYWGQGTLV TVSS

BMS2h-758-1 (SEQ ID NO: 439)
EVQLLESGGG LVQPGGSLRL SCAASGFTFG DYGMNWVRQA PGKGLEWVSH ISSNGRFTYY
ADSVKGRFTI SRDNSKNMLY LRMNSLRAED TAVYYCAETS GY-------- YEYWGQGTLV TVSS

BMS2h-758-2 (SEQ ID NO: 440)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-3 (SEQ ID NO: 441)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS SY-------- FEYWGQGTLV TVSS
```

TABLE 1-continued

Anti-human CD40L VH Domain Amino Acid Sequences

```
BMS2h-758-4 (SEQ ID NO: 442)
EVQLLESGGG LVQPGGSLRL SCAASGFTFG DYGMNWVRQA PGKGLEWVSH ISSNGRFTYY
ADSVKGRFTI SRDNSKNTLF LQMNSLRAED TAVYYCAETS GY-------- YEYWGHGTLV TVSS

BMS2h-758-5 (SEQ ID NO: 443)
EVQLLESGGG LVQPGGSLRL SCAASGFAFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-6 (SEQ ID NO: 444)
EVQLLESGGG LVQPGGSLRL SCAASGFTFG DYGMNWVRQA PGKGLEWVSH ISSNGRFIYY
ADSVKGRFTI SRDNSKNTLY LQMNSLRAED TAVYYCAETS GY-------- FEYWGQGTLV TVSS

BMS2h-759 (SEQ ID NO: 445)
EVQLLESGGG LVQPGGSLRL SCAASGFTFR EYVMGWVRQA PGKGLEWVST INGLGNVTYY
ADSVKGRFTI SRDNTKNTLY LQMNSLRAEE TAVYYCAIQL PN-------- FDYWGQGTLV TVSS

BMS2h-760 (SEQ ID NO: 446)
EVQLLESGGG LVQPGGSLRL SCAASGFTFG NDGMWWVRQA PGKGLEWVSF INVDGRETYY
ADSVKGRFTI SRDNSKNTLY LQMNSLRAED TAVYYCAEWS PGRVQ----- FDYWGQGTLV TVSS

BMS2h-761 (SEQ ID NO: 447)
EVQLLESGGG LVQPGGSLRL SCAASGFTFG GWDMAWVRQA PGKGLEWVSS IAHEGGETYY
ADSVKGRFTI SRDNSKNTLY LQMNSLRAED TAVYYCAKYV PGSPL----- FDYWGQRTLV TVSS

BMS2h-762 (SEQ ID NO: 448)
EVQLLESGGG LVQPGGSLRL SCAASGFTFD QGWMYWVRQA PGKGLEWVSG IGSNGPRTSY
ADSVKGRFTI SRDNSKNTLY LQMNSLRAED TAVYYCAKSG EY-------- FDYWGQGTLV TVSS

BMS2h-763 (SEQ ID NO: 449)
EVQLLESGGG LVQPGGSLRL SCAASGFTFR QSDMWVRQA PGKGLEWVSV IGNNGEFTYY
ADSVKGRFTI SRDNSKNTLY LQMNSLRAED TAVYYCAKDN WLL------- FDYWGQGTLV TVSS

BMS2h-764 (SEQ ID NO: 450)
EVQLLESGGG LVQPGGSLRL SCAASGFTFD LSTMYWVRQA PGKGLEWVST IGGDGSHTYY
ADSVKGRFTI SRDNSKNTLY LQMNSLRAED TAVYYCAEGT QY-------- FDYWGQGTLV TVSS

BMS2h-765 (SEQ ID NO: 451)
EVQLLESGGG LVQPGGSLRL SCAASGFTFS AYTMEWVRQA PGKGLEWVSS IGVTGYDTYY
ADSVKGRFTI SRDNSKNTLY LQMNSLRAED TAVYYCAKGG QG-------- FDYWGQGTLV TVSS

BMS2h-766 (SEQ ID NO: 452)
EVQLLESGGG LVQPGGSLRL SCAASGFTFG DYGMSWVRQA PGKGLEWVSY IDPLGRLTYY
ADSVKGRFTI SRDNSKNTLY LQMNSLRAED TAVYYCAEDL SSLQYGVSPN FDYWGQGTLV TVSS

BMS2h-767 (SEQ ID NO: 453)
EVQLLESGGG LVQPGGSLRL SCAASGFTFF HYSMSWVRQA PGKGLEWVSS IGPVGRETYY
ADSVKGRFTI SRDNSKNTLY LQMNSLRAED TAVYYCAKMI QSPLFKD--- FDYWGQGTLV TVSS

BMS2h-768 (SEQ ID NO: 454)
EVQLLESGGG LVQPGGSLRL SCAASGFTFE WYDMYWVRQA PGKGLEWVSR IDSGGNQTYY
ADSVKGRFTI SRDNSKNTLY LQMNSLRAED TAVYYCAEAS LWKWRL---- FDYWGQGTLV TVSS

BMS2h-77 (SEQ ID NO: 455)
EVQLLESGGG LVQPGGSLRL SCAASGFTFE EYGMAWVRQA PGKGLEWVST ISPLGISTYY
ADSVKGRFTI SRDNSKNTLY LQMNSLRAED TAVYYCAKHA TSQESLRS-FDYWGQGTLV TVSS

BMS2h-770 (SEQ ID NO: 456)
EVQLLESGGG LVQPGGSLRL SCAASGFTFS KYEMMWVRQA PGKGLEWVSA ISGSGGSTYY
ADSVKGRFTI SRDNSKNTLY LQMNSLRAED TAVYYCAKGP LPDAFWTRG- FDYWGQGTLV TVSS

BMS2h-771 (SEQ ID NO: 457)
EVQLLESGGG LVQPGGSLRL SCAASGFTFG TYSMAWVRQA PGKGLEWVST IDRHGLATYY
ADSVKGRFTI SRDNSKNTLY LQMNSLRAED TAVYYCAKTP GSSWQTV--- FGYWGQGTLV TVSS

BMS2h-772 (SEQ ID NO: 458)
EVQLLESGGG LVQPGGSLRL SCAASGFTFE SYPMGWVRQA PGKGLEWVSS IDHHGHSTYY
ADSAKGRFTI SRDNSKNTLY LQMNSLRAED TAVYYCAKLL RVSMIFG--- FDYWGQGTLV TVSS

BMS2h-773 (SEQ ID NO: 459)
EVQLLESGGG LVQPGGSLRL SCAASGFTFV QYGMSWVRQA PGKGLEWVSW ISSSGTYTYY
ADSVKGRFTI SRDNSKNTLY LQMNSLRAED TAVYYCAETS RM-------- FDYWGQGTLV TVSS

BMS2h-774 (SEQ ID NO: 460)
EVQLLESGGG LVQPGGSLRL SCAASGFTFR EYDMGWVRQA PGKGLEWVSL ISPPGRTTYY
ADSVKGRFTI SRDNSKNTLY LQMNSLRAED TAVYYCAKVV ILGYTNR--- FDYWGQGTLV TVSS
```

TABLE 1-continued

Anti-human CD40L VH Domain Amino Acid Sequences

```
BMS2h-775 (SEQ ID NO: 461)
EVQLLESGGG LVQPGGSLRL SCAASGFTFP NYGMLWVRQA PGKGLEWVSS INSSGMETYY
ADSVKGRFTI SRDNSKNTLY LQMNSLRAED TAVYYCAKFF RLNDHNSVFG FDYWGQGTLV TVSS

BMS2h-776 (SEQ ID NO: 462)
EVQLLESGGG LVQPGGSLRL SCAASGFTFK DYKMMWIRQA PGKGLEWVSS IVGSGSMTYY
ADSVKGRFTI SRDNSKNTLY LQMNSLRAED TAVYYCAKGP GY-------- FDYWGQGTLV TVSS

BMS2h-777 (SEQ ID NO: 463)
EVQLLESGGG LVQPGGSLRL SCAASGFTFH NYAMGWVRRA PGKGLEWVSS IDEHGTITYY
ADSVKGRFTI SRDNSKNTLY LQMNSLRAED TAVYYCAKDS LDRVWI---- FDYWGQGTLV TVSS

BMS2h-778 (SEQ ID NO: 464)
EVQLLESGGG LVQPGGSLRL SCAASGFTFA DYPMTWVRQA PGKGLEWVSS IYSAGSPTYY
ADSVKGRFTI SRDNSKNTLY LQMNSLRAED TAVYYCAKLY HREPILFG-FDYWGQGTLV TVSS

BMS2h-78 (SEQ ID NO: 465)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG HR-------- FDYWGQGTLV TVSS

BMS2h-780 (SEQ ID NO: 466)
EVQLLESGGG LVQPGGSLRL SCAASGFTFG SYTMMWVRQA PGKGLEWVSE IDRTGERTYY
ADSVKGRFTI SRDNSKNTLY LQMNSLRAED TAVYYCAEPG FASLP----- FDYWGQGTLV TVSS

BMS2h-781 (SEQ ID NO: 467)
EVQLLESGGG LVQPGGSLRL SCAASGFTFT DYTMYWVRQA PGKGLEWVSK ISPSGRSTYY
ADSVKGRFTI SRDNSKNTLY LQMNSLRAED TAVYYCAKDP FG-------- FDYWGQGTLV TVSS

BMS2h-782 (SEQ ID NO: 468)
EVQLLESGGG LVQPGGSLRL SCAASGFTFD DAEMFWVRQA PGKGLEWVSS IDARGLTTYY
ADPVKGRFTI SRDNSKNTLY LQMNSLRAED TAVYYCAEAT SAMYP----- FDYWGQGTLV TVSS

BMS2h-783 (SEQ ID NO: 469)
EVQLLESGGG LVQPGGSLRL SCAASGFTFR DYDMGWVRQA PGKGLEWVST ISPLGHFTYY
ADSVKGRFTI SRDNSKNTLY LQMNSLRAED TAVYYCAKSF FHEYTEG--- FDYWGQGTLV TVSS

BMS2h-784 (SEQ ID NO: 470)
EVQLLESGGG LVQPGGSLRL SCAASGFTFD RAGMGWVRQA PGKGLEWVSL IGRGGDITYY
ADSVKGRFTI SRDNSKNTLY LQMNSLRAED TAVYYCAKIR NLHWDVGRQ- FDYWGQGTLV TVSS

BMS2h-80 (SEQ ID NO: 471)
EVQLLESGGG LVQPGGSLRL SCAASGFTFG RYQMAWVRQA PGKGLEWVSS ISSDGGGTYY
ADSVKGRFTI SRDNSKNTLY LQMNSLRAED TAVYYCAKPS RR-------- FDYWGQGTLV TVSS

BMS2h-81 (SEQ ID NO: 472)
EVQLLESGGG LVQPGGFLRL SCAASGFTFE LYPMAWVRQA PGKGLEWVSS ISPVGFLTYY
ADSVKGRFTI SRDNSKNTLY LQMNSLRAED TAVYYCAKGH EGSYTPRSA- FDYWGQGTLV TVSS

BMS2h-82 (SEQ ID NO: 473)
EVQLLESGGG LVQPGGSLRL SCAASGFTFV AYPMAWVRQA PGKGLEWVST IAPLGGNTYY
ADSVKGRFTI SRDNSKNTLY LQMNSLRAED TAVYYCAKRP EGLQIDSQN- FDYWGQGTLV TVSS

BMS2h-83 (SEQ ID NO: 474)
EVQLLESGGG LVQPGGSLRL SCAASGFTFA LYQMAWVRQA PGKGLEWVSS IDSSGSDTYY
ADSVKGRFTI SRDNSKNTLY LQMNSLRAED TAVYYCAKPE RD-------- FDYWGQGTLV TVSS

BMS2h-84 (SEQ ID NO: 475)
EVQLLESGGG LVQPGGSLRL SCAASGFTFR QYQMAWARQA PGKGLEWVST IASDGVSTYY
ADSVKGRFTI SRDNSKNTLY LQMNSLRAED TAVYYCAKVG RD-------- FDYWGQGTLV TVSS

BMS2h-85 (SEQ ID NO: 476)
EVQLLESGGG LVQPGGSLRL SCAASGFTFE QYDMRWVRQA PGKGLEWVSW IDEAGHETYY
ADSVKGRFTI SRDNSRNTLY LQMNSLRAED TAVYYCAKGM DG-------- FDYWGQGTLV TVSS

BMS2h-92 (SEQ ID NO: 477)
EVQLLESGGG LVQPGGSLRL SCAASGFTFV DYPMGWVRQA PGKGLEWVST ISTGGFSTYY
ADSVKGRFTI SRDNSKNTLY LQMNSLRAED TAVYYCAKAR YYYLSQIKN- FDYWGQGTLV TVSS

BMS2h-93 (SEQ ID NO: 478)
EVQLLESGGG LVQPGGSLRL SCAASGFTFD IYGMTWVRQA PGKGLEWVSS ISPLGLVTYY
ADPVKGRFTI SRDNSKNTLY LQMNSLRAED TAVYYCAKLK EHGDVP---- FDYWGQGTLV TVSS

BMS2h-94 (SEQ ID NO: 479)
EVQLLESGGG LVQPGGSLRL SCAASGFTFE LYPMSWVRQA PGKGLEWVST ISPTGLLTYY
ADSVKGRFTI SRDNSKNTLY LQMNSLRAED TAVYYCAKFK RSGKTDDTN- FDYWGQGTLV TVSS
```

TABLE 1-continued

Anti-human CD40L VH Domain Amino Acid Sequences

BMS2h-95 (SEQ ID NO: 480)
EVQLLESGGG LVQPGGSLRL SCAASGFTFR EYDMLWVRQA PGKGLEWVST IVGDGNGTYY
ADSVKGRFTI SRDNSKNTLY LQMNSLRAED TAVYYCAKQD RQ-------- FDYWGQGTLV TVSS

BMS2h-97 (SEQ ID NO: 481)
EVQLLESGGG LVQPGGSLRL SCAASGFTFE EYGMSWVRQA PGKGLEWVST ISPIGVTTYY
ADSVKGRFTI SRDNSKNTLY LQMNSLRAED TAVYYCAKNA YDRKSN---- FDYWGQGTLV TVSS

BMS2h-98 (SEQ ID NO: 482)
EVQLLESGGG LVQPGGSLRL SCAASGFTFD RYVMVWVRQA PGKDLEWVSG ITPSGRRTYY
ADSVKGRFTI SRDNSKDTLY LQMNSLRAED TAVYYCAKVL GRHFDPLLPS FDYWGQGTLV TVSS

BMS2h-99 (SEQ ID NO: 483)
EVQLLESGGG LVQPGGSLRL SCAASGFTFE DYAMSWVRQA PGKGLEWVST ITPGGFWTYY
ADSVKGRFTI SRDNSKNTLY LQMNSLRAED TAVYYCAKTS SGELQLVED- FDYWGQGTLV TVSS

TABLE 2

Human Anti-CD40L VH Domain Encoding Nucleotide Sequences

BMS2h-10 (SEQ ID NO: 484)
GAGGTGCAGCTGTTGGAGTCTGGGGGAGGCTTAGTACAGCCTGGGGGGTCCCTGCGTCTC
TCCTGTGCAGCCTCCGGATTCACCTTTATTGCTTATGATATGAGTTGGGTCCGCCAGGCT
CCAGGGAAGGGTCTGGAGTGGGTCTCATGGATTGATGAGTGGGGTCTGCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAAGACG
CCTGAGGAGTTTGACTACTGGGGTCAGGGAACCCTGGTCACCGTCTCGAGC

BMS2h-11 (SEQ ID NO: 485)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGAGATGAGTTGGGTCCGCCAGGCT
CCAGGGAAGGGTCTAGAGTGGGTCTCAGGGATTGATGGTGAGGGTTCTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCGGGG
AGGAGTTTTGACTACTGGGGTCAGGGAACCCTGGTCACCGTCTCGAGC

BMS2h-111 (SEQ ID NO: 486)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCGTTATCCTATGACGTGGGTCCGCCAGGCT
CCAGGGAAGGGTCTAGAGTGGGTCTCAACGATTCATGGTTCTGGTAGTGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGCCG
TATACTAGTCGGCATAATAGTCTTGGGCATTTTGACTACTGGGGTCAGGGAACCCTGGTC
ACCGTCTCGAGC

BMS2h-112 (SEQ ID NO: 487)
GAGGTGCAGCTGTTGGAGTCTGGGGGAGGCTTGGTACAGCCTGGGGGGTCCCTGCGTCTC
TCCTGTGCAGCCTCCGGATTCACCTTTATGGATTATCCTATGGGTGGGTCCGCCAGGCT
CCAGGGAAGGGTCTAGAGTGGGTCTCATCTATTGGGCCTGTTGGTATGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATATGGG
GGGACTAGTGGTAGGCATAATACTAAGTTTGACTACTGGGGTCAGGGAACCCTGGTCACC
GTCTCGAGC

BMS2h-113 (SEQ ID NO: 488)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGAGTATCCTATGAGTTGGGTCCGCCAGGCT
CCAGGGAAGGGTCTAGAGTGGGTCTCAGTTATTTCTCCTCTTGGTTTTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGACT
GGTGGGAGTGGTATTTTGAATTCTTCTTTTGACTACTGGGGTCAGGGAACCCTGGTCACC
GTCTCGAGC

BMS2h-114 (SEQ ID NO: 489)
GAGGTGCAGCTGTTGGAGTCTGGGGGAGGCTTGGTACAGCCTGGGGGGTCCCTGCGTCTC
TCCTGTGCAGCCTCCGGATTTAGGGTTAGCAATTACGATTTGACCTGGGTCCGCCAGGCT
CCAGGGAAGGGTCTAGAGTGGGTATCAACCATTAGTGCCACAAACGGTAGCACATACTAC
GCAGACTCCGTGAAGGGCCGGTTCACCATCTCCCGTGACAATTCCAAGAACACGCTGTAT
CTGCAAATGAACAGCCTGCGTGCCGAGGACACCGCGGTATATTATTGCGCGGCAGTGACG
TGGTGGTTGTTGCGTCATAACGACAACTTGGGGTTTTGGGGTCAGGGAACCCTGGTCACC
GTCTCGAGC

TABLE 2-continued

Human Anti-CD40L VH Domain Encoding Nucleotide Sequences

BMS2h-115 (SEQ ID NO: 490)
GAGGTGCAGCTGTTGGAGTCTGGGGGAGGCTTGGTACAGCCTGGGGGGTCCCTGCGTCTC
TCCTGTGCAGCCTCCGGATTTAGCATTAGCTATAAGAATATGGCCTGGGTCCGCCAGGCT
CCAGGGAAGGGTCTAGAGTGGGTATCAGCCATTAAGGCGGCAAACGGTAGCACATACTAC
GCAGACTCCGTGAAGGGCCGGTTCACCATCTCCCGTGACAATTCCAAGAACACGCTGTAT
CTGCAAATGAACAGCCTGCGTGCCGAGGACACCGCGGTATATTATTGCGCGACAGGGAGT
CAGAAGAAGCGGACCTACACGTTCGACTTTTGGGGTCAGGGAACCCTGGTCACCGTCTCG
AGC

BMS2h-12 (SEQ ID NO: 491)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGTTGTATGAGATGGCGTGGGTCCGCCAGGCT
CCAGGGAAGGGTCTAGAGTGGGTCTCAGGGATTGATATTTTGGGTTCGAGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGATCTG
TCGTGGCAGGGTTTTGACTACTGGGGTCAGGGAACCCTGGTCACCGTCTCGAGC

BMS2h-120 (SEQ ID NO: 492)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGTCTTATACGATGGGTTGGGTCCGCCAGGCT
CCAGGGAAGGGTCTAGAGTGGGTCTCATCTATTAATCCTATGGGTTATCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACATGGG
GTGGGGAAGGGTACTAAGCCGCATAATTTTGACTACTGGGGTCAGGGAACCCTGGTCACC
GTCTCGAGC

BMS2h-121 (SEQ ID NO: 493)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCTGTATAGGATGTCTTGGGTCCGCCAGGCT
CCAGGGAAGGGTCTAGAGTGGGTCTCAGAGATTAGTGGTAGTGGTTTTCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTCTG
CATGATAAGACTCAGCATCATCAGGAGTTTGACTACTGGGGTCAGGGAACCCTGGTCACC
GTCTCGAGC

BMS2h-123 (SEQ ID NO: 494)
GAGGTGCAGCTGTTGGAGTCTGGGGGAGGCTTGGTACAGCCTGGGGGGTCCCTGCGTCTC
TCCTGTGCAGCCTCCGGATTCACCTTTATTGAGTATCCTATGCGGTGGGTCCGCCAGGCT
CCAGGGAAGGGTCTAGAGTGGGTCTCACTTATTTCTCCGTCTGGTGTGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGAT
GAGTCTAGTACTTTTGACTACTGGGGTCAGGGAACCCTGGTCACCGTCTCGAGC

BMS2h-124 (SEQ ID NO: 495)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGCGGTATGATATGGATTGGGTCCGCCAGGCT
CCAGGGAAGGGTCTAGAGTGGGTCTCAACGATTGGGAGTTCAGGGTTATCCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAAGGATG
CCTGGTTATTTTCCTGGGTTTGCTCGGCAGTTTGACTACTGGGGTCAGGGAACCCTGGTC
ACCGTCTCGAGC

BMS2h-125 (SEQ ID NO: 496)
GAGGTGCAGCTGTTGGAGTCTGGGGGAGGCTTGGTACAGCCTGGGGGGTCCCTGCGTCTC
TCCTGTGCAGCCTCCGGATTCACCTTTTGGCGGTATGCTATGGGGTCCGCCAGGCT
CCAGGGAAGGGTCTAGAGTGGGTCTCAACGATTAATGATGAGGGTCGGGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAAGCGG
GTGTCTAGTTCTGTGAATGCTCCGTATGAGTTTGACTACTGGGGTCAGGGAACCCTGGTC
ACCGTCTCGAGC

BMS2h-126 (SEQ ID NO: 497)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGAATTATAGTATGAGTTGGGTCCGCCAGGCC
CCAGGGAAGGGTCTAGAGTGGGTCTCATCGATTGATCGTCTTGGTACGCATACATACTAC
GCAGACTCCGTGAAGGGCCGGTTCACCATCTCCCGCGACAATTCCAAGAATACGCTGTAT
CTGCAAATGAACAGCCTGCGTGCCGAGGATACCGCGGTATATTACTGTGCGAAAGTGCTG
GCTGATCTTATTGCTGGGCATGCGGAGTTTGACTACTGGGGTCAGGGAACCCTGGTCACC
GTCTCGAGC

BMS2h-127 (SEQ ID NO: 498)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGTCGTATGATATGGCGTGGGTCCGCCAGGCT
CCAGGGAAGGGTCTAGAGTGGGTCTCAGGGATTTCGAGGTCTGGTTCTATGACATACTAC
GCAGACTCCGTGAAGGGCCGGTTCACCATCTCCCGCGACAATTCCAAGAACACGCTGTAT
TTGCAAATGAACAGCCTGCGTGCCGAGGACACCGCGGTATATTACTGTGCGAAAGGTGTT

TABLE 2-continued

Human Anti-CD40L VH Domain Encoding Nucleotide Sequences

GATGCGCATGTTTATTATATGGAGCCTTTTTTTGACTACTGGGGTCAGGGAACCCTGGTC
ACCGTCTCGAGC

BMS2h-128 (SEQ ID NO: 499)
GAGGTGCAGCTGTTGGAGTCTGGGGGAGGCTTGGTACAGCCTGGGGGTCCCTGCGTCTC
TCCTGTGCAGCCTCCGGATTCACCTTTGAGAGGTATCAGATGGCGTGGTCCGCCAGGCT
CCAGGGAAGGGTCTAGAGTGGGTCTCAACGATTAGTTCTGATGGTGGGGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGT
ACTGTTTTTGACTACTGGGGTCAGGGAACCCTGGTCACCGTCTCGAGC

BMS2h-129 (SEQ ID NO: 500)
GAGGTGCAGCTGTTGGAGTCTGGGGGAGGCTTGGTACAGCCTGGGGGTCCCTGCGTCTC
TCCTGTGCAGCCTCCGGATTCACATTTCCGAAGTATGAGATGGCGTGGGTCCGCCAGGCT
CCAGGGAAGGGTCTAGAGTGGGTCTCATCTATTGATGGTGGTAAGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCGGAT
CAGTTTTTTGACTACTGGGGTCAGGGAACCCTGGTCACCGTCTCGAGC

BMS2h-13 (SEQ ID NO: 501)
GAGGTGCAGCTGTTGGAGTCTGGGGGAGGCTTGGTACAGCCTGGGGGTCCCTGCGTCTC
TCCTGTGCAGCCTCCGGATTCACCTTTTCTTATTATTCGATGTATTGGGTCCGCCAGGCT
CCAGGGAAGGGTCTAGAGTGGGTCTCATCGATTTCGCCTTTTGGTTGGGGTACATACTAC
GCAGACTCCGTGAAGGGCCGGTTCACCATCTCCCGCGACAATTCCAAGGACACGCTGTAT
CTGCAAATGAACAGCCTGCGTGCCGAGGACACCGCGGTATATTACTGTGCGAAATATGGG
GAGACGAGTGGTCCGATTTCTGAGAATTTTGACTACTGGGGTCAGGGAACCCTGGTCACC
GTCTCGAGC

BMS2h-130 (SEQ ID NO: 502)
GAGGTGCAGCTGTTGGAGTCTGGGGGAGGCTTGGTACAGCCTGGGGGTCCCTGCGTCTC
TCCTGTACAGCCTCCGGATTCACCTTTGCGGGTTATCAGATGTCGTGGTCCGCCAGGCT
CCAGGGAAGGGTCTAGAGTGGGTCTCAAGTATTACTAATGAGGGTGTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
AAGTATTTTGACTACTGGGGTCAGGGAACCCTGGTCACCGTCTCGAGC

BMS2h-131 (SEQ ID NO: 503)
GAGGTGCAGCTGTTGGAGTCTGGGGGAGGCTTGGTACAGCCTGGGGGTCCCTGCGTCTC
TCCTGTGCAGCCTCCGGATTCACCTTTGGGGAGTATGAGATGGTGTGGGTCCGCCAGGCT
CCAGGGAAGGGTCTGGAGTGGGTCTCATCTATTACGTCGGATGGTCTGAGTACATACTAC
GCAGACTCCGTGAAGGGCCGGTTCACCATCTCCCGCGACAATTCCAAGAACACGCTGTAT
CTGCAAATGAACAGCCTGCGTGCTGAGGACACCGCGGTATATTACTGTGCGAAACCGGGT
ATTCGTTTTGACTACTGGGGTCAGGGAACCCTGGTCACCGTCTCGAGC

BMS2h-132 (SEQ ID NO: 504)
GAGGTGCAGCTGTTGGAGTCTGGGGGAGGCTTGGTACAGCCTGGGGGTCCCTGCGTCTC
TCCTGTGCAGCCTCCGGATTCACCTTTGCTGATTATGATATGGCTTGGGTCCGCCAGGCT
CCAGGGAAGGGTCTAGAGTGGGTCTCAGGTATTGTTGATGATGGTCTTATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGAT
GTTGCTTTTGACTACTGGGGTCAGGGGACCCTGGTCACCGTCTCGAAC

BMS2h-133 (SEQ ID NO: 505)
GAGGTGCAGCTGTTGGAGTCTGGGGGAGGCTTGGTACAGCCTGGGGGTCCCTGCGTCTC
TCCTGTGCAGCCTCCGGATTCACCTTTATTGGTTATGCTATGGCGTGGGTCCGCCAGGCT
CCAGGGAAGGGTCTAGAGTGGGTCTCAAGTATTGGTCCTTTGGTCGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGCCT
GCTGGTACGAGTAGTCATAGTGTGGATTTTGACTACTGGGGTCAGGGAACCCTGGTCACC
GTCTCGAGC

BMS2h-134 (SEQ ID NO: 506)
GAGGTGCAGCTGTTGGAGTCTGGGGGAGGCTTGGTACAGCCTGGGGGTCCCTGCGTCTC
TCCTGTGCAGCCTCCGGATTCACCTTTGCGGATTATGAGATGACTTGGGTCCGCCAGGCT
CCAGGGAAGGGTCTAGAGTGGGTCTCATCTATTACTAGTGATGGTGTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGTCG
GTTCAGTTTGACTACTGGGGTCAGGGAACCCTGGTCACCGTCTCGAGC

BMS2h-135 (SEQ ID NO: 507)
GAGGTGCAGCTGTTGGAGTCTGGGGGAGGCTTGGTACAGCCTGGGGGTCCCTGCGTCTC
TCCTGTGCAGCCTCCGGATTCACCTTTCGTAGGTATGTTATGGGGTGGGTCCGCCAGGCT
CCAGGGAAGGGTCTAGAGTGGGTCTCATGGATTGAGGCTGATGGTCGTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGCTT
ACGGATCAGCATGTTATTGAGTTTGACTACTGGGGTCAGGGAACCCTGGTCACCGTCTCG
AGC

TABLE 2-continued

Human Anti-CD40L VH Domain Encoding Nucleotide Sequences

BMS2h-136 (SEQ ID NO: 508)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGTTATCGTATGGGGTGGGTCCGCCAGGCT
CCAGGGAAGGGTCTAGAGTGGGTCTCATCGATTGCTCCGGATGGTAATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTTGG
GGGGATGCAGTTTGACTACTGGGGTCAGGGAACCCTGGTCACCGTCTCGAGC

BMS2h-137 (SEQ ID NO: 509)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTCGTATCCGATGGGTTGGGTCCGCCAGGCT
CCAGGGAAGGGTCTAGAGTGGGTCTCAAGTATTGGTCCTATTGGTTTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAATGAAG
TCGCCTTATAAGCCGCAGTTTGACTACTGGGGTCAGGGAACCCTGGTCACCGTCTCGAGC

BMS2h-138 (SEQ ID NO: 510)
GAGGTGCAGCTGTTGGAGTCTGGGGGAGGCTTGGTACAGCCTGGGGGGTCCCTGCGTCTC
TCCTGTGCAGCCTCCGGATTCACCTTTTTGGCTTATTGGATGGTTTGGGTCCGCCAGGCT
CCAGGGAAGGGTCTAGAGTGGGTCTCATCTATTTCTCCGTCGGGTACGCATACATACTAC
GCAGACTCCGTGAAGGGCCGGTTCACCATCTCCCGCGACAATTCCAAGAACACGCTGTAT
CTGCAAATGAACAGCCTGCGTGTCGAGGACACCGCGGTATATTACTGTGCGAAATATACT
GAGCCGGGGTTGGGTTCTTTTGACTACTGGGGTCAGGGAACCCTGGTCACCGTCTCGAGC

BMS2h-139 (SEQ ID NO: 511)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGAATTATGAGATGGGTTCCGCCAGGCT
CCAGGGAAGGGTCTAGAGTGGGTCTCAGTGATTTCTGAGGTGGGTTCTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTCAT
GATAGTTCGATTGGGTTTGACTACTGGGGTCAGGGAACCCTGGTCACCGTCTCGAGC

BMS2h-14 (SEQ ID NO: 512)
GAGGTGCAGCTGTTGGAGTCTGGGGGAGGCTTGGTACAGCCTGGGGGGTCCCTGCGTCTC
TCCTGTGCAGCCTCCGGATTCACCTTTTGGTCTTATGATATGACGTGGGTCCGCCAGGCT
CCAGGGAAGGGTCTAGAGTGGGTCTCATCTATTATGGCTTCGGGTGATGATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGGAT
CGGGATTTTGACTACTGGGGTCAGGGAACCCTGGTCACCGTCTCGAGC

BMS2h-15 (SEQ ID NO: 513)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGTTATGTCGTGGGTCCGCCAGGCT
CCAGGGAAGGGTCTGGAGTGGGTCTCAACTATTTCTCCTATTGGTCTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATTTCCT
TTGATTATTCTTCCTGATTTTGACTACTGGGGTCAGGGAACCCTGGTCACCGTCTCGAGC

BMS2h-16 (SEQ ID NO: 514)
GAGGTGCAGCTGTTGGAGTCTGGGGGAGGCCTGGTACAGCCTGGGGGGTCCCTGCGTCTC
TCCTGTGCAGCCTCCGGATTCACCTTTATGGAGTATGCGATGATTTGGGTCCGCCAGGCT
CCAGGGAAGGGTCTAGAGTGGGTCTCAATTATTTCTCCGCTTGGTTTGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATCAG
GATTCGTCTGATAGTCAGTATACGAATTTTGACTACTGGGGTCAGGGAACCCTGGTCACC
GTCTCGAGC

BMS2h-17 (SEQ ID NO: 515)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTATGGGATGGGGTGGGCCGCCAGGCT
CCAGGGAAGGGTCTAGAGTGGGTCTCAAGTATTGGTCCTCTGGGTCTTTGGACATACTAC
GCAGACTCCGCGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCCCG
CTTGAGGGTTTGATTACGAATTTTGACTACTGGGGTCAGGGAACCCTGGTCACCGTCTCG
AGC

BMS2h-176 (SEQ ID NO: 516)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGCGTATGAGATGGGTGGGTCCGCCAGGCT
CCAGGGAAGGGTCTAGAGTGGGTCTCAATTATTGATTGGGATGGTAATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGGG
GATAATGTTGGTATTTTTGACTACTGGGGTCAGGGAACCCTGGTCACCGTCTCGAGC

BMS2h-177 (SEQ ID NO: 517)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATTATATGGTGTGGGTCCGCCAGGCT
CCAGGGAAGGGTCTAGAGTGGGTCTCAGCGATTGATGAGTGGGGTTTTGCGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATTGG
GAGTTTACGTCTGATACGTCGCGTTTTGACTACTGGGGTCAGGGAACCCTGGTCACCGTC
TCGAGC

BMS2h-178 (SEQ ID NO: 518)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTTTGATATGGCTTGGGTCCGCCAGGCT
CCAGGGAAGGGTCTAGAGTGGGTCTCATCTATTAATGATCAGGGTTCTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGAT
CAGTTTTTTGACTACTGGGGTCAGGGAACCCTGGTCACCGTCTCGAGC

BMS2h-179 (SEQ ID NO: 519)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGCTTATGATATGATGTGGGTCCGCCAGGCT
CCAGGGAAGGGTCTAGAGTGGGTCTCACGGATTAGTCCTCAGGGTCAGCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
GGGCAGTCGCGGATTCCTATGAGGTTTGACTACTGGGGTCAGGGAACCCTGGTCACCGTC
TCGAGC

BMS2h-18 (SEQ ID NO: 520)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTGAGTATGATATGACGTGGGTCCGCCAGGCT
CCAGGGAAGGGTCTGGAGTGGGTCTCATATATTAGTTCTGATGGTTATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGCAT
GGGAGTCCGCGGGAGTTTGACTACTGGGGTCAGGGAACCCTGGTCACCGTCTCGAGC

BMS2h-180 (SEQ ID NO: 521)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGATTATGAGATGGGGTGGGTCCGCCAGGCT
CCAGGGAAGGGTCTAGAGTGGGTCTCAACGATTACTAGTTTGGGTGAGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
CGTATTTTTGACTACTGGGGTCAGGGAACCCTGGTCACCGTCTCGAGC

BMS2h-181 (SEQ ID NO: 522)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTTTTATCCTATGATGTGGGTCCGCCAGGCT
CCAGGGAAGGGTCTAGAGTGGGTCTCATGGATTGATGCTACGGGTACGAGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGGTAAT
TATGGGAGTTCGTATACTATGGGGGTTTTTGACTACTGGGGTCAGGGAACCCTGGTCACC
GTCTCGAGC

BMS2h-182 (SEQ ID NO: 523)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGAGTATCCGATGTATTGGGTCCGCCAGGCT
CCAGGGAAGGGTCTAGAGTGGGTCTCATCGATTGGTCCTTCTGGTCCGAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCTCCG
TATTTTGATGTTATTCCTAGTTATTTTGACTACTGGGGTCAGGGAACCCTGGTCACCGTC
TCGAGC

BMS2h-183 (SEQ ID NO: 524)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGGATTACGGTATGGGTTGGGTCCGCCAGGCT
CCAGGGAAGGGTCTAGAGTGGGTCTCATCTATTCAGTCGTCGGGTTTGCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACGGGCT
AATTCTCGTAGGGGTTTTGACTACTGGGGTCAGGGAACCCTGGTCACCGTCTCGAGC

BMS2h-184 (SEQ ID NO: 525)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGATTATGAGATGATGTGGGTCCGCCAGGCT
CCAGGGAAGGGTCTAGAGTGGGTCTCATCTATTACTAGTCATGGTGGGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGAT
AAGGATTTTGACTACTGGGGTCAGGGAACCCTGGTCACCGTCTCGAGC

BMS2h-185 (SEQ ID NO: 526)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGCATTATCCGATGTCGTGGGTCCGCCAGGCT
CCAGGGAAGGGTCTAGAGTGGGTCTCATCGATTGGTAGGCTGGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACGTGCT

TABLE 2-continued

Human Anti-CD40L VH Domain Encoding Nucleotide Sequences

ACGCCTGTGCCGATTAAGGGTTTGTTTGACTACTGGGGTCAGGGAACCCTGGTCACCGTC
TCGAGC

BMS2h-186 (SEQ ID NO: 527)
GAGGTGCAGCTGTTGGAGTCTGGGGGAGGCTTGGTACAGCCTGGGGGGTCCCTGCGTCTC
TCCTGTGCAGCCTCCGGACTCACCTTTGGGAGGTATGAGATGGCGTGGGTCCGCCAGGCT
CCAGGGAAGGGTCTAGAGTGGGTCTCAAGTATTGATTCGGATGGTTGGGTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGCAACCGGAT
TCGTTGTTTGACTACTGGGGTCAGGGAACCCTGGTCACCGTCTCGAGC

BMS2h-187 (SEQ ID NO: 528)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTAGTTATTCTATGGTGTGGGTCCGCCAGGCT
CCAGGGAAGGGTCTAGAGTGGGTCTCAGGTATTAATCGGGGTGGTACTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTGG
AGGAGGGGGTTTGACTACTGGGGTCAGGGAACCCTGGTCACCGTCTCGAGC

BMS2h-188 (SEQ ID NO: 529)
GAGGTGCAGCTGTTGGAGTCTGGGGGAGGCTTGGTACAGCCTGGGGGGTCCCTGCGTCTC
TCCTGTGCAGCCTCCGGATTCACCTTTACGCGTTATAGGATGTCTTGGGTCCGCCAGGCT
CCAGGGAAGGGTCTGGAGTGGGTCTCAGGGATTTCGAGGGATGGTTATCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTATG
ACTGCGTCGTTTGACTACTGGGGTCAGGGAACCCTGGTCACCGTCTCGAGC

BMS2h-189 (SEQ ID NO: 530)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGATGTATCCGATGGGGTGGGTCCGCCAGGCT
CCAGGGAAGGGTCTAGAGTGGGTCTCAATGATTGAGCCGGCTGGTGATCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATCAG
GAGCAGCCTTGGTTTGACTACTGGGGTCAGGGAACCCTGGTCACCGTCTCGAGC

BMS2h-19 (SEQ ID NO: 531)
GAGGTGCAGCTGTTGGAGTCTGGGGGAGGCTTGGTACAGCCTGGGGGGTCCCTGCGTCTC
TCCTGTGCAGCCTCCGGATTCCCCTTTCCGCAGTATCAGATGCGTGGGTCCGCCAGGCT
CCAGGGAAGGGTCTAGAGTGGGTCTCAATGATTACTTCTGATGGTCTTGATACATATTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGAG
CCTCTTTTTGACTACTGGGGTCAGGGAACCCTGGTCACCGTCTCGAGC

BMS2h-190 (SEQ ID NO: 532)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTATGTATGATATGCATTGGGTCCGCCAGGCT
CCAGGGAAGGGTCTAGAGTGGGTCTCAACGATTTTGTCTGATGGTACGGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATGGG
GCTATGTTTGACTACTGGGGTCAGGGAACCCTGGTCACCGTCTCGAGC

BMS2h-191 (SEQ ID NO: 533)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTTGTATCCGATGACGTGGGTCCGCCAGGCT
CCAGGGAAGGGTCTAGAGTGGGTCTCATCTATTGATGCGGGGGGTCATGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGATTGG
TGGGATTATCTGTTTGACTACTGGGGTCAGGGAACCCTGGTCACCGTCTCGAGC

BMS2h-192 (SEQ ID NO: 534)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGCGGTATCCGATGAGTTGGGTCCGCCAGGCT
CCAGGGAAGGGTCTAGAGTGGGTCTCATCTATTAATCGTTCGGGTATGCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGGGCAT
CAGGCGCCGTTTGACTACTGGGGTCAGGGAACCCTGGTCACCGTCTCGAGC

BMS2h-193 (SEQ ID NO: 535)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGGGTATGCTATGTCTTGGGTCCGCCAGGCT
CCAGGGAAGGGTCTAGAGTGGGTCTCAACTATTAATGCGAATGGTATTCGGACATACTAC
GCCGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGGG
GTTTGGAGGTGGGGACTGGGCATAAGTTTGACTACTGGGGTCAGGGAACCCTGGTCACC
GTCTCGAGC

TABLE 2-continued

Human Anti-CD40L VH Domain Encoding Nucleotide Sequences

BMS2h-194 (SEQ ID NO: 536)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGCAGTATGATATGCGGTGGGTCCGCCAGGCT
CCAGGGAAGGGTCTAGAGTGGGTCTCAACGATTTCGCAGAATGGTACTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGAGG
ACTGGTAGGTATTTTGACTACTGGGGTCAGGGAACCCTGGTCACCGTCTCGAGC

BMS2h-195 (SEQ ID NO: 537)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGACTTATGATATGGGGTGGGTCCGCCAGGCT
CCAGGGAAGGGTCTAGAGTGGGTCTCAAGGATTAATTGGCAGGGTGATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGG
TTTGGTCATTATGTTGATGGTCTTGGGTTTGACTACTGGGGTCAGGGAACCCTGGTCACC
GTCTCGAGC

BMS2h-196 (SEQ ID NO: 538)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGGGTATGAGATGGCGTGGGTCCGCCAGGCT
CCAGGGAAGGGTCTAGAGTGGGTCTCATCTATTACTGATATGGGTGATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGG
ACTGCGTTTGACTACTGGGGTCCGGGAACCCTGGTCACCGTCTCGAGC

BMS2h-197 (SEQ ID NO: 539)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGAAGTATAAGATGTGGTGGGTCCGCCAGGCT
CCAGGGAAGGGTCTAGAGTGGGTCTCAAGTATTACTCCGAAGGGTCATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAAGGCCG
ATGACTCCGTTTGACTACTGGGGTCAGGGAACCCTGGTCACCGTCTCGAGC

BMS2h-198 (SEQ ID NO: 540)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCGGTATAATATGTCTTGGGTCCGCCAGGCT
CCAGGGAAGGGTCTAGAGTGGGTCTCATCTATTCGGCCGCGGGTGGGAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGCGG
CGGGAGGGGTATACTGGTTCTAAGTTTGACTACTGGGGTCAGGGAACCCTGGTCACCGTC
TCGAGC

BMS2h-199 (SEQ ID NO: 541)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGAGGTATGGTATGACTTGGGTCCGCCAGGCT
CCAGGGAAGGGTCTGGAGTGGGTCTCAAGTATTTGGCCGAGGGGTCAGAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGAAT
AGTCGGTATGTTTTTGACTACTGGGGTCAGGGAACCCTGGTCACCGTCTCGAGC

BMS2h-2 (SEQ ID NO: 542)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGATTATGAGATGATGTGGGTCCGCCAGGCT
CCAGGGAAGGGTCTAGAGTGGGTCTCAACTATTACTTCGGATGGTATTTCTACATACTAC
GCAGACTCCGTGAAGGGCCGGTTCACCATCTTCCGCGACAATTCCAAGAACACGCTGTAT
CTGCAAATGAACAGCCTGCGTGCCGAGGATACCGCGGTATATTACTGTGCGAAAAGTGGG
AGGTTTTTTGACTACTGGGGTCAGGGAACCCTGGTCACCGTCTCGAGC

BMS2h-20 (SEQ ID NO: 543)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGGTTATCAGATGGCTTGGGTCCGCCAGGCT
CCAGGGAAGGGTCTAGAGTGGGTCTCAGGTATTAGTTCGGAGGGTCTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGGGG
CGTAGGTTTGACTACTGGGGTCAGGGAACCCTGGTCACCGTCTCGAGC

BMS2h-200 (SEQ ID NO: 544)
GAGGTGCAGCTGTTGGAGTCTGGGGGAGGCTTGGTACAGCCTGGGGGGTCCCTGCGTCTC
TCCTGTGCAGCCTCCGGATTCACCTTTACTAATTATAGTATGGGTTGGGTCCGCCAGGCT
CCAGGGAAGGGTCTAGAGTGGGTCTCAACTATTCGTCCTAATGGTACTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACGGTCG
TCTGCGCATCTTCAGAGGTTTGACTACTGGGGTCAGGGAACCCTGGTCACCGTCTCGAGC

BMS2h-201 (SEQ ID NO: 545)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATTATTCGATGGGTTGGGTCCGCCAGGCT

TABLE 2-continued

Human Anti-CD40L VH Domain Encoding Nucleotide Sequences

CCAGGGAAGGGTCTAGAGTGGGTCTCATCGATTGGTCGTCATGGTGGGCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAAGGGG
AGTACTTATCCTAGGTTTGACTACTGGGGTCAGGGAACCCTGGTCACCGTCTCGAGC

BMS2h-202 (SEQ ID NO: 546)
GAGGTGCAGCTGTTGGAGTCTGGGGGAGGCTTGGTACAGCCTGGGGGGTCCCTGCGTCTC
TCCTGTACAGCCTCCGGATTCACCTTTTCGCATTATGAGATGGGGTGGGTCCGCCAGGCT
CCAGGGAAGGGTCTAGAGTGGGTCTCAAGTATTGAGCCTTTTGGTGGTGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGTGTAT
CCTCAGGGTTCTTTTGACTACTGGGGTCAGGGAACCCTGGTCACCGTCTCGAGC

BMS2h-203 (SEQ ID NO: 547)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATACTATGGGGTGGGTCCGTCAGGCT
CCAGGGAAGGGTCTAGAGTGGGTCTCATCTATTCGGCCTGATGGTAAGATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGTTTAT
TCTTCGTGTGCGATGTGTACTCCGCTTTTGTTTGACTACTGGGGTCAGGGAACCCTGGTC
ACCGTCTCGAGC

BMS2h-204 (SEQ ID NO: 548)
GAGGTGCAGCTGTTGGAGTCTGGGGGGGGCTTGGTACAGCCTGGGGGGTCCCTGCGTCTC
TCCTGTGCAGCCTCCGGATTCACCTTTAAGCGGTATTCGATGGCGTGGGTCCGCCAGGCT
CCAGGGAAGGGTCTAGAGTGGGTCTCAGATATTGGGCCGAGGGGTTTTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTGGGT
CGTGGTCAGCGTGATACTAGTCAGCCGTTTGACTACTGGGGTCAGGGAACCCTGGTCACC
GTCTCGAGC

BMS2h-205 (SEQ ID NO: 549)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTCTTATCAGATGGCTTGGGTCCGCCAGGCT
CCAGGGAAGGGTCTAGAGTGGGTCTCAGGGATTACTTCGGGTGGTCTTAGTACGTACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
AGGGGTTTTGACTACTGGGGTCAGGGAACCCTGGTCACCGTCTCGAGC

BMS2h-206 (SEQ ID NO: 550)
GAGGTGCAGCTGTTGGAGTCTGGGGGAGGCTTGGTACAGCCTGGTGGGTCCCTGCGTCTC
TCCTGTGCAGCCTCCGGATTCACCTTTGCTTCTTATGAGATGACTTGGGTCCGCCAGGCT
CCAGGGAAGGGTCTAGAGTGGGTCTCAGGGATTTCTTCTGATGGTCTGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
GTGTTGTTTGACTACTGGGGTCAGGGAACCCTGGTCACCGTCTCGAGC

BMS2h-207 (SEQ ID NO: 551)
GAGGTGCAGCTGTTGGAGTCTGGGGGAGGCTTGGTACAGCCTGGGGGGTCCCTGCGTCTC
TCCTGTGCAGCCTCTGGATTCACCTTTGATAAGTATTTGATGTCGTGGGTCCGCCAGGCT
CCAGGGAAGGGTCTGGAGTGGGTCTCAGGTATTGAGCCTCTGGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGAGGCT
TCGGGGGATTTTGACTACTGGGGTCAGGGAACCCTGGTCACCGTCTCGAGC

BMS2h-208 (SEQ ID NO: 552)
GAGGTGCAGCTGTTGGAGTCTGGGGGAGGCTTGGTACAGCCTGGGGGGTCCCTGCGTCTC
TCCTGTGCAGCCTCCGGGTTCACCTTTACTGAGTATGAGATGTCTTGGGTCCGCCAGGCT
CCAGGGAAGGGTCTAGAGTGGGTCTCAAGTATTGATAATGTGGGTAGTAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGGG
AAGCTTTTTGACTACTGGGGTCAGGGAACCCTGGTCACCGTCTCGAGC

BMS2h-209 (SEQ ID NO: 553)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGATTATGAGATGTGGTGGGTCCGCCAGGCT
CCAGGGAAGGGTCTAGAGTGGGTCTCAGCGATTTCTAGGCAGGGTTTTGCTACATACTAC
GCAGACTCCGTGAAAGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCTG
GAGCGGGATGATTTTGACTACTGGGGTCAGGGAACCCTGGTCACCGTCTCGAGC

BMS2h-21 (SEQ ID NO: 554)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGAATTATGAGATGGGGTGGGCCCGCCAGGCT
CCAGGGAAGGGTCTAGAGTGGGTCTCAGTTATTTCTGAGTGGGTTATTCTACATACTAC
GCAGACTCCGCGAAGGGCCGGTTCACCATCTCCCGCGACAATTCCAAGAACACGCTGTAT
CTGCAAATGAACAGCCTGCGTGCCGAGGCACACCGCGGTATATTACTGTGCGAAACTTGTG
GGTGGGACTCAGTATGAGTTTGACTACTGGGGTCAGGGAACCCTGGTCACCGTCTCGAGC

TABLE 2-continued

Human Anti-CD40L VH Domain Encoding Nucleotide Sequences

BMS2h-22 (SEQ ID NO: 555)
GAGGTGCAGCTGTTGGAGTCTGGGGGAGGCTTGGTACAGCCTGGGGGGTCCCTGCGTCTC
TCCTGTGCAGCCTCCGGATTCACCTTTCATAATTATGAGATGTCGTGGGTCCGCCAGGCT
CCAGGGAAGGGTCTAGAGTGGGTCTCAAGTATTTCTTCGGGTGGTTCTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
GTTAAGTTTGACTACTGGGGTCAGGGAACCCTGGTCACCGTCTCGAGC

BMS2h-23 (SEQ ID NO: 556)
GAGGTGCAGCTGTTGGAGTCCGGGGGAGGCTTGGTACAGCCTGGGGGGTCCCTGCGTCTC
TCCTGTGCAGCCTCCGGATTCACCTTTGGGCTGTATGAGATGACGTGGGTCCGCCAGGCT
CCAGGGAAGGGTCTAGAGTGGGTCTCAAGTATTACGGGTGATGGTATTTCGACATACTAC
GCAGACTCCGTGAAGGGCCGGTTCACCATCTCCCGCGACAATTCCAGGAACACGCTGTAT
CTGCAAATGAACAGCCTGCGTGCCGAGGACACCGCGGTATATTACTGTGCGAAAGCTGGG
AGGAAGTTTGACTACTGGGGTCAGGGAACCCTGGTCACCGTCTCGAGC

BMS2h-24 (SEQ ID NO: 557)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATCAGATGGCGTGGGTCCGCCAGGCT
CCAGGGAAGGGTCTAGAGTGGGTCTCAAGTATTACTAGTGAGGGTGGTTCGACATACTAC
GCAGACTCCGTGAAGGGCCGGTTCACCATCTCCCGCGACAATTCCAAGAACACACTGTAT
CTGCAAATGAACAGCCTGCGTGCCGAGGACACCGCGGTATATTACTGTGCGAAACCGGGT
AAGAATTTTGACTACTGGGGTCAGGGAACCCTGGTCACCGTCTCGAGC

BMS2h-24-1 (SEQ ID NO: 558)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATCAGATGGCGTGGGTTCGCCAGGCT
CCAGGGAAGGGACTAGAGTGGGTCTCAAGTATTACTAGTGAGGGTGGTTCGACATACTAC
GCAGACTCCGTGAAGGGCCGGTTCACCATCTCCCGCGACAATTCCAAGAACACAGTGTAT
CTGCAAATGAACAGCCTGCGTGCCGAGGACACCGCGGTATATTACTGTGCGAAACCGGGT
AAGAATTTCGACTACTGGGGTCAGGGAACCCTGGTCACCGTCTCGAGC

BMS2h-25 (SEQ ID NO: 559)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATTATGAGATGACGTGGGTCCGCCAGGCT
CCAGGGAAGGGTCTAGAGTGGGTCTCAACTATTACGTCGCAGGGTACTAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
CGTTCTTTTGACTACTGGGGTCAGGGAACCCTGGTCACCGTCTCGAGC

BMS2h-26 (SEQ ID NO: 560)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTAGTTATGAGATGACTTGGGTCCGCCAGGCT
CCAGGGAAGGGTCTGGAGTGGGTCTCATCTATTACGTCGGATGGTGGTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
AAGACGTTTGACTACTGGGGTCAGGGAACCCTGGTCACCGTCTCGAGC

BMS2h-27 (SEQ ID NO: 561)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTTGTATGAGATGACTTGGGTCCGCCAGGCT
CCAGGGAAGGGTCTAGAGTGGGTCTCATCTATTACTAGTGATGGTGTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGAT
TCTCCGTTTGACTACTGGGGTCAGGGAACCCTGGTCACCGTCTCGAGC

BMS2h-28 (SEQ ID NO: 562)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATTATGATATGGCTTGGGTCCGCCAGGCT
CCAGGGAAGGGTCTAGAGTGGGTCTCAACTATTAGTGATAATGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
CGTGATTTTGACTACTGGGGTCAGGGAACCCTGGTCACCGTCTCGAGC

BMS2h-29 (SEQ ID NO: 563)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTCGTTATCAGATGGCTTGGGTCCGCCAGGCT
CCAGGGAAGGGTCTAGAGTGGGTCTCATCTATTTCTTCTGATGGTGGGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGGG
CGGGCGTTTGACTACTGGGGTCAGGGAACCCTGGTCACCGTCTCGAGC

BMS2h-30 (SEQ ID NO: 564)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGAGGTATCAGATGGCTTGGGTCCGCCAGGCT
CCAGGGAAGGGTCTGGAGTGGGTCTCAACTATTTCTGATGATGGTGATTCGACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAACTGGAT
AAGTTGTTTGACTACTGGGGTCAGGGAACCCTGGTCACCGTCTCGAGC

BMS2h-300 (SEQ ID NO: 565)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATGATGAGATGACGTGGGTCCGCCAGGCT
CCAGGGAAGGGTCTAGAGTGGGTCTCAGCTATTGATACGACGGGTGGGCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
AAGGAGTTTGACTACTGGGGTCAGGGAACCCTGGTCACCGTCTCGAGC

BMS2h-301 (SEQ ID NO: 566)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGAGAGTGAGATGAGTTGGGTCCGCCAGGCT
CCAGGGAAGGGTCTAGAGTGGGTCTCAAGTATTCTTGATGAGGGTTCTGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
AAGGATTTTGACTACTGGGGTCAGGGAACCCTGGTCACCGTCTCGAGC

BMS2h-302 (SEQ ID NO: 567)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGAGGAGGAGATGAGTTGGGTCCGCCAGGCT
CCAGGGAAGGGTCTAGAGTGGGTCTCAGCGATTACTGATGATGGTGATGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTAAT
GCGGGTGCTTTTGACTACTGGGGTCAGGGAACCCTGGTCACCGTCTCGAGC

BMS2h-303 (SEQ ID NO: 568)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGTGTATGATATGGCTTGGGTCCGCCAGGCT
CCAGGGAAGGGTCTAGAGTGGGTCTCAGGGATTGTTAATGATGGTTCTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
AAGGATTTTGACTACTGGGGTCAGGGAACCCTGGTCACCGTCTCGAGC

BMS2h-304 (SEQ ID NO: 569)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATACGGAGATGACTTGGGTCCGCCAGGCT
CCAGGGAAGGGTCTAGAGTGGGTCTCATCGATTGCGGATGATGGTTCTAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
CAGGCTTTTGACTACTGGGGTCAGGGAACCCTGGTCACCGTCTCGAGC

BMS2h-31 (SEQ ID NO: 570)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATCAGATGGCGTGGGTCCGCCAGGCT
CCAGGGAAGGGTCTAGAGTGGGTCTCAACGATTTCGGATGATGGTTCTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
CTTTATTTTGACTACTGGGGTCAGGGAACCCTGGTCACCGTCTCGAGC

BMS2h-32 (SEQ ID NO: 571)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGTGTATCAGATGGGTTGGGTCCGCCAGGCT
CCAGGGAAGGGTCTAGAGTGGGTCTCATTTATTGTGCCTGGGGGTGATTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACGTGG
CCGGAGTTTGACTACTGGGGTCAGGGAACCCTGGTCACCGTCTCGAGC

BMS2h-4 (SEQ ID NO: 572)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATTATGAGATGACGTGGGTCCGCCAGGCT
CCAGGGAAGGGTCTAGAGTGGGTCTCATCTATTACGAGTGATGGTACTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTAAT
CCGCCGTTTGACTACTGGGGTCAGGGAACCCTGGTCACCGTCTCGAGC

BMS2h-40 (SEQ ID NO: 573)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCGTATGATATGGGTTGGGTCCGCCAGGCT
CCAGGGAAGGGTCTAGAGTGGGTCTCACAGATTGGGAGGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTCGT
CGGTATGCTATTTTTACTTTTGATCGGGGTCAGGGAACCCTGGTCACCGTCTCGAGC

BMS2h-400 (SEQ ID NO: 574)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGCAGTATCCGATGGTGTGGGTCCGCCAGGCT

TABLE 2-continued

Human Anti-CD40L VH Domain Encoding Nucleotide Sequences

CCAGGGAAGGGTCTAGAGTGGGTCTCAACGATTTCTACTAATGGTGTGAGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGACG
GATATTATTTCGTCTTCGGAGTTTGACTACTGGGGTCAGGGAACCCTGGTCACCGTCTCG
AGC

BMS2h-401 (SEQ ID NO: 575)
GAGGTGCAGCTGTTGGAGTCTGGGGGAGGCTTGGTACAGCCTGGGGGGTCCCTGCGTCTC
TCCTGTGCAGCCTCCGGATTCACCTTTTTTAATTATGATATGTCTTGGGTCCGCCAGGCT
CCAGGGAAGGGTCTAGAGTGGGTCTCAGCTATTAGTGGTAGTGGTGGTAGCACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTTTT
GTGTGGTCGGCTGATATTGATTTTGACTACTGGGGTCAGGGAACCCTGGTCACC
GTCTCGAGC

BMS2h-402 (SEQ ID NO: 576)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGTGGTATGATATGAGTTGGGTCCGCCAGGCT
CCAGGGAAGGGTCTAGAGTGGGTCTCACATATTGCGAGTTGGGGTGGTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTGACG
GTGAAGGATGGGGGGTATCTGATGGATTTTGACTACTGGGGTCAGGGAACCCTGGTCACC
GTCTCGAGC

BMS2h-403 (SEQ ID NO: 577)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGAGTATGCTATGCGTGGGTCCGCCAGGCT
CCAGGGAAGGGTCTGGAGTGGGTCTCAAGTATTGGGCGGGATGGTGCGGTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGAAG
GCGGCGAAGGAGCGGGGTTCTTGGTTTGACTACTGGGGTCAGGGAACCCTGGTCACCGTC
TCGAGC

BMS2h-404 (SEQ ID NO: 578)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGGCTTATCAGATGCAGTGGGTCCGCCAGGCT
CCAGGGAAGGGTCTTGAGTGGGTCTCAACTATTAGTCCTAATGGTCTTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGTTG
AGTTCTTTTGACTACTGGGGTCAGGGAACCCTGGTCACCGTCTCGAGC

BMS2h-407 (SEQ ID NO: 579)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTATGTATTCGATGGCTTGGGTCCGCCAGGCT
CCAGGGAAGGGTCTAGAGTGGGTCTCAGGTATTTCGCCTCGTGGTGTTGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACTAAT
TGGAATGGTGTGGATCTGTTTGACTACTGGGGTCAGGGAACCCTGGTCACCGTCTCGAGC

BMS2h-408 (SEQ ID NO: 580)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTACGTATATGATGAGTTGGGTCCGCCAGGCT
CCAGGGAAGGGTCTAGAGTGGGTCTCAACTATTAATACGAATGGTCGTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGAT
AGTAAATATGTCGTTTTTTGACTACTGGGGTCAGGGAACCCTGGTCACCGTCTCGAGC

BMS2h-409 (SEQ ID NO: 581)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTTATTCGATGACGTGGGTCCGCCAGGCT
CCAGGGAAGGGTCTAGAGTGGGTCTCATCTATTAATGCGTCGGGTACTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATGGT
AATAGGTCTGAGGTTTTTTTTGACTACTGGGGTCAGGGAACCCTGGTCACCGTCTCGAGC

BMS2h-41 (SEQ ID NO: 582)
GAGGTGCAGCTGTTGGAGTCTGGGGGAGGCTTGGTACAGCCTGGGGGGTCCCTGCGTCTC
TCCTGTGCAGCCTCCGGATTCACCTTTTTGAGTATGAGATGACGTGGGTCCGCCAGGCT
CCAGGGAAGGGTCTAGAGTGGGTCTCATCTATTGCGAATGATGGTTCGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
CGGCAGTTTGACTACTGGGGTCAGGGAACCCTGGTCACCGTCTCGAGC

BMS2h-410 (SEQ ID NO: 583)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGGATTATTTGATGGCGTGGGTCCGCCAGGCT
CCAGGGAAGGGTCTAGAGTGGGTCTCAGAGATTAATCAGGATGGTACTGTTACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGGAAAGTTCT
CCGTATTTTGACTACTGGGGTCAGGGAACCCTGGTCACCGTCTCGAGC

BMS2h-411 (SEQ ID NO: 584)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATTATGCGATGTCGTGGGTCCGCCAGGCT
CCAGGGAAGGGTCTAGAGTGGGTCTCATCTATTAGTCGGGATGGTCATGTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTTTCT
TCTAAGGGGGGGACGTTTGCTAGTTCTTTTGACTACTGGGGTCAGGGAACCCTGGTCACC
GTCTCGAGC

BMS2h-412 (SEQ ID NO: 585)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGCTGTTCCGATGACGTGGGTCCGCCAGGCT
CCAGGGAAGGGTCTAGAGTGGGTCTCAGCGATTACGGATGATGGTCTTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCAT
ATTTATGGGATTATTTTGACTACTGGGGTCAGGGAACCCTGGTCACCGTCTCGAGC

BMS2h-413 (SEQ ID NO: 586)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCTTTATAGGATGATGTGGGTCCGCCAGGCT
CCAGGGAAGGGTCTAGAGTGGGTCTCAGCTATTAGTAGTGATGGTGATACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACATTGG
TTGGGTACTACGTTGTCTTTGAGGGATTTTGACTACTGGGGTCAGGGAACCCTGGTCACC
GTCTCGAGC

BMS2h-414 (SEQ ID NO: 587)
GAGGTGCAGCTGTTGGAGTCTGGGGGAGGCTTGGTACAGCCTGGGGGGTCCCTGCGTCTC
TCCTGTGCAGCCTCCGGATTCACCTTTTATCGTTATACGATGGCGTGGGTCCGCCAGGCT
CCAGGGAAGGGTCTAGAGTGGGTCTCACAGATTTCGCCTAGGGGTAATATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGTGGT
GTGGCGGGGGCGGAGTCGCCTGAGTATTTTGACTACTGGGGTCAGGGAACCCTGGTCACC
GTCTCGAGC

BMS2h-415 (SEQ ID NO: 588)
GAGGTGCAGCTGTTGGAGTCTGGGGGAGGTTTGGTGCAGCCTGGGGGGTCCCTGCGTCTC
TCCTGTGCAGCCTCCGGATTCACCTTTTTGGGTTATTATATGAGTTGGATCCGCCAGGCT
CCAGGGAAGGGTCTAGAGTGGGTCTCAACGATTGGGCCGATTGGTGGTGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGAG
AATATTTATGGTCCTTTTGACTACTGGGGTCAGGGAACCCTGGTCACCGTCTCGAGC

BMS2h-416 (SEQ ID NO: 589)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCAGTATGATATGGCTTGGGTCCGCCAGGCT
CCAGGGAAGGGTCTAGAGTGGGTCTCAGAGATTAGTCGTGATGGTGGGCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGAGTAT
CCTTATTTTGACTACTGGGGTCAGGGAACCCTGGTCACCGTCTCGAGC

BMS2h-417 (SEQ ID NO: 590)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGCAGTATAGTATGGTGTGGGTCCGCCAGGCT
CCAGGGAAGGGTCTTGAGTGGGTCTCAACTATTTCGCCTCTGGGTTCTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAATGAGT
AAGTTGTTGCTGTCGAGGGAGTTTGACTACTGGGGTCAGGGAACCCTGGTCACCGTCTCG
AGC

BMS2h-418 (SEQ ID NO: 591)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTATGTATTCGATGGCTTGGGTCCGCCAGGCT
CCAGGGAAGGGTCTAGAGTGGGTCTCAGGTATTTCGCCTCGTGGTGTTGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTAAT
TGGAATGGTGTGGATCTGTTTGACTACTGGGGTCAGGGAACCCTGGTCACCGTCTCGAGC

BMS2h-419 (SEQ ID NO: 592)
GAGGTGCAGCTGTTGGAGTCTGGGGGAGGCTTGGTACAGCCTGGGGGGTCCCTGCGTCTC
TCCTGTGCAGCCTCCGGATTCACCTTTACGCGTCATGGTATGGCGTGGGTCCGCCAGGCT
CCAGGGAAGGGTCTAGAGTGGGTCTCAACGATTACGCCTACTGGTAATACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATGCT
CATGATGAGGGGTATTTTGACTACTGGGGTCAGGGAACCCTGGTCACCGTCTCGAGC

TABLE 2-continued

Human Anti-CD40L VH Domain Encoding Nucleotide Sequences

BMS2h-42 (SEQ ID NO: 593)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTCCGTATGAGATGACTTGGGTCCGCCAGGCT
CCAGGGAAGGGTCTAGAGTGGGTCTCATCGATTGTTGGTGATGGTCTGGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGAT
CGGGTTTTTGACTACTGGGGTCAGGGAACCCTGGTCACCGTCTCGAGC

BMS2h-420 (SEQ ID NO: 594)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAGTACGCCTATGATGTGGGTCCGCCAGGCT
CCAGGGAAGGGTCTAGAGTGGGTCTCAGAGATTAGGGATACGGGTCTGGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAGTGTTTCG
TTTGACTACTGGGGTCAGGGAACCCTGGTCACCGTCTCGAGC

BMS2h-421 (SEQ ID NO: 595)
GAGGTGCAGCTGTTGGAGTCTGGGGGAGGCTTGGTACAGCCTGGGGGGTCCCTGCGTCTC
TCCTGTGCAGCCTCCGGATTCACCTTTCATCTGGGGATATGCATTGGGTCCGCCAGGCT
CCAGGGAAGGGTCTAGAGTGGGTCTCATCGATTAGTGGGACGGGTCATACTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTATG
AATGATCAGGGGTTTGACTACTGGGGTCAGGGAACCCTGGTCACCGTCTCGAGC

BMS2h-422 (SEQ ID NO: 596)
GAGGTGCAGCTGTTGGAGTCTGGGGGAGGCTTGGTACAGCCTGGGGGGTCCCTGCGTCTC
TCCTGTGCAGCCTCCGGATTCACCTTTATGGATGAGGATATGTTGTGGGTCCGCCAGGCT
CCAGGGAAGGGTCTAGAGTGGGTCTCAAGGATTAATTCGCTGGGTACTCATACATACTAC
GCAGACTCCGTGAAGGGCCGATTCACCATCTCCCGCGACAATTCCAAGAACACGCTGTAT
CTGCAAATGAACAGCCTGCGTGCCGAGGATACCGCGGTATATTACTGTGCGAAATCGTTT
ATGATGTTTGACTACTGGGGTCAGGGAACCCTGGTCACCGTCTCGAGC

BMS2h-423 (SEQ ID NO: 597)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTAATTATCAGATGCATTGGGTCCGCCAGGCT
CCAGGGAAGGGTCTAGAGTGGGTCTCAGGTATTGATGCGACTGGTCGGGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAGATCTACT
AGGTCATTTGACTACTGGGGTCAGGGAACCCTGGTCACCGTCTCGAGC

BMS2h-424 (SEQ ID NO: 598)
GAGGTGCAGCTGTTGGAGTCTGGGGGAGGCTTGGTACAGCCTGGGGGTCCCTGCGTCTC
TCCTGTGCAGCCTCCGGATTCACCTTTACGAATGCGATATGGTGTGGGTCCGCCAGGCT
CCAGGGAAGGGTCTAGAGTGGGTCTCAAGTATTAGTGGTAGTGGTGGTAGCACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTAT
TTGACTTCGCATTTTGACTACTGGGGTCAGGGAACCCTGGTCACCGTCTCGAGC

BMS2h-425 (SEQ ID NO: 599)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGGATTATTCTATGGCTTGGGTCCGCCAGGCT
CCAGGGAAGGGTCTAGAGTGGGTCTCAACTATTACTCCGTCGGGTCTTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGTCT
CAGGCGGTTACTCGGTCTTTTGACTACTGGGGTCAGGGAACCCTGGTCACCGTCTCGAGC

BMS2h-426 (SEQ ID NO: 600)
GAGGTGCAGCTGTTGGAGTCTGGGGGAGACTTGGTACAGCCTGGGGGGTCCCTGCGTCTC
TCCTGTGCAGCCTCCGGATTCACCTTTTCTGATGAGGGTATGATGTGGGTCCGCCAGGCT
CCAGGGAAGGGTCTAGAGTGGGTCTCAGAGATTAATCAGCAGGGTTCGGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGATT
GGGATGTTTGACTACTGGGGTCAGGGAACCCTGGTCACCGTCTCGAGC

BMS2h-427 (SEQ ID NO: 601)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGATCAGCCGATGGTGTGGGTCCGCCAGGCT
CCAGGGAAGGGTCTAGAGTGGGTCTCATCGATTGGGGCGGTGGCCTACATACTAC
GCAGACTCCGTGAAGGGCCGGTTCACCGTCTCCCGCGACAATTCCAAGAACACGCTGTAT
CTGCAAATGAACAGCCTGCGTGCCGAGGACACCGCGGTATATTACTGTGCGAAATGGTTT
GATATTATTGCTTGGGATCCTTTTAGTTTTGACTACTGGGGTCAGGGAACCCTGGTCACC
GTCTCGAGC

BMS2h-428 (SEQ ID NO: 602)
GAGGTGCAGCTGTTGGAGTCTGGGGGAGGCTTGGTACAGCCTGGGGGGTCCCTGCGTCTC
TCCTGTGCAGCCTCCGGATTCACCTTTAATCAGTATCCTATGATGTGGGTTCGCCAGGCT
CCAGGGAAGGGTCTAGAGTGGGTCTCAAGTATTACTCCTTCTGGTTTTTTGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAATGAAT
CCTTTTATTACTACGTTTGACTACTGGGGTCAGGGAACCCTGGTGACCGTCTCGAGC

BMS2h-429 (SEQ ID NO: 603)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTGAT
TATTCGCTTCGTTTTGACTACTGGGGTCAGGGAACCCTGGTCACCGTCTCGAGC

BMS2h-43 (SEQ ID NO: 604)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTCTTATGAGATGGCGTGGGTCCGCCAGGCT
CCAGGGAAGGGTCTAGAGTGGGTCTCATCGATTGGTAGTGATGGTGGGCCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACTCCGCGGTATATTACTGTGCGAAACCTGAT
AGGGCTTTTGACTACTGGGGTCAGGGAACCCTGGTCACCGTCTCGAGC

BMS2h-430 (SEQ ID NO: 605)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGCGGAGCAGATGACTTGGGCCTGCCAGGCT
CCAGGGAAGGGTCTAGAGTGGGTCTCAACTATTACTCCGCATGGTGATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGCGG
ACTTTGGTTGATTGGCTACGAGTGAGTCGTTTGACTACTGGGGTCAGGGAACCCTGGTC
ACCGTCTCGAGC

BMS2h-44 (SEQ ID NO: 606)
GAGGTGCAGCTGTTGGAGTCTGGGGGAGGCTTGGTACAGCCTGGGGGGTCCCTGCGTCTC
TCCTGTGCAGCCTCCGGATTCACCTTTACGTCTTATGAGATGGGGTGGGTCCGCCAGGCT
CCAGGGAAGGGTCTAGAGTGGGTCTCATCTATTGAGCCTACTGGTATTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTCAT
TTTACTGAGCTTGGTTTTGACTACTGGGGTCAGGGAACCCTGGTCACCGTCTCGAGC

BMS2h-449 (SEQ ID NO: 607)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGGGAGCAGATGCGTTGGGTCCGCCAGGCT
CCAGGGAAGGGTCTAGAGTGGGTCTCAACGATTACGCTGCCTGGTCCGTATACATTCTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGAAT
GGGACGTTTTTTGACTACTGGGGTCAGGGAACCCTGGTCACCGTCTCGAGC

BMS2h-45 (SEQ ID NO: 608)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATTATGCGACAGGGCGTGGGTCCGCCAGGCT
CCAGGGAAGGGTCTAGAGTGGGTCTCAAAGATTGGGCGCAGGGTCTTCATACATACTAC
GCAGGCTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACAGACG
ACGATGGATTATGAGAGGTTTGACTACTGGGGTCAGGGAACCCTGGTCACCGTCTCGAGC

BMS2h-450 (SEQ ID NO: 609)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGAGGTTGATATGTGTGGGTCCGCCAGGCT
CCAGGGAAGGGTCTGAGTGGGTCTCAGCTATTGGTAATAATGGTCTTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGGCT
CTGTCGTATAGGCCTCCTGTTTTTGACTACTGGGTCAGGGAACCCTGGTCACCGTCTCG
AGC

BMS2h-451 (SEQ ID NO: 610)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGGATGATACTATGTCGTGGGTCCGCCAGGCT
CCAGGGAAGGGTCTAGAGTGGGTCTCAACGATTACGCTTAAGGGTCCGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGAGG
GATGGGTTGTATTTTGACTACTGGGGTCAGGGAACCCTGGTCACCGTCTCGAGC

BMS2h-452 (SEQ ID NO: 611)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTCGTCTCCGATGCGTTGGGTCCGCCAGGCT
CCAGGGAAGGGTCTAGAGTGGGTCTCAAGTATTGGTCGGGATGGTAGTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTTCG
CCTTATCGGCGGTTTGACTACTGGGGTCAGGGAACCCTGGTCACCGTCTCGAGC

TABLE 2-continued

Human Anti-CD40L VH Domain Encoding Nucleotide Sequences

BMS2h-453 (SEQ ID NO: 612)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGATTATTCGATGGTTTGGGTCCGCCAGGCT
CCAGGGAAGGGTCTAGAGTGGGTCTCAACTATTGTGAGTCATGGTGGTACTACATACTAC
GCAGACTCCGTGAAGGGCCGATTCACCATCTCCCGCGACAATTCCAAGAACACGCTGTAT
CTGCAAATGAACAGCCTGCGTGCCGAGGACACCGCGGTATATTACTGTGCGAAAGGTAAG
GGTTATAATGCGCAGTATTTTGACTACTGGGGTCAGGGAACCCTGGTCACCGTCTCGAGC

BMS2h-454 (SEQ ID NO: 613)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTGAT
TATTCGCTTCGTTTTGACTACTGGGGTCAGGGAACCCTGGTCACCGTCTCGAGC

BMS2h-455 (SEQ ID NO: 614)
GAGGTGCAGCTGTTGGAGTCTGGGGGAGGCTTGGTACAGCCTGGGGGGTCCCTGCGTCTC
TCCTGTGCAGCCTCCGGATTCACCTTTAATGATTATGATATGATTTGGGTCCGCCAGGCT
CCAGGGAAGGGTCTAGAGTGGGTCTCAACTATTAGTTCGCATGGTGATAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTGAT
GTTTTTTTTGACTACTGGGGTCAGGGAACCCTGGTCACCGTCTCGAGC

BMS2h-456 (SEQ ID NO: 615)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAATGGTCG
GATTCTTTTGACTACAGGGGTCAGGGAACCCTGGTCACCGTCTCGAGC

BMS2h-457 (SEQ ID NO: 616)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGATTATGAGATGGCTTGGGTCCGCCAGGCT
CCAGGGAAGGGTCTAGAGTGGGTCTCAGGGATTCAGTCTAATGGTAATATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTAAT
TCTCAGGTTGAGTATTTTGACTACTGGGGTCAGGGAACCCTGGTCACCGTCTCGAGC

BMS2h-458 (SEQ ID NO: 617)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGTGGAGCCTATGTCTTGGGTCCGCCAGGCT
CCAGGGAAGGGTCTAGAGTGGGTCTCAAATATTGGTCGTGATGGTTCGATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGGGG
AAGCATGGTACTTTTGACTACTGGGGTCAGGGAACCCTGGTCACCGTCTCGAGC

BMS2h-459 (SEQ ID NO: 618)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGGAGTATCGGATGATGTGGGTCCGCCAGGCT
CCAGGGAAGGGTCTGGAGTGGGTCTCATGGATTGATGAGCGGGGTTCGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGGCGG
AAGGGTACTAAGCAGTTTGACTACTGGGGTCAGGGAACCCTGGTCACCGTCTCGAGC

BMS2h-46 (SEQ ID NO: 619)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGTTGTATGCTATGGCGTGGGTCCGCCAGGCT
CCAGGGAAGGGTCTAGAGTGGGTCTCAGGTATTGGTGCTGTGGGTGAGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGAGGCT
AATAATCTTTCTGATAATCTTGTGTTTGACTACTGGGGTCAGGGAACCCTGGTCACCGTC
TCGAGC

BMS2h-460 (SEQ ID NO: 620)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGTCG
GTTGAGTGGTTTGACTACTGGGGTCAGGGAACCCTGGTCACCGTCTCGAGC

BMS2h-461 (SEQ ID NO: 621)
GAGGTGCAGCTGTTGGAGTCTGGGGGAGGCTTGGTACAGCCTGGGGGGTCCCTGCGTCTC
TCCTGTGCAGCCTCCGGATTCACCTTTAATAGTTATACGATGAATTGGGTCCGCCAGGCT
CCAGGGAAGGGTCTGGAGTGGGTCTCAAGTATTAATCCTTGGGGTAGTCGGACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGATACCGCGGTATATTACTGTGCGAAAGGTCTG
GTGCTGTTTGACTACTGGGGTCAGGGAACCCTGGTCACCGTCTCGAGC

BMS2h-462 0 (SEQ ID NO: 622)
GAGGTGCAGCTGTTGGAGTCTGGGGGAGGCTTGGTACAGCCTGGGGGTCCCTGCGTCTC
TCCTGTGCAGCCTCCGGATTCACCTTTGATGGTGATATGATGTCTTGGGTCCGCCAGGCT
CCAGGGAAGGGTCTAGAGTGGGTCTCATCGATTACTCAGCTTGGTAGTAGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACAGAAT
TGGGCGGACTCTTACTTTTGACTACTGGGGTCAGGGAACCCTGGTCACCGTCTCGAGC

BMS2h-463 (SEQ ID NO: 623)
GAGGTGCAGCTGTTGGAGTCTGGGGGAGGCTTGGTACAGCCTGGGGGTCCCTGCGTCTC
TCCTGCGCAGCCTCCGGATTCACCTTTAATGCTTATGGGATGATGTGGGTCCGCCAGGCT
CCAGGGAAGGGTCTAGAGTGGGTCTCATCTATTCTTTCTGATGGTGTTATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGTGCT
CGGGGTGCGAATTTTTTTGACTACTGGGGTCAGGGAACCCTGGTCACCGTCTCGAGC

BMS2h-464 (SEQ ID NO: 624)
GAGGTGCAGCTGTTGGAGTCTGGGGGAGGCTTGGTACAGCCTGGGGGTCCCTGCGTCTC
TCCTGTGCAGCCTCCGGATTCACCTTTGGGCATTATATGATGGTGTGGGTCCGCCAGGCT
CCAGGGAAGGGTCTGGAGTGGGTCTCATCTATTACGCCTCATGGTACGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAATTTAAT
GCTATTTTTAGTGAGGCGTTTGACTACTGGGGTCAGGGAACCCTGGTCACCGTCTCGAGC

BMS2h-465 (SEQ ID NO: 625)
GAGGTGCAGCTGTTGGAGTCTGGGGGAGGCTTGGTACAGCCTGGGGGTCCCTGCGTCTC
TCCTGTGCAGCCTCCGGATTCACCTTTAGGGATTATTCTATGGCTTGGGTCCGCCAGGCT
CCAGGGAAGGGTCTAGAGTGGGTCTCAACTATTACTCCGTCGGGTCTTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAATGGTCT
CAGGCGGTTACTCGGTCTTTTGACTACTGGGGTCAGGGAACCCTGGTCACCGTCTCGAGC

BMS2h-466 (SEQ ID NO: 626)
GAGGTGCAGCTGTTGGAGTCTGGGGGAGGCTTGGTACAGCCTGGGGGTCCCTGCGTCTC
TCCTGTGCAGCCTCCGGATTCACCTTTGATCTTTATGCGATGGCTTGGGTCCGCCAGGCT
CCAGGGAAGGGTCTAGAGTGGGTCTCAATGATTGGGAGGGATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACGCGGTATATTACTGTGCGAAATTGGCT
GGTTCGCTGAGGGGTCGTTTTGACTACTGGGGTCAGGGAACCCTGGTCACCGTCTCGAGC

BMS2h-467 (SEQ ID NO: 627)
GAGGTGCAGCTGTTGGAGTCTGGGGGAGGCTTGGTACAGCCTGGGGGTCCCTGCGTCTC
TCCTGTGCAGCCTCCGGATTCACCTTTAATAAGGCTAGTATGGGTTGGGTCCGCCAGGCT
CCAGGGAAGGGTCTAGAGTGGGTCTCAACTATTACGCCTCATGGTTCGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACAGCGG
TGGGGTGTTGAGTTTGACTACTGGGGTCAGGGAACCCTGGTCACCGTCTCGAGC

BMS2h-468 (SEQ ID NO: 628)
GAGGTGCAGCTGTTGGAGTCTGGGGGAGGCTTGGTACAGCCTGGGGGTCCCTGCGTCTC
TCCTGTGCAGCCTCCGGATTCACCTTTCAGGGGTATAGTATGGGTTGGGTCCGCCAGGCT
CCAGGGAAGGGTCTAGAGTGGGTCTCATCTATTGCTGGGCGTGGTGGTGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTTG
TATATTTATCATAGTCGTTTGACTACTGGGGTCAGGGAACCCTGGTCACCGTCTCGAGC

BMS2h-469 (SEQ ID NO: 629)
GAGGTGCAGCTGTTGGAGTCTGGGGGAGGCTTGGTACAGCCTGGGGGCTCCCTGCGTCTC
TCCTGTGCAGCCTCCGGATTCACCTTTCCTGGTATGGAGATGTCGTGGGTCCGCCAGGCT
CCAGGGAAGGGTCTAGAGTGGGTCTCAGCTATTACTGGGACTGGTAGTACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTAT
CATCCGTTTGACTACTGGGGTCAGGGAACCCTGGTCACCGTCTCGAGC

BMS2h-470 (SEQ ID NO: 630)
GAGGTGCAGCTGTTGGAGTCTGGGGGAGGCTTGGTACAGCCTGGGGGTCCCTGCGTCTC
TCCTGTGCAGCCTCCGGATTCACCTTTCCGATGGTGGCTATGTCTTGGGTCCGCCAGGCT
CCAGGGAAGGGTCTAGAGTGGGTCTCATCTATTGCTCGGGATGGTAATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACGCCGCGGTATATTACTGTGCGAAAGTTTCG
CCGACTGGTTTTGACTACTGGGGTCAGGGAACCCTGGTCACCGTCTCGAGC

BMS2h-471 (SEQ ID NO: 631)
GAGGTGCAGCTGTTGGAGTCTGGGGGAGGCTTGGTACAGCCTGGGGGTCCCTGCGTCTC
TCCTGTGCAGCCTCCGGATTCACCTTTGGGCATCAGGATATGTCGTGGGTCCGCCAGGCT

TABLE 2-continued

Human Anti-CD40L VH Domain Encoding Nucleotide Sequences

CCAGGGAAGGGTCTAGAGTGGGTCTCAGGGATTACGGATGATGGTGAGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTGAT
TATGATTTTGACTACTGGGGTCAGGGAACCCTGGTCACCGTCTCGAGC

BMS2h-472 (SEQ ID NO: 632)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGAGTATAATATGATGTGGGTCCGCCAGGCT
CCAGGGAAGGGTCTAGAGTGGGTCTCACAGATTACGAGGGATGGTTCTAGGACATACTAC
GCAGACTCCGTGAGGGGCCGGTTCACCATCTCCCGCGACAATTCCAGGAACACGCTGTAT
CTGCAAATGAACAGCCTGCGTGCCGAGGACTCCGCGGTATATTACTGTGCGAAACTGTCG
AATATTGGGTTTGACTACTGGGGTCAGGGAACCCTGGTCACCGTCTCGAGC

BMS2h-473 (SEQ ID NO: 633)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATTCTATGATTTGGGCCCGCCAGGCT
CCAGGGAAGGGTCTAGAGTGGGTCTCATCGATTACGCCGTATGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAACTGAT
TATTTGTTTGACTACTGGGGTCAGGGAACCCTGGTCACCGTCTCGAGC

BMS2h-474 (SEQ ID NO: 634)
GAGGTGCAGCTGTTGGAGTCTGGGGGAGGCTTGGTACAGCCTGGGGGGTCCCTGCGTCTC
TCCTGTGCAGCCTCCGGATTCACCTTTGATACGTATAGTATGATGTGGGTCCGCCAGGCT
CCAGGGAAGGGTCTTGAGTGGGTCTCAACTATTACTCCTTATGGTAGTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGGGT
CTGGTGTTTGACTACTGGGGTCAGGGAACCCTGGTCACCGTCTCGAGC

BMS2h-475 (SEQ ID NO: 635)
GAGGTGCAGCTGTTGGAGTCTGGGGGAGGCTTGGTACAGCCTGGGGGGTCCCTGCGACTC
TCCTGTGCAGCCTCCGGATTCACCTTTACTACGGGTCCTATGATGTGGGTCCGCCAGGCT
CCAGGGAAGGGTCTAGAGTGGGTCTCAGCGATTGGTATTGGGGGTGATACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTCATTACTGTGCGAAATTGACT
CCGTCTAATCAGTTTGACTACTGGGGTCAGGGAACCCTGGTCACCGTCTCGAGC

BMS2h-476 (SEQ ID NO: 636)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGCAGTATCAGATGATGTGGGTTCGCCAGGCT
CCAGGGAAGGGTCTAGAGTGGGTCTCAAGTATTACTCCTTCGGTTTTTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGAAT
CCTTTTATTAGTACGTTTGACTACTGGGGTCAGGGAACCCTGGTCACCGTCTCGAGC

BMS2h-477 (SEQ ID NO: 637)
GAGGTGCAGCTGTTGGAGTCTGGGGGAGGCTTGGTACAGCCTGGGGGTCCCTGCGTCTC
TCCTGTGCAGCCTCCGGATTCACCTTTCCTAATTATGATATGGTTTGGGTCCGCCAGGCT
CCAGGGAAGGGTCTAGAGTGGGTCTCATCGATTTCTGCTTTGGGTAATGTTACATACTAC
GCAGACTCCGTGAAGGGCCGGTTCACCATCTCCCGCGACAATTCCAAGAACACGCTGTAT
CTGCAAACGAACAGCCTGCGTGCCGAGGACACTGCGGTATATTACTGTGCGAAATGGCGT
AGTGCTATTACTGGTAATTTTGACTACTGGGGTCAGGGAACCCTGGTCACCGTCTCGAGC

BMS2h-478 (SEQ ID NO: 638)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGAGTATCAGATGTCTTGGGTCCGCCAGGCT
CCAGGGAAGGGTCTAGAGTGGGTCTCAACTATTTCGCCGTCGGGTATGAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGCGG
TCGGTTGTTCGTCCTTGGCCGGGTGTGTTTGACTACTGGGGTCAGGGAACCCTGGTCACC
GTCTCGAGC

BMS2h-479 (SEQ ID NO: 639)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGATGAGAGTGGGATGGTTTCGCCAGGCT
CCAGGGAAGGGTCTAGAGTGGGTCTCATCGATTACTCCTCATGGTACTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTTCAT
CTTAAGTTGTATGAGTCTCATTTTGACTACTGGGGTCAGGGAACCCTGGTCACCGTCTCG
AGC

BMS2h-480 (SEQ ID NO: 640)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTGGTGAGATGGGTTGGGTCCGCCAGGCT
CCAGGGAAGGGTCTAGAGTGGGTCTCAATGATTCCGATGGATGGTAGTGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGG
AGTACGTTTGACTACTGGGGTCAGGGAACCCTGGTCACCGTCTCGAGC

TABLE 2-continued

Human Anti-CD40L VH Domain Encoding Nucleotide Sequences

BMS2h-481 (SEQ ID NO: 641)
GAGGTGCAGCTGTTGGAGTCTGGGGGAGGCTTGGTACAGCCTGGGGGGTCCCTGCGTCTC
TCCTGTGCAGCCTCCGGATTCACCTTTGATTTTATGCCGATGGCGTGGGTCCGCCAGGCT
CCAGGGAAGGGTCTAGAGTGGGTCTCATCTATTGGGAGGGATGGTGCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTTGCT
TCGCCGGCGCAGTTTGACTACTGGGGTCAGGGAACCCTGGTCACCGTCTCGAGC

BMS2h-482 (SEQ ID NO: 642)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATGAGCCTATGCTGTGGGTCCGCCAGGCT
CCAGGGAAGGGTCTAGAGTGGGTCTCATCTATTGGGGGTACGGGTACGACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTAAT
CAGGGTGATTTTATTAATCGGTTTCACTACTGGGGTCAGGGAACCCTGGTCACCGTCTCG
AGC

BMS2h-483 (SEQ ID NO: 643)
GAGGTGCAGCTGTTGGAGTCTGGGGGAGGCTTGGTACAGCCTGGGGGGTCCCTGCGTCTC
TCCTGTGCAGCCTCCGGATTCACCTTTCATGCGTATAATATGGCGTGGGTCCGCCAGGCT
CCAGGGAAGGGTCTAGAGTGGGTCTCAACGATTTCTCCGCGGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGCCG
CCGCCTTCGTCTCATTTTGACTACTGGGGTCAGGGAACCCTGGTCACCGTCTCGAGC

BMS2h-5 (SEQ ID NO: 644)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGGTATGAGATGGCGTGGGTCCGCCAGGCT
CCAGGGAAGGGTCTAGAGTGGGTCTCATCTATTACGAGTGATGGTACGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
CTGCGTTTTGACTACTGGGGTCAGGGAACCCTGGTCACCGTCTCGAGC

BMS2h-505 (SEQ ID NO: 645)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTTATATGATGTATTGGGTCCACCAGGCT
CCGGGGAAGGGTCTAGAGTGGGTCTCATCTATTTCTCCTCAGGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACTTCGT
GAGCTTCCTCGTCTGTTTGACTACTGGGGTCAGGGAACCCTGGTCACCGTCTCGAGC

BMS2h-506 (SEQ ID NO: 646)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAGTTATGCTATGGGTTGGGTCCGCCAGGCT
CCAGGGAAGGGTCTAGAGTGGGTCTCATCGATTGATGCGAGTGGTGGTCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGAAT
GGGAAGAAGTTTCCTTTTACTAAGTATTTTGACTACTGGGGTCAGGGAACCCTGGTCACC
GTCTCGAGC

BMS2h-507 (SEQ ID NO: 647)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTAGTGTGCATATGCGTGGGTCCGCCAGGCT
CCAGGGAAGGGTCTAGAGTGGGTCTCAGGGATTAATCTGACGGGTGTTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGTGCT
ACTACTAGGCAGGCGCATCCGTTGTATTTTGACTACTGGGGTCAGGGAACCCTGGTCACC
GTCTCGAGC

BMS2h-515 (SEQ ID NO: 648)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGAGGGTGAGATGTATTGGGTCCGCCAGGCT
CCAGGGAAGGGTCTAGAGTGGGTCTCAACGATTTCGACTAATGGTCTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCTACT
CGTGATCTGGGTTTTGCCTACTGGGGTCAGGGAACCCTGGTCACCGTCTCGAGC

BMS2h-516 (SEQ ID NO: 649)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGAGATGGCTTGGGCCCGCCAGGCT
CCAGGGAAGGGTCTAGAGTGGGTCTCATTTATTTCTCCTCGTGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGCT
AAGACTTTTGACTACTGGGGTCAGGGAACCCTGGTCACCGTCTCGAGC

TABLE 2-continued

Human Anti-CD40L VH Domain Encoding Nucleotide Sequences

BMS2h-517 (SEQ ID NO: 650)
GAGGTGCAGCTGTTGGAGTCTGGGGGAGGCTTGGTACAGCCTGGGGGGTCCCTGCGTCTC
TCCTGTGCAGCCTCCGGATTCACCTTTGATACGTATGAGATGCTTTGGGTCCGCCAGGCT
CCAGGGAAGGGTCTAGAGTGGGTCTCACGTATTTCTGTTGATGGTAGTATTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAACGCGG
ATGCGTTTTGACTACTGGGGTCAGGGAACCCTGGTCACCGTCTCGAGC

BMS2h-518 (SEQ ID NO: 651)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTTCGTATGCTATGTCGTGGGTCCGCCAGGCT
CCAGGGAAGGGTCTAGAGTGGGTCTCAAATATTTCTCGTGATGGTTCGAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGCGCAG
TCTGGGGGGCTTCGGTCGGTTTGACTACGTTTGACTACTGGGGTCAGGGAACCCTGGTC
ACCGTCTCGAGC

BMS2h-519 (SEQ ID NO: 652)
GAGGTGCAGCTGTTGGAGTCTGGGGGAGGCTTGGTACAGCCTGGGGGGTCCCTGCGTCTC
TCCTGTGCAGACTCCGGATTCACCTTTAGCAGCTATGCCATGAGCTGGGTCCGCCAGGCT
CCAGGGAAGGGTCTAGAGTGGGTCTCATCTATTGGGAGGGATGGTGCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGG
CCGAAGGGTATTGCGTTTGACTACTGGGGTCAGGGAACCCTGGTCACCGTCTCGAGC

BMS2h-520 (SEQ ID NO: 653)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTCCGCATGCTATGGCTTGGGTCCGCCAGGCT
CCAGGGAAGGGTCTGGAGTGGGTCTCAGGTATTGATGGGGGGGGTTCGATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGGAT
CCTCCGTTTGACTACTGGGGTCAGGGAACCCTGGTCACCGTCTCGAGC

BMS2h-521 (SEQ ID NO: 654)
GAGGTGCAGCTGTTGGAGTCTGGGGGAGGCTTGGTACAGCCTGGGGGGTCCCTGCGTCTC
TCCTGCGCAGCCTCCGGATTCACCTTTCATGCGGGGGAGATGCATTGGGTCCGCCAGGCT
CCAGGGAAGGGTCTAGAGTGGGTCTCATCGATTACGCTGCCTGGTGATATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGAAT
ACTGGGTATACTTTTGACTACTGGGGTCAGGGAACCCTGGTCACCGTCTCGAGC

BMS2h-522 (SEQ ID NO: 655)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGAATTATGGTATGTCGTGGGTCCGCCAGGCT
CCAGGGAAGGGTCTAGAGTGGGTCTCAAGTATTTCGTGGGATGGTTCTCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGCAAAATACG
CGGCTTTTTGACTACTGGGGTCAGGGAACCCTGGTCACCGTCTCGAGC

BMS2h-523 (SEQ ID NO: 656)
GAGGTGCAGCTGTTGGAGTCTGGGGGAGGCTTGGTACAGCCTGGGGGGTCCCTGCGTCTC
TCCTGTGCAGCCTCCGGATTCACCTTTCATGATGCGGATATGCTGTGGGTCCGCCAGGCT
CCAGGGAAGGGTCTAGAGTGGGTCTCAGGTATTTTGTCTCCGGGTGAGGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTGGT
CTGCCGTTTGACTACTGGGGTCAGGGAACCCTGGTCACCGTCTCGAGC

BMS2h-524 (SEQ ID NO: 657)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTACTGATCAGATGAATTGGGTCCGCCAGGCT
CCAGGGAAGGGTCTAGAGTGGGTCTCAAGTATTTCTCCTAGTGGTGCGTATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGGTCTT
GGTGCTTTTGACTACTGGGGTCAGGGAACCCTGGTCACCGTCTCGAGC

BMS2h-525 (SEQ ID NO: 658)
GAGGTGCAGCTGTTGGAGTCTGGGGGAGGCTTGGTACAGCCTGGGGGGTCCCTGCGTCTC
TCCTGTGCAGCCTCCGGATTCATCTTTGAGCAGTATCAGATGGTTTGGGTCCGCCAGGCT
CCAGGGAAGGGTCTAGAGTGGGTCTCATGGATTTCGCCTGATGGTACGCATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTAGT
TTGCGTAAGATGGGAAGTTTGACTACTGGGGTCAGGGAACCCTGGTCACCGTCTCGAGC

BMS2h-526 (SEQ ID NO: 659)
GAGGTGCAGCTGTTGGAATCTGGGGGAGGCTTGGTACAGCCTGGGGGGTCCCTGCGTCTC
TCCTGTGCAGCCTCCGGATTCACCTTTCAGGATGAGCAGATGGCGTGGGTCCGCCAGGCT
CCAGGGAAGGGTCTAGAGTGGGTCTCAAGTATTGCGTCTGATGGTATGTCTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAATAGCCTGCGTGCCGAGGACACCGCGGTATATTACTGTGCGCAACCTGGG
AAGAATTTTGACCACTGGGGTCAGGGAACCCTGGTCACCGTCTCGAGC

BMS2h-527 (SEQ ID NO: 660)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGCGATGAGTTGGGTCCGCCAGGCT
CCAGGGAAGGGTCTAGAGTGGGTCTCATCGATTACTACTGGGGGTGAGCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACGTTGG
AATCTGTATACGGAGTCTTTTGACTACTGGGGTCAGGGAACCCTGGTCACCGTCTCGAGC

BMS2h-528 (SEQ ID NO: 661)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGGTCAGCCGATGGATTGGGTCCGCCAGGCT
CCAGGGAAGGGTCTAGAGTGGGTCTCATCTATTGCTCCTGATGGTATTCATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAATTTG
GGTCAGGGTTTTGACTACTGGGGTCAGGGAACCCTGGTCACCGTCTCGAGC

BMS2h-529 (SEQ ID NO: 662)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCGGTATCAGATGACGTGGGTCCGCCAGGCT
CCAGGGAAGGGTCTAGAGTGGGTCTCAAGTATTTCTCCTAGTGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGAAG
GCGCTTTTTGACTACTGGGGTCAGGGAACCCTGGTCACCGTCTCGAGC

BMS2h-530 (SEQ ID NO: 663)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTCATTCGACTATGTATTGGGTCCGCCAGGCT
CCAGGGAAGGGTCTAGAGTGGGTCTCACTTATTTTGCCGTCGGGTAGTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTTCT
GATGAGCGTTTTGACTACTGGGGTCAGGGAACCCTGGTCACCGTCTCGAGC

BMS2h-531 (SEQ ID NO: 664)
GAGGTGCAGCTGTCGGAGTCTGGGGGAGGCTTGGTACAGCCTGGGGGGTCCCTGCGTCTC
TCCTGTGCAGCCTCCGGATTCACCTTTGGTGATGGGAATATGGATTGGGTCCGCCAGGCT
CCAGGGAAGGGTCTAGAGTGGGTCTCAGGTATTTCTAGTGATGGTGTGACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATAGG
GGTCAGGGGTTTGACTACTGGGGTCAGGGAACCCTGGTCACCGTCTCGAGC

BMS2h-532 (SEQ ID NO: 665)
GAGGTGCAGCTGTTGGAGTCTGGGGGAGGCTTGGTACAGCCTGGGGGGTCCCTGCGTCTC
TCCTGTGCAGCTTCCGGATTCACCTTTGATGATTATATGATGTGGTGGGTCCGCCAGGCT
CCAGGGAAGGGTCTAGAGTGGGTCTCATCTATTAGTCCGCATGGTGTTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGTTG
CATACGTTTGACTACTGGGGTCAGGGAACCCTGGTCACCGTCTCGAGC

BMS2h-533 (SEQ ID NO: 666)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGAATTATACGATGGCGTGGGGCCGCCAGGCT
CCAGGGAAGGGTCTAGAGTGGGTCTCATTTATTGCTGGTCGGGTAATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
AGTACTGCGACGTATAATAATGGTCAGTTTGACTACTGGGGTCAGGGAACCCTGGTCACC
GTCTCGAGC

BMS2h-534 (SEQ ID NO: 667)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGAGTATAGTATGGTGTGGGTCCGCCAGGCT
CCAGGGAAGGGTCTGGAGTGGGTCTCATCTATTAGTGGGAGTGGTCGTGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGCTT
AAGCTGGTTAGGGCTCCTAATCCGTTTGACTACTGGGGTCAGGGAACCCTGGTCACCGTC
TCGAGC

BMS2h-535 (SEQ ID NO: 668)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATCAGATGGCGTGGGTCCGCCAGGCT
CCAGGGAAGGGTCTAGAGTGGGTCTCAGGTATTTCTAAGACTGGTCATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTTCG
CATTCGTTGGGGCCTCTTTTTGACTACTGGGGTCAGGGAACCCTGGTCACCGTCTCGAGC

TABLE 2-continued

Human Anti-CD40L VH Domain Encoding Nucleotide Sequences

BMS2h-54 (SEQ ID NO: 669)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGCGTATAGGATGGCTTGGGTCCGCCAGGCT
CCAGGGAAGGGTCTAGAGTGGGTCTCATGGATTTCGCCTTCTGGTTCGGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACTTTG
ACGGATTCGCCGTCGGGGCATTATGAGTTTGACTACTGGGGTCAGGGAACCCTGGTCACC
GTCTCGAGC

BMS2h-55 (SEQ ID NO: 670)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGCGGTATGAGATGGGGTGGGTCCGCCAGGCT
CCAGGGAAGGGTCTAGAGTGGGTCTCACGGATTACTGCTCAGGGTCTTGGGACATACTAC
GCAGACTCCGTGAAGGGCCGGTTCACCATCTCCCGCGACAACTCCAAGAACACGCTGTAT
CTGCAAATGAACAGCCTGCGTGCCGAGGATACCGCGGTATATTACTGTGCGAAATATCTT
ACTGATTTTAGTAGTGGGCATCAGGAGTTTGACTACTGGGGTCAGGGAACCCTGGTCACC
GTCTCGAGC

BMS2h-553 (SEQ ID NO: 671)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGATTATGGTATGTCGTGGGTCCGCCAGGTT
CCAGGGAAGGGTCTGGAGTGGGTCTCAGGTATTAGTCATAATGGTATGTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATATTGG
CCGTCTACTAGTTGGGAGACTGATTTTGACTACTGGGGTCAGGGAACCCTGGTCACCGTC
TCGAGC

BMS2h-554 (SEQ ID NO: 672)
GAGGTGCAGCTGTTGGAGTCTGGGGGAGGCTCGGTACAGCCTGGGGGGTCCCTGCGTCTC
TCCTGTGCAGCCTCCGGATTCACCTTTGGGAATGAGCCTATGGCTTGGGTCCGCCAGGCT
CCAGGGAAGGGTCTAGAGTGGGTCTCAAGTATTGAGATGCAGGGTAAGAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATAGG
GGTCAGGGGTTTGACTACTGGGGTCAGGGAACCCTGGTCACCGTCTCGAGC

BMS2h-555 1 (SEQ ID NO: 673)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGAGGAGGAGATGAGTTGGGTCCGCCAGGCT
CCAGGGAAGGGTCTAGAGTGGGTCTCATGTATTGATAATCTGGGTAGTCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACGCCGCGGTATATTACTGTGCGAAAACGATT
TCTCATCAGTATGATAGGTTTGACTACTGGGGTCAGGGAACCCTGGTCACCGTCTCGAGC

BMS2h-556 (SEQ ID NO: 674)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGAGGAGGAGATGAGTTGGGTCCGCCAGGCT
CCAGGGAAGGGTCTAGAGTGGGTCTCATCGATTGATGAGGGGGGTCGGTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGACG
CCGCATAAGCAGTTGTCGTTTGACTACTGGGGTCAGGGAACCCTGGTCACCGTCTCGAGC

BMS2h-557 (SEQ ID NO: 675)
GAGGTGCAGCTGTTGGAGTCTGGGGGAGGCTTGGTACAGCCTGGGGGGTCCCTGCGTCTC
TCCTGTGCAGCCTCCGGATTCAGCTTTGCTGATGAGTATATGGTTTGGGCCCGCCAGGCT
CCAGGGAAGGGTCTAGAGTGGGTCTCAGAGATTGATCCGTTGGGTACTGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATGGG
ACGGCTTTTGACTACTGGGGTCAGGGAACCCTGGTCACCGTCTCGAGC

BMS2h-558 (SEQ ID NO: 676)
GAGGTGCAGCTGTTGGAGTCTGGGGGAGGCTTGGTACAGCCTGGGGGGTCCCTGCGCCTC
TCCTGTGCAGCCTCCGGATTCACCTTTTCTACGCATGATATGATGTGGGTCCGCCAGGCT
CCAGGGAAGGGTCTAGAGTGGGTCTCATCGATTTCTGATGATGGTATTAGTACATACTAC
GCAGACTCCGTGAAGGGCCGGTTCACCATTTCCCGCGACAATTCCAAGAACACGCTGTAT
CTGCAAATGAACAGCCTGCGTGCCGAGGATACCGCGGTATATTACTGTGCGAAACCTGAT
ATGTCTCTTATTGAGTTTGACTACTGGGGTCAGGGAACCCTGGTCACCGTCTCGAGC

BMS2h-559 (SEQ ID NO: 677)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGTACTCCGATGGTTTGGGTCCGCCAGGCT
CCAGGGAAGGGTCTAGAGTGGGTCTCAGGGATTAGTGGTGATGGTAGGAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGGAACCTTAT
GCGCTTACTTCGTCTAAGCCTTTTGACTACTGGGGTCAGGGAACCCTGGTCACCGTCTCG
AGC

TABLE 2-continued

Human Anti-CD40L VH Domain Encoding Nucleotide Sequences

BMS2h-56 (SEQ ID NO: 678)
GAGGTGCAGCTGTTGGAGTCTGGGGGAGGCTTGGTACAGCCTGGGGGGTCCCTGCGTCTC
TCCTGTGCAGCCTCCGGATTCACCTTTAATGATTATACTATGGGTTGGGTCCGCCAGGCT
CCAGGGAAGGGTCTAGAGTGGGTCTCATGGATTCATGGGACTGGTGGTCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTTTG
GCTGATAGGAGTGGGGGGGTTGTTGAGTTTGACTACTGGGGTCAGGGAACCCTGGTCACC
GTCTCGAGC

BMS2h-560 (SEQ ID NO: 679)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGCGGAGACGATGGCTTGGGTCCGCCAGGCT
CCAGGGAAGGGTCTAGAGTGGGTCTCATGTATTAGTAATGATGGTAATACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGAGTCT
CTGATTAGTCCTGGTCTTTTTGACTACTGGGGTCAGGGAACCCTGGTCACCGTCTCGAGC

BMS2h-561 (SEQ ID NO: 680)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGGTGAGTATATGAATTGGGTCCGCCAGGCT
CCAGGGAAGGGTCTAGAGTGGGTCTCAACTATTAATGAGACTGGTTATATGACATACTAC
GCAGACTCCGTGAAGGGCCGGTTCACCATCTCCCGCGACAATTCCAAGAACACGCTGTAT
CTGCAAATGAATAGCCTGCGTGCCGAGGACACCGCGGTATATTACTGTGCGAAACTTTCT
ACGAGGGGGGTGCCTTTTGACTACTGGGGTCAGGGAACCCTGGTCACCGTCTCGAGC

BMS2h-562 (SEQ ID NO: 681)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGTCGTATGATATGGGTTGGGTCCGCCAGGCT
CCAGGGAAGGGTCTAGAGTGGGTCTCAACGATTTCGCCTATGGGTGTTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCTAAT
CAGCATGCTCATGATCCTTTTGACTACTGGGGTCAGGGAACCCTGGTCACCGTCTCGAGC

BMS2h-563 (SEQ ID NO: 682)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGATATGGGTTGGGTCCGCCAGGCT
CCAGGGAAGGGTCTGGAGTGGGTCTCAAGTATTTCGCCTATGGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTGCT
TTGACTGAGCCTATGTTTGACTACTGGGGTCAGGGAACCCTGGTCACCGTCTCGAGC

BMS2h-564 (SEQ ID NO: 683)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTGATTATGATATGGGTTGGGTCCGCCAGGCT
CCAGGGAAGGGTCTAGAGTGGGTCTCAACTATTTCTCCTCTTGGTCATTTTACATACTAC
GCAGACTCCGTGAAGGGCCGGTCCACCATCTCCCGCGACAATTCCAAGAACACGCTGTAT
CTGCAAATGAACAGCCTGCGTGCCGAGGATACCGCGGTATATTACTGTGCGAAAGCTGAG
GAGGCTTTTGACTACTGGGGTCAGGGAACCCTGGTCACCGTCTCGAGC

BMS2h-565 (SEQ ID NO: 684)
GAGGTGCAGCTGTTGGAGTCTGGGGGAGGCTTGGTACAGCCTGGGGGGTCCCTGCGCCTC
TCCTGTGCAGCCTCCGGATTCGCCTTTCCTAGGTATGGTATGACGTGGGTCCGCCAGGCT
CCAGGGAAGGGTCTAGAGTGGGTCTCAAATATTGATCAGTTTGGTATGAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGAGTAT
GCTTCGTTTGACTACTGGGGTCAGGGAACCCTGGTCACCGTCTCGAGC

BMS2h-566 (SEQ ID NO: 685)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAAGTATGATATGGGTTGGGTCCGCCAGGCT
CCAGGGAAGGGTCTAGAGTGGGTCTCAACGATTTCGCCTATGGGTGTTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGCGG
GGTAATACTTCGGATTTTGACTACTGGGGTCAGGGAACCCTGGTCACCGTCTCGAGC

BMS2h-567 (SEQ ID NO: 686)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATGATATGGCGTGGGTCCGCCAGGCT
CCAGGGAAGGGTCTAGAGTGGGTCTCAACTATTTCTGGGGCGGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTTTT
CCGCGTGATGAGTTTGACTACTGGGGTCAGGGAACCCTGGTCACCGTCTCGAGC

BMS2h-568 (SEQ ID NO: 687)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGAAGTATGAGATGAGGTGGGTCCGCCAGGCT
CCAGGGAAGGGTCTAGAGTGGGTCTCAGAGATTGGTCTGGATGGTTCGCCTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGGGG
GATCCGAATGGTTTTGACTACTGGGGTCAGGGAACCCTGGTCACCGTCTCGAGC

BMS2h-569 (SEQ ID NO: 688)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGACTAGTGAGATGGATTGGGTCCGCCAGGCT
CCAGGGAAGGGTCTGGAGTGGGTCTCAGGTATTGGGCCTGATGGTTTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATGCG
GATTGGTTTGACTACTGGGGTCAGGGAACCCTGGTCACCGTCTCGAGC

BMS2h-57 (SEQ ID NO: 689)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGAGTATGATATGTATTGGGTCCGCCAGGCT
CCAGGGAAGGGTCTAGAGTGGGTCTCATGGATTGATACTGATGGTGGGGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
CTGAAGTTTGACTACTGGGGTCAGGGAACCCTGGTCACCGTCTCGAGC

BMS2h-570 (SEQ ID NO: 690)
GAGGTGCAGCTGTTGGAGTCTGGGGGAGGCCTGGTACAGCCTGGGGGGTCCCTGCGTCTC
TCCTGTACAGCCTCCGGATTCACCTTTGAGAATGCTTCTATGCAGTGGGTCCGCCAGGCT
CCAGGGAAGGGTCTAGAGTGGGTCTCATCTATTGAGGGGCAGGGTAATGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGTTCG
TCTTGGTCTTTTGACTACTGGGGTCAGGGAACCCTGGTCACCGTCTCGAGC

BMS2h-571 (SEQ ID NO: 691)
GAGGTGCAGCTGTTGGAGTCTGGGGGAGGCTTGGTACAGCCTGGGGGGTCCCTGCGTCTC
TCCTGTGCAGCCTCCGGATTCACCTTTACGCGTAATGAGATGGGGTGGGTCCGCCAGGCT
CCAGGGAAGGGTCTAGAGTGGGTCTCAACTATTACGCCGACTGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGGAT
CCTGGTAATAGGTATTTTGACTACTGGGGTCAGGGAACCCTGGTCACCGTCTCGAGC

BMS2h-572 (SEQ ID NO: 692)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-1 (SEQ ID NO: 693)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGTTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGGACCCTGGTCACCGTCTCGAGC

BMS2h-572-10 (SEQ ID NO: 694)
GAGGTGCAGCTGTTGGAGTCTGGTGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCGTCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTCTGACTACCGGGGTCAGGGAACCCTGGTCACCGTCTCGAGC

BMS2h-572-11 (SEQ ID NO: 695)
GAGGTGCAGCTGTTGGAGTCTGGGGGAGGCTTGGTACAGCCTGGGGGGTCCCTGCGTCTC
TCCTGTGCAGCCTCAGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGATTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCAGGTCACCGTCTCGAGC

BMS2h-572-12 (SEQ ID NO: 696)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGCCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTCTGACTACCGGGGTCAGGGAACCCTGGTCACCGTCTCGAGC

TABLE 2-continued

Human Anti-CD40L VH Domain Encoding Nucleotide Sequences

BMS2h-572-13 (SEQ ID NO: 697)
GAGGTGCAGTTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGCCCGCCAGGCT
CCAGGGAAGGGTCTAGAGTGGGTCTCAGGTATTGAGGGTCCTGGTGATGTTACATACTAC
GCAGACTCCGTGAAGGACCGGTTCACCATCTCCCGCGACAATTCCAAGAACACGCTGTAT
CTGCTAATGAACAGCCTGCGTGCCGAGGACACCGCGGTATATTACTGTGCGAAAGTAGGG
AAGGAGAGTAATTTTGACTACTGGGGTCAGGGAACCCTGGTCACCGTCTCGAGC

BMS2h-572-14 (SEQ ID NO: 698)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGCATTGAGGGTCCTGGTGATGTTACATACTAC
GCAGACTCAGTGAAGGGCCGGTTCACCATCTCCCGCGACAATACCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTCTCGAGC

BMS2h-572-15 (SEQ ID NO: 699)
GAGGTGCGGCTATTGGAGTCTGGGGGAGGCTTGGTACAGCCTGGGGGGTCCCTGCGTCTC
TCCTGTGCAGCCTCCGGATTCAACTTTAATTGGCAGCTGATGGGTTGGATCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCCAGTATATTACTGTGCGAAAGTTGGG
AAGGAGAGTAATTCTGACTACCGGGGTCAGGGAACCCTGGTCACCGTCTCGAGC

BMS2h-572-16 (SEQ ID NO: 700)
GAGGTGCAGCTGTTGGAGTCTGGGGGAGGCTTGGTACAGCCTGGGGGGTCACTGCGTCTC
TCCTGTGTAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-17 (SEQ ID NO: 701)
GAGGTGCAGCTGTTGGAGTCTGGGGGAGGCTTGGTACAGACTGGGGGGTCCCTGCGTCTC
TCCTGTGCAGCCTCCGGATTCACCTATAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGATGACACCGCGGTATATTACTGTGTGAAAGTTGGG
AAGGAGAGTAATTTTGACTACCGGGGTCACGGAACCCTGGTCACCGTCTCGAGC

BMS2h-572-18 (SEQ ID NO: 702)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAAGGCT
CCTGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-19 (SEQ ID NO: 703)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATACCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-2 (SEQ ID NO: 704)
GAGGTGCAGCTGTTGGAGTCTGGGGGAGGCTTGGTACAGCCTGGGGGGTCCCTGCGCCTC
TCCTGTGCAGCCTCCGGATTCACCTTTAATTGGCAGCTGATGGGTTGGGTCCGCCAGGCT
CCAGGGAAGGGTCTTGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAAGTTTGACTACCTGGGTCAGGGAACCCTGGTCACCGTCTCGAGC

BMS2h-572-21 (SEQ ID NO: 705)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGAATCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATCTTGACTACCGGGGTCAGGGAACCCTGGTCACCGTCTCGAGC

BMS2h-572-22 (SEQ ID NO: 706)
GAGGTGCAGCTGTTTGAGTCTGGGGGAGGCTCGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAAGTTGGG
AAGGAGAGTAATTCTGACTACCGGGGTCAGGGGACCCTGGTCACCGTCTCGAGC

BMS2h-572-23 (SEQ ID NO: 707)
GAGGTGCAGCTGTTGGAGTCTGGGGGAGGCTTGGTACAGCCTGGGGGGTCCCTGCGTCTC
ACCTGTGCAGCCTCCGGATTCACCTTTAATTGGCAGCTGATGGGTTGGGTCCGCCAGGCT
CCAGGGAAGGGTCTAGAGTGGGTCTCGGGTATTGAGGGTCCTGGTGATGTTACATACTAC
GCAGACTCCGTGAAGGGCCGGTTCATCATCTCCCGCGACAATTCCAAGAACACGCTATAT
CTGCAAATGAACAGCCTGCGTGCCGAGGACACCGCGGTATATTACTGTGCGAAAGTTGGG
AAGGAGAGTAATTCTGACTACCGGGGTCAGGGAACCCTGGTCACCGTCTCGAGC

BMS2h-572-24 (SEQ ID NO: 708)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCGGACTCCGTGAAGGGCCGGTTCACCATCTCCCGCGACAATTCCACGAACACGCTGTAT
CTGCAAATGAACAGCCTGCGTGCCGAGGACACCGCGGTATATTACTGTGCGAAAGTTGGG
AAGGAGAGTGAATTTGACTACCGGGGTCAGGGAACCCTGGTCACCGTCTCGAGC

BMS2h-572-3 (SEQ ID NO: 709)
GAGGTGCGGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCACCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATCTTGACTACCGGGGTCAGGGAACCCTGGTCACCGTCTCGAGC

BMS2h-572-4 (SEQ ID NO: 710)
GAGGTGCAGCTGTTGGTGTCTGGGGGAGGCCTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-5 (SEQ ID NO: 711)
GAGGTGCAGCTGTTGGTGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACATGCTGTAT
CTGCAAATGAACGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-6 (SEQ ID NO: 712)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCAGGCT
CCAGGGAAGGGTCTAGAGTGGGTCTCAGGTATTGAGGGTCCAGGTGATGTTACATACTAC
GCAGACTCCGTGAAGGCCGGTTCACCATCTCCCGCGACAATTCCAAGAACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-601 (SEQ ID NO: 713)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTCATGGGGTGGGCCCGGCAGGCT
CCAGGGAAGGGTCTAGAGTGGGTCTCAGGTATTGAGGGTCCAGGTGATGTTACATACTAC
GCAGACCCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-602 (SEQ ID NO: 714)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCACCTGATGGGGTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAGTTCTGACTACCGGGGTCAGGGAACCCTGGTCACCGTATCGAGC

BMS2h-572-603 (SEQ ID NO: 715)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGCACCTGATGGCCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-604 (SEQ ID NO: 716)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTGATGGGCTGGGTCCGGCAGGCT

TABLE 2-continued

Human Anti-CD40L VH Domain Encoding Nucleotide Sequences

CCAGGGAAGGGTCTCGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-605 (SEQ ID NO: 717)
GAGGTGCAGCTGTTGGAGTCTGGGGGAGGCTTGGTGCAGCCTGGGGGGTCCCTGCGTCTC
TCCTGTGCAGCCTCCGGATTCACCTTTAAGTGGCAGCTGATGGCCTGGGCCCGGCAGGCT
CCAGGGAAGGGTCTAGAGTGGGTCTCAGGTATTGAGGGTCCAGGTGATATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-606 (SEQ ID NO: 718)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGCACTTGATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-607 (SEQ ID NO: 719)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTCATGGGGTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-608 (SEQ ID NO: 720)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGGAGCTGATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-609 (SEQ ID NO: 721)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGCAGCTCATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-610 (SEQ ID NO: 722)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

BMS2h-572-611 (SEQ ID NO: 723)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCGGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTCGGG
AAGGACAGCAAGTCGGACTACCGGGGTCAGGGAACCCTGGTCACCGTATCGAGC

BMS2h-572-612 (SEQ ID NO: 724)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTCGGG
AAGGACAGCAACTCGGACTACCGGGGTCAGGGAACCCTGGTCACCGTATCGAGC

BMS2h-572-613 (SEQ ID NO: 725)
GAGGTGCAGCTGTTGGAGTCTGGGGGAGGCTTGGCACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

TABLE 2-continued

Human Anti-CD40L VH Domain Encoding Nucleotide Sequences

BMS2h-572-614 (SEQ ID NO: 726)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AAGGACGCCAAGTCGGACTACCGGGGTCAGGGAACCCTGGTCACCGTATCGAGC

BMS2h-572-615 (SEQ ID NO: 727)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGCCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AAGGACAAGAACTCGGACTACCGGGGTCAGGGAACCCTGGTCACCGTATCGAGC

BMS2h-572-616 (SEQ ID NO: 728)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AAGGAGAGCAAGTCCGACTACCGGGGTCAGGGAACCCTGGTCACCGTATCGAGC

BMS2h-572-617 (SEQ ID NO: 729)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AGGGACAGCAAGTCGGACTACCGGGGTCAGGGAACCCTGGTCACCGTATCGAGC

BMS2h-572-618 (SEQ ID NO: 730)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCGGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTCGGG
AAGTACAGCAACTCGGACTACCGGGGTCAGGGAACCCTGGTCACCGTATCGAGC

BMS2h-572-619 (SEQ ID NO: 731)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAGGTCGGACTACCGGGGTCAGGGAACCCTGGTCACCGTATCGAGC

BMS2h-572-620 (SEQ ID NO: 732)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGG
AAGGACGACAGCTCGGACTACCGGGGTCAGGGAACCCTGGTCACCGTATCGAGC

BMS2h-572-621 (SEQ ID NO: 733)
GAGGTGCAGCTGTTGGAGTTTGGGGGAGGCTTGGTACAGCCTGGGGGGTCCTTGCGTTTT
TCCTGTGCAGCTTCCGGATTCACCTTTAATTGGCAGCTGATGGGTTGGTTCCGGCAGGCT
CCAGGGAAGGGTTTAGAGTGGGTTTCAGGTATTGAGGGTCCAGGTGATGTTACATATTAC
GCAGATTCCGTGAAGGGCCGGTTCACCATTTCCCGCGACAATTCCAAGAACACGCTGTAT
CTGCAAATGAACAGCTTGCGTGCCGAGGATACCGCGGTATATTACTGTGTGAAAGTGGGG
AGGGACAGCAATTCGGACTACCGGGGTCAGGGAACCCTGGTCACCGTATCGAGC

BMS2h-572-622 (SEQ ID NO: 734)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGG
AAGGACAGCACCTCGGACTACCGGGGTCAGGGAACCCTGGTCACCGTATCGAGC

BMS2h-572-623 (SEQ ID NO: 735)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGTGAAAGTGGGG
AAGGAGAGCAGCTCGGACTACCGGGGTCAGGGAACCCTGGTCACCGTATCGAGC

BMS2h-572-624 (SEQ ID NO: 736)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTTCCGCGACAATTCCAAGAACACGCTGTAT
CTGCAAATGAACAGCCTGCGTGCCGAGGATACCGCGGTATATTACTGTGTGAAAGTGGGC
AAGGACAGCGCGTCCGACTACCGGGGTCAGGGAACCCTGGTCACCGTATCGAGC

BMS2h-572-625 (SEQ ID NO: 737)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTCGGC
AACGACAGCTACTCGGACTACCGGGGTCAGGGAACCCTGGTCACCGTATCGAGC

BMS2h-572-626 (SEQ ID NO: 738)
GAGGTGCAGCTGTTGGAGTCTGGGGGAGGCTTGGTACAGCCTGGGGGGTCCCTGCGTCTC
TCCTGTGCAGCCTCTGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACGGCCTGCGTGCCGAGGACACCGCGGTATATTACTGTGTGAAAGTGGGG
AAGGACAGCAGCTCGGACTACCGGGGTCAGGGAACCCTGGTCACCGTATCGAGC

BMS2h-572-627 (SEQ ID NO: 739)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGATATATTACTGTGTGAAAGTGGGC
AAGGACAGCGCGTCGGACTACCGGGGTCAGGGAACCCTGGTCACCGTATCGAGC

BMS2h-572-630 (SEQ ID NO: 740)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTGATGGGCTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AAGGACGCCAAGTCGGACTACCGGGGTCAGGGAACCCTGGTCACCGTATCGAGC

BMS2h-572-631 (SEQ ID NO: 741)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTGATGGGCTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAGGTCGGACTACCGGGGTCAGGGAACCCTGGTCACCGTATCGAGC

BMS2h-572-632 (SEQ ID NO: 742)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTGATGGGCTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

BMS2h-572-633 (SEQ ID NO: 743)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGGAGCTGATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGTGAAAGTGGGG
AAGGACGCCAAGTCGGACTACCGGGGTCAGGGAACCCTGGTCACCGTATCGAGC

BMS2h-572-634 (SEQ ID NO: 744)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGGAGCTGATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAGGTCGGACTACCGGGGTCAGGGAACCCTGGTCACCGTATCGAGC

BMS2h-572-635 (SEQ ID NO: 745)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGGAGCTGATGGGCTGGGCCCGGCAGGCT

TABLE 2-continued

Human Anti-CD40L VH Domain Encoding Nucleotide Sequences

CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

BMS2h-572-7 (SEQ ID NO: 746)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGATGGGCCCGCCAGGCT
CCAGGGAAGGGTCTAGAGTGGGTCTCAGGTATTGAGGGTCCTGGTGATGTTACATACTAC
GCAGACTCCGTGAAGGGTCGGTTCACCATCTCCCGCGACAATTCCAAGAACACGCTGTAT
CTACAAATGAACAGCCTGCGTGCCGAGGACTCCGCGGTATATTACTGTGCGAAAGTTGGG
AAGGAGAGTAATTTTGACTACCTGGGTCAGGGAACCCTGGTCACCGTCTCGAGC

BMS2h-572-8 (SEQ ID NO: 747)
GAGGTGCAGCTGTTGGAGTCTGGGGGAGGCTTGGTACAGCCTGGGGGGTCCCTGCGTCTC
TCCTGTGTAGCCTCCGGATTCACCTTTAATTGGCAGCTGATGGGTTGGGTCCGCCAGGCG
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTCGGG
AAGGAGAGTAATTCTGACTACCGGGGTCAGGGAACCCTGGTCACCGTTTCGAGC

BMS2h-572-9 (SEQ ID NO: 748)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTCTGACTACCGGGGTCAGGGAACCCTGGTCACCGTCTCGAGC

BMS2h-573 (SEQ ID NO: 749)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGGGTGGGAGATGGGTTGGGTCCGCCAGGCT
CCAGGGAAGGGTCTAGAGTGGGTCTCATCTATTGATGAGTCTGGTCTTAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGGTGCG
CCGCAGTATCAGATTACATTTGACTACTGGGGTCAGGGAACCCTGGTCACCGTCTCGAGC

BMS2h-574 (SEQ ID NO: 750)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTAATTATGGGATGTATTGGGTCCGCCAGGCT
CCAGGGAAGGGTCTAGAGTGGGTCTCATATATTTCGCGGAGGGGTTTGTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGTCG
CATTATATGAATAATGGGTTTGACTACTGGGGTCAGGGAACCCTGGTCACCGTCTCGAGC

BMS2h-575 (SEQ ID NO: 751)
GAGGTGCAGCTGTTGGAGTCTGGGGGAGGCTTGGTACAGCCTGGGGGGTCCCTGCGTCTC
TCCTGTGCAGCCTCCGGATTCACCTTTGTGGATTATACGAGTCTTGGGTCCGCCAGGCT
CCAGGGAAGGGTCTGGAGTGGGTCTCATCTATTAGTCCGATTGGTACTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
TATGGGATGGAGGATGGTCTGACGTGGTTTGACTACTGGGGTCAGGGAACCCTGGTCACC
GTCTCGAGC

BMS2h-576 (SEQ ID NO: 752)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGCGTATGATATGCAGTGGGTCCGCCAGGCT
CCAGGGAAGGGTCTGGAGTGGGTCTCAACGATTACGTCGGAGGGTCTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTAGT
GATTTGTTTGACTACTGGGGTCAGGGAACCCTGGTCACCGTCTCGAGC

BMS2h-577 (SEQ ID NO: 753)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGGTATGATATGGGTTGGGTCCGCCAGGCT
CCAGGGAAGGGTCTAGAGTGGGTCTCAACTATTTCTCGTGGGGGTTGGTTCACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGACG
AGTCAGTCGTCTACGGGGAGTTTTGACTACTGGGGTCAGGGAACCCTGGTCACCGTCTCG
AGC

BMS2h-578 (SEQ ID NO: 754)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTCGGTATGATATGCTTTGGGCCCGCCAGGCT
CCAGGGAAGGGTCTAGAGTGGGTCTCAGAGATTTCGCCTACGGGTGCTCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACTTGGT
TCGACTTTTGACTACTGGGGTCAGGGAACCCTGGTCACCGTCTCGAGC

TABLE 2-continued

Human Anti-CD40L VH Domain Encoding Nucleotide Sequences

BMS2h-579 (SEQ ID NO: 755)
GAGGTGCAGCTGTTGGAGTCTGGGGGAGGCTTGGTACAGCCTGGGGGGTCCCTGCGTCTC
TCCTGTGCAGCCTCCGGATTCACCTTTTTTCCGTATTATATGAGTTGGGTCCGCCAGGCT
CCAGGGAAGGGTCTAGAGTGGGTCTCATCTATTTCGGGTACGGGTGGGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGACG
CAGAATGCGACGCTTTTTGACTACTGGGGTCAGGGAACCCTGGTCACCGTCTCGAGC

BMS2h-58 (SEQ ID NO: 756)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGTTTATACTATGGCGTGGGTCCGCCAGGCT
CCAGGGAAGGGTCTGGAGTGGGTCTCAACGATTGATGAGTCTGGTCGTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
GTTTGGTTTGACTACTGGGGTCAGGGAACCCTGGTCACCGTCTCGAGC

BMS2h-580 (SEQ ID NO: 757)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGTTTTATAAGATGGGGTGGGTCCGCCAGGCT
CCAGGGAAGGGTCTAGAGTGGGTCTCAACGATTACTCCTAAGGGTCATCATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTTTT
AAGGGTAAGGGTTGGACTCGTCCGAGTGGGTTTGACTACTGGGGTCAGGGAACCCTGGTC
ACCGTCTCGAGC

BMS2h-581 (SEQ ID NO: 758)
GAGGTGCAGCTGTTGGAGTCTGGGGGAGGCTTGGTACAGCCTGGGGGGTCCCTGCGTCTC
TCCTGTGCAGCCTCCGGATTCACCTTTAATGAGTATAGTATGATGTGGGTCCGCCAGGCT
CCAGGGAAGGGTCTAGAGTGGGTCTCATCTATTGGGAGGCGTGGTTGGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTGTG
CTGCTGGATTCTACTAAGTTTGACTACTGGGGTCAGGGAACCCTGGTCACCGTCTCGAGC

BMS2h-582 (SEQ ID NO: 759)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGAGTATCCGATGACTTGGGTCCGCCAGGCT
CCAGGGAAGGGTCTAGAGTGGGTCTCAACTATTTCTGCGCGGTGGTCCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTAGG
CATTGGCTTCGTAATGGTCGTTTTGACTACTGGGGTCAGGGAACCCTGGTCACCGTCTCG
AGC

BMS2h-583 (SEQ ID NO: 760)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTATGCAGTCGATGCAGTGGGTCCGCCAGGCT
CCAGGGAAGGGTCTAGAGTGGGTCTCAAGTATTACTGATGATGGTACTAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
CGGGTTTTTGACTACTGGGGTCAGGGAACCCTGGTCACCGTCTCGAGC

BMS2h-584 (SEQ ID NO: 761)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGCGGCTGTATATGCAGTGGGTCCGCCAGGCT
CCAGGGAAGGGTCTAGAGTGGGTCTCACTGATTACTAATGATGGTATTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGT
GATCGTTTTGACTACTGGGGTCAGGGAACCCTGGTCACCGTCTCGAGC

BMS2h-586 (SEQ ID NO: 762)
GAGGTGCAGCTGTTGGAGTCTGGGGGAGGCTTGGTACAGCCTGGGGGGTCCCTGCGTCTC
TCCTGTGCAGCCTCCGGATTCACCTTTAATAAGTATAGGATGCAGTGGGTCCGCCAGGCT
CCAGGGAAGGGTCTAGAGTGGGTCTCAAGTATTGATAGTTCTGGTGAGCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGAGGTT
CCGATGGGGAATCAGACTTTTTTTGACTACTGGGGTCAGGGAACCCTGGTCACCGTCTCG
AGC

BMS2h-587 (SEQ ID NO: 763)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGATTATACTATGGGGTGGGTCCGCCAGGCT
CCAGGGAAGGGTCTAGAGTGGGTCTCATCGATTACGTCTCAGGGTGCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTACG
GGTACGGATTCGTCGTTTGACTACTGGGGTCAGGGAACCCTGGTCACCGTCTCGAGC

TABLE 2-continued

Human Anti-CD40L VH Domain Encoding Nucleotide Sequences

BMS2h-588 (SEQ ID NO: 764)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTATGAGATGTCTTGGGTCCGCCAGGCT
CCAGGGAAGGGTCTGGAGTGGGTCTCATGTATTGGGCCGGGGGGTAAGCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTGGAT
GGGCATTTTGACTACTGGGGTCAGGGAACCCTGGTCACCGTCTCGAGC

BMS2h-589 (SEQ ID NO: 765)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTCAGTATGATATGGGGTGGGTCCGCCAGGCT
CCAGGGAAGGGTCTAGAGTGGGTCTCAACGATTTCTTCGAGGGGTTGGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCCG
GGGGGTCGTCGGCGGTTTGACTACTGGGGTCAGGGAACCCTGGTCACCGTCTCGAGC

BMS2h-59 (SEQ ID NO: 766)
GAGGTGCAGCTGTTGGAGTCTGGGGGAGGCTTGGTACAGCCTGGGGGGTCCCTGCGTCTC
TCCTGTGCAGCCTCCGGATTCACCTTTCTGGATTATGCGATGGGTTGGGTCCGCCAGGCT
CCAGGGAAGGGTCTGGAGTGGGTCTCAACTATTTCTCCGATGGGTATGGGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGAGT
GCTATTTCGTTTACTTCTGATATTTCTAATTTTGACTACTGGGGTCAGGGAACCCTGGTC
ACCGTCTCGAGC

BMS2h-590 (SEQ ID NO: 767)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATCCGATGTCTTGGGTCCGCCAGGCT
CCAGGGAAGGGTCTAGAGTGGGTCTCAAGTATTTCTTGGTCTGGTTTTCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACCTGGT
GTTGCGAGGATGCCTACTGGGATTGCTTTTGACTACTGGGGTCAGGGAACCCTGGTCACC
GTCTCGAGC

BMS2h-591 (SEQ ID NO: 768)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGCTTATGAGATGCAGTGGGTCCGCCAGGCT
CCAGGGAAGGGTCTAGAGTGGGTCTCATCTATTGATAGTGCTGGTACTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTCTATTACTGTGCGGAACCTTTT
GGGATGTTTGACTACTGGGGTCAGGGAACCCTGGTCACCGTCTCGAGC

BMS2h-592 (SEQ ID NO: 769)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGAGTATCCGATGAAGTGGGTCCGCCAGGCT
CCAGGGAAGGGTCTAGAGTGGGTCTCAACGATTGATCGGCAGGGTGATCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGGTG
CGGAGGGGTCTTCCTCGTCCGAGTCGTTATTTTGACTACTGGGGTCAGGGAACCCTGGTC
ACCGTCTCGAGC

BMS2h-593 (SEQ ID NO: 770)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGATATGGGTTGGGTCCGCCAGGCT
CCAGGGAAGGGTCTGGAGTGGGTCTCAAGTATTTCGCCTATGGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCTG
AGTGTGTATTCGGGTCTTGATTTTGACTACTGGGGTCAGGGAACCCTGGTCACCGTCTCG
AGC

BMS2h-594 (SEQ ID NO: 771)
GAGGTGCAGCTGTTGGAGTCTGGGGGAGGCCTGGTACAGCCTGGGGGGTCCCTGCGTCTC
TCCTGCGCAGCCTCCGGATTCACCTTTTCTCATTATGATATGGGTTGGGTCCGCCAGGCT
CCAGGGAAGGGTCTGGAGTGGGTCTCAGATATTGATTATATTGGTAAGACTACATACTAC
GCAGACTCCGTGAAGGGCCGGTTCACCATCTCTCGCGACAATTCCAAGAACACGCTGTAT
CTGCAAATGAACAGCCTGCGTGCCGAGGACACCGCGGTATATTACTGTGCGAAAGCTTCG
GATGAGGTGGGTGTTAATACTTCCAAGTTTGACTACTGGGGTCAGGGAACCCTGGTCACC
GTCTCGAGC

BMS2h-595 (SEQ ID NO: 772)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGCGGTATGATATGGGGTGGGTCCGCCAGGCT
CCAGGGAAGGGTCTAGAGTGGGTCTCAACTATTTCTCCTACTGGTGTGTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTTT
GAGGATTTTGACTACTGGGGTCAGGGAACCCTGGTCACCGTCTCGAGC

TABLE 2-continued

Human Anti-CD40L VH Domain Encoding Nucleotide Sequences

BMS2h-596 (SEQ ID NO: 773)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGCTTATCCGATGAGTTGGGTCCGCCAGGCT
CCAGGGAAGGGTCTAGAGTGGGTCTCACTGATTTCTCATACGGGTCATGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGCAT
TGGCCTTTTGACTACCGGGGTCAGGGAACCCTGATCACCGTCTCGAGC

BMS2h-597 0 (SEQ ID NO: 774)
GAGGTGCAGCTGTTGGAGTCTGGGGGAGGCTTGGTACAGCCAGGGGGGTCCCTGCGCCTC
TCCTGTGCAGCCTCCGGATTCACCTTTGAGGATGAGTGGATGAGTTGGGTCCGCCAGGCT
CCAGGGAAGGGTCTAGAGTGGGTCTCAGATATTAGCCCGGGTGGTTGGACTACATACTAC
GCCGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTTAT
CGTCCGTTTGATGAGTTTGACTACTGGGGTCAGGGAACCCTGGTCACCGTCTCGAGC

BMS2h-598 (SEQ ID NO: 775)
GAGGTGCAGCTGTTGGAGTCTGGGGGAGGCTTGGTACAGCCTGGGGGGTCCCTGCGTCTC
TCCTGTGCAGCCTCCGGAGTCACCTTTGATGCTATTGAGATGTCTTGGGTCCGCCAGGCT
CCAGGGAAGGGTCTGGAGTGGGTCTCATCGATTTCGCGTCATGGTGAGTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGATGCT
TGGTCTCGGCATTTTGACTACTGGGGTCAGGGAACCCTGGTCACCGTCTCGAGC

BMS2h-599 (SEQ ID NO: 776)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAGTACGGATATGAGTCCGCCAGGCT
CCAGGGAAGGGTCTAGAGTGGGTCTCAGGTATTTTGGATAATGGTAGTAATACATACTAC
GCAGACTCCGTGAAGGGCCGGTTCACCATCTCCCGCGACAATTCCAAGAACATGCTGTAT
CTGCAAATGAATAGCCTGCGTGCCGAGGATACCGCGGTATATTACTGTGCGAAAGGGGCG
AGGGATTTTGACTACTGGGGTCAGGGAACCCTGGTCACCGTCTCGAGC

BMS2h-600 (SEQ ID NO: 777)
GAGGTGCAGCTGTTGGAGTCTGGGGGAGGCTTGGTACAGCCTGGGGGGTCCCTGCGTCTC
TCCTGTGCAGCTTCCGGATTCACCTTTGGTAGGCAGAGTATGCAGTGGGTCCGCCAGGCT
CCAGGGAAGGGTCTAGAGTGGGTCTCAAGTATTGATGATGATGGTTTTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGAT
CCGTGGGGTTTTGACTACTGGGGTCAGGGAACCCTGGTCACCGTCTCGAGC

BMS2h-601 (SEQ ID NO: 778)
GAGGTGCAGCTGTTGGAGTCTGGGGGAGGCTTGGTACAGCCTGGGGGGTCCCTGCGTCTC
TCCTGTACAGCCTCCGGATTCACCTTTAGTGATACGCAGATGGCGTGGGTCCGCCAGGCT
CCAGGGAAGGGTCTAGAGTGGGTCTCAGGTATTGATGATGGGGGTGTGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGAT
CGTCATTTTGACTACTGGGGTCAGGGAACCCTGGTCACCGTCTCGAGC

BMS2h-602 (SEQ ID NO: 779)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGAGTACGACGATGGGGTGGGTCCGCCAGGCT
CCAGGGAAGGGTCTGGAGTGGGTCTCAGTGATTTCGGATGATGGTGGTTTTACATACTAC
GCAGACTCCGTGAAGGGCCGGTTCACCATCTCCCGCGACAATTCCAGGAACACGCTGTAT
CTGCAAATGAACAGCCTGCGTGCCGAGGACACCGCGGTATATTACTGTGCGAAAGTTGAT
GGTTATGGTGTTTTTGACTACTGGGGTCAGGGAACCCTGGTCACCGTCTCGAGC

BMS2h-603 (SEQ ID NO: 780)
GAGGTGCAGCTGTTGGAGTCTGGGGGAGGCTTGGTACAGCCTGGGGGGTCCCTGCGTCTC
TCCTGTGCAGCCTCCGGATTCACCTTTCGGAGTGGGGATATGAATTGGGTCCGCCAGGCT
CCAGGGAAGGGTCTAGAGTGGGTCTCAACTATTACGAATGATGGTACGTCTACATACTAC
GCAGACTCCGTGAAGGGCCGGTTCACCATCTCCCGCGACAATTCCAAGAATACGCTGTAT
CTGCAAATGAACAGCCTGCGTGCCGAGGACACCGCGGTATATTACTGTGCGAAATCTGAT
TCTGATTTTGACTACTGGGGTCAGGGAACCCTGGTCACCGTCTCGAGC

BMS2h-61 (SEQ ID NO: 781)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGCTTATGCTATGACGTGGGTCCGCCAGGCT
CCAGGGAAGGGTCTAGAGTGGGTCTCATATATTAGTCCGAATGGTACGGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTCGGAATATGTG
GGGATGCGTTGGAATTCTTTTGACTACTGGGGTCAGGGAACCCTGGTCACCGTCTCGAGC

BMS2h-62 (SEQ ID NO: 782)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGAGTTATGAGATGGCTTGGGTCCGCCAGGCT
CCAGGGAAGGGTCTAGAGTGGGTCTCATCTATTACGAGTCTTGGTACTTCTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGT
AGGAAGTTTGACTACTGGGGTCAGGGAACCCTGGTCACCGTCTCGAGC

BMS2h-65 (SEQ ID NO: 783)
GAGGTGCAGCTGTTGGAGTCTGGGGGAGGCTTGGTACAGCCTGGGGGGTCCCTGCGTCTC
TCCTGTGCAGCCTCCGGATTCACCTTTAATGAGTATGAGATGACGTGGGTCCGCCAGGCT
CCAGGGAAGGGTCTAGAGTGGGTCTCAACGATTACTAGTGAGGGTAGTGGGACATACTAC
GCAGACTCCGTAAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTAAT
GGTAAGTTTGACTACTGGGGTCAGGGAACCCTGGTCACCGTCTCGAGC

BMS2h-66 (SEQ ID NO: 784)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGATTATGAGATGTTGTGGGTCCGCCAGGCT
CCAGGGAAGGGTCTGGAGTGGGTCTCAACTATTACTAGTGAGGGTCATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGG
ACTTCGTTTGACTACTGGGGTCAGGGAACCCTGGTCACCGTCTCGAGC

BMS2h-67 (SEQ ID NO: 785)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGAGATGAGTTGGGTCCGCCAGGCT
CCAGGGAAGGGTCTAGAGTGGGTCTCAACGATTGATTCTGATGGTAGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGT
GTGAAGTTTGACTACTGGGGTCAGGGAACCCTGGTCACCGTCTCGAGC

BMS2h-68 (SEQ ID NO: 786)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGATTATGAGATGACTTGGGTCCGCCAGGCT
CCAGGGAAGGGTCTAGAGTGGGTCTCATCTATTTCTTCTACTGGTCAGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGT
AATAAGTTTGACTACTGGGGTCAGGGAACCCTGGTCACCGTCTCGAGC

BMS2h-69 (SEQ ID NO: 787)
GAGGTGCAGCTGTTGGAGTCTGGGGGAGGCTTGGTACAGCCTGGGGGGTCCCTGCGTCTC
TCCTGTGCAGCCTCCGGATTCACCTTTCTTGATTATGGTATGGCTTGGGTCCGCCAGGCT
CCAGGGAAGGGTCTAGAGTGGGTCTCAGCTATTTCGCCTCTTGGTCTTAGTACATACTAC
GCAGACTCCGTGAAGAGCCGGTTCACCATCTCCCGCGACAATTCCAAGAACACGCTGTAT
CTGCAAATGAACAGCCTGCGTGCCGAGGATACCGCGGTATATTACTGTGCGAAAGAGGTG
AGGGTGGGTAGGGGTGTTCATCCTCCGAAGTTTGACTACTGGGGTCAGGGAACCCTGGTC
ACCGTCTCGAGC

BMS2h-7 (SEQ ID NO: 788)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTTGTATGAGATGACTTGGGTCCGCCAGGCT
CCAGGGAAGGGTCTAGAGTGGGTCTCATCTATTACTAGTGATGGTGTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTGGG
GTGATTTTTGACTACTGGGGTCAGGGAACCCTGGTCACCGTCTCGAGC

BMS2h-70 (SEQ ID NO: 789)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGAATTATGCTATGTCGTGGGTCCGCCAGGCT
CCAGGGAAGGGTCTAGAGTGGGTCTCAACGATTGCTCCGCTGGGTGTTCCGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAAAGAAG
GTTGGGGCGTGGCTGCAGTCGCGGAGTTTTGACTACTGGGGTCAGGGAACCCTGGTCACC
GTCTCGAGC

BMS2h-701 (SEQ ID NO: 790)
GAGGTGCAGCTGTTGGAGTCTGGGGGAGGCTTGGTACAGCCTGGGGGGTCCCTGCGTCTC
TCCTGTGCAGCCTCCGGATTCACCTTTATGGATTATGAGATGCATTGGGTCCGCCAGGCT
CCAGGGAAGGGTCTAGAGTGGGTCTCAACGATTGGTGCTTCTGGTCATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATCTT
GATATGCTGCTGTTTGGGTTTGACTACTGGGGTCAGGGAACCCTGGTCACCGTCTCGAGC

BMS2h-702 (SEQ ID NO: 791)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGAGTATGAGATGATGTGGGTCCGCCAGGCT
CCAGGGAAGGGTCTAGAGTGGGTCTCACGTATTGCTGGTAATGGTTCTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGATAATGCTT
TCTCATTTTGACTACTGGGGTCAGGGAACCCTGGTCACCGTCTCGAGC

TABLE 2-continued

Human Anti-CD40L VH Domain Encoding Nucleotide Sequences

BMS2h-703 (SEQ ID NO: 792)
GAGGTGCAGCTGTTGGAGTCTGGGGGAGGCTTGGTACAGCCTGGGGGGTCCCTGCGTCTC
TCCTGTGCAGCCTCCGGATTCACCTTTTATAATTATGATATGAGTTGGGTCCGCCAGGCT
CCAGGGAAGGGTCTAGAGTGGGTCTCAGGTATTGATTCGATGGGTCTTGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGGGTCT
AATGCGAGTGATTGGGTTGTTTTTGACTACTGGGGTCAGGGAACCCTGGTCACCGTCTCG
AGC

BMS2h-704 (SEQ ID NO: 793)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGTCGTATCATATGACTTGGGTCCGCCAGGCT
CCAGGGAAGGGTCTAGAGTGGGTCTCATCGATTGCGGATACGGGTGATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACTGCGGTATATTACTGTGCGAAATTGCGT
GGGATGGCTCGGGTTTGGGGGTTTGACTACTGGGGTCAGGGAACCCTGGTCACCGTCTCG
AGC

BMS2h-705 (SEQ ID NO: 794)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTTATTATGATATGATGTGGGTCCGCCAGGCT
CCAGGGAAGGGTCTAGAGTGGATCTCATCTATTTCGGATCGTGGTCTTCAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATTTACG
GAGATTCCGTTGGATTGGTTGGAGGTGTTTGACTACTGGGGTCAGGGAACCCTGGTCACC
GTCTCGAGC

BMS2h-706 (SEQ ID NO: 795)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGAGTTATAAGATGTTGTGGGTCCGCCAGGCT
CCAGGGAAGGGTCTAGAGTGGGTCTCATCGATTACTAATTCTGGTACTGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGATG
TATCCGGATTTGGAGATTGTGCATTTTGACTACTGGGGTCAGGGAACCCTGGTCACCGTC
TCGAGC

BMS2h-707 (SEQ ID NO: 796)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGACTTATCGTATGAGTTGGGTCCGCCAGGCT
CCAGGGAAGGGTCTAGAGTGGGTCTCAGCTATTGATCAGGAGGGTTCTGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAAATAGT
GGGACGAGGCCGGGGCTTCGGTTTGACTACTGGGGTCAGGGAACCCTGGTCACCGTCTCG
AGC

BMS2h-708 (SEQ ID NO: 797)
GAGGTGCAGCTGTTGGAGTCTGGGGGAGGCTTGGTACAGCCTGGGGGGTCCCTGCGCCTC
TCCTGTGCAGCCTCCGGATTCACCTTTAGTAGTTATGATATGCTTTGGGTCCGCCAGGCT
CCAGGGAAGGGTCTAGAGTGGGTCTCACGGATTGATGCGAGTGGTTATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGCAATTGTTG
AAGCTGTCGTTGAATCCTAATTTTGACTACTGGGGTCAGGGAACCCTGGTCACCGTCTCG
AGC

BMS2h-709 1 (SEQ ID NO: 798)
GAGGTGCAGCTGTTGGAGTCTGGGGGAGGCTTGGTACAGCCTGGGGGGTCCCTGCGTCTC
TCCTGTGCAGCCTCCGGATTCACCTTTAGCAGCTATGCCATGAGCTGGGTCCGCCAGGCT
CCAGGGAAGGGTCTAGAGTGGGTCTCATCGATTCATAATACTGGTTTGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGACT
CAGCATCGTTTTGTTGTTTTTGACTACTGGGGTCAGGGAACCCTGGTCACCGTCTCGAGC

BMS2h-71 (SEQ ID NO: 799)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTTATCCTATGTCGTGGGTCCGCCAGGCT
CCAGGGAAGGGTCTAGAGTGGGTCTCAACTATTAGTCCTTTGGGTCCTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACTGTTG
ATGGGGGAGTATTTGAATTCTAGGACGTTTGACTACTGGGGTCAGGGAACCCTGGTCACC
GTCTCGAGC

BMS2h-710 (SEQ ID NO: 800)
GAGGTGCAGCTGTTGGAGTCTGGGGGAGGCTTGGTACAGCCTGGGGGGTCCCTGCGTCTC
TCCTGTGCAGCCTCCGGATTCACCTTTAATACGTATAGTATGTCTTGGGTCCGCCAGGCT
CCAGGGAAGGGTCTGGAGTGGGTCTCATGGATTGATGCTGATGGTTGGGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGCAAACTGGG
CATACGTTTGACTACTGGGGTCAGGGAACCCTGGTCACCGTCTCGAGC

TABLE 2-continued

Human Anti-CD40L VH Domain Encoding Nucleotide Sequences

BMS2h-711 (SEQ ID NO: 801)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGATGGGGAGATGGGTTGGGCCCGCCAGGCT
CCAGGGAAGGGTCTAGAGTGGGTCTCAAGGATTGTGGATCCTGGTGATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGT
GATCAGTTTGACTACTGGGGTCAGGGAACCCTGGTCACCGTCTCGAGC

BMS2h-712 (SEQ ID NO: 802)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTGAGTATGAGATGAAGTGGGTCCGCCAGGCT
CCAGGGAAGGGTCTAGAGTGGGTCTCAACTATTACTCCGTCGGGTGGTCATACATACTAC
GCAGACTCCGTGAAGGGCCGGTTCACCATCTCCCGCGACAATTCCAAGAACACGCTGTAT
CTGCAAATGAACAGCCTGCGTGCCGAGGACGCCGCGGTATATTACTGTGCGATACCTCTT
TCTAGTTTTGACTACTGGGGTCGGGGAACCCTGGTCACCGTCTCGAGC

BMS2h-713 (SEQ ID NO: 803)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTAATTATGTGATGATTTGGGTCCGCCAGGCT
CCAGGGAAGGGTCTAGAGTGGGTCTCACTTATTAATGGTGCTGGTGATATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGGGGGT
GCGCGTTCGTTTGGGGTTCCGCCTAATTTTGACTACTGGGGTCAGGGAACCCTGGTCACC
GTCTCGAGC

BMS2h-714 (SEQ ID NO: 804)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGATGGGGAGATGGGTTGGGCCCGCCAGGCT
CCAGGGAAGGGTCTAGAGTGGGTCTCAAGGATTGTGGATCCTGGTGATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGT
GATCAGTTTGACTACTGGGGTCAGGGAACCCTGGTCACCGTCTCGAGC

BMS2h-715 (SEQ ID NO: 805)
GAGGTGCAGCTGTTGGAGTCTGGGGGAGGCTTGGTACAGCCTGGGGGGTCCCTGCGTCTC
TCCTGTGTAGCCTCCGGATTCACCTTTACGCTGTATAATATGTCTTGGGTCCGCCAGGCT
CCAGGGAAGGGTCTGGAGTGGGTCTCAGTTATTTCTAGTAAGGGTGATAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGCAAACGAGT
AGTGTTTTTGACTACTGGGGTCAGGGAACCCTGGTCACCGTCTCGAGC

BMS2h-716 (SEQ ID NO: 806)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGCGTATTATATGAGTTGGGTCCGCCAGGCT
CCAGGGAAGGGTCTAGAGTGGGTCTCAGGTATTGTTAATAATGGTTTGTTGACATACTAC
GCAGACTCCGTGAAGGGCCGGTTCACCATCTCCCGCGACAATTCCAAGAACATGCTGTAT
CTGCAAATGAACAGCCTGCGTGCCGAGGACACCGCGGTATATTACTGTGCGAAATCGGCT
GTTCATCCTTCGTATAGGGCGGAGTTGTTCGACTACTGGGGTCAGGGAACCCTGGTCACC
GTCTCGAGC

BMS2h-717 (SEQ ID NO: 807)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTTCGTATGAGATGGCGTGGGTCCGCCAGGCT
CCAGGGAAGGGTCTAGAGTGGGTCTCACGTATTGAGCCTGATGGTAGTAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCCG
GATAATTTTACTATGTTTGACTACTGGGGTCAGGGAACCCTGGTCACCGTCTCGAGC

BMS2h-718 (SEQ ID NO: 808)
GAGGTGCAGCTGTTGGAGTCTGGGGGAGGCTTGGTACAGCCTGGGGGGTCCCTGCGTCTC
TCCTGTGCAGCCTCCGGATTCACCTTTAATAAGTATATGATGGGGTGGGTCCGCCAGGCT
CCAGGGAAGGGTCTAGAGTGGGTCTCATCTATTGATAGTCTTGGTCATTATACATACTAC
GCAGACTCTGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGCGGAG
TTTCCGTTTGACTACTGGGGTCAGGGAACCCTGGTCACCGTCTCGAGC

BMS2h-719 (SEQ ID NO: 809)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGACGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCAGGGAACCCTGGTCACCGTCTCGAGC

BMS2h-719-1 (SEQ ID NO: 810)
GAGGTGCAGCTGTTGGAGTCTGGGGGAGGCATGGTACAGCCTGGGGGGTCCCTGCGTCTC
TCCTGTGCAGCCTCCGGATTCACCTTTAAGAGGTATGAGATGATGTGGGTCCGCCAGGCT

TABLE 2-continued

Human Anti-CD40L VH Domain Encoding Nucleotide Sequences

CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCAGGGAACCCAGGTCACCGTCTCGAGC

BMS2h-719-10 (SEQ ID NO: 811)
GAGGTGCAGCTGTTGGAGTCTGGGGGAGGCATGGTGCAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCAGGGAACCCAGGTCACCGTCTCGAGC

BMS2h-719-11 (SEQ ID NO: 812)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCAAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCGAGAACACGCTGTAT
CTGCAAATGAACAGCCTGCGTGCCGAGGATACCGCGGTATATTACTGTGCGGATCCGTTT
ACTGAGTTTGACTATTGGGGTCAGGGTACCCTGGTCACCGTCTCGAGC

BMS2h-719-12 (SEQ ID NO: 813)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCGTCTCCCGCGACAATTCCAAGAACACGCTGTAT
CTGCAAATGAACAGCCTGCGTGCCGAGGATACCGCGGTATATTACTGTGCGGACCCGTTT
ACTGAGTTTGACTACTGGGGTCAGGGAACCCTGGTCACCGTCTCGAGC

BMS2h-719-13 (SEQ ID NO: 814)
GAGGTGCAGCTGTTGGAGTCGGGGGGAGGCTTGGTACAGCCTGGGGGGTCCCTGCGTCTC
TCGTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATACCAAGAACACGCTGTAT
CTACAGATGAACAGCCTGCGTGCCGAGGATACCGCGGTATATTACTGTGCGGACCCGTTT
ACTGAGCTTGACTACTGGGGTCATGGAACCCTGGTCACCGTCTCGAGC

BMS2h-719-14 (SEQ ID NO: 815)
GAGGTGCAGCTGTTGGAGTCTGGGGGAGGCTTGGTACGGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTTCTGTGCAGATCCGTTT
ACTGAGTTTGACTACTGGGGTCAGGGAACCCTGGTCACCGTCTCGAGC

BMS2h-719-15 (SEQ ID NO: 816)
GAGGTGCAGCTGTTGGAGTCTGGGGGAGGCTTGGTACAGCCTGGGGGGTCCCTGCGTCTC
TCCTGTGCAGCCTCCGGATTCGCCTTTAAGAGGTATGAGATGACATGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCATATGAACAGCCTGCGTGCCGAGGATACCGCGGTATATTACTGTGCGGATCCGTTT
ACTGAGATTGACTACTGGGGTCAGGGAACCCTGGTCACCGTCTCGAGC

BMS2h-719-16 (SEQ ID NO: 817)
GAGGTGCAGCTGTTGGAGTCTGGGGGAGGCTTGGTACAGCCTGGGGGGTCCCTGCGTCTC
TCCTGTGCAGCCTCCGGATTCCCCTTTAAGAGGTATGAGATGACGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACCGGGCTCAGGGAACCCTGGTCACCGTCTCGAGC

BMS2h-719-17 (SEQ ID NO: 818)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGTCGTGGGTCCGCCAGGCT
CCAGGGAAGGGTCTGGAGTGGGTCTCTTCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGATCCGTTT
ACTGAGATTGACTACTGGGGTCAGGGAACCCAGGTCACCGTCTCGAGC

BMS2h-719-18 (SEQ ID NO: 819)
GAGGTGCAGCTGTTGGAGTCTGGGGGAGGCTTGGTACATCCTGGGGGGTCCCTGCGTCTC
TCCTGTGCAGCTTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGACGAGGATACCGCGGTATATTACTGTGCGGAACCGTTT
ACTGAGTTTGACTACGGGGGTCAGGGAACCCTGGTCACCGTCTCGAGC

TABLE 2-continued

Human Anti-CD40L VH Domain Encoding Nucleotide Sequences

BMS2h-719-19 (SEQ ID NO: 820)
GAGGTGCAGCTGTTGGAGTCTGGGGGAGGCTGGGTACAGCCTGGGGGGTCCCTGCGTCTC
TCCTGTGCAGCCTCAGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGATCCGTTT
ACTGAGTTTGACTACTGGGGTCAGGGAACCCTGGTCACCGTCTCGAGC

BMS2h-719-2 (SEQ ID NO: 821)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-20 (SEQ ID NO: 822)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGACGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACTCTGTAT
CTGCAAATGAACAGCCTGCGTGCCGAGGATACCGCGGTATATTACTGTGCGGAACCGTTT
ACTGAGATTGACTACCGGGGTCAGGGAACCCTGGTCACCGTCTCGAGC

BMS2h-719-202 (SEQ ID NO: 823)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAAGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-203 (SEQ ID NO: 824)
GAGGTGCAGCTGTTGGAGTCTGGGGGAGGCTTGGTACAGCCTGGGGGGTCCCTGCGTCTC
TCCTGTGCAGCCTCCGGATTCACCTTTAACAGCTATGAGATGATGTGGGTCCGCCAGGCT
CCAGGGAAGGGTCTAGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-21 (SEQ ID NO: 825)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGATCCATTT
ACTGAGTTTGACTACTGGGGTCAGGGAACCCTGGTCACCGTCTCGAGC

BMS2h-719-213 (SEQ ID NO: 826)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGACCCGTTC
ACGGAGATGGACTACTGGGGTCATGGAACCCTGGTCACCGTCTCGAGC

BMS2h-719-214 (SEQ ID NO: 827)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGACCCGTTC
ACGGAGTTCGACTACTGGGGTCATGGAACCCTGGTCACCGTCTCGAGC

BMS2h-719-215 (SEQ ID NO: 828)
GAGGTGCAGCTGTTGGAGTCTGGGGGAGGCTTGGTACAGCCTGGGGGGTCCCTGCGTCTA
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAGCCGTTC
ACGGAGTTGGACTACTGGGGTCATGGAACCCTGGTCACCGTCTCGAGC

BMS2h-719-218 (SEQ ID NO: 829)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCC
CCAGGGAAGGGTCTGGAGTGGGTCTCATCGATTTCGTCCGACGGTTCTTCACGTACTAC
GCCGAGTCGGTCAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-225 (SEQ ID NO: 830)
GAGGTGCAGCTGTTGGAGTCTGGGGGAGGCTTGGTACAGCCTGGGGGGTCCCTGCGTCTC
TCCTGTGCAGCCTCCGGATTCACCTTTAACACGTATGAGATGCAGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-226 (SEQ ID NO: 831)
GAGGTGCAGCTGTTGGAGTCTGGGGGAGGCTTGGTACAGCCTGGGGGGTCCCTGCGTCTC
TCCTGTGCAGCCTCCGGATTCACCTTTAACAAGTATGAGATGATGTGGGCCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAGGAACACGCTGTAT
CTGCAAATGAACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-3 (SEQ ID NO: 832)
GAGGTGCAGCTGTCGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAATACGCTGTAT
CTGCAAATGAACAGCCTGCGTGCCGAGGATACCGCGGTATATTACTGTGCGGATCCGTTT
ACTGAGTTTGACTACTGGGGTCAGGGAACCCTGGTCACCGTCTCGAGC

BMS2h-719-4 (SEQ ID NO: 833)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGACT
CCAGGGAAGGGTCTGGAGTGGGTCTCATCTATTTCGTCGGATGGTTCTTTTACATACTAC
GCAGACTCCGTGAAGGGGCGGTTCACCATCTCCCGCGACAATTCCAAGAACACGCTGTAT
CTGCAAATGAACAGCCTGCGTGCCGAGGATACCCAGTATATTACTGTGCGGAACCGTTT
ACTGAGTTTGACTACTGGGGTCAGGGAACCCTGGTCACCGTCTCAAGC

BMS2h-719-5 (SEQ ID NO: 834)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGGAAATGAACAGCATGCGTGCCGAGGATACCGCGGTATATTACTGTGCGGAACCGTTT
ACTGAGTTTGACAACTGGGGTCAGGGAACCCTCGTCACCGTCTCGAGC

BMS2h-719-6 (SEQ ID NO: 835)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCAGAACCGTTT
ACTGAGTTTGACTACTGGGGTCAGGGAACCCAGGTCACCGTCTCGAGC

BMS2h-719-7 (SEQ ID NO: 836)
GAGGTGCAGCTGTTGGAGTCTGGGGGAGGCTTGGTACAGCCTGGGGGGTCCCTGCGTCTC
TCCTGTGCAGCCTCCGGATTCAACTTTAAGAGGTATGAGATGACGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCAGACCCGTTT
ACTGAGTTTGACTACTGGGGTCAGGGAACCCTGGTCACCGTCTCGAGC

BMS2h-719-8 (SEQ ID NO: 837)
GAGGTGCAGCTGTTGGAGTCTGGGGGAGACTTGGTACAGCCTGGGGGGTCCCTGCGTCTC
TCCTGTGCAGCCTCCGGATTCACCTTTAAGAGGTATGAGATGATGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCACGCGACAATTCCAAGAACACGCTGTAT
CTGCAAATGAACAGCCTGCGTGCCGAGGATACCGCGGTATATTACTGTGCGGAACCGTTT
ACTGAGTTTGACTACAGGGGTCAGGGAACCCTGGTCACCGTCTCGAGC

BMS2h-719-9 (SEQ ID NO: 838)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATGAGATGTCGTGGGTCCGCCAGGCT
CCAGGGAAGGGTCTGGAGTGGGTCTCATCTATTTCGTCGGATGGTTCTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAACCGTTT
ACTGAGTTTGACTACTGGGGTCGGGGAACCCTGGTCACCGTCTCGAGC

BMS2h-72 (SEQ ID NO: 839)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGCGTATCCTATGTCGTGGGTCCGCCAGGCT

TABLE 2-continued

Human Anti-CD40L VH Domain Encoding Nucleotide Sequences

CCAGGGAAGGGTCTAGAGTGGGTCTCAAGTATTTCCCCTCTTGGTTTGTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTTAGT
GCTGGGGCGGAGACTCATGTTTATCGGCTTTTTGACTACTGGGGTCAGGGAACCCTGGTC
ACCGTCTCGAGC

BMS2h-720 (SEQ ID NO: 840)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATTATGAGATGATGTGGGTCCGCCAGGCT
CCAGGGAAGGGTCTAGAGTGGGTCTCATCTATTGGGGTGTTGGGTCATACGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACTTATG
TCGTTGAGGACGTTTGAGAATCTTTTTGACTACTGGGGTCAGGGAACCCTGGTCACCGTC
TCGAGC

BMS2h-722 (SEQ ID NO: 841)
GAGGTGCAGCTGTTGGAGTCTGGGGGAGGCTTGGTACAGCCTGGGGGGTCCCTGCGTCTC
TCCTGTGCAGCCTCCGGATTCACCTTTACGAAGTATCCTATGGCTTGGGTCCGCCAGGCT
CCAGGGAAGGGTCTAGAGTGGGTCTCAGGTATTGATGCTAATGGTAATAGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGGGACT
TGGCGTAGGCATTTTGCGATTTTTGACTACTGGGTCAGGGAACCCTGGTCACCGTCTCG
AGC

BMS2h-723 (SEQ ID NO: 842)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCTGTATGATATGATGTGGGTCCGCCAGGCT
CCAGGGAAGGGTCTAGAGTGGGTCTCATCTATTTCTGATCTGGGTACGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAATGGT
TTTAGGGTTTACGAGTAATGATCGTAGGTTTGACTACTGGGGTCAGGGAACCCTGGTCACC
GTCTCGAGC

BMS2h-724 (SEQ ID NO: 843)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGGTGGGGATATGTGGTGGGTCCGCCAGGCT
CCAGGGAAGGGTCTAGAGTGGGTCTCAATGATTGAGGGTGGTGGTGTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACTTGAT
CTTCGGACGGGTCAGTTTGACTACTGGGGTCAGGGAACCCTGGTCACCGTCTCGAGC

BMS2h-725 (SEQ ID NO: 844)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACCGTCG
GATCCTACTAAGTTTGACTACTGGGGTCAGGGAACCCTGGTCACCGTCTCGAGC

BMS2h-725-1 (SEQ ID NO: 845)
GAGGTGCAGCTGTTGGAGTCTGGGGGAGGCTTGGTACAGCCTGGGGGGTCCCTGCATCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTTCTGTGCGGATCCGTCG
GATCCTACTAAGTTTGACTACTGGGGTCAGGGAACCCTGGTCACCGTCTCGAGC

BMS2h-725-10 (SEQ ID NO: 846)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGTGACAATTCCAAGAACACGCTGTAT
CTGCAAATGAACAGCCTGCGTGCCGAGGACACCGCGGTATATTACTGTGCGGATCCGTCG
GATCCTACTAAGTTTGACTACTGGGGTCAGGGAACCCTGGTCACCGTCTCGAGC

BMS2h-725-11 (SEQ ID NO: 847)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAGCAGCCTGCGTGCCGAGGACACCGCGGTATATTACTGTGCGGATCCGTCG
GATCCTACTAAGTTTGACTACTGGGGTCAGGGAACCCTGGTCACCGTCTCGAGC

BMS2h-725-12 (SEQ ID NO: 848)
GAGGTGCAGCTGTTGGAGTCTGGGGGTGGCTTGGTACAGCCTGGGGGGTCCCTGCGTCTC
TCCTGTGCAGCCTCCGGATTCACCTTCCCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACGATTCCAAGAACACGCTGTAT

TABLE 2-continued

Human Anti-CD40L VH Domain Encoding Nucleotide Sequences

CTGCAAATGAACAGCCTGCGTGTCGAGGACACCGCGGTATATTACTGTGCGGAACCGTCG
GATCCTACTATGTTTGTCTACTGGGGTCAGGGAACCCTTGTCACCGTCTCGAGC

BMS2h-725-13 (SEQ ID NO: 849)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGCTGGGTCCGCCAGGCT
CCAGGGAAGGGTCTGGAGTGGGTCTCTCTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACCGTCG
GATCCTACTATGTTTGTCTACTGGGGTCAGGGAACCCTGGTCACCGTCTCGAGC

BMS2h-725-14 (SEQ ID NO: 850)
GAGGTGCAGCTGTTGGAGTCTGGGGGAGGCTTGGTACAGCCTGGGGGGTCCCTGCGTCTC
TCCTGTGCAGCATCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGTGACAATTCCAAGAACACGCTGTAT
CTGCAAATGAACAGCCTGCGTGCCGAGGACACCGCGGTATATTACTGTGCGGATCCGTCA
GATCCTACTATGTTTGACTACTGGGGTCAGGGAACCCTGGTCACCGTCTCGAGC

BMS2h-725-15 (SEQ ID NO: 851)
GAGGTGCAGCTGTTGGAGTCTGGGGGGGGCATGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCATGCGTGCCGAGGACACCGCGGTATATTACTGTGCGGATCCGTCG
GATCCTACTAAGTTTGACTACTGGGGTCAGGGAACCCTGGTCACCGTCTCGAGC

BMS2h-725-16 (SEQ ID NO: 852)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCACACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACCGTCG
GATCCTACTATGTTTGACTACTGGGGTCAGGGAACCCTGGTCACCGTCTCGAGC

BMS2h-725-17 (SEQ ID NO: 853)
GAGGTGCAGCTGTTGGAGTCTGGGGGAGGCTTGGTGCAGCCTGGGGGTCCCTGCGTCTC
TCCTGTGCAGCCTCCGGATTCACCTTTACGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACACTGTAT
CTGCAAATGAACAGCCTGCGTGCCGAGGACACCGCGGTATATTACTGCGCGGAACCGTCG
GATCCTACTAAGTTAGACTACTGGGGTCAGGGAACCCTGGTCACCGTCTCGAGC

BMS2h-725-18 (SEQ ID NO: 854)
GAGGTGCAGCTGTCGGAGTCTGGGGGAGGCTTGGTACAGCCTGGGGGGTCCCTGCGTCTC
ACCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGATCCGTCG
GATCCTACTAAGTTTGTCTACTGGGGTCAGGGAACCCTGGTCACCGTCTCGAGC

BMS2h-725-19 (SEQ ID NO: 855)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCAGATCCGTCG
GATCCTACTAAGTTTGTCTACTGGGGTCAGGGAACCCTGGTCACCGTCTCGAGC

BMS2h-725-2 (SEQ ID NO: 856)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGCGCGGAACCGTCG
GATCCTACTAAGTTTGTCTACTGGGGTCAGGGAACCCCGGTCACCGTCTCGAGC

BMS2h-725-3 (SEQ ID NO: 857)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCGCTTATTGGGGATCGTGGTTCTTGGACATACTAC
GCAGACTCCGTGAAGGGCCGGTTCACCATCTCCCGCGACAATTCCAGGAACATGCTGTAT
CTGCAAATGAAAAGCCTGCGTGCCGAGGACACCGCGGTATATTACTGCGCGGATCCGTCG
GATCCTACTAAGTTTGTCTACTGGGGTCAAGGAACCCAGGTCACCGTCTCGAGC

BMS2h-725-4 (SEQ ID NO: 858)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT

TABLE 2-continued

Human Anti-CD40L VH Domain Encoding Nucleotide Sequences

CCAGGGAAGGGTCTGGAGTGGGTCTCACTTATTGGGGATCGTGGTTCTTGGACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGGATCCGTCG
GATCCTACTAAGTTTGTCTACTGGGGTCAGGGAACCCTGGTCACCGTCTCGAGC

BMS2h-725-5 (SEQ ID NO: 859)
GAGGTGCAGCTGTTGGAGTCTGGGGGAGGCTTGTTACAGCCTGGGGGGTCCCTGCGTCTC
TCCTGTGCAGCCTCCGGATTCACCTTTTCGGATTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGGAACCGTCG
GATCCTACTAAGTTCGACTACTGGGGTCGGGGAACCCTGGTCACCGTCTCGAGC

BMS2h-725-6 (SEQ ID NO: 860)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCACGCGACAATTCCAAGAACACGCTGTAT
CTGCAAATGAACAGCCTGCGTGCCGAGGACACCGCGGTATATTACTGTGCGGAACCGTCC
GATCCTACTAAGTTTGTCTACTGGGGTCAGGGAACCCTGGTCACCGTCTCGAGC

BMS2h-725-7 (SEQ ID NO: 861)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTACTTGGACATATTAC
GCAGACCCCGTGAAGGGCCGGTTCACCATCTCCGCGACAATTCCAAGAACACACTGTAT
CTGCAAATGAACAGCCTGCGTGCCGAGGACACTGCGGTATATTATTGTGCGGATCCGTCG
GATCCTACTAAGTTTGACTACTGGGGTCAGGGAACCCTGGTCACCGTCTCGAGC

BMS2h-725-8 (SEQ ID NO: 862)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCGTCTCCGCGACAATTCCAAGAACACGCTGTAT
CTGCAAATGAACAGCCTGCGTGCCGAGGACACCGCGGTATATTACTGTGCGGAACCGTCG
GATCCTACTAAGTTTGACTACTGGGGTCAGGGAACCCTGGTCACCGTCTCGAGC

BMS2h-725-9 (SEQ ID NO: 863)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTCCGCCAGGCT
CCAGGGATGGGTCTGGAGTGGGTCTCACTTATTGGGGATCGTGGTTCTTGGACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGGAACCGTCG
GATCCTACTAAGTTTGACTACTGGGGTCAGGGAACCCTGGTCACCGTCTCGAGC

BMS2h-726 (SEQ ID NO: 864)
GAGGTGCAGCTGTTGGAGTCTGGGGGAGGCTTGGTACAGCCCGGGGGGTCCCTGCGTCTC
TCCTGTGCAGCCTCCGGATTCACCTTTGATAATTATAAGTGTATTGGGTCCGCCAGGCT
CCAGGGAAGGGTCTGGAGTGGGTCTCAAGTATTTCGGAGATAGGTAATCTGACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGATAGCTCTG
ACGCGTTTTGACTACTGGGGTCAGGGAACCCTGGTCACCGTCTCGAGC

BMS2h-727 (SEQ ID NO: 865)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGAGTTATCGTATGTATTGGGTCCGCCAGGCT
CCAGGGAAGGGTCTGGAGTGGGTCTCATATATTGATCCGCCGGGTAGTCGTACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGAAAAGTTTG
AATTTGTCGTTTCCTTATATTAATTTTGACTACTGGGGTCAGGGAACCCTGGTCACCGTC
TCGAGC

BMS2h-728 (SEQ ID NO: 866)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCGGTATGAGATGTGTGGTCCGCCAGGCT
CCAGGGAAGGGTCTAGAGTGGGTCTCACGTATTTCTCATTCGGGTCGGACGACATACTAC
GCAGACTCCGTGAAGGGCCGGTTCACCATCTCCGCGACAATTCCAAGAACACGCTGTAT
CTGCAAATGAACAGCCTGCGTGCCGAGGACACCGCGGTATATTACTGTGCGCAATTGGAT
GGTCCGTTTGACTACTGGGGTCAGGGAACCCTGGTCACCGTCTCGAGC

BMS2h-729 (SEQ ID NO: 867)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGAGGTATTATATGGATTGGGTCCGCCAGGCT
CCAGGGAAGGGTCTAGAGTGGGTCTCAAGGATTAATCATAATGGTTCTGTTACATACTAC
GCAGACTCCGTGAAGGGCCGGTTCACCATCTCCGCGACAATTCCAAGAACACGCTGTAT
CTGCAAATGAACAGCCTGCGTGCCGAGGATACCGCGGTATATTACTGTGCGAAAATGCCG
CAGGGTACTTCTGATTGGTATTATTTTGACTACTGGGGTCAGGGAACCCTGGTCACCGTC
TCGAGC

TABLE 2-continued

Human Anti-CD40L VH Domain Encoding Nucleotide Sequences

BMS2h-73 (SEQ ID NO: 868)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTAAGTATGATATGTCTTGGGTCCGCCAGGCT
CCAGGGAAGGGTCTAGAGTGGGTCTCAACTATTCTGGAGGATGGTCTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
CGTTTGTTTGACTACTGGGGTCAGGGAACCCTGGTCACCGTCTCGAGC

BMS2h-74 (SEQ ID NO: 869)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGATTATCCTATGACGTGGGTCCGCCAGGCT
CCAGGGAAGGGTCTGGAGTGGGTCTCAACTATTCTGTCTCCGGGTACGGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTGAG
AAGGATTTTGACTACTGGGGTCAGGGAACCCTGGTCACCGTCTCGAGC

BMS2h-741 (SEQ ID NO: 870)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTGGTGAGATGGGTTGGGTCCGCCAGGCT
CCAGGGAAGGGTCTAGAGTGGGTCTCAATGATTCCGATGGATGGTAGTGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGGGT
GAGGTGTTTGACTACTGGGGTCAGGGAACCCTGGTCACCGTCTCGAGC

BMS2h-742 (SEQ ID NO: 871)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGGAGTATCATATGAAGTGGGCCCGCCAGGCT
CCAGGGAAGGGTCTAGAGTGGGTCTCAGGGATTAGTAGGGATGGTATGAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGATACAGCTT
GCTTTGTTTGACTACTGGGGTCAGGGAACCCTGGTCACCGTCTCGAGC

BMS2h-743 (SEQ ID NO: 872)
GAGGTGCAGCTGTTGGAGTCTGGGGGAGGCTTGGTACAGCCTGGGGGGTCCCTGCGCCTC
TCCTGTGCAGCCTCCGGATTCACCTTTCGTGATTATGAGATGCTTTGGGCCCGCCAGGCT
CCAGGGAAGGGTCTAGAGTGGGTCTCAGGTATTCTTCCGTCGGGTGGGGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCTGGT
TCGGGGAATGGGCCTATTCTTTTTGACTACTGGGGTCAGGGAACCCTGGTCACCGTCTCG
AGC

BMS2h-744 (SEQ ID NO: 873)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGAGCATGATATGTTTTGGGTCCGCCAGGCT
CCAGGGAAGGGTCTAGAGTGGGTCTCAGGGATTGGGGCTGAGGGTGTTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACCGACG
ATGTCTAATGGTTCTCAGTCGCGTTTTGACTACTGGGGTCAGGGAACCCTGGTCACCGTC
TCGAGC

BMS2h-745 (SEQ ID NO: 874)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-1 (SEQ ID NO: 875)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTTTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-10 (SEQ ID NO: 876)
GAGGTGCAGCTGTTGGAGTCTGGGGGAGGCTTGGTACAGCCTGGGGGGTCCCTTCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAACAACCTGCGTGCCGAAGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

TABLE 2-continued

Human Anti-CD40L VH Domain Encoding Nucleotide Sequences

BMS2h-745-11 (SEQ ID NO: 877)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGATCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTTCAAGAACACGCTGTAT
CTGCAGATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-12 (SEQ ID NO: 878)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCAGATTCCGTGAAGGGCCGGTTCACCATCTCCCGCGACAATTCCATGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGTCTACTGGGGTCAGGGAACCCTGGTCACC
GTCTCGAGC

BMS2h-745-13 (SEQ ID NO: 879)
GAGGTGCAGCTGTTGGAGTCTGGGGGAGGCTTGGTACAGCCTGGGGGGTCCTTGCGTCTC
TCCTGTGCAGCCTCCGGATTCACCTTTGATAACACTGAGATGGCTTGGATCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-14 (SEQ ID NO: 880)
GAGGTGCAGCTGTTGGAGTCTGGGGGAGGCTTGGTACAGCCTGGGGGGTCCCTGCGTCTC
TCCTGTGCAGCCTCCGGGTTCACCTTTGATAATACTGAGATGGCTTGGATCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCTGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-15 (SEQ ID NO: 881)
GAGGTGCAGCTGTTGGAGTCTGGGGGAGGCTTGGTACAGCCAGGGGGGTCCCTGCGTCTC
TCCTGTGCAGCCTCTGGATTCACCTTTGATAATACTGAGATGGCTTGGATCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTCCAAGAACGCGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCTGGGAACCCTGGTCACC
GTCTCGAGC

BMS2h-745-16 (SEQ ID NO: 882)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATACCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGTCTACTGGGGTCAGGGAACCCTGGTCACC
GTCTCGAGC

BMS2h-745-17 (SEQ ID NO: 883)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCCTGGATCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATTCCAAGAACAGGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGCACCCTGGTCACC
GTTTCGAGC

BMS2h-745-18 (SEQ ID NO: 884)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATCACTGTGCGAAAATTCGT
AATCTGCATTGGGATGTGGGGAGGCAGTTTGACTACTGGGGTCAGGGAACCCTCGTCACC
GTCTCGAGC

BMS2h-745-19 (SEQ ID NO: 885)
GAGGTGCAGCTGTTGGAGTCTGGGGGAGGCTTGGTACAGCCTGAGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT

TABLE 2-continued

Human Anti-CD40L VH Domain Encoding Nucleotide Sequences

AATCTGCATTGGGATGTGGGGAGGCAGTTTGACTACTGGGGTCAGGGAACCCTGGTCACC
GTCTCGAGC

BMS2h-745-2 (SEQ ID NO: 886)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTAGTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCAGAGGACTCCGCGGTATATTACTGTGCGAAAATTCGT
AATCTGCATTGGGATGTGGGGAGGCAGTTTGTCTACTGGGGTCAGGGAACCCTGGTCACC
GTCTCGAGC

BMS2h-745-3 (SEQ ID NO: 887)
GAGGTGCAGCTGTTGGAGTCTGGGGGAGGCTTGGTAGAGCCTGGGGGGTCCCTGCGTCTC
TCCTGTGCAGCCTCCGGATTCACCTTTGATAATACTGAGATGGCTTGGGTCCGCCAGGCT
CCTGGGAAGGGTCTCGAGTGGGTCTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAGCAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-4 (SEQ ID NO: 888)
GAGGTGCAGCTGTTGGAGTCTGGGGGAGGCCTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTAGTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATCACTGTGCGAAAATTCGT
AATCTGCATTGGGATGTGGGGAGGCAGTTTGACTACTGGGGTCAGGGAACCCTGGTCACC
GTCTCGAGC

BMS2h-745-5 (SEQ ID NO: 889)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCTGACTCCGTGAAGGGCCGGTTCATCATCTCCCGCGACAATTCCAAGAACACGCTGAAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-6 (SEQ ID NO: 890)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGATCCGCCAGGCT
CCAGGGAGGGGTCTAGAGTGGGTCTCAGGTGTTACTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAATTTGACTACTGGGGTCAGGGAACCCTGGTCACC
GTCTCGAGC

BMS2h-745-7 (SEQ ID NO: 891)
GAGGTGCAGCTGTTGGAGTCAGGGGGAGGCTTGGTACAGCCTGGGGGGTCCCTGCGTCTC
TCCTGTGAAGCCTCCGGATTCACCTTTGATAATACTGAGATGGCTTGGATCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATACCAAGAACACGCTGTAT
CTGCAAATGAACAGCCTGCGTGCCGAGGACACCGCGGTATATTATTGTGCGAAAATTCGT
AATCTGCATTGGGATGTGGGGAGGCAGTTTGACTACTGGGGTCAGGGAACCCTGGTCACC
GTCTCGAGT

BMS2h-745-8 (SEQ ID NO: 892)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGATCCGCCAGGCT
CCAGGGAAGGGTCTAGAGTGGGTCTCAGGTATTACTGAGGATGGATCGTACATACTAC
GCAGACTCCGTGAAGGGCCGGTTCACCATCTCCCGCGACAATTCCAAGAGCTCGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCCAGC

BMS2h-745-9 (SEQ ID NO: 893)
GAGGTGCAGCTGTTGGAGTCTGGGGGAGGCTCGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTACTGAGGATGGTAATCGTACATACTAC
GCAGACTCCGTGAAGGGCCGGTTCACCATCTCCCGCGACAATTCCAAGAACACTCTGTAT
CTGCAAATGAACAGCCTGCGTGCCGAGGACACCGCGGTATATTACTGTGCGAAAATTCGT
AATCTGCATTGGGATGTGGGGAGGCAGTTTGTCTACTGGGGTCAGGGAACCCTGGTCACC
GTCTCGAGC

BMS2h-746 (SEQ ID NO: 894)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGTCGGCTGAGATGGGGTGGGTCCGCCAGGCT

TABLE 2-continued

Human Anti-CD40L VH Domain Encoding Nucleotide Sequences

CCAGGGAAGGGTCTAGAGTGGGTCTCAGGTATTTCGAGGCCTGGTCAGGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-747 (SEQ ID NO: 895)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGATGGTACTATGGGTGGGCCCGCCAGGCT
CCAGGGAAGGGTCTAGAGTGGGTCTCACTTATTTTGCCGTCGGGTAGTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATTCG
CTGACTAATCGTCCGTTTGACTACTGGGGTCAGGGAACCCTGGTCACCGTCTCGAGC

BMS2h-748 (SEQ ID NO: 896)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAAGTATGATATGCGGTGGGCCCGCCAGGCT
CCAGGGAAGGGTCTAGAGTGGGTCTCAGATATTGATGCTGTTGGTACTCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGATACCGGGG
GGGACGTTTGACTACTGGGGTCAGGGAACCCTGGTCACCGTCTCGAGC

BMS2h-749 (SEQ ID NO: 897)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGATGTATGGTATGATGTGGGCCCGCCAGGCT
CCAGGGAAGGGTCTAGAGTGGGTCTCATCTATTGAGGGTGCGGGTCATGCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACTGCGGTATATTACTGTGCGATAGTGCTT
GGTATGTTTGACTACTGGGGTCAGGGAACCCTGGTCACCGTCTCGAGC

BMS2h-75 (SEQ ID NO: 898)
GAGGTGCAGCTGTTGGAGTCTGGGGGAGGCTTGGTACAGCCTGGGGGGTCCCTGCGTCTC
TCCTGTGCAGCCTCCGGATTCACCTTTTTGCAGTATCCGATGGGTTGGGTCCGCCAGGCT
CCAGGGAAGGGTCTAGAGTGGGTCTCAACTATTTCTCCTGTTGGTTTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATTGTTT
GAGGGGTCGAGGATTCAGCGTGATGTGGGTTTTGACTACTGGGGTCAGGGAACCCTGGTC
ACCGTCTCGAGC

BMS2h-750 (SEQ ID NO: 899)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGAAGTATCAGATGGGTTGGGCCCGCCAGGCT
CCAGGGAAGGGTCTAGAGTGGGTCTCATCGATTCGGGGGTCTGGTCTTGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTGCAT
ACTACGCTGCATACGGAGGTGATTGGGTTTGACTACTGGGGTCAGGGAACCCTGGTCACC
GTCTCGAGC

BMS2h-751 (SEQ ID NO: 900)
GAGGTGCAGCTGTTGGAGTCTGGGGGAGGCTTGGTACAGCCTGGGGGGGTCCCTGCGTCTC
TCCTGTGCAGCCTCCGGATTCACCTTTAGTCAGTATACGATGTATTGGGCCCGCCAGGCT
CCAGGGAAGGGTCTAGAGTGGGTCTCAGAGATTTCTCATAGTGGTTCTAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGATATCGGGG
CTGCATTTTGACTACTGGGGTCAGGGAACCCTGGTCACCGTCTCGAGC

BMS2h-752 (SEQ ID NO: 901)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGATTATGCGATGGCTTGGGTCCGCCAGGCT
CCAGGGAAGGGTCTGGAGTGGGTCTCACGTATTGGTGTGGAGGGTGGGGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGTTG
CGGCTTTATCGTCTGGGGTTTGACTACTGGGGTCAGGGAACCCTGGTCACCGTCTCGAGC

BMS2h-753 (SEQ ID NO: 902)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTAAGTATGATATGACGTGGGTCCGCCAGGCT
CCAGGGAAGGGTCTAGAGTGGGTCTCAAAGATTAATTCTGATGGTGGTCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGTTG
CATGGTAGGGGGTTTGTTATTTTTGACTACTGGGGTCAGGGAACCCTGGTCACCGTCTCG
AGC

BMS2h-754 (SEQ ID NO: 903)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGCGGTATGATATGGTGTGGGTCCGCCAGGCT
CCAGGGAAGGGTCTAGAGTGGGTCTCACGGATTAATTCTATGGGTCTGGCTACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGATACCGCGGTATATTACTGTGCGAAAGATTAT
TCGGTTGCGCCGCATGGGTATCCTTTGGGTTTTGACTACTGGGGTCAGGGAACCCTGGTC
ACCGTCTCGAGC

BMS2h-755 (SEQ ID NO: 904)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGATTATTCGATGATGTGGGTCCGCCAGGCT
CCAGGGAAGGGTCTAGAGTGGGTCTCAACGATTACTGATAATGGTACGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATATG
TCGCTTGCTACTTATCTGCAGTTTTTTGACTACTGGGGTCAGGGAACCCTGGTCACCGTC
TCGAGC

BMS2h-756 (SEQ ID NO: 905)
GAGGTGCAGCTGTTGGAGTCTGGGGGAGGCTTGGTACAGCCTGGGGGGTCCCTGCGTCTC
TCCTGTGCAGCCTCCGGATTCACCTTTATGGAGTATGATATGCTTTGGGTCCGCCAGGCT
CCAGGGAAGGCTCTAGAGTGGGTCTCACGTATTTCGTCGGATGGTCTTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGTG
AGTGCGCTTGCTCCTTTTGATATTGGTTTTGACTACTGGGGTCAGGGAACCCTGGTCACC
GTCTCGAGC

BMS2h-757 (SEQ ID NO: 906)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGAGTATAATATGGCTTGGGTCCGCCAGGCT
CCAGGGAAGGGTCTGGAGTGGGTCTCAAGTATTAATTTTGCTGGTCGGACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTGTCT
CTTCCTTTTGGATATTTTTCTTTTGACTACTGGGGTCAGGGAACCCTGGTCACCGTCTCG
AGC

BMS2h-758 (SEQ ID NO: 907)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
GGTTATTTTGACTACTGGGGTCAGGGAACCCTGGTCACCGTCTCGAGC

BMS2h-758-1 (SEQ ID NO: 908)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACATGCTGTAT
CTGCGAATGAACAGCCTGCGTGCCGAGGACACCGCGGTATATTACTGTGCGGAAACTAGT
GGTTATTATGAATACTGGGGTCAGGGAACCCTGGTCACCGTCTCGAGC

BMS2h-758-2 (SEQ ID NO: 909)
GAGGTGCAGCTGTTGGAGTCTGGGGGAGGCTTGGTACAGCCTGGGGGGTCCCTGCGCCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
GGTTATTTTGAATACTGGGGTCAGGGAACCCTGGTCACCGTCTCGAGC

BMS2h-758-3 (SEQ ID NO: 910)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCC
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
AGTTATTTTGAATACTGGGGTCAGGGAACCCTGGTCACCGTCTCGAGC

BMS2h-758-4 (SEQ ID NO: 911)
GAGGTGCAGCTGTTGGAGTCTGGGGGAGGCTTGGTACAGCCTGGGGGGTCCCTGCGTCTC
TCCTGTGCAGCCTCCGGGTTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTTT
CTGCAAATGAACAGCCTGCGTGCCGAGGACACCGCGGTATATTACTGTGCGGAAACTAGT
GGTTATTATGAGTACTGGGGTCATGGAACCCTGGTCACCGTCTCGAGC

BMS2h-758-5 (SEQ ID NO: 912)
GAGGTGCAGCTGTTGGAGTCTGGGGGAGGCTTGGTCCAGCCTGGGGGGTCCCTGCGTCTC
TCCTGTGCTGCCTCCGGATTCGCCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
GGTTATTTTGAATACTGGGGTCAGGGAACCCTGGTCACCGTCTCGAGC

TABLE 2-continued

Human Anti-CD40L VH Domain Encoding Nucleotide Sequences

BMS2h-758-6 (SEQ ID NO: 913)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTATATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
GGTTACTTTGAATACTGGGGTCAGGGAACCCTGGTCACCGTCTCGAGC

BMS2h-759 (SEQ ID NO: 914)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGGAGTATGTTATGGGGTGGGTCCGCCAGGCT
CCAGGGAAGGGTCTAGAGTGGGTCTCAACTATTAATGGTTTGGGTAATGTTACATACTAC
GCAGACTCCGTGAAGGGCCGGTTCACCATCTCCCGCGACAATACCAAGAACACGCTGTAT
CTGCAAATGAACAGCCTGCGTGCCGAGGAGACCGCGGTATATTACTGTGCGATACAGCTG
CCTAATTTTGACTACTGGGGTCAGGGAACCCTGGTCACCGTCTCGAGC

BMS2h-760 (SEQ ID NO: 915)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATGATGGGATGTGGTGGGTCCGCCAGGCT
CCAGGGAAGGGTCTAGAGTGGGTCTCATTTATTAATGTTGATGGTAGGGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAATGGTCT
CCTGGGCGGGTTCAGTTTGACTACTGGGGTCAGGGAACCCTGGTCACCGTCTCGAGC

BMS2h-761 (SEQ ID NO: 916)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGGTTGGGATATGGCGTGGGTCCGCCAGGCT
CCAGGGAAGGGTCTAGAGTGGGTCTCAAGTATTGCTCATGAGGGTGGTGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATGTT
CCTGGGTCTCCTCTGTTTGACTACTGGGGTCAGAGAACCCTGGTCACCGTCTCGAGC

BMS2h-762 (SEQ ID NO: 917)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCAGGGTTGGATGTATTGGGTCCGCCAGGCT
CCAGGGAAGGGTCTAGAGTGGGTCTCAGGGATTGTTCGAATGGTCCTCGGACATCCTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGGGG
GAGTATTTTGACTACTGGGGTCAGGGAACCCTGGTCACCGTCTCGAGC

BMS2h-763 (SEQ ID NO: 918)
GAGGTGCAGCTGTTGGAGTCTGGGGGAGGCTTGGTACAGCCTGGGGGGTCCCTGCGTCTC
TCCTGTGCAGCCTCCGGATTCACCTTTAGGCAGAGTGATATGTGGTCCGCCAGGCT
CCAGGGAAGGGTCTAGAGTGGGTCTCAGTTATTGGTAATAATGGTGAGTTTACATACTAC
GCAGACTCGGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATAAT
TGGCTGTTGTTTGACTACTGGGGTCAGGGAACCCTGGTCACCGTCTCGAGC

BMS2h-764 (SEQ ID NO: 919)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCTTAGTACTATGTATTGGGTCCGCCAGGCT
CCAGGGAAGGGTCTCAACTATTGGTGGGATGGTAGTCATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGGAAGGTACG
CAGTATTTTGACTACTGGGGTCAGGGAACCCTGGTCACCGTCTCGAGC

BMS2h-765 (SEQ ID NO: 920)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCGTATACGATGGAGTGGGTCCGCCAGGCT
CCAGGGAAGGGTCTAGAGTGGGTCTCAAGTATTGGGGTTACGGGTTATGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTGGT
CAGGGTTTTGACTACTGGGGTCAGGGAACCCTGGTCACCGTCTCGAGC

BMS2h-766 (SEQ ID NO: 921)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGATTATGGGATGTCTTGGGTCCGCCAGGCT
CCAGGGAAGGGTCTAGAGTGGGTCTCATATATTGATCCTCTGGGTCGTCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGATTTG
TCGTCGCTGCAGTATGGGGTGTCGCCTAATTTTGACTACTGGGGTCAGGGAACCCTGGTC
ACCGTCTCGAGC

BMS2h-767 (SEQ ID NO: 922)
GAGGTGCAGCTGTTGGAGTCTGGGGGAGGCTTGGTACAGCCTGGGGGGTCCCTGCGTCTC
TCCTGTGCAGCCTCCGGATTCACCTTTTTTCATTATTCTATGAGTTGGGTCCGCCAGGCT
CCAGGGAAGGGTCTAGAGTGGGTCTCATCTATTGGTCCGGTTGGTCGGGAGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATGATT
CAGTCGCCGTTGTTTAAGGATTTTGACTACTGGGGTCAGGGAACCCTGGTCACCGTCTCG
AGC

BMS2h-768 (SEQ ID NO: 923)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGTGGTATGATATGTATTGGGTCCGCCAGGCT
CCAGGGAAGGGTCTAGAGTGGGTCTCACGTATTGATAGTGGGGGTAATCAGACATACTAC
GCAGACTCCGTGAAGGGCCGGTTCACCATCTCCCGCGACAATTCCAAGAACACGCTGTAT
CTGCAAATGAATAGCCTGCGTGCCGAGGACACCGCGGTATATTACTGTGCGGAAGCGTCG
CTTTGGAAGTGGAGGTTGTTTGACTACTGGGGTCAGGGAACCCTGGTCACCGTCTCGAGC

BMS2h-77 (SEQ ID NO: 924)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGGTATGGCGTGGGTCCGCCAGGCT
CCAGGGAAGGGTCTAGAGTGGGTCTCAACTATTTCTCCGCTGGGTATTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATGCT
ACGTCTCAGGAGTCTTTGCGGTCTTTTGACTACTGGGGTCAGGGAACCCTGGTCACCGTC
TCGAGC

BMS2h-770 (SEQ ID NO: 925)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAAGTATGAGATGATGTGGGTCCGCCAGGCT
CCAGGGAAGGGTCTAGAGTGGGTCTCAGCTATTAGTGGTAGTGGTGGTAGCACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCCT
CTGCCTGATGCGTTTTGGACTAGGGGTTTTGACTACTGGGGTCAGGGAACCCTGGTCACC
GTCTCGAGC

BMS2h-771 (SEQ ID NO: 926)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTACTTATTCTATGGCGTGGGTCCGCCAGGCT
CCAGGGAAGGGTCTAGAGTGGGTCTCAACTATTGATCGGCATGGTTTGGCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACTCCT
GGTTCTTCTTGGCAGACTGTTTTTGGCTACTGGGGTCAGGGAACCCTGGTCACCGTCTCG
AGC

BMS2h-772 (SEQ ID NO: 927)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGTCGTATCCTATGGGTTGGGTCCGCCAGGCT
CCAGGGAAGGGTCTAGAGTGGGTCTCAAGTATTGATCATCATGGTCATTCGACATACTAC
GCAGACTCCGCGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGCTT
AGGGTTTCGATGATTTTTGGTTTTGACTACTGGGGTCAGGGAACCCTGGTCACCGTCTCG
AGC

BMS2h-773 (SEQ ID NO: 928)
GAGGTGCAGCTGTTGGAGTCTGGGGGAGGCTTGGTACAGCCTGGGGGGTCCCTGCGTCTC
TCCTGTGCAGCCTCCGGATTCACCTTTGTGCAGTATGGGATGAGTCGGCCGCCAGGCT
CCAGGGAAGGGTCTAGAGTGGGTCTCATGGATTAGTAGTAGTGGTACGTATACATACTAC
GCAGACTCCGTGAAGGGCCGGTTCACCATCTCCCGCGACAATTCCAAGAACACGCTGTAT
CTGCAAATGAACAGCCTACGTGCCGAGGACACCGCGGTATATTACTGTGCGGAAACGTCT
AGGATGTTTGACTACTGGGGTCAGGGAACCCTGGTCACCGTCTCGAGC

BMS2h-774 (SEQ ID NO: 929)
GAGGTGCAGCTGTTGGAGTCTGGGGGAGGCTTGGTACAGCCTGGGGGGTCCCTGCGTCTC
TCCTGTGCGGCCTCCGGATTCACCTTTCGGGAGTATGATATGGGTTGGGTCCGCCAGGCT
CCAGGGAAGGGTCTAGAGTGGGTCTCACTTATTTCGCCTCCTGGTCGTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGTTGTG
ATTTGGGTTATACGAATAGGTTTGACTACTGGGGTCAGGGAACCCTGGTCACCGTCTCG
AGC

BMS2h-775 (SEQ ID NO: 930)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTAATTACGGGATGTTGTGGGTCCGCCAGGCT
CCAGGGAAGGGTCTAGAGTGGGTCTCATCGATTAATTCTTCGGGTATGGAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATTTTTT
CGTCTGAATGATCATAATTCTGTGTTTGGTTTTGACTACTGGGGTCAGGGAACCCTGGTC
ACCGTCTCGAGC

BMS2h-776 (SEQ ID NO: 931)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGATTATAAGATGATGTGGATCCGCCAGGCT

TABLE 2-continued

Human Anti-CD40L VH Domain Encoding Nucleotide Sequences

CCAGGGAAGGGTCTAGAGTGGGTCTCATCGATTGTTGGGTCTGGTTCGATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGCCT
GGTTATTTTGACTACTGGGGTCAGGGAACCCTGGTCACCGTCTCGAGC

BMS2h-777 (SEQ ID NO: 932)
GAGGTGCAGCTGTTGGAGTCTGGGGGAGGCTTGGTACAGCCTGGGGGGTCCCTGCGTCTC
TCCTGTGCAGCCTCCGGATTCACCTTTCATAATTATGCTATGGGTGGGTCCGCCGGGCT
CCAGGGAAGGGTCTAGAGTGGGTCTCAAGTATTGATGAGCATGGTACTATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATAGT
CTGGATCGGGTTTGGATTTTTGACTACTGGGGTCAGGGAACCCTGGTCACCGTCTCGAGC

BMS2h-778 (SEQ ID NO: 933)
GAGGTGCAGCTGTTGGAGTCTGGGGGGGGCTTGGTACAGCCTGGGGGGTCCCTGCGTCTC
TCCTGTGCAGCCTCCGGATTCACCTTTGCTGATTATCCGATGACTTGGGTCCGCCAGGCT
CCAGGGAAGGGTCTAGAGTGGGTCTCAAGTATTTATTCTGCGGGTTCTCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAACTTTAT
CATCGGGAGCCGATTCTTTTTGGGTTTGACTACTGGGGTCAGGGAACCCTGGTCACCGTC
TCGAGC

BMS2h-78 (SEQ ID NO: 934)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGAGGTATCAGATGGCGTGGGTCCGCCAGGCT
CCGGGGAAGGGTCTAGAGTGGGTCTCAACGATTAGTTCTGATGGTGGGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGGT
CATCGGTTTGACTACTGGGGTCAGGGAACCCTGGTCACCGTCTCGAGC

BMS2h-780 (SEQ ID NO: 935)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTTCTTATACTATGATGTGGGTCCGCCAGGCT
CCAGGGAAGGGTCTAGAGTGGGTCTCAGAGATTGATCGGACGGGTGAGCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACCTGGG
TTTGCTTCTCTTCCTTTTGACTACTGGGGTCAGGGAACCCTGGTCACCGTCTCGAGC

BMS2h-781 (SEQ ID NO: 936)
GAGGTGCAGCTGTTGGAGTCTGGGGGAGGCTTGGTACAGCCTGGGGGGTCCCTGCGTCTC
TCCTGTGCAGCCTCCGGATTCACCTTTACGGATTATACTATGTATTGGGTCCGCCAGGCT
CCAGGGAAGGGTCTAGAGTGGGTCTCAAAGATTTCTCCGAGTGGTCGTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGATCCG
TTTGGGTTTGACTACTGGGGTCAGGGAACCCTGGTCACCGTCTCGAGC

BMS2h-782 (SEQ ID NO: 937)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGATGCGGAGATGTTTTGGGTCCGCCAGGCT
CCAGGGAAGGGTCTAGAGTGGGTCTCATCTATTGATGCTCGTGGTTTGACGACATACTAC
GCAGACCCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGCGACG
TCGGCTATGTATCCTTTTGACTACTGGGGTCAGGGAACCCTGGTCACCGTCTCGAGC

BMS2h-783 (SEQ ID NO: 938)
GAGGTGCAGCTGTTGGAGTCTGGGGGAGGCTTGGTACAGCCTGGGGGGTCCCTGCGTCTC
TCCTGTGCAGCCTCCGGATTCACCTTTCGTGATTATGATATGGGTTGGGTCCGCCAGGCT
CCAGGGAAGGGTCTAGAGTGGGTCTCAACTATTTCTCCTCTTGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATCTGGG
TTTCATGAGTATACTGAGGGGTTTGACTACTGGGGTCAGGGAACCCTGGTCACCGTCTCG
AGC

BMS2h-784 (SEQ ID NO: 939)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCGTGCGGGTATGGGTGGGTCCGCCAGGCT
CCAGGGAAGGGTCTAGAGTGGGTCTCACTGATTGGGCGTGGTGGTGATATTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-80 (SEQ ID NO: 940)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTCGTTATCAGATGGCTTGGGTCCGCCAGGCT
CCAGGGAAGGGTCTAGAGTGGGTCTCATCTATTTCTTCTGATGGTGGGGGGACATACTAC
GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAACCGTCT
CGTCGGTTTGACTACTGGGGTCAGGGAACCCTGGTCACCGTCTCGAGC

BMS2h-81 (SEQ ID NO: 941)
GAGGTGCAGCTGTTGGAGTCTGGGGGAGGCTTGGTACAGCCTGGGGGGTCCTGCGTCTC
TCCTGTGCAGCCTCCGGATTCACCTTTGAGTTGTATCCGATGGCGTGGGTCCGCCAGGCT
CCAGGGAAGGGTCTGGAGTGGGTCTCATCGATTTCTCCGGTTGGTTTTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGGGCAT
GAGGGGTCGTATACTCCGCGGTCGGCTTTTGACTACTGGGGTCAGGGAACCCTGGTCACC
GTCTCGAGC

BMS2h-82 (SEQ ID NO: 942)
GAGGTGCAGCTGTTGGAGTCTGGGGGAGGCTTGGTACAGCCTGGGGGGTCCTGCGTCTC
TCCTGTGCAGCCTCCGGATTCACCTTTGTGGCGTATCCTATGCGTGGGTCCGCCAGGCT
CCAGGGAAGGGTCTGGAGTGGGTCTCAACTATTGCGCCTCTGGGTGGTAATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACGGCCG
GAGGGGCTGCAGATTGATTCTCAGAATTTTGACTACTGGGGTCAGGGAACCCTGGTCACC
GTCTCGAGC

BMS2h-83 (SEQ ID NO: 943)
GAGGTGCAGCTGTTGGAGTCTGGGGGAGGCTTGGTACAGCCTGGGGGGTCCTGCGTCTC
TCCTGTGCAGCCTCCGGATTCACCTTTGCGTTGTATCAGATGGCTTGGGTCCGCCAGGCT
CCAGGGAAGGGTCTAGAGTGGGTCTCATCGATTGATTCTTCTGGTAGTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAG
CGTGATTTTGACTACTGGGGTCAGGGAACCCTGGTCACCGTCTCGAGC

BMS2h-84 (SEQ ID NO: 944)
GAGGTGCAGCTGTTGGAGTCTGGGGGAGGCTTGGTACAGCCTGGGGGGTCCTGCGTCTC
TCCTGTGCAGCCTCCGGATTCACCTTTAGGCAGTACCAGATGGCTTGGGCCCGCCAGGCT
CCAGGGAAGGGTCTAGAGTGGGTCTCAACGATTGCGTCGGATGGTGTTTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGT
CGTGATTTTGACTACTGGGGTCAGGGAACCCTGGTCACCGTCTCGAGC

BMS2h-85 (SEQ ID NO: 945)
GAGGTGCAGCTGTTGGAGTCTGGGGGAGGCTTGGTACAGCCTGGGGGGTCCTGCGTCTC
TCCTGTGCAGCCTCCGGATTCACCTTTGAGCAGTATGATATGAGGTGGGTCCGCCAGGCT
CCAGGGAAGGGTCTAGAGTGGGTCTCATGGATTGATGAGGCGGGTCATGAGACATACTAT
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGATG
GATGGGTTTGACTACTGGGGTCAGGGAACCCTGGTCACCGTCTCGAGC

BMS2h-92 (SEQ ID NO: 946)
GAGGTGCAGCTGTTGGAGTCTGGGGGAGGCTTGGTACAGCCTGGGGGGTCCTGCGTCTC
TCCTGTGCAGCCTCCGGATTCACCTTTGTTGATTATCCGATGGGTTGGGTCCGCCAGGCT
CCAGGGAAGGGTCTAGAGTGGGTCTCAACGATTTCTACGGGGGGTTTTTCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGCGG
TATTATTATCTTAGTCAGATTAAGAATTTTGACTACTGGGGTCAGGGAACCCTGGTCACC
GTCTCGAGC

BMS2h-93 (SEQ ID NO: 947)
GAGGTGCAGCTGTTGGAGTCTGGGGGAGGCTTGGTACAGCCTGGGGGGTCCTGCGTCTC
TCCTGTGCAGCCTCCGGATTCACCTTTGATATTTATGGGATGACTTGGGTCCGCCAGGCT
CCAGGGAAGGGTCTGGAGTGGGTCTCAAGTATTTCGCCTCTTGGTCTTGTTACATACTAC
GCAGACCCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTGAAG
GAGCATGGGGATGTTCCTTTTGACTACTGGGGTCAGGGAACCCTGGTCACCGTCTCGAGC

BMS2h-94 (SEQ ID NO: 948)
GAGGTGCAGCTGTTGGAGTCTGGGGGAGGCTTGGTACAGCCTGGGGGGTCCTGCGTCTC
TCCTGTGCAGCCTCCGGATTCACCTTTGAGCTTTATCCGATGATTTGGGTCCGCCAGGCT
CCAGGGAAGGGTCTAGAGTGGGTCTCAACTATTTCTCCTACGGGTTTGTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTAAG
AGGAGTGGGAAGACTGATGATACTAATTTTGACTACTGGGGTCAGGGAACCCTGGTCACC
GTCTCGAGC

BMS2h-95 (SEQ ID NO: 949)
GAGGTGCAGCTGTTGGAGTCTGGGGGAGGCTTGGTACAGCCTGGGGGGTCCTGCGTCTC
TCCTGTGCAGCCTCCGGATTCACCTTTCGGGAGTATGATATGCTGTGGGTCCGCCAGGCT
CCAGGGAAGGGTCTAGAGTGGGTCTCAACGATTGTGGGGATGGTAATGGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACAGGAT
CGTCAGTTTGACTACTGGGGTCAGGGAACCCTGGTCACCGTCTCGAGC

TABLE 2-continued

Human Anti-CD40L VH Domain Encoding Nucleotide Sequences

BMS2h-97 (SEQ ID NO: 950)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGGTATGAGTTGGGTCCGCCAGGCT
CCAGGGAAGGGTCTAGAGTGGGTCTCAACGATTTCGCCTATTGGTGTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAAATGCT
TATGATCGGAAGTCTAATTTTGACTACTGGGGTCAGGGAACCCTGGTCACCGTCTCGAGC

BMS2h-98 (SEQ ID NO: 951)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCGGTATGTGATGGTGTGGGTCCGCCAGGCT
CCAGGGAAGGATCTAGAGTGGGTCTCAGGTATTACTCCGAGTGGTAGGAGGACATACTAC
GCAGACTCCGTGAAGGGCCGGTTCACCATCTCCCGCGACAATTCCAAGGACACGCTGTAT
CTGCAAATGAACAGCCTGCGTGCCGAGGACACCGCGGTATATTACTGTGCGAAAGTGTTG
GGGCGTCATTTTGATCCTCTTCTGCCTTCGTTTGACTACTGGGGTCAGGGAACCCTGGTC
ACCGTCTCGAGC

BMS2h-99 (SEQ ID NO: 952)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTATGCTATGAGTTGGGTCCGCCAGGCT
CCAGGGAAGGGTCTAGAGTGGGTCTCAACTATTACTCCGGGTGGTTTTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAACGTCT
AGTGGGGAGTTGCAGTTGGTTGAGGATTTTGACTACTGGGGTCAGGGAACCCTGGTCACC
GTCTCGAGC

TABLE 3

Anti-human CD40L VK Domain Amino Acid Sequences

BMS2h-100 (SEQ ID NO: 953)
DIQMTQSPSS LSASVGDRVT ITCRASQNIK HSLRWYQQKP GKAPRLLIYH RSQLQSGVPS
RFSGSGSGTD FTLTISSLQP EDFATYYCQQ VRHRPYTFGQ GTKVEIKR

BMS2h-101 (SEQ ID NO: 954)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VALFPYTFGQ GTKVEIKR

BMS2h-102 (SEQ ID NO: 955)
DIQMTQSPSS LSASVGDRVT ITCRASQHIG HHLRWYQQKP GKAPKLLIYH RSHLQSGVPS
RFSGSGSGTD FTLTISSLQP EDSATYYCQQ WDRPPYTFGQ GTKVEIKR

BMS2h-103 (SEQ ID NO: 956)
DIQMTQSPSS LSASVGDRVT ITCRASQAIG HRLRWYQQKP GKAPKLLIYH
RSKLQSGVPS RFSGSGSGTD FTLTISSLQP EDFATYYCQQ VRAVPYTFGQ GTKVEIKR

BMS2h-104 (SEQ ID NO: 957)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VRFSPYTFGQ GTKVEIKR

BMS2h-105 (SEQ ID NO: 958)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ SYARPVTFGQ GTKVEIKR

BMS2h-106 (SEQ ID NO: 959)
DIQMTQSPSS LSASVGDRVT ITCRASQSIN HRLYWYQQKP GKAPKLLIYH RSRLQSGVPS
RFSGSGSGTD FTLTISSLQP EDFATYYCQQ YKVRPNTFGQ GTKVEIKR

BMS2h-107 (SEQ ID NO: 960)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ TYSSPHTFGQ GTKVEIKR

BMS2h-108 (SEQ ID NO: 961)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ RAVRPFTFGQ GTKVEIKR

BMS2h-109 (SEQ ID NO: 962)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ TYYRPLTFGQ GTKVEIKR

BMS2h-110 (SEQ ID NO: 963)
DIQMTQSPAS LSASVGDRVT ITCRASQDID PMLRWYQQKP GKAPKLLIYA GSILQSGVPS
RFSGSGSGTD FTLTISSLQP EDFATYYCQQ TSIRPYTFGQ GTKVEIKR

TABLE 3-continued

Anti-human CD40L VK Domain Amino Acid Sequences

BMS2h-116 (SEQ ID NO: 964)
DIQMTQSPSS LSASVGDRVT ITCRASQPIG PDLLWYQQKP GKAPKLLIYQ TSILQSGVPS
RFSGSGSGTD FTLTISSLQP EDFATYYCQQ YWAFPVTFGQ GTKVEIKR

BMS2h-116-1 (SEQ ID NO: 965)
DIQMTQSPSS LSASVGDRVT ITCRASQPIG PDILWYQQKP GKAPKLLIYQ TSILQSGVPS
RFSGSESGTD FTLTISSLQP EDFATYYCQQ YWAFPVTFGQ GTKVEIKR

BMS2h-116-10 (SEQ ID NO: 966)
DIQITQSPSS LSASVGDRVT ITCRASQPIG PDLLWYQQKP GKAPKLLIYQ TSILRSGVPS
RFSGSGSGTD FTLTISSLQP EDLATYYCQQ YWAFPVTFGQ GTKVEIKR

BMS2h-116-11 (SEQ ID NO: 967)
DIQMTQSPSS LSASVGDRVT ITCRASQPIG PDLLWYQQKP GKAPKLLIYQ TSILRSGVPS
RFSGRGSGTD FTLTISSLQP EDFATYYCQQ YWAFPVTFGQ GTKVEIKR

BMS2h-116-12 (SEQ ID NO: 968)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWTFPVTFGQ GTKVEIKR

BMS2h-116-13 (SEQ ID NO: 969)
DIQMTQSPSS LSASVGDRVT ITCRASQPIG PDLLWYQQKP GKAPKLLIYQ TSILRSGVPS
RFSGSGSETD FTLTISNLQP EDFATYYCQQ YWAFPVTFGQ GTKVVIKR

BMS2h-116-1312 (SEQ ID NO: 970)
DIQMTQSPSS LSASVGDRVT ITCRASQPIG PDLLWYQQKP GKAPKLLIYQ TSILRSGVPS
RFSGSGSETD FTLTISNLQP EDLATYYCQQ YWAFPVTFGK GTKVVIKR

BMS2h-116-1313 (SEQ ID NO: 971)
DIQMTQSPSS LSASVGDRVT ITCRASQPIG PDLLWYQQKP GKAPKLLIYQ TSILRSGVPS
RFSGSGSETD FTLTISNLQP EDFATYYCQQ YWAFPVTFGR GTKVVIKR

BMS2h-116-1314 (SEQ ID NO: 972)
DIQMTQSPSS LSASVGDRVT ITCRASQPIG PDLLWYRQKP GKAPKLLIYQ TSILRSGVPS
RFSGSGSETD FTLTISNLQP EDFATYYCQQ YWAFPVTFGQ GTKVVIKR

BMS2h-116-1319 (SEQ ID NO: 973)
DIQMTQSPSS LSASVGDRVT ITCRASQPIG PDLLWYQQKP GKAPKLLIYQ TSIMRSGVPS
RFSGSGSETD FTLTISNLQP EDFATYYCQQ YWTFPVTFGQ GTKVEIKR

BMS2h-116-1320 (SEQ ID NO: 974)
DIQMTQSPSS LSAYVGDRVT ITCRASQPIG PDLLWYQQKP GKAPKLLIYQ TSILRSGVPS
RFSGSGSETD FTLTISNLQP EDFAKYYCQQ YWAFPVTFGQ GTKVVIKR

BMS2h-116-138 (SEQ ID NO: 975)
DIQMTQSPSS LSASVGDRVT ITCRASQPIG PDLLWYQQKP GKAPKLLIYQ TSILRSGVPS
RFSGSGSETD FTLTISNLQP VDFATYYCQQ YWAFPVTFGQ GTKVVIKR

BMS2h-116-14 (SEQ ID NO: 976)
DIQMTQSPSS LSASVGDRVT ITCRASQPIG PDLLWFQQKP GKAPKLLIYQ TSILQSGVPS
RFSGSESGTD FTLTISSLQP EDFATYYCQQ YWAFPVTFGQ GTKVEIKR

BMS2h-116-15 (SEQ ID NO: 977)
DIQMTQSPSS LSASVGDRVT ITCRASQPIG PDLLWYRQKP GKAPKLLIYQ TSILQSGVPS
RFSGSGSGTD FTLTISSLQP EDFATYYCQQ YWTFPVTFGQ GTKVEIKR

BMS2h-116-16 (SEQ ID NO: 978)
DIQMTQSPSS LSASVGDRVT ITCRASQPID PDLLWYQQKP GKAPKLLIYQ TSILQSGVPS
RFSGSGSGTV FTLTISSLQP EDFATYYCQQ YWAFPVTFGQ GTKVEIKR

BMS2h-116-17 (SEQ ID NO: 979)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWAFPVTFGQ GTKVEIKR

BMS2h-116-2 (SEQ ID NO: 980)
DIQMTQSPSS LSASVGDRVT ITCRASQPIE PDLLWYQQKP GKAPKLLIYQ TSILQSGVPS
RFSGSGSGTD FTLTISSLQP EDFATYYCQQ YWASPVTFGQ GTKVEIKR

BMS2h-116-3 (SEQ ID NO: 981)
DIQMTQSPSS LSASVGDRVT ITCRASQPIG PDLLWYQQKP GKAPKLLIYQ
TSILQSGVPS RFSGSESGTD FTLTISSLQP EDIATYYCQQ YWAFPVTFGQ GTRVEIKR

BMS2h-116-4 (SEQ ID NO: 982)
DIQMTQSPSS LSASVGDRVT ITCRASQPIG PDLLWYQQKP GKAPKLLIYQ TSILQSGVPS
RFSGSESGTD FTLTISSLQP EDFATYYCQQ YWAFPVTFGQ GTKVEIKR

TABLE 3-continued

Anti-human CD40L VK Domain Amino Acid Sequences

BMS2h-116-5 (SEQ ID NO: 983)
DIQMTQSPSS LSASVGDRVA ITCRASQPIG PDILWYQQKP GKAPKLLIYQ TSILRSGVPS
RFSGSGSGTD FTLTISSLQP EDSATYYCQQ YWAFPVTFGQ GTKVEIKR

BMS2h-116-6 (SEQ ID NO: 984)
DIQMTQSPSS LSASVGDRVT ITCRASQPIG PDLLWYQQKP GKAPKLLIYQ TSILRSGVPS
RFSGSGSVTD FTLTISSLQP EDFATYYCQQ YWAFPVTFGQ GTKVGIKR

BMS2h-116-7 (SEQ ID NO: 985)
DIQMTQSPSS LSASVGDRVT ITCRASQPID PDLLWYQQKP GKAPKLLIYQ TSILQSGVPS
RFSGSGSRTD FTLTISSLQP EDFATYYCQQ YWAFPVTFGQ GTKVEIKR

BMS2h-116-8 (SEQ ID NO: 986)
DIQMTQSPSS LSASVGDRVT ITCRASQPIG PDLLWYQQKP GKAPKLLIYQ TSILQSGVPS
RFSGSGSGTD FTLTISGLQP EDFATYYCQQ YWAFPVTFGQ GTKVEIKR

BMS2h-116-9 (SEQ ID NO: 987)
DIQMTQSPSS LSASVGDRVT ITCRASMPIG PDLLWYQQKP GKAPKLLIYQ TSILRSGVPS
RFSGSESGTD FTLTISSLQP EDFATYYCQQ YWAFPVTFGQ GTKVEIKR

BMS2h-141 (SEQ ID NO: 988)
DIQMTQSPSS LSASVGDRVT ITCRASQWIG DTLTWYQQKL GKAPKLLIYG GSELQSGVPP
RFSGSGSGTD FTLTISSLQP EDFATYYCQQ CISSPCTFGQ GTKVEIKR

BMS2h-142 (SEQ ID NO: 989)
DIQMTQSPSS LSASVGDRVT ITCRASQFIG DSLSWYQQKP GKAPKLLIYF SSILQSGVPS
RFSGSGSGTD FTLTISSLQP EDFATYYCQQ YHTSPTTFGR GTKVKIKR

BMS2h-143 (SEQ ID NO: 990)
DIQMTQSPSS LSASVGDRVT ITCRASQTIE TNLEWYQQKP GKAPKLLIYD SSQLQSGVPS
RFSGSGSGTD FTLTISSLQP EDLATYYCQQ YHGYPTTFGQ GTKVEIKR

BMS2h-144 (SEQ ID NO: 991)
DIQMTQSPSS LSASVGDRVT ITCRASQMID QDLEWYQQKP GKAPKLLIYN ASWLQSGVPS
RFSGSGSGTD FTLTISSLQP EDFATYYCQQ YHGYPITFGQ GTKVEIKR

BMS2h-145 (SEQ ID NO: 992)
DIQMTQSPSS LSASVGDRVT ITCRASQTIY TSLSWYQQKP GKAPKLLIHY GSVLQSGVPS
RFSGSGSGTD FTLTISSLQP EDSATYYCQQ VHQAPTTFGQ GTKVEIKR

BMS2h-146 (SEQ ID NO: 993)
DIRMTQSPSS LSASVGDRVT ITCRASQWIG DSLAWYQQKP GKAPKLLIYG ISELQSGVPS
RFSGSGSGTD FTLTISSLQP EDSATYYCQL SSSMPHTFGQ GTKVEIKR

BMS2h-147 (SEQ ID NO: 994)
DIQMTQSPSS LSASVGDRVT ITCRASQEIE TNLEWYQQKP GKAPKLLIYD SSHLQSGVPS
RFSGSGSGTD FTLTISSLQP EDFATYYCQQ YHQNPPTFGQ GTKVEIKR

BMS2h-149 (SEQ ID NO: 995)
DIQMTQSPSS LSASVGDRVT ITCRASQWIG RQLVWYQQKP GKAPKLLIYG ATELQSGVPS
RFSGSGSGTD FTLTISSLQP EDFATYYCQQ QSKGPLTFGH GTKVEIKR

BMS2h-150 (SEQ ID NO: 996)
DIQMTQSPSS LSASVGDRVT ITCRASQGIG TDLNWYQQKP GKAPKLLIYM GSYLQSGVPS
RFSGSGSGTD FTLTISSLQP EDFATYYCQQ IYSFPITFGQ GTKVEIKR

BMS2h-154 (SEQ ID NO: 997)
DIQMTQSPSS LSASVGDRVT ITCRASQDIE EMLHWYQQKP GKAPKLLIYF GSLLQSGVPS
RFSGSRSGTD FTLTISSLQP EDFATYYCQQ HHTRPYTFGQ GTKVEIKR

BMS2h-155 (SEQ ID NO: 998)
DIQMTQSPSS LSASVGDRVT ITCRASQDIG MDLEWYQQIP GKVPKLLIYD ASYLQSGVPS
RFSGSGSGTD FTLTISSLQP EDFATYYCQQ YHKLPATFGQ GTKVEIKR

BMS2h-156 (SEQ ID NO: 999)
DIQMTQSPSS LSASVGDRVT ITCRASQDIM DNLEWYQQKP GKAPKLLIYA ASWLQSGVPS
RFSGSGSGTD FTLTISSLQP EDFATYYCQQ YHKLPVTFGQ GTKVEIKR

BMS2h-157 (SEQ ID NO: 1000)
DIQMTQSPSS LSASVGDRVT ITCRASQNIG EDLEWYQQKP GNAPKLLIYS ASHLQSGVPS
RFSGSGSGTD FTLTISSLQP EDFATYYCQQ YSSYPVTFGQ GTKVEIKR

BMS2h-158 (SEQ ID NO: 1001)
DIQMTQSPSS LSASVGDRVT ITCRASQPID EDLEWYQQKP GNAPKLLIYS ASYLQSGVPS
RFSGSGSGTD FTLTISRLQP EDFATYYCQQ YHLLPATFGQ GTKVEIKR

TABLE 3-continued

Anti-human CD40L VK Domain Amino Acid Sequences

BMS2h-159 (SEQ ID NO: 1002)
DIQMIQSPSS LSASVGDRVT ITCRASQDIN EDLEWYQQKP GKAPKLLIYN ASMLQSGVPS
RFSGSGSGTD FTLTISSLQP KDFATYYCQQ YHTNPTTFGQ GTKVEIKR

BMS2h-160 (SEQ ID NO: 1003)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YHMSPVTFGQ GTKVEIKR

BMS2h-161 (SEQ ID NO: 1004)
DIQMTQSPSS LSASVGDRVT ITCRASQDID SDLEWYQQKP GKAPMLLIYS SSDLQSGVPS
RFSGSGSGTD FTLTISSLQP EDFATYYCQQ YHSLPVTFGQ GTKVEIKR

BMS2h-162 (SEQ ID NO: 1005)
DIQMTQSPSS LSASVGDRVT ITCRASQDIS DDLEWYQQKP GKAPKLLIYN SSFLQSGVPS
RFSGSGSGAD FTLTISSLQP EDFATYYCQQ YHSLPVTFGQ GTKVEIKR

BMS2h-163 (SEQ ID NO: 1006)
DIQMTQSPSS LSASVGDRVT ITCRASQDIE GNLEWYQQKP GKAPKLLIYD SSQLQSGVPS
RFSGSGSGTD FTLTISSLQP EDFATYYCQQ YHHLPTTFGQ GTKVEIKR

BMS2h-164 (SEQ ID NO: 1007)
DIQMTQSPSS LSASVGDRVT ITCRASQSID TDLEWYQQKP GKAPKLLIYD GSWLQSGVPS
RFSGSGSGTD FTLTISSLQP EDFATYYCQQ YRWIPVTFGQ GTKVEIKR

BMS2h-165 (SEQ ID NO: 1008)
DIQMTQSPSS LSASVGDRVT ITCRASQSIS TDLEWYQQKL GKAPKLLIYD ASLLQSGVPS
RFSGSGSGTD FTLTISSLQP EDFATYYCQQ YSSLPVTFGQ GTKVEIKR

BMS2h-166 (SEQ ID NO: 1009)
DIQMTQSPSS LSASVGDRVT ITCRASQPIT TSLEWYQQKP GKAPKLLIYD ASMLQSGVPS
RFSGSGSGTD FTLTISSLQP EDFATYYCQQ YWVTPVTFGQ GTKVEIKR

BMS2h-167 (SEQ ID NO: 1010)
DIQMTQSPSS LSASVGDRVT ITCRASQNIH TNLEWYQQKP GKAPKLLIYD GSMLQSGVPS
RFSGSGSGTD FTLTISSLQP EDFATYYCQQ YSANPVTFGQ GTKVGIKR

BMS2h-168 (SEQ ID NO: 1011)
DIQMTQSPSS LSASVGDRVT ITCRASQWIH TDLEWYQQKP GKAPKLLIYD GSMLQSGVPS
RFSGSGSGTD FTLTISSLQP EDFATYYCQQ YSVSPVTFGQ GTKVEIKR

BMS2h-169 (SEQ ID NO: 1012)
DIQMTQSPSS LSASVGDRVT ITCRASQSID NNLEWYQQKP GEAPKLLIYD GSLLQSGVPS
RFSGSGSGTD FTLTISSLQP EDFATYYCQQ YHLHPVTFGQ GTKVEIKR

BMS2h-170 (SEQ ID NO: 1013)
DIQMTQSPSS LSASVGDRVT ITCRASQDID TNLEWYQQKP GEAPKLLIYD RSTLQSGVPS
RFSGSGSGTD FTLTISSLQP EDFATYYCQQ YDSYPVTFGQ GTKVEIKR

BMS2h-171 (SEQ ID NO: 1014)
DIQMTQSPSS LSASVGDRVT ITCRASQSIE SNLEWYQQKP GKAPKLLIYN ASELQSGVPS
RFSGSGSGTD FTLTISSLRP EDFATYYCQQ YDQWPTTFGQ GTKVEIKR

BMS2h-172 (SEQ ID NO: 1015)
DIQMTQSPSS LSASVGDRVT ITCRASQAIG NTLRWYQQKP GKAPKLLIYL SSRLQSGVPS
RFSGSGSGTD FTLTISSLQP EDFATYYCQQ LKKPPYTFGQ GTKVEIKR

BMS2h-173 (SEQ ID NO: 1016)
DIQMTQSPSS LSASVGDRVT ITCRASQKIK NRLAWYQQKP GKAPKLLIYE VSHLQSGVPS
RFSGSGSGTD FTLTIGSLQP EDFATYYCQQ RRQSPYTFGQ GTKVEIKR

BMS2h-174 (SEQ ID NO: 1017)
DIQMTQSPSS LSASVGDRVT ITCRASEDIG EELFWYQQKP GKAPKLLIYS ASTLQSEVPS
RFSGSGSGTD FTLTISSLQH EDFATYYCQQ VYEWPYTFGQ GTKVEIKR

BMS2h-175 (SEQ ID NO: 1018)
DIQMTQSPSS LSASVGDRVT ITCRASQPIS GGLRWYQQKP GKAPKLLIYS TSMLQSGVPS
RFSGSGSGTD FTLTISSLQP EDFATYYCQQ LYSAPYTFGQ GTKVEIKR

BMS2h-305 (SEQ ID NO: 1019)
DIQMTQSPSS LSASVGDRVT ITCRASQDID QDLEWYQQKP GKAPKLLIYN VSLLQSGVPS
RFSGSGSGTD FTLTISSLQP EDFATYYCQQ YSMNPVTFGQ GTKVEIKR

BMS2h-306 (SEQ ID NO: 1020)
DIQMTQSPSS LSASVGDRVT ITCRASQDIG NQLKWYQQKP GKAPKLLIYQ ASGLQSGVPS
RFSGSGSGTD FTLTISSLQP EDFATYYCQQ YDLRPQTFGQ GTKVEIKR

TABLE 3-continued

Anti-human CD40L VK Domain Amino Acid Sequences

BMS2h-307 (SEQ ID NO: 1021)
DIQMTQSPSF LSASVGDRVT ITCRASQKIS TSLEWYQQKP GKAPRLLIYD SSWLQSGVPS
RFSGSGSGTD FTLTISSLQP EDFATYYCQQ YEYNPITFGQ GTKVEIKR

BMS2h-33 (SEQ ID NO: 1022)
DIQMTQSPSS LSASVGDRVT ITCRASQTIG ESLHWYQQKP GKAPRLLIYF ASLLQSGVPS
RFSGSGSGTD FTLTISSLQP EDFATYYCQQ HHMLPSTFGQ GTKVEIKR

BMS2h-35 (SEQ ID NO: 1023)
DIQMTQSPSS LSASVGDRVT ITCRASQFIG DSLSWYQQKP GKAPKLLIYF SSILQSGVPS
RFSGSGSGTD FTLTISSLQP EDFATYYCQQ YMDIPITFGQ GTKVEIKR

BMS2h-36 (SEQ ID NO: 1024)
DIQMTQSPSS LSASVGDRVT ITCRASQDID HNLEWYQQKP GKAPKLLIYD SSMLQSGVPS
RFSGSGSGTD FTLTISSLQP EDFATYYCQQ YHSIPVTFGQ GTKVEIKR

BMS2h-37 (SEQ ID NO: 1025)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YHSLPATFGQ GTKVEIKR

BMS2h-38 (SEQ ID NO: 1026)
DIQMTQSPSS LSASVGDRVT ITCRASQDIG NNLEWYQQKP GKAPRLLIYH GSWLQSGVPS
RFSGSGSGTD FTLTISSLQP EDFATYYCQQ YDFNPTTFGQ GTKVEIKR

BMS2h-39 (SEQ ID NO: 1027)
DIQMTQSPSS LSASVGDCVT ITCRASQNID GLLWWYQQKP GKAPKLLIYA GSGLQSGVPS
RFSGSGSGTD FTLTISSLQP EDFATYYCQQ KAFEPFTFGQ GTKVEIKR

BMS2h-405 (SEQ ID NO: 1028)
DIQMTQTPSS LSASVGDRVT ITCRASQSIG HDLEWYQQKP GKAPKLLIYN VSWLQSGVPS
RFSGSGSGTD FTLTISSLQP EDFATYYCQQ YSHNPPTFGQ GTKVEIKR

BMS2h-406 (SEQ ID NO: 1029)
DIQMTQSPSS LSASVGDRVT ITCRASQHIE NDLEWYQQKP GKAPKLLIYS ASHLQSGVPS
RFSGSGSGTD FTLTISSLQP EDFATYYCQQ YHLQPTTFGP GTKVEIKR

BMS2h-431 (SEQ ID NO: 1030)
DIQMTQSPSS LSASVGDRVT ITCRASQVIE GSLNWYQQKP GKAPKLLIYH RSILQSGVPS
RFSGRGSGTD FTLTISSLQP EDFATYYCQQ TYQLPLTFGQ GTKVEIKR

BMS2h-432 (SEQ ID NO: 1031)
DIQMTQSPSS LSASVGDRVT ITCRASRPIN GKLFWYQQKP GKAPKLLIAF ASALQSGVPS
RFSGSGSGTD FTLTISSLQP EDFATYYCVQ QAVYPITFGQ GTKVEIKR

BMS2h-433 (SEQ ID NO: 1032)
DIQMTQSPSS LSASVGDRVT ITCRASQAIE TNLEWYQQKP GKAPKLLIYD GSLLQSGVPS
RFSGRGSGTD FTLTISSLQP EDFATYYCQQ YHYQPATFGQ GTKVEIKR

BMS2h-434 (SEQ ID NO: 1033)
DIQMTQSPSS LSASVGDRVT ITCRASQDIE HDLEWYQQKP GKAPKLLIYS ASQLQSGVPS
RFSGSGSGTD FTLTISSLQP EDFATYYCQQ YQQQPTTFGQ GTKVEIKR

BMS2h-435 (SEQ ID NO: 1034)
DIQMTQSPSS LSASVGDRVT ITCRASSQIE ESLWWYQQKP GKAPKLLIAD VSLLQSGVPS
RFSGSGSGTD FTLTISSLQP EDFATYYCAQ GVVEPRTFGQ GTKVEIKR

BMS2h-436 (SEQ ID NO: 1035)
DIQMTQSPSS LSASVGDRVT ITCRASQYIG LDLEWYQQKP GKAPKLLIYA ASWLQSGVPS
RFSGSGSGTD FTLTISSLQP EDFATYYCQQ YFRQPITFGQ GTKVEIKR

BMS2h-437 (SEQ ID NO: 1036)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVEIKR

BMS2h-437-1 (SEQ ID NO: 1037)
DIQLTQSPTS LSATVGDRVT ITCRASTPIG TMLDWYQQKP GKAPKLLIGH SSWLQSGVPS
RFSGSGSGTD FTLTISSLQP EDFATYYCGQ HVRHPATFGQ GTKVEIKR

BMS2h-437-2 (SEQ ID NO: 1038)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVGIKR

BMS2h-437-3 (SEQ ID NO: 1039)
DIQMTQSPSS LSASVGDRVT ITCRVSTPIG TMLDWYQQKP GKAPKLLIGH SSWLQSGVPP
RFSGSGSGTD FTLTISSLQP EDFATYYCGQ HVRPPATFGQ GTKVEIKR

TABLE 3-continued

Anti-human CD40L VK Domain Amino Acid Sequences

BMS2h-437-4 (SEQ ID NO: 1040)
DIQMTQSPSS LSASVGDRVT ITCRASTPIG TMLDWYQQKP GKAPKLLIGH SSWLQSGVPS
RFSGCGSGTD FTLTISSLQP EDFATYYCGQ HVRPPATFGQ GTKVEIKR

BMS2h-437-5 (SEQ ID NO: 1041)
DIQMTQSPSS LSASVGDRVT ITCRASTPIG TMIDWYQQKP GKAPKLLIGH SSWLQSGVPS
RFSGSGSGTD FTLTISSLQP EDFATYYCGQ HVRPPATFGK GTKVEIKR

BMS2h-438 (SEQ ID NO: 1042)
DIQMTQSPSS LSASVGDRVT ITCRASQYID TNLEWYQQKP GKAPRLLIYD GSQLQSGVPS
RFSGSGSGTD FTLIISSLQP EDFATYYCQQ YQVVPVTFGQ GTKVEIKR

BMS2h-439 (SEQ ID NO: 1043)
DIQMTQSPSS LSASVGDRVT ITCRASQSIS SYLNWYQQKP GKAPRLLIVD SSGLQSGVPS
RFSGSGSGTD FTLTISSLQP EDFATYYCGQ DRWSPATFGQ GTKVEIKR

BMS2h-440 (SEQ ID NO: 1044)
DIQMTQSPSS LSASVGDRVT ITCRASSRIQ HMLSWYQQKP GKAPKLLIGG HSGLQSGVPS
RFSGSGSGTD FTLTISSLQP EDFATYYCAQ SCAWPLTFGQ GTKVEIKR

BMS2h-441 (SEQ ID NO: 1045)
DIQMTQSPSS LSASVGDRVT ITCRASRGID GDLWWYQQKP GKAPKLLIAD SSLLQSGVPS
RFSGSGSGTD FTLTISSLQP EDFATYYCGQ GAVRPMTFGQ GTKVEIKR

BMS2h-442 (SEQ ID NO: 1046)
DIQMTQSPSS LSASVGDRVT ITCRASRGID TDLWWYQQKP GKAPKLLIAD SSLLQSGVPS
RFSGSGSGTD FTLTISSLQP EDFATYYCGQ GAVRPMTFGQ GTKVEIKR

BMS2h-443 (SEQ ID NO: 1047)
DIQMTQSPSS LSASVGDRVT ITCRASYTIP VALDWYQQKP GKAPKLLIAD ASLLQSGVPS
RFSGSGSGTD FTLTISSLQP EDFATYYCAQ GWPGPQTFGQ GTKVEIKR

BMS2h-444 (SEQ ID NO: 1048)
DIQMTQSPSS LSASVGDRVT ITCRASQSIA TDLEWYQQKP GKAPKLLIYD TSMLQSGVPS
RFSGSGSGTD FTLTISSLQP EDFATYYCQQ YSYNPSTFGQ GTKVEIKR

BMS2h-445 (SEQ ID NO: 1049)
DIQMTQSPSS LSASVGDRVT ITCRASVPIT EGLSWYQQKP GKAPKLLIQA NSWLQSGVPS
RFSGSGSGTD FTLTISSLQP EDFATYYCGQ WEHVPATFGQ GTKVEIKR

BMS2h-446 (SEQ ID NO: 1050)
DIQMTQSPSS LSASVGDRVT ITCRASSMIL YGLDWYQQKP GKAPKLLIGG TSALQSGVPS
RFSGSGSGTD FTLTISSLQP EDFATYYCGQ WETVPATFGQ GTKVEIKR

BMS2h-447 (SEQ ID NO: 1051)
DIQMTQSPSS LSASVGDRVT ITCRASQPIN GLLIWYQQKP GKAPKLLIYA MSSLQSGVPS
RFSGSGSGTD FTLTISSLQP EDFATYYCQQ LARIPFTFGQ GTKVGIKR

BMS2h-448 (SEQ ID NO: 1052)
DIQMTQSPSS LSASVGDRVT ITCRASQLIR TYLAWYQQKP GKAPKLLIYQ SSQLQSGVPS
RFSGSGSGTD FTLTISSLQP EDFATYYCQQ YNSYPDTFGQ GTKVEIKR

BMS2h-47 (SEQ ID NO: 1053)
DIQMTQSPSS LSASVGDRVT ITCRASQWIG DSLSWYQQKP GKAPKLLIYF GSYLQSGVPS
RFSGSGSGTD FTLTISSLQP EDFATYYCQQ YLHTPSTFGQ GTKVEIKR

BMS2h-484 (SEQ ID NO: 1054)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YGFNPPTFGQ GTKVEIKR

BMS2h-485 (SEQ ID NO: 1055)
DIQMTQSPSS LSASVGDRVT ITCRASSPIE YGLDWYQQKP GKAPKLLIGG GSALQSGVPS
RFSGSGSGTD FTLTISSLQP EDFATYYCGQ WEVQPATFGQ GTKVEIKR

BMS2h-486 (SEQ ID NO: 1056)
DIQMTQSPSS LSASVGDRVT ITCRASQRID TDLEWYQQKP GKAPKLLIYD SSQLQSGVPS
RFSGSGSGTD FTLTISSLQP EDFATYYCQQ YHSAPATFGQ GTKVEIKR

BMS2h-487 (SEQ ID NO: 1057)
DIQMTQSPSS LSASVGDRVT ITCRASGWIG MSLEWHQQKP GKAPKLLIRG ASSLQSGVPS
RFSGSGSGTD FTLTISSLQP EDFATYYCSQ SRWPPVTFGQ GTKVEIKR

BMS2h-488 (SEQ ID NO: 1058)
DIQMTQSPSS LSASVGDRVT ITCRASRNIS NALSWYQQKP GKAPKLLILG ASWLQSGVPS
RFSGSGSGTD FTLTISSLQP EDFATYYCTQ VWDRPFTFGQ GTKVEIKR

TABLE 3-continued

Anti-human CD40L VK Domain Amino Acid Sequences

BMS2h-489 (SEQ ID NO: 1059)
DIQMTQSPSS LSASVGDRVT ITCRASQDIM SALSWYQQKP GKAPKLLIYS TSILQSGVPS
RFSGSGSGTD FTLTISSLQP EDFATYYCQQ VYLLPVTFGQ GTKVEIKR

BMS2h-490 (SEQ ID NO: 1060)
DIQMTQSPSS LSASVGDRVT ITCRASQEIG IDLEWYQQKP GKAPKLLIYA ASYLQSGVPS
RFSSSGSGTD FTLTISSLQP EDFATYYCQQ YASNPPTFGR GTKVEIKR

BMS2h-491 (SEQ ID NO: 1061)
DIQMTQSPSS LSASVGDRVT ITCRASQMIG DWLNWYQQKP GKAPKLLIYR SSELQSGVPS
RFSGSGSGTD FTLTISSLQP EDFATYYCQQ LYFWPRTFGQ GTKVEIKR

BMS2h-492 (SEQ ID NO: 1062)
DIQMTQSPSS LSASVGDRVT ITCRASQAIE LNLEWYQQKP GKAPKLLIYD ASMLQSGVPS
RFSGSGSGTD FTLTISSLQP EDFATYYCQQ YDVYPPTFGQ GTKVEIKR

BMS2h-492-1 (SEQ ID NO: 1063)
DIQMTQSPSS LSASVGDRVT ITCRASQAIE HNLEWYQQKP GKAPKLLIYD ASMLQSGVPS
RFSGSGSGTD FTLTISSLQP EDLATYYCQQ YDAYPPTYGQ GTKVEIKR

BMS2h-492-2 (SEQ ID NO: 1064)
DIQMTQSPSS LSASVGDRVT ITCRASRAIE TNLEWYQQKP GKAPKLLFYD ASMLQSGVPS
RFGGSGSGTD FTLTISSLQP EDFATYYCLQ YDVYPPTFGQ GTKVEIKR

BMS2h-492-3 (SEQ ID NO: 1065)
DIQMTQSPSS LSATVGDRVT ITCRASQAIE TNLEWYQQKP GKAPKLLIYD ASMLQSGVPS
RFSGSGSGTD FTLTISSLQP EDFATYYCQQ YDAYPPTFGQ GTKVEIKR

BMS2h-492-4 (SEQ ID NO: 1066)
DIQMTQSPSS LSASVGDRVT ITCRASQAIE HNLEWYQQKP GKAPKLLIYD ASMLQSGVPS
RFSGRGSGTD FTLTISSLQP EDFATYYCQQ YDAYPPTFGQ GTKVEIKR

BMS2h-492-5 (SEQ ID NO: 1067)
DIQMNQSPSS LSASVGDRVS ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-492-6 (SEQ ID NO: 1068)
DIQMTQSPSS LSASVGDRVT ITCRASQAIE SNLEWYQQKP GKAPKLLIYD ASMLQSGVPS
RFSGSGSGTD FTLTISSLQP EDFATYYCQQ YDVYPPTFGQ GTKVEIKR

BMS2h-492-7 (SEQ ID NO: 1069)
DIQMTQSPSS LSASVGDRVT ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-493 (SEQ ID NO: 1070)
DIQMTQSPSS LSASVGDRVT ITCRASQGID EDLEWYQQKP GKAPRLLIYS SSWLQSGVPS
RFSGSGSGTD FTLTISSLQP EDFATYYCQQ YFQYPPTFGQ GTKVEIKR

BMS2h-494 (SEQ ID NO: 1071)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YFQYPPTFGQ GTKVEIKR

BMS2h-494-1 (SEQ ID NO: 1072)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YSQYPPTFGQ GTKVEIKR

BMS2h-494-2 (SEQ ID NO: 1073)
DIQMTQSPSS LSASVGDRVT ITCRASQSIE EDLEWYQQKP GKAPRLLIYS SSWLQSGVPS
RFSGSGSGTD FTLTISSLQP EDFATYYCQQ YFQYPPTFGH GTKVEIKR

BMS2h-494-3 (SEQ ID NO: 1074)
DIQMTQSPSS LSASVGDRVT ITCRASQSID EDLEWYQQKP GKAPRLLIYS SSWLQSGVPS
RFSGSGSGTD FTLTISSLQP EDFATYFCQQ YFQYPPTFGQ GTKVEIKR

BMS2h-494-4 (SEQ ID NO: 1075)
EIQMTQSPSS LSASVGDRVT MTCRASQSID KDLEWYQQKP GKAPRLLIYS SSWLQRGVPS
RFSGSGSGTD FTLTISSLRP EDFATYYCQQ YFQYPPTLGQ GTKVEIKR

BMS2h-494-5 (SEQ ID NO: 1076)
DIQMTQSPSS LSASVGDRVT ITCRASQSID EDLEWYQQKP GKAPRLLIYS SSWLQSGVPS
RFSGSGSGTD FTLTISGLQP EDIATYYCKQ YSQYPPTFGQ GTKVEIKR

BMS2h-494-6 (SEQ ID NO: 1077)
DIQMTQSPPS LSASVGDRVT ITCRASQSID KDLEWYQQKP GKAPRLLIYS SSWLQRGVPS
RFSGSGSGTD FTLTISSLQP EDFATYHCQQ YFQYPPTFGQ GTKVEIKR

TABLE 3-continued

Anti-human CD40L VK Domain Amino Acid Sequences

BMS2h-495 (SEQ ID NO: 1078)
DIQMTQSPSS LSASVGDRVT ITCRASEYIN AELAWYQQKP GKAPKLLIYG SSGLQSGVPS
RFSGSGSGTD FTLTISSLQP EDFATYYCLQ NAMWPITFGQ GTKVEIKR

BMS2h-496 (SEQ ID NO: 1079)
DIQMTQSPSS LSASVGDRVT ITCRASLDIN NGLIWYQQKP GKAPRLLILG ASGLQSGVPS
RFSGSGSGTD FTLTISSLQP EDFATYYCSQ VRSRPFTFGQ GTKVEIKR

BMS2h-497 (SEQ ID NO: 1080)
DIQMTQSPSS LSASVGDRVT ITCRASQDIL SALAWYQQKP GKAPKLLIYG SSVLQSGVPS
RFSGSGSGTD FTLTISSLQP EDFATYYCQQ NYSLPITFGQ GTKVEIKR

BMS2h-498 (SEQ ID NO: 1081)
DIQMTQSPSS LSASVGDRVT ITCRASSPIE SYLRWYQQKP GKAPKLLIRY VSVLQSGVPS
RFSGSGSGTD FTLTISSLQP EDFATYYCGQ WFRAPVTFGQ GTKVEIKR

BMS2h-499 (SEQ ID NO: 1082)
DIQMTQSPSS LSASVGDRVT ITCRVSESIN AELHWYQQKP GKAPKLLISG FSGLQSGVPS
RFSGSGSGTD FTLTISSLQP EDFATYYCVQ FAMWPFTFGQ GTKVEIKR

BMS2h-500 (SEQ ID NO: 1083)
DIQMTQSPSS LSASVGDRVT ITCRASMMIR FGLDWYQQKP GKAPKLLIGG GSSLQSGVPS
RFSGSGSGTD FTLTISSLQP EDFATYYCGQ HERWPATFGQ GTKVEIKR

BMS2h-501 (SEQ ID NO: 1084)
DIQMTQSPSS LSASVGDRVT ITCRASQSIG TLLRWYQQKP GKAPKLLIYL TSVLQSGVPS
RFSGSGSGTD FTLTISSLQP EDFATYYCQQ MVYRPYTFGQ GTKVEIKR

BMS2h-502 (SEQ ID NO: 1085)
DIQMTQSPSS LSASVGDRVT ITCRASQTIE TNLEWYQQKP GKAPKLLIYD SSQLQSGVPS
RFSGSGSGTD FTLTISSLQP EDFATYYCQQ YDKVPATFGQ GTKVEIKR

BMS2h-503 (SEQ ID NO: 1086)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPPTFGQ GTKVEIKR

BMS2h-503-1 (SEQ ID NO: 1087)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPQTFGQ GTKVEIKR

BMS2h-503-2 (SEQ ID NO: 1088)
DIQMTQSPSS LSASVGDRVT ITCRASHDIQ RYLSWYQQKP GKAPKLLILW GSQLQSGVPS
RFSGSGSGTD FTLTISSLQP EDFATYYCGQ WWAPPQTFGQ GTKVEIKR

BMS2h-504 (SEQ ID NO: 1089)
DIQMTQSPSS LSASVGDRVT ITCRASQYID TNLEWYQQKP GKAPKLLIYD GSLLQSGVPS
RFSGSGSGTD FTLTISSLQP EDFATYYCGQ GAVVPVTFGQ GTKVEIKR

BMS2h-508 (SEQ ID NO: 1090)
DIQMTQSPSS LSASVGDRVT ITCRASQDIA FDLEWYQQKP GKAPKLLIYS ASMLQSGVPS
RFSGSGSGSD FTLTISSLQP EDFATYYCQQ YNLQPPTFGQ GTKVEIKR

BMS2h-509 (SEQ ID NO: 1091)
DIQMTQSPSS LSASVGDRVT ITCRASQNIA TLLRWYQQKP GKAPKLLIYA GSMLQSGVPS
RFSGSGSGTD FTLTISSLQP EDFATYYCQQ MWQRPYTFGQ GTKVEIKR

BMS2h-51 (SEQ ID NO: 1092)
DIQMTQSPSS LSASVGDRVT ITCRASQPIV DELDWYQQKP GKAPKLLIYA ASILQSGVPS
RFSGSGSGTD FTLTISSLQP EDFATYYCHQ WSTYPTTFGQ GTKVEIKR

BMS2h-510 (SEQ ID NO: 1093)
DIQMTQSPSS LSASVGDRVT ITCRASQSIS SYLNWYQQKP GKAPKLLIDG VSGLQSGVPS
RFSGSGSGTD FTLTISSLQP EDFATYYCGQ DWDWPRTFGQ GTKVEIKR

BMS2h-511 (SEQ ID NO: 1094)
DIQMTQSPSS LSASVGDRVT ITCRASRNIR DWLRWYQQKP GKAPKLLIDW GSVLQSGVPS
RFSGSGSGTD FTLTISSLQP EDFATYYCAQ TWDDPLTFGQ GTKVEIKR

BMS2h-511-1 (SEQ ID NO: 1095)
DIQMTQSPSS LSAFVGDRVT ITCRASRNIR DWLRWYQQKP GKAPKLLIDW GSELQSGVPS
RFSGSGSGTD FTLTISSLQP EDFATYYCAQ TWYDPLTFGH GTKVEIKR

BMS2h-512 (SEQ ID NO: 1096)
DIQMTQSPSS LSASVGDRVT ITCRASIDIH GGLTWYQQKP GKAPKLLIVG VSGLQSGVPS
RFSGSGSGTD FTLTISNLQP EDFATYYCAQ VWRRPFTFGQ GTKVEIKR

TABLE 3-continued

Anti-human CD40L VK Domain Amino Acid Sequences

BMS2h-513 (SEQ ID NO: 1097)
DIQMTQSPSS LSASVGDRVT ITCRASQDIG SSLSWYQQKP GKAPKLLIYA SSLLQSGVPS
RFSGSGSGTD FTLTISSLQP EDFATYYCQQ TYALPVTFGQ GTKVEIKR

BMS2h-514 (SEQ ID NO: 1098)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YKYLPVTFGQ GTKVEIKR

BMS2h-52 (SEQ ID NO: 1099)
DIQMTQSPSS LSASVGDRVT ITCRASQDIG SALRWYQQKP GKAPKLLIYL GSDLQSGVPS
RFSGSGSGTD FTLTISSLQP EDFATYYCQQ TQYFPTTFGQ GTKVEIKR

BMS2h-53 (SEQ ID NO: 1100)
DIQMTQSPSS LSASVGDRVT ITCRASQAIY GGLRWYQQKP GKAPKLLIYG ESMLQSGVPS
RFSGSGSGTD FTLTISSLHP EDFATYYCQQ VHKPFTFGQ GTKVEIKR

BMS2h-536 (SEQ ID NO: 1101)
DIQMTQSPSS LSASVGDRVT ITCRASQRIG VWLDWYQQKP GKAPKLLIYD GSFLQSGVPS
RFSGSGSGTD FTLTISSLQP EDFATYYCQQ TFSSPSTFGQ GTKVEIKR

BMS2h-537 (SEQ ID NO: 1102)
DIQMTQSPSS LSASVGDRVP ITCRASQWIG DELYWYQQKP GKAPKLLIYS SSTLQSGVPS
RFSGSGSGTD FTLTISSLQP EDFATYYCQQ SFQFPYTFGQ GTKVEIKR

BMS2h-538 (SEQ ID NO: 1103)
DIQMTQSPSS LSASVGDRVT ITCRASSNIT GPLEWYQQKP GKAPKLLIPG WSTLQSGVPS
RFSGSGSGTD FTLTISSLQP EDFATYYCGQ VWGEPVTFGQ GTKVEIKR

BMS2h-539 (SEQ ID NO: 1104)
DIQMTQSPSS LSASIGDRVT ITCRASQRIA YGLHWYQQKP GKAPRLLIGG RSGLQSGVPS
RFSGSGSGTD FTLTISSLQP EDFATYYCVQ PGMPPDTFGQ GTKVEIKR

BMS2h-540 (SEQ ID NO: 1105)
DIQMTQSPSS LSASVGDRVT ITCRASKQIV GGLSWYQQKP GKAPKLLIGR HSGLQSGVPS
RFSGSGSGTD FTLTISSLQP EDFATYYCVQ GVWAPGTFGQ GTKVEIKR

BMS2h-541 (SEQ ID NO: 1106)
DIQMTQSPSS LSASVGDRVT ITCRASPAIA AKLDWYQQKP GKAPKLLIGA DSGLQSGVPS
RFSGSGSGTD FTLTISSLQP EDFATYYCGQ LWAGPPTFGQ GTKVEIKR

BMS2h-542 (SEQ ID NO: 1107)
DIQMTQSPSS LSASVGDRVT ITCRASRTIA DGLDWYQQKP GKAPKLLIGA YSGLQSGVPS
RFSGSGSGTD FTLTISSLQP EDFATYYCGQ LWEGPPTFGQ GTKVEIKR

BMS2h-543 (SEQ ID NO: 1108)
DIQMTQSPSS LSASVGDRVT ITCRASQRIY GFLDWYQQKP GKAPKLLIYG VSSLQSGVPS
RFSGSGSGTD FTLTISSLQP EDFATYYCQQ TLAWPFTFGQ GTKVEIKR

BMS2h-544 (SEQ ID NO: 1109)
DIQMTQSPSS LSASVGDRVT ITCRASQDIR DWLMWYQQKP GKAPKLLIYW GSFLQSGVPS
RFSGSGSGTD FTLTISSLQP EDFATYYCQQ LYDTPYTFGQ GTKVEIKR

BMS2h-545 (SEQ ID NO: 1110)
DIQMTQSPSS LSASVGDRVT ITCRASQNIN TGLDWYQQKP GKAPKLLIYD SSALQSGVPS
RFSGSGSGTD FTLTISSLQP EDFATYYCQQ TSYYPYTFGQ GTKVEIKR

BMS2h-546 (SEQ ID NO: 1111)
DIQMTQSPSS LSASVGDRVT ITCRASQKIF GWLDWYQQKP GKAPKLLIYG TSKLQSGVPS
RFSGSGSGTD FTLTISSLQP EDFATYYCQQ VYSLPYTFGQ GTKVEIKR

BMS2h-547 (SEQ ID NO: 1112)
DIQMTQSPSS LSASVGDRVT ITCRASSNIG ADLDWYQQKP GKAPKLLIGG ASGLQSGVPS
RFSGSGSGTD FTLTISSLQP EDFATYYCGQ LWNGPPTFGQ GTKVEIKR

BMS2h-548 (SEQ ID NO: 1113)
DIQMTQSPSS LSASVGDRVT ITCRASSPIY DGLDWYQQKP GKAPKLLISG ASWLQSGVPS
RFSGSGSGTD FTLTISSLQP EDFATYYCGQ LWLGPPTFGQ GTKVEIKQ

BMS2h-549 (SEQ ID NO: 1114)
DIQMTQSPSS LSASVGDRVT ITCRASSRIY NGLHWYQQKP GKAPKLLIGG RSGLQSGVPS
RFSGSGSGTD FTLTISSLQP EDFATYYCAQ VGEAPSTFGQ GTKVEIKR

BMS2h-550 (SEQ ID NO: 1115)
DIQMTQSPSS LSASVGDRVT ITCRASRFIN EELDWYQQKP GKAPKLLISW SSWLQSGVPS
RFSGSGSGTD FTLTISSLQP EDFATYYCVQ PGGGPGTFGQ GTKVEIKR

TABLE 3-continued

Anti-human CD40L VK Domain Amino Acid Sequences

BMS2h-551 (SEQ ID NO: 1116)
DIQMTQSPSS LSASVGDRVT ITCRASRDIL DELDWYQQKP GKAPRLLIGG GSGLQSGVPS
RFSGSGSGTD FTLTISSLQP EDFATYYCGQ LWHGPPTFGQ GTKVEIKR

BMS2h-552 (SEQ ID NO: 1117)
DIQMTQSPSS LSASVGDRVT ITCRASSPIY TGLHWYQQKP GKAPKLLIGG RSGLQSGVPS
RFSGSGSGTD FTLTISSLQP EDFATYYCMQ VGTAPATFGQ GTKVEIKR

BMS2h-585 (SEQ ID NO: 1118)
DIRMTQSPSS LSASVGDRVT ITCRASQNIS RRLLWYQQKP GKAPKLLIYS SSRLQSGVPS
RFGGSGSGTD FTLTISSLQP EDFATYYCQQ TYSYPHTFGQ GTKVEIKR

BMS2h-604 (SEQ ID NO: 1119)
DIQMTQSPSS LSASVGDRVT ITCRASSPIP QDLYWYQQKP GKAPKLLIVG ISQLQSGVPS
RFSGSGSGTD FTLTISSLQP EDFATYYCGQ LWSAPATFGQ GTKVEIKR

BMS2h-605 (SEQ ID NO: 1120)
DIQMTQSPSS LSASVGDRVT ITCRASKSID GMLDWYQQKP GKAPKLLIPG FSGLQSGVPS
RFSGSGSGTD FTLTISSLQP EDFATYYCGQ SVEAPWTFGQ GTKVEIKR

BMS2h-606 (SEQ ID NO: 1121)
DIQMTQSPSS LSASVGDRVT ITCRASRYIA HPLDWYQQKP GKAPKLLIPG SSVLQSGVPS
RFSGSGSGTD FTLTISSLQP EDFATYYCGQ SVVVPWTFGQ GTKVEIKR

BMS2h-607 (SEQ ID NO: 1122)
DIQMTQSPSS LSASVGDRVT ITCRASRTIE GGLDWYQQKP GKAPKLLIMG GSGLQSGVPS
RFSGSGSGTD FTLTISSLQP EDFATYYCGQ LWVGPPTFGQ GTKVEIKR

BMS2h-608 (SEQ ID NO: 1123)
DIQMTQSPSS LSASVGDRVT ITCRASKFIR DELYWYQQKP GKAPRLLIGG SSLLQSGVPS
RFSGSGSGTD FTLTISSLQP EDFATYYCGQ LWRAPATFGQ GTKVEIKR

BMS2h-609 (SEQ ID NO: 1124)
DIQMTQSPSS LSASVGDRVT ITCRASKPIY GGLEWYQQKP GKAPRLLIGG GSVLQSGVPS
RFSGSGSGTD FTLTISSLQP EDFATYYCGQ VWGGPVTFGQ GTKVEIKR

BMS2h-610 (SEQ ID NO: 1125)
DIRMTQSPSS LSASVGDRVT ITCRASRPIS GCLDWYQQKP GKAPKLLIDG ASGLQSGVPS
RFSGSGSGTD FTLTISSLQP EDFATYYCGQ WWEYPPTFGQ GTKVEIKR

BMS2h-611 (SEQ ID NO: 1126)
DIQMTQSPSS LSASVGDRVT ITCRASKPIV RDLEWYQQKP GKAPKLLIHG VSTLQSGVPS
RFSGSGSGTD FTLTISSLQP EDFATYYCGQ LEAAPATFGQ GTKVEIKR

BMS2h-612 (SEQ ID NO: 1127)
DIQMTQSPSS LSASVGDRVT ITCRASRDIG DWLYWYQQKP GKAPRLLIVW ASVLQSGVPS
RFSGSGSGTD FTLTISSLQP EDFATYYCAQ WGTPPTTFGQ GTKVEIKR

BMS2h-613 (SEQ ID NO: 1128)
DIQMTQSPSS LSASVGDRVT ITCRASNRIE YGLDWYQQKP GKAPKLLISG SSRLQSGVPS
RFSSSGSGTD FTLTISSLQP EDFATYYCGQ LEAAPATFGQ GTKVEIKR

BMS2h-614 (SEQ ID NO: 1129)
DIQMTQSPSS LSASVGDRVT ITCRASRNIG HFLDWYQQKP GKAPKLLILG GSSLQSGVPS
RFSGSGSGTD FTLTISSLQP EDFATYYCGQ LVEPPATFGQ GTKVEIKR

BMS2h-615 (SEQ ID NO: 1130)
DIQMTQSPSS LSASVGDRVT ITCRASSSIY SDLYWYQQKP GKAPKLLIDG WSGLQSGVPS
RFSGSGSGTD FTLTISSLQP EDFATYYCGQ LHRAPATFGQ GTKVEIKR

BMS2h-616 (SEQ ID NO: 1131)
DIQMTQSPSS LSASVGDRVT ITCRASRFIT DRLDWYQQKP GKAPKLLIGG VSGLQSGVPS
RFSGSGSGTD FTLTISSLQP EDFATYYCGQ SSELPWTFGQ GTKVEIKR

BMS2h-617 (SEQ ID NO: 1132)
DIQMTQSPSS LSASVGDRVT ITCRASRKIG SELYWYQQKP GKAPKLLIGG RSRLQSGVPS
RFSGSGSGTD FTLTISSLQP EDFATYYCGQ LWEPPATFGQ GTKVEIKR

BMS2h-618 (SEQ ID NO: 1133)
DIQMTQSPSS LSASVGDRVT ITCRASRNIG NGLDWYQQKP GKAPKLLIGE GSRLQSGVPS
RFSGSGSGTD FTLTISSLQP EDFATYYCGQ LWHTPPTFGQ GTKVEIKR

BMS2h-619 (SEQ ID NO: 1134)
DIQMTQSPSS LSASVGDRVT ITCRASRNIY GWLSWYQQKP GKAPRLLIGG WSGLQSGVPS
RFSGSGSGTD FTLTISSLQP EDFATYYCAQ DYTLPGTFGQ GTKVEIKR

TABLE 3-continued

Anti-human CD40L VK Domain Amino Acid Sequences

BMS2h-730 (SEQ ID NO: 1135)
DIQMTQSPSS LSASVGDRVT ITCRASQDIK DWLHWYQQKP GKAPKLLIYF ASGLQSGVPS
RFSGSGSGTD FTLTISSLQP EDSATYYCQQ HYSTPYTSGQ GTKVEIKR

BMS2h-731 (SEQ ID NO: 1136)
DIQMTQSPPS LSASVGDRVT ITCRASQLIS SHLDWYQQKP GKAPKLLVYD ASELQSGVPS
RFSGSGSGTD FTLTISSLQP EDFATYYCQQ HRSLPFTFGQ GTKVEIKR

BMS2h-732 (SEQ ID NO: 1137)
DIQMTQSPSS LSASVGDRVT ITCRASQWIG GALAWYQQKP GKAPRLLIYQ ISVLQSGIPS
RFSGSGSGTD FTLTISSLQP EDFATYYCQQ YIRSPFTFGQ GTKVEIKR

BMS2h-733 (SEQ ID NO: 1138)
DIQMTQSPSS LSASVGDRVT ITCRASQSIG AALNWYQQKP GKAPKLLIYG LSSLQSGVPS
RFSGSGSGTD FTLTISSLQP EDFATYYCQQ LFRLPLTFGQ GTKVEIKR

BMS2h-734 (SEQ ID NO: 1139)
DIQMTQSPSS LSASVGDRVT ITCRASQPIG GRLVWYQQKP GKAPKLLIYG SSILQSGVPS
RFSGSGSGTD FTLTISSLQP EDFATYYCQQ YAEAPITFGQ GTKVEIKR

BMS2h-735 (SEQ ID NO: 1140)
DIQMTQSPSS LSASVGDRVT ITCRASQNIG SSLIWYQQKP GKAPTLLIYY SSKLQSGVPS
RFSGSGSGTD FTLTISSLQP EDFATYYCQQ SLSSPYTVGQ GTKVEIKR

BMS2h-736 (SEQ ID NO: 1141)
DIQMTQSPSS LSASVGDRVT ITCRASQWIG SELAWYQQKP GKAPKLLIYW TSNLQSGVPS
RFSGSGSGTD FTLTISNLQP EDFATYYCQQ ILETPLTFGQ GTKVEIKR

BMS2h-737 (SEQ ID NO: 1142)
DIQMTQSPSS LSASVGDRVT ITCRASQKIW DALYWYQQKP GKAPKLLIYR GSILQSGVPS
RFSGSGSGTD FTLTISSLQP EDFATYYCQQ FYRWPHTFGQ GTKVEIKR

BMS2h-738 (SEQ ID NO: 1143)
DIQMTQSPSS LSASVGDRVT ITCRASQHIE DSLRWYQQKP GKAPKLLIYY GSVLQSGVPS
RFSGSGSGTD FTLTISSLQP EDFATYYCQQ MYKFPITFGQ GTKVEIKR

BMS2h-739 (SEQ ID NO: 1144)
DIQTTQSPSS LSASVGDRVT ITCRASQRIN SSLLWYQQKP GKAPKLLIYD TSTLQSGVPS
RFSGSRSGTD FTLTISSLQP EDFATYYCQQ IWGSPPTFGQ GTKVEIKR

BMS2h-740 (SEQ ID NO: 1145)
DIQMTQSPSS LSASVGDRVT ITCRASQSIP VGLNWYQQKP GKAPRLLIYS GSTLQSGVPS
RFSGSGSGTD FTLTISSLQP EDFATYYCQQ DWYYPNTFGQ GTKVEIKR

BMS2h-785 (SEQ ID NO: 1146)
DIQMTQSPSS LSASVGDRVT ITCRASQPIY GWLNWYQQKP GKAPKLLIYL TSGLQSGVPS
RFSGSGSGTD FTLTISSLQP EDFATYYCQQ IHSSPFTFGQ GTKVEIKR

BMS2h-8 (SEQ ID NO: 1147)
DIQMTQSPSS LSASVGDRVT ITCRASQFID TSLEWYQQKP GKAPKLLIYD GSHLQSGVPS
RFSGSGSGTD FTLTISSLQP EDLATYYCQQ YWVLPLTFGQ GTKVEIKR

BMS2h-86 (SEQ ID NO: 1148)
DIQMTQSPSS LSASVGDRVT ITCRASQDIG DALFWYQQKP GKAPKLLIYY SSMLQSGVPS
RFSGGGSGTD FTLTISSLQP EDFATYYCQQ RHSTPATFGQ GTKVEIKR

BMS2h-87 (SEQ ID NO: 1149)
DIQMTQSPSS LSASVGDRVT ITCRASQDID ESLMWYQQKP GKAPRLLIYG VSYLQSGVPS
RFSGSGSGTD FTLTISSLQP EDFATYYCQQ RWKAPFTFGQ GTKVEIKR

BMS2h-88 (SEQ ID NO: 1150)
DIQMTQSPSS LSASVGDRVT ITCRASQEIV EDLYWYQQKP GKAAKLLIYG ASWLQSGVPS
RFSGSGSGTD FTLTISSLQP EDFATYYCQQ TRRRPYTFGQ GTKVEIKR

BMS2h-89 (SEQ ID NO: 1151)
DIQMTQSPAS LSASVGDRVT ITCRASQDID PMLRWYQQKP GKAPKLLIYA GSILQSGVPS
RFSGSGSGTD FTLTISSLQP EDFATYYCQQ TLVTPYTFGQ GTKVEIKR

BMS2h-90 (SEQ ID NO: 1152)
DIQMTQSPSS LSASVGDRVT ITCRASQSIS DALFWYQQKP GKAPRLLIYY GSVLQSGVPS
RFSGSGSGTD FTLTISSLQP EDFATYYCQQ RFQEPVTFGQ GTKVEIKR

BMS2h-91 (SEQ ID NO: 1153)
DIQMTQSPSS LSASVGDRVT ITCRASQQIS DELNWYQQKP GKAPKLLIYA VSILQSGVPS
RFSGSGSGTD FTLTISSLQP EDFATYYCQQ WLSFPSTFGQ GTKVEIKR

TABLE 4

Human Anti-CD40L VK Domain Encoding Nucleotide Sequences

BMS2h-100 (SEQ ID NO: 1154)
GACATCCAGATGACCCAGTCTCCATCCTCCCTGTCTGCATCTGTAGGAGACCGTGTCACC
ATCACTTGCCGAGCAAGTCAGAATATTAAGCATTCGTTACGGTGGTACCAGCAGAAACCA
GGGAAAGCCCCTAGGCTCCTGATCTATCATCGTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTAGGCATCGTCCTTATACGTTCGGCCAA
GGGACCAAGGTGGAAATCAAACGG

BMS2h-101 (SEQ ID NO: 1155)
GACATCCAGATGACCCAGTCTCCATCCTCTCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTGCTTTGTTTCCCTATACGTTCGGCCAA
GGGACCAAGGTGGAAATCAAACGG

BMS2h-102 (SEQ ID NO: 1156)
GACATCCAGATGACCCAGTCTCCATCCTCCCTGTCTGCATCTGTAGGAGACCGTGTCACC
ATCACTTGCCGGGCAAGTCAGCATATTGGTCATCATTTAAGGTGGTACCAGCAGAAACCA
GGGAAAGCCCCCAAGCTCCTGATCTATCATAGGTCCCATTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGTGGGATAGGCCGCCTTATACGTTCGGCCAA
GGGACCAAGGTGGAAATCAAACGG

BMS2h-103 (SEQ ID NO: 1157)
GACATCCAGATGACCCAGTCCCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTGCGGGCTGTGCCTTATACGTTTGGCCAA
GGGACCAAGGTGGAAATTAAACGG

BMS2h-104 (SEQ ID NO: 1158)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTCGTTTTTCTCCTTATACGTTCGGCCAA
GGGACCAAGGTGGAAATCAAACGG

BMS2h-105 (SEQ ID NO: 1159)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTTATGCTAGGCCTGTGACGTTCGGCCAA
GGGACCAAGGTGGAAATCAAACGG

BMS2h-106 (SEQ ID NO: 1160)
GACATCCAGATGACCCAGTCTCCATCCTCCCTGTCTGCATCTGTAGGAGACCGTGTCACC
ATCACTTGCCGGGCAAGTCAAAGTATTAATCATAGGTTATATTGGTACCAGCAGAAACCA
GGGAAAGCCCCTAAGCTCCTGATCTATCATCGGTCCAGGTTGCAAAGTGGGGTCCCATCA
CGTTTCAGTGGCAGTGGATCTGGGACAGATTTCACTCTCACCATCAGCAGTCTGCAACCT
GAGGATTTTGCTACGTACTACTGTCAACAGTATAAGGTTAGGCCTAATACGTTCGGCCAA
GGGACCAAGGTGGAAATCAAACGG

BMS2h-107 (SEQ ID NO: 1161)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATTTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTTATTCGTCTCCTCATACGTTCGGCCAA
GGGACCAAGGTGGAAATCAAACGG

BMS2h-108 (SEQ ID NO: 1162)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTACAACCT
GAAGATTTTGCTACGTACTACTGTCAACAGAGGGCGGTGAGGCCTTTTACGTTCGGCCAA
GGGACCAAAGTGGAAATCAAACGG

BMS2h-109 (SEQ ID NO: 1163)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGACTTATTATCGTCCTCTTACGTTCGGCCAA
GGGACCAAGGTGGAAATCAAACGG

BMS2h-110 (SEQ ID NO: 1164)
GACATCCAGATGACCCAGTCTCCAGCCTCCCTGTCTGCATCTGTAGGAGACCGTGTCACC
ATCACTTGCCGGGCAAGTCAGGATATTGATCCTATGTTAAGGTGGTACCAGCAGAAACCA
GGGAAAGCCCCTAAGCTCCTGATCTATGCGGGTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTAGTATTAGGCCTTATACGTTCGGCCAA
GGGACCAAGGTGGAAATCAAACGG

BMS2h-116 (SEQ ID NO: 1165)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-1 (SEQ ID NO: 1166)
GACATCCAGATGACCCAGTCTCCATCCTCCCTGTCTGCATCTGTAGGAGACCGTGTCACC
ATCACTTGCCGGGCAAGTCAGCCTATTGGTCCTGATATACTGTGGTACCAGCAGAAACCA
GGGAAAGCCCCTAAGCTCCTGATCTATCAGACGTCCATCTTGCAAAGTGGGGTCCCATCA
CGTTTCAGTGGCAGTGAATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-10 (SEQ ID NO: 1167)
GACATCCAGATAACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATATTGCGAAGTGGAGTCCCATCA
CGTTTCAGTGGCAGTGGGTCTGGGACAGATTTCACTCTCACCATCAGCAGTCTGCAACCT
GAAGATCTTGCTACGTACTACTGTCAACAGTATTGGGCTTTTCCTGTGACGTTCGGCCAA
GGGACCAAGGTGGAAATCAAACGG

BMS2h-116-11 (SEQ ID NO: 1168)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTTCTGATCTATCAGACGTCCATTTTGCGAAGTGGGGTCCCATCA
CGTTTCAGTGGCAGAGGATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-12 (SEQ ID NO: 1169)
GACATCCAGATGACCCAGTCTCCATCCTCCCTGTCTGCATCTGTAGGAGACCGTGTCACC
ATCACTTGCCGGGCAAGTCAACCTATTGGTCCTGATTTACTGTGGTACCAGCAGAAACCA
GGGAAAGCCCCTAAGCTCTTGATCTATCAGACGTCCATTTTGCGAAGTGGGGTCCCATCA
CGTTTCAGTGGCAGCGGATCTGGGACTGATTTCACTCTCACCATCAGCAGTCTGCAACCT
GAAGATTTTGCTACGTACTACTGTCAACAGTATTGGACTTTTCCTGTGACGTTCGGCCAA
GGGACCAAGGTGGAAATCAAACGG

BMS2h-116-13 (SEQ ID NO: 1170)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGAGACAGATTTCACTCTCACCATCAGCAATCTGCAACCT
GAAGATTTTGCTACGTACTACTGTCAACAGTATTGGGCTTTTCCTGTGACGTTCGGCCAA
GGGACCAAGGTGGTAATCAAACGG

BMS2h-116-1312 (SEQ ID NO: 1171)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGAGACAGATTTCACTCTCACCATCAGCAATCTGCAACCT
GAAGATCTTGCTACGTACTACTGTCAACAGTATTGGGCTTTTCCTGTGACGTTCGGCAAA
GGGACCAAGGTGGTAATCAAACGG

BMS2h-116-1313 (SEQ ID NO: 1172)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGAGACAGATTTCACTCTCACCATCAGCAATCTGCAACCT
GAAGATTTTGCTACGTACTACTGTCAACAGTATTGGGCTTTTCCTGTGACGTTCGGCCGA
GGGACCAAGGTGGTAATCAAACGG

BMS2h-116-1314 (SEQ ID NO: 1173)
GACATCCAGATGACCCAGTCTCCATCCTCCCTGTCTGCATCTGTAGGAGACCGTGTCACC
ATCACTTGCCGAGCAAGTCAGCCTATTGGTCCTGATTTACTGTGGTACCGGCAGAAACCA

TABLE 4-continued

Human Anti-CD40L VK Domain Encoding Nucleotide Sequences

GGGAAAGCCCCTAAGCTCCTGATCTATCAGACGTCCATTTTGCGAAGTGGTGTCCCATCA
CGTTTCAGTGGCAGTGGATCTGAGACAGATTTCACTCTCACCATCAGCAATCTGCAACCT
GAAGATTTTGCTACGTACTACTGTCAACAGTATTGGGCTTTTCCTGTGACGTTCGGCCAA
GGGACCAAGGTGGTAATCAAACGG

BMS2h-116-1319 (SEQ ID NO: 1174)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTATGCGAAGTGGGGTCCCATCA
CGTTTCAGTGGCAGTGGATCTGAGACAGATTTCACTCTCACCATCAGCAATCTGCAACCT
GAAGATTTTGCTACGTACTACTGTCAACAGTATTGGACTTTTCCTGTGACGTTCGGCCAA
GGGACCAAGGTGGAAATCAAACGG

BMS2h-116-1320 (SEQ ID NO: 1175)
GACATCCAGATGACCCAGTCTCCATCCTCCCTGTCTGCATATGTAGGAGACCGTGTCACC
ATCACTTGCCGGGCAAGTCAGCCTATTGGTCCTGATTTACTTTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGAGACAGATTTCACCCTCACCATCAGCAATCTGCAACCT
GAAGATTTTGCTAAGTACTACTGTCAACAGTATTGGGCTTTTCCTGTGACGTTCGGCCAA
GGGACCAAGGTGGTGATCAAACGG

BMS2h-116-138 (SEQ ID NO: 1176)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGAGACAGATTTCACTCTCACCATCAGCAATCTGCAACCT
GTAGATTTTGCTACGTACTACTGTCAACAGTATTGGGCTTTTCCTGTGACGTTCGGCCAA
GGGACCAAGGTAGTAATCAAACGG

BMS2h-116-14 (SEQ ID NO: 1177)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTTCCAGCAGAAACCA
GGGAAAGCCCCTAAGCTCCTGATCTATCAGACGTCCATTTTGCAAAGTGGGGTCCCATCA
CGTTTCAGTGGCAGTGAATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-15 (SEQ ID NO: 1178)
GACATCCAGATGACCCAGTCTCCATCCTCCCTGTCTGCATCTGTAGGAGACCGTGTCACC
ATCACTTGCCGGGCAAGTCAGCCTATCGGTCCTGATTTACTGTGGTACCGGCAGAAACCA
GGGAAAGCCCCTAAGCTCCTGATCTATCAGACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTGGACTTTTCCTGTGACGTTCGGCCAA
GGGACCAAGGTGGAAATCAAACGG

BMS2h-116-16 (SEQ ID NO: 1179)
GACATCCAGATGACCCAGTCTCCATCCTCCCTGTCTGCATCTGTAGGAGACCGTGTCACC
ATCACTTGCCGGGCAAGTCAGCCTATTGATCCTGACTTACTGTGGTACCAGCAGAAACCA
GGTAAAGCCCCTAAGCTCCTGATCTATCAGACGTCCATTTTGCAAAGTGGGGTCCCATCA
CGTTTCAGTGGCAGTGGATCTGGGACAGTTTTCACTCTCACCATCAGCAGTCTGCAACCT
GAAGATTTTGCTACGTACTACTGTCAACAGTATTGGGCATTTCCTGTGACGTTCGGCCAA
GGGACCAAGGTGGAAATCAAACGG

BMS2h-116-17 (SEQ ID NO: 1180)
GACATCCAGATGACCCAGTCTCCATCCTCCCTGTCTGCATCAGTAGGAGACCGTGTCACC
ATCACTTGCCGGGCAAGTCAGCCTATTGGTCCTGATTTACTGTGGTACCAGCAGAAGCCA
GGGAAAGCCCCTAAGCTCCTGATCTATCAGACGTCCATTTTGCGAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-2 (SEQ ID NO: 1181)
GACATCCAGATGACCCAGTCTCCATCATCCCTGTCTGCATCTGTAGGAGACCGTGTCACC
ATCACTTGCCGGGCAAGTCAGCCTATTGAACCTGATTTACTGTGGTACCAGCAGAAACCA
GGGAAAGCCCCTAAGCTCCTGATCTATCAGACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTGGGCTTCTCCTGTGACGTTCGGCCAA
GGGACCAAGGTGGAAATCAAACGG

BMS2h-116-3 (SEQ ID NO: 1182)
GACATCCAGATGACCCAGTCACCATCCTCCCTGTCTGCATCTGTAGGAGACCGTGTCACC
ATCACTTGCCGGGCTAGTCAGCCTATTGGTCCTGATTTACTGTGGTACCAGCAGAAACCA
GGGAAAGCCCCTAAGCTCCTGATCTATCAGACGTCCATTTTGCAAAGTGGGGTCCCATCA
CGTTTCAGCGGCAGTGAATCCGGGACAGATTTCACTCTCACCATCAGCAGTCTGCAACCT
GAAGATATTGCAACGTACTACTGTCAACAGTATTGGGCTTTTCCTGTGACGTTCGGCCAA
GGGACCAGGGTGGAAATCAAACGG

TABLE 4-continued

Human Anti-CD40L VK Domain Encoding Nucleotide Sequences

BMS2h-116-4 (SEQ ID NO: 1183)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCAAAGTGGGGTCCCTTCA
CGTTTCAGTGGCAGTGAATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-5 (SEQ ID NO: 1184)
GACATCCAGATGACCCAGTCTCCATCCTCCCTGTCTGCATCTGTAGGAGACCGTGTCGCC
ATCACTTGCCGGGCAAGTCAGCCTATTGGTCCTGATATACTGTGGTACCAGCAGAAACCA
GGGAAAGCCCCTAAGCTCCTGATCTATCAGACGTCCATTTTGCGAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGTATTGGGCTTTTCCTGTGACGTTCGGTCAA
GGGACCAAGGTGGAAATCAAACGG

BMS2h-116-6 (SEQ ID NO: 1185)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCGAAGTGGGGTCCCGTCA
CGTTTCAGTGGCAGTGGATCTGTGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGGAATCAAGCGG

BMS2h-116-7 (SEQ ID NO: 1186)
GACATCCAGATGACCCAGTCTCCATCCTCCCTGTCTGCATCTGTAGGAGACCGTGTCACC
ATCACTTGCCGGGCAAGTCAGCCTATTGATCCTGATTTACTGTGGTACCAGCAGAAACCA
GGGAAAGCCCCTAAGCTCCTGATCTATCAGACGTCCATTTTGCAAAGTGGGGTCCCATCA
CGTTTCAGTGGCAGTGGATCTAGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-116-8 (SEQ ID NO: 1187)
GACATCCAGATGACCCAGTCTCCATCCTCCCTGTCTGCATCTGTAGGAGACCGTGTCACC
ATCACTTGCCGGGCAAGTCAGCCTATTGGTCCTGATTTACTGTGGTACCAGCAGAAACCA
GGGAAAGCCCCTAAGCTCCTGATCTATCAGACGTCCATTTTGCAAAGTGGGGTCCCATCA
CGTTTCAGTGGCAGTGGATCTGGGACAGATTTCACTCTCACCATCAGCGGTCTGCAACCT
GAAGATTTTGCTACGTACTACTGTCAGCAGTATTGGGCTTTTCCTGTGACGTTCGGCCAA
GGGACCAAGGTGGAAATCAAACGG

BMS2h-116-9 (SEQ ID NO: 1188)
GACATCCAGATGACCCAGTCTCCATCCTCCCTGTCTGCATCTGTAGGAGACCGTGTCACC
ATCACTTGCCGGGCAAGTATGCCTATTGGTCCTGATTTACTGTGGTACCAGCAGAAACCA
GGGAAGGCCCCTAAGCTCCTGATCTATCAGACGTCCATTTTGCGAAGTGGGGTCCCATCA
CGTTTCAGTGGCAGTGAATCTGGGACAGATTTCACTCTCACCATCAGCAGTCTGCAACCT
GAAGATTTTGCTACGTACTACTGTCAACAGTATTGGGCTTTTCCTGTGACGTTCGGCCAA
GGGACCAAGGTGGAAATCAAACGG

BMS2h-141 (SEQ ID NO: 1189)
GACATCCAGATGACCCAGTCTCCATCCTCCCTGTCTGCATCTGTAGGAGACCGTGTCACC
ATCACTTGCCGGGCAAGTCAGTGGATTGGGGATACGTTAACGTGGTACCAGCAGAAACTA
GGGAAAGCCCCTAAGCTCCTGATCTATGGTGGTTCCGAGTTGCAAAGTGGGGTCCCACCA
CGTTTCAGTGGCAGTGGATCTGGGACAGATTTCACTCTCACCATCAGCAGTCTGCAACCT
GAAGATTTTGCTACGTACTACTGTCAACAGTGTATTAGTAGTCCTTGTACGTTCGGCCAA
GGGACCAAGGTGGAAATCAAACGG

BMS2h-142 (SEQ ID NO: 1190)
GACATCCAGATGACCCAGTCTCCATCCTCCCTGTCTGCATCTGTAGGAGACCGTGTCACC
ATCACTTGCCGGGCAAGTCAGTTTATTGGTGATTCTTTATCTTGGTACCAGCAGAAACCA
GGGAAAGCCCCTAAGCTCCTGATCTATTTTTCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATACTTCGCCTACTACGTTCGGCCGA
GGGACCAAGGTGAAAATCAAACGG

BMS2h-143 (SEQ ID NO: 1191)
GACATCCAGATGACCCAGTCTCCATCCTCCCTGTCCGCATCTGTAGGAGACCGTGTCACC
ATCACTTGCCGGGCAAGTCAGACTATTGAGACTAATTTAGAGTGGTACCAGCAGAAACCA
GGGAAAGCCCCTAAGCTCCTGATCTATGATTCTTCCCAGTTGCAAAGTGGGGTCCCATCA
CGTTTCAGTGGCAGTGGATCTGGGACAGATTTTACTCTCACCATCAGCAGTCTGCAACCT
GAAGATTTAGCTACGTACTACTGTCAACAGTATCATGGGTATCCTACGACGTTCGGCCAA
GGGACCAAGGTGGAAATCAAACGG

BMS2h-144 (SEQ ID NO: 1192)
GACATCCAGATGACCCAGTCTCCATCCTCCCTGTCTGCATCTGTAGGAGACCGTGTCACC
ATCACTTGCCGGGCAAGTCAGATGATTGATCAGGATTTAGAGTGGTACCAGCAGAAACCA
GGGAAAGCCCCTAAGCTCCTGATCTATAATGCGTCCTGGTTGCAAAGTGGGGTCCCATCA
CGTTTCAGCGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGTATCATGGTTATCCTATTACGTTCGGCCAA
GGGACCAAGGTGGAAATCAAACGG

BMS2h-145 (SEQ ID NO: 1193)
GACATCCAGATGACCCAGTCTCCATCCTCCCTGTCTGCATCTGTAGGAGACCGTGTCACC
ATCACTTGCCGGGCAAGTCAGACGATTTATACTTCGTTAAGTTGGTATCAGCAGAAACCA
GGGAAAGCCCCTAAGCTCCTGATCCATTATGGTTCCGTGTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGGTTCATCAGGCTCCTACGACGTTCGGCCAA
GGGACCAAGGTGGAAATCAAACGG

BMS2h-146 (SEQ ID NO: 1194)
GACATCCGGATGACCCAGTCTCCATCCTCCCTGTCTGCATCTGTAGGAGACCGTGTCACC
ATCACTTGCCGGGCAAGTCAGTGGATTGGGGATTCTTTAGCGTGGTACCAGCAGAAGCCA
GGGAAAGCCCCTAAGCTCCTGATCTATGGTATTTCCGAGTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACTGTCTAGTAGTATGCCTCATACGTTCGGCCAA
GGGACCAAGGTGGAAATCAAACGG

BMS2h-147 (SEQ ID NO: 1195)
GACATCCAGATGACCCAGTCTCCATCCTCCCTGTCTGCATCTGTAGGAGACCGTGTCACC
ATCACTTGCCGGGCAAGTCAGGAGATTGAGACGAATTTAGAGTGGTACCAGCAGAAACCA
GGGAAAGCCCCTAAGCTCCTGATCTATGATTCGTCCCATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATCAGAATCCTCCGACGTTCGGCCAA
GGAACCAAGGTGGAAATCAAACGG

BMS2h-149 (SEQ ID NO: 1196)
GACATCCAGATGACCCAGTCTCCATCCTCCCTGTCTGCATCTGTAGGAGACCGTGTCACC
ATCACTTGCCGGGCAAGTCAGTGGATTGGGAGGCAGTTAGTTTGGTACCAGCAGAAACCA
GGGAAAGCCCCTAAGCTCCTGATCTATGGGGCGACCGAGTTGCAAAGTGGGGTCCCATCA
CGTTTTAGTGGCAGTGGATCTGGGACAGATTTCACTCTCACCATCAGCAGTCTGCAACCT
GAAGATTTTGCTACGTACTACTGTCAACAGCAGTCGAAGGGTCCTCTTACGTTCGGCCAT
GGGACCAAGGTGGAAATCAAACGG

BMS2h-150 (SEQ ID NO: 1197)
GACATCCAGATGACCCAGTCTCCATCCTCCCTGTCTGCATCTGTAGGAGACCGTGTCACC
ATCACTTGCCGGGCAAGTCAGGGGATTGGTACTGATTTAAATTGGTATCAGCAGAAACCA
GGGAAAGCCCCTAAGCTCCTGATCTATATGGGTTCCTATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATTTATTCTTTTCCTATTACGTTCGGCCAA
GGGACCAAGGTGGAAATCAAACGG

BMS2h-154 (SEQ ID NO: 1198)
GACATCCAGATGACCCAGTCTCCATCCTCCCTGTCTGCATCTGTAGGAGACCGTGTCACC
ATCACTTGCCGGGCAAGTCAGGATATTGAGGAGATGTTACATTGGTATCAGCAGAAACCA
GGGAAAGCCCCTAAGCTCCTGATCTATTTTGGTTCCCTGTTGCAAAGTGGGGTCCCATCA
CGTTTCAGTGGCAGTAGATCTGGGACAGATTTCACTCTCACCATCAGCAGTCTGCAACCT
GAAGATTTTGCTACGTACTACTGTCAACAGCATCATACTCGTCCTTATACGTTCGGCCAA
GGGACCAAGGTGGAAATCAAACGG

BMS2h-155 (SEQ ID NO: 1199)
GACATCCAGATGACCCAGTCTCCATCCTCCCTGTCTGCATCTGTAGGAGACCGTGTCACC
ATCACTTGCCGGGCAAGTCAGGATATTGGGATGGATTTAGAGTGGTACCAGCAGATACCA
GGGAAAGTCCCTAAGCTCCTGATCTATGATGCGTCCTATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATAAGCTTCCTGCGACGTTTGGCCAA
GGGACCAAGGTGGAAATCAAACGG

BMS2h-156 (SEQ ID NO: 1200)
GACATCCAGATGACCCAGTCTCCATCCTCCCTGTCTGCATCTGTAGGAGACCGTGTCACC
ATCACTTGCCGGGCAAGTCAGGATATTATGGATAATTTAGAGTGGTATCAGCAGAAACCA
GGGAAAGCCCCTAAGCTCCTGATCTATGCGGCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATAAGTTGCCTGTGACGTTCGGCCAA
GGGACCAAGGTGGAAATCAAACGG

BMS2h-157 (SEQ ID NO: 1201)
GACATCCAGATGACCCAGTCTCCATCCTCCCTGTCTGCATCTGTAGGAGACCGTGTCACC
ATCACTTGCCGAGCAAGTCAGAATATTGGGGAGGATTTAGAGTGGTACCAGCAGAAACCA
GGGAATGCCCCTAAGCTCCTGATCTATAGTGCGTCCCATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTCTAGTTATCCTGTTACGTTCGGCCAA
GGGACCAAGGTGGAAATCAAACGG

BMS2h-158 (SEQ ID NO: 1202)
GACATCCAGATGACCCAGTCTCCATCCTCCCTGTCTGCATCCGTAGGAGACCGTGTCACC
ATCACTTGCCGGGCAAGTCAGCCGATTGATGAGGATTTAGAGTGGTACCAGCAGAAACCA

TABLE 4-continued

Human Anti-CD40L VK Domain Encoding Nucleotide Sequences

GGGAATGCCCCTAAGCTCCTGATCTATAGTGCGTCCTATTTGCAAAGTGGGGTCCCATCA
CGTTTCAGTGGCAGTGGATCTGGGACAGATTTCACTCTCACCATCAGCAGACTGCAACCT
GAAGATTTTGCTACGTACTACTGTCAACAGTATCATCTTCTGCCTGCTACGTTCGGCCAA
GGGACCAAGGTGGAAATCAAACGG

BMS2h-159 (SEQ ID NO: 1203)
GACATCCAGATGATCCAGTCTCCATCCTCCCTGTCTGCATCTGTAGGAGACCGTGTCACC
ATCACTTGCCGGGCAAGTCAGGATATTAATGAGGATTTAGAGTGGTATCAGCAGAAACCA
GGGAAAGCCCCTAAGCTCCTGATCTATAATGCTTCCATGTTGCAAAGCGGGGTCCCATCA
CGTTTCAGTGGCAGTGGATCTGGGACAGATTTCACTCTCACCATCAGCAGTCTGCAACCT
AAAGATTTTGCTACGTACTACTGTCAACAGTATCATACTAATCCTACTACGTTCGGCCAA
GGGACCAAGGTGGAAATCAAACGG

BMS2h-160 (SEQ ID NO: 1204)
GACATCCAGATGACCCAGTCTCCATCCTCCCTGTCTGCATCTGTAGGAGACCGTGTCACC
ATCACTTGCCGGGCAAGTCAGGATATTGAGGCGGATTTAGAGTGGTACCAGCAGAAACCA
GGGAAAGCCCCTAAGCTCCTGATCTATCATTCTTCCGAGTTGCAAAGTGGGGTCCCATCA
CGTTTCAGTGGAAGTGGATCTGGGACAGATTTCACTCTCACCATCAGCAGTCTGCAACCT
GAAGATTTTGCTACGTACTACTGTCAACAGTATCATATGTCGCCTGTGACGTTCGGCCAA
GGGACCAAGGTGGAAATCAAACGG

BMS2h-161 (SEQ ID NO: 1205)
GACATCCAGATGACCCAGTCTCCATCCTCCCTGTCTGCATCTGTAGGAGACCGTGTCACC
ATCACTTGCCGGGCAAGTCAGGATATTGATAGTGATTTAGAGTGGTACCAGCAGAAACCA
GGGAAAGCCCCTATGCTCCTGATCTATTCTTCGTCCGATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATAGTCTGCCTGTTACGTTCGGCCAA
GGGACCAAGGTGGAAATCAAACGG

BMS2h-162 (SEQ ID NO: 1206)
GACATCCAGATGACCCAGTCTCCATCCTCCCTGTCTGCATCTGTAGGAGACCGTGTCACC
ATCACTTGCCGGGCAAGTCAGGATATTTCGGATGATTTAGAGTGGTACCAGCAGAAACCA
GGGAAAGCCCCTAAGCTCCTGATCTATAATTCGTCCTTTTTGCAAAGTGGGGTCCCATCA
CGTTTCAGTGGCAGTGGATCTGGGGCAGATTTCACTCTCACCATCAGCAGTCTGCAACCT
GAAGATTTTGCTACGTACTACTGTCAACAGTATCATAGTTTGCCTGTTACGTTCGGCCAA
GGGACCAAGGTGGAAATCAAACGG

BMS2h-163 (SEQ ID NO: 1207)
GACATCCAGATGACCCAGTCTCCATCCTCCCTGTCTGCATCTGTAGGAGACCGTGTCACC
ATCACTTGCCGGGCAAGTCAGGATATTGAGGGTAATTTAGAGTGGTACCAGCAGAAACCA
GGGAAAGCCCCTAAGCTCCTGATCTATGATTCGTCCCAGTTGCAAAGTGGGGTCCCATCA
CGTTTCAGTGGCAGTGGGTCTGGGACAGATTTCACTCTCACCATCAGCAGTCTGCAACCT
GAAGATTTTGCTACGTACTACTGTCAACAGTATCATCATCTTCCTACGACGTTCGGCCAA
GGGACCAAGGTGGAAATCAAACGG

BMS2h-164 (SEQ ID NO: 1208)
GACATCCAGATGACCCAGTCTCCATCCTCCCTGTCTGCATCTGTAGGAGACCGTGTCACC
ATCACTTGCCGGGCAAGTCAGAGTATTGATACGGATTTAGAGTGGTATCAGCAGAAACCA
GGGAAAGCCCCTAAGCTCCTGATCTATGATGGGTCCTGGTTGCAAAGTGGGGTCCCATCA
CGTTTCAGTGGCAGTGGATCTGGGACAGATTTTACTCTCACCATCAGCAGTCTGCAACCT
GAAGATTTTGCTACGTACTACTGTCAACAGTATCGGTGGATTCCTGTTACGTTCGGCCAA
GGGACCAAGGTGGAAATCAAACGG

BMS2h-165 (SEQ ID NO: 1209)
GACATCCAGATGACCCAGTCTCCATCCTCCCTGTCTGCATCTGTAGGAGACCGTGTCACC
ATCACTTGCCGGGCAAGTCAGAGTATTAGTACTGATTTAGAGTGGTACCAGCAGAAACTA
GGGAAAGCCCCTAAGCTCCTGATCTATGATGCTTCCCTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTCGAGTCTGCCTGTTACGTTCGGCCAA
GGGACCAAGGTGGAAATCAAACGG

BMS2h-166 (SEQ ID NO: 1210)
GACATCCAGATGACCCAGTCTCCATCCTCCCTGTCTGCATCTGTAGGAGACCGTGTCACC
ATCACTTGCCGGGCAAGTCAGCCTATTACGACGTCTTTAGAGTGGTACCAGCAGAAACCA
GGGAAAGCCCCTAAGCTCCTGATCTATGATGCGTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTGGGTTACGCCTGTTACGTTCGGCCAA
GGGACCAAGGTGGAAATCAAACGG

BMS2h-167 (SEQ ID NO: 1211)
GACATCCAGATGACCCAGTCTCCATCCTCCCTGTCTGCATCTGTAGGAGACCGTGTCACC
ATCACCTGCCGGGCAAGTCAGAATATTCATACGAATTTAGAGTGGTATCAGCAGAAACCA
GGGAAAGCCCCTAAGCTCCTGATCTATGATGGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTCGGCTAATCCTGTTACGTTCGGCCAA
GGGACCAAGGTGGGAATCAAACGG

TABLE 4-continued

Human Anti-CD40L VK Domain Encoding Nucleotide Sequences

BMS2h-168 (SEQ ID NO: 1212)
GACATCCAGATGACCCAGTCTCCATCCTCCCTGTCTGCATCTGTAGGAGACCGTGTCACC
ATCACTTGCCGGGCAAGTCAGTGGATTCATACGGATTTAGAGTGGTATCAGCAGAAACCA
GGGAAAGCCCCTAAGCTCCTGATCTATGATGGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATAGTGTGTCGCCTGTTACGTTCGGCCAA
GGGACCAAGGTGGAAATCAAACGG

BMS2h-169 (SEQ ID NO: 1213)
GACATCCAGATGACCCAGTCTCCATCCTCCCTGTCTGCATCTGTAGGAGACCGTGTCACC
ATCACTTGCCGGGCAAGTCAGAGTATTGATAATAATTTAGAGTGGTACCAGCAGAAACCA
GGGGAAGCCCCTAAGCTCCTGATCTATGATGGGTCCCTTTTGCAAAGTGGGGTCCCATCA
CGTTTCAGTGGCAGTGGATCTGGGACAGATTTCACTCTTACCATCAGCAGTCTGCAACCT
GAAGATTTTGCTACGTACTACTGTCAACAGTATCATCTTCATCCTGTTACGTTCGGCCAA
GGGACCAAGGTGGAAATCAAACGG

BMS2h-170 (SEQ ID NO: 1214)
GACATCCAGATGACCCAGTCTCCATCCTCCCTGTCTGCATCTGTAGGAGACCGTGTCACC
ATCACTTGCCGGGCAAGTCAGGATATTGATACGAATTTAGAGTGGTATCAGCAGAAACCA
GGGGAAGCCCCTAAGCTCCTGATCTATGATCGTTCCACGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGATTCTTATCCTGTGACGTTCGGCCAA
GGGACCAAGGTGGAAATCAAACGG

BMS2h-171 (SEQ ID NO: 1215)
GACATCCAGATGACCCAGTCTCCATCCTCCCTGTCTGCATCTGTAGGAGACCGTGTCACC
ATCACTTGCCGGGCAAGTCAGTCTATTGAGTCTAATTTAGAGTGGTACCAGCAGAAACCA
GGGAAAGCCCCTAAGCTCCTGATCTATAATGCGTCCGAGTTGCAAAGTGGGGTCCCATCA
CGTTTCAGTGGCAGTGGATCTGGGACAGATTTCACTCTCACCATCAGCAGTCTGCGACCT
GAAGATTTTGCTACGTACTACTGTCAACAGTATGATCAGTGGCCTACGACGTTCGGCCAA
GGGACCAAGGTGGAAATCAAACGG

BMS2h-172 (SEQ ID NO: 1216)
GACATCCAGATGACCCAGTCTCCATCCTCCCTGTCTGCATCTGTAGGAGACCGTGTCACT
ATCACTTGCCGGGCAAGTCAGGCTATTGGTAATACTTTACGGTGGTACCAGCAGAAACCA
GGGAAAGCCCCTAAGCTCCTGATCTATCTTAGTTCCAGGTTGCAAAGTGGGGTCCCATCA
CGTTTCAGTGGCAGTGGATCTGGGACAGATTTTACTCTCACCATCAGCAGTCTGCAACCT
GAAGATTTTGCTACGTACTACTGTCAACAGCTGAAGAAGCCTCCTTATACGTTCGGCCAA
GGGACCAAGGTGGAAATCAAACGG

BMS2h-173 (SEQ ID NO: 1217)
GACATCCAGATGACCCAGTCTCCATCCTCCCTGTCTGCATCTGTAGGAGACCGTGTCACC
ATCACTTGCCGGGCAAGTCAGAAGATTAAGAATCGGTTAGCGTGGTACCAGCAGAAACCA
GGGAAAGCCCCTAAGCTCCTGATCTATGAGGTTTCCCATTTGCAAAGTGGGGTCCCATCA
CGTTTCAGTGGCAGTGGATCTGGGACAGATTTCACTCTCACCATCGGCAGTCTGCAACCT
GAAGATTTTGCTACGTACTACTGTCAACAGAGGAGGCAGTCGCCTTATACGTTCGGCCAA
GGGACCAAGGTGGAAATCAAACGG

BMS2h-174 (SEQ ID NO: 1218)
GACATCCAGATGACCCAGTCTCCATCCTCCCTGTCTGCATCTGTAGGAGACCGTGTCACC
ATCACTTGCCGGGCAAGTGAGGATATTGGGGAGGAGTTATTTTGGTATCAGCAGAAACCA
GGGAAAGCCCCTAAGCTCCTGATCTATTCGGCGTCCACGTTGCAAAGTGAGGTCCCATCA
CGTTTCAGTGGCAGTGGATCTGGGACAGATTTCACTCTCACCATCAGCAGTCTGCAACAT
GAAGATTTTGCTACGTACTACTGTCAACAGGTTTATGAGTGGCCTTATACGTTCGGCCAA
GGGACCAAGGTGGAAATCAAACGG

BMS2h-175 (SEQ ID NO: 1219)
GACATCCAGATGACCCAGTCTCCATCCTCCCTGTCTGCATCTGTAGGAGACCGTGTCACC
ATCACTTGCCGGGCAAGTCAGCCTATTTCTGGGGGTTTAAGGTGGTACCAGCAGAAACCA
GGGAAAGCCCCTAAGCTCCTGATCTATTCTACTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCTTTATTCTGCTCCTTATACGTTCGGCCAA
GGGACCAAGGTGGAAATCAAACGG

BMS2h-305 (SEQ ID NO: 1220)
GACATCCAGATGACCCAGTCTCCATCCTCCCTGTCTGCATCTGTAGGAGACCGTGTCACC
ATCACTTGCCGGGCAAGTCAGGATATTGATCAGGATTTAGAGTGGTACCAGCAGAAACCA
GGGAAAGCCCCTAAGCTCCTGATCTATAATGTTTCCCTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTCTATGAATCCTGTTACGTTCGGCCAA
GGGACCAAGGTGGAAATCAAACGG

BMS2h-306 (SEQ ID NO: 1221)
GACATCCAGATGACCCAGTCTCCATCCTCCCTGTCTGCATCTGTAGGAGACCGTGTCACC
ATCACTTGCCGGGCAAGTCAGGATATTGGGAATCAGTTAAAGTGGTACCAGCAGAAACCA
GGGAAAGCCCCTAAGCTCCTGATCTATCAGGCTTCCGGGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGTATGATTTGAGGCCTCAGACGTTCGGCCAA
GGGACCAAGGTGGAAATCAAACGG

BMS2h-307 (SEQ ID NO: 1222)
GACATCCAGATGACCCAGTCTCCATCCTTCCTGTCTGCATCTGTAGGTGACCGTGTCACC
ATCACTTGCCGGGCGAGTCAGAAGATTTCTACGTCTTTAGAGTGGTATCAGCAGAAACCA
GGGAAAGCCCCTAGGCTCCTGATCTATGATTCTTCCTGGTTGCAAAGTGGGGTCCCATCA
CGTTTCAGTGGCAGTGGATCTGGGACAGATTTCACTCTCACCATTAGCAGTCTGCAACCT
GAAGATTTTGCTACGTACTACTGTCAACAGTATGAGTATAATCCTATTACGTTCGGCCAA
GGGACCAAGGTGGAAATCAAACGG

BMS2h-33 (SEQ ID NO: 1223)
GACATCCAGATGACCCAGTCTCCATCCTCCCTGTCTGCATCTGTAGGAGACCGTGTCACC
ATCACTTGCCGGGCAAGTCAGACGATTGGGGAGAGTTTACATTGGTACCAGCAGAAACCA
GGGAAAGCCCCTAGGCTCCTGATCTATTTTGCTTCCCTGTTGCAAAGTGGGTCCCATCG
CGTTTCAGTGGCAGTGGATCTGGGACAGATTTTACTCTCACCATCAGCAGTCTGCAACCT
GAAGATTTTGCTACGTACTACTGTCAACAGCATCATATGCTTCCTTCTACGTTCGGCCAA
GGGACCAAGGTGGAAATCAAACGG

BMS2h-35 (SEQ ID NO: 1224)
GACATCCAAATGACCCAGTCTCCATCCTCCCTGTCTGCATCTGTAGGAGACCGTGTCACC
ATCACTTGCCGGGCAAGTCAGTTTATTGGTGATTCTTTATCTTGGTACCAGCAGAAACCA
GGGAAAGCCCCTAAGCTCCTGATCTATTTTTCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGGATATTCCTATTACGTTCGGCCAA
GGGACCAAGGTGGAAATCAAACGG

BMS2h-36 (SEQ ID NO: 1225)
GACATCCAGATGACCCAGTCTCCATCCTCCCTGTCTGCATCTGTAGGAGACCGTGTCACC
ATCACTTGCCGGGCAAGTCAGGATATTGATCATAATTTAGAGTGGTATCAGCAGAAACCA
GGGAAAGCCCCTAAGCTCCTGATCTATGATAGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATTCTATTCCTGTTACGTTCGGCCAA
GGGACCAAGGTGGAAATCAAACGG

BMS2h-37 (SEQ ID NO: 1226)
GACATCCAGATGACCCAGTCTCCATCCTCCCTGTCTGCATCTGTAGGAGACCGTGTCACC
ATCACTTGCCGGGCAAGTCAGCAGATTGAGACGAATTTAGAGTGGTATCAGCAGAAACCA
GGGAAAGCCCCTAAGCTCCTGATCTATGATGGTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATAGTTTGCCTGCTACGTTCGGCCAA
GGGACCAAGGTGGAAATCAAACGG

BMS2h-38 (SEQ ID NO: 1227)
GACATCCAGATGACCCAGTCTCCATCCTCCCTGTCTGCATCTGTAGGAGACCGTGTCACC
ATCACTTGCCGGGCAAGTCAGGATATTGGTAATAATTTAGAGTGGTACCAGCAGAAACCA
GGGAAAGCCCCTAGGCTCCTGATCTATCATGGGTCCTGGTTGCAAAGTGGGGTCCCATCG
CGTTTCAGTGGCAGTGGATCTGGGACAGATTTCACTCTTACCATCAGCAGTCTGCAACCT
GAAGATTTTGCTACGTACTACTGTCAACAGTATGATTTTAATCCTACTACGTTCGGCCAA
GGGACCAAGGTGGAAATCAAACGG

BMS2h-39 (SEQ ID NO: 1228)
GACATCCAGATGACCCAGTCTCCATCCTCCCTGTCTGCATCTGTAGGAGACTGTGTCACC
ATCACTTGCCGGGCAAGTCAGAATATTGATGGTCTGTTATGGTGGTATCAGCAGAAACCA
GGGAAAGCCCCTAAGCTCCTGATCTATGCGGGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGAAGGCTTTTGAGCCTTTTACGTTCGGCCAA
GGGACCAAGGTGGAAATCAAACGG

BMS2h-405 (SEQ ID NO: 1229)
GACATCCAGATGACCCAGACTCCATCCTCCCTGTCTGCATCTGTAGGAGACCGTGTCACC
ATCACTTGCCGGGCAAGTCAGAGTATTGGTCATGATTTAGAGTGGTACCAGCAGAAACCA
GGGAAAGCCCCTAAGCTCCTGATCTATAATGTGTCCTGGTTGCAAAGTGGGGTCCCATCA
CGTTTCAGTGGCAGTGGATCTGGGACAGATTTACTCTCACCATCAGCAGTCTGCAACCT
GAAGATTTTGCTACGTACTACTGTCAACAGTATAGTCATAATCCTCCTACGTTCGGCCAA
GGGACCAAGGTGGAAATCAAACGG

BMS2h-406 (SEQ ID NO: 1230)
GACATCCAGATGACCCAGTCTCCATCCTCCCTGTCTGCATCTGTAGGAGACCGTGTCACT
ATCACTTGCCGGGCAAGTCAGCATATTGAGAATGATTTAGAGTGGTACCAGCAGAAACCA
GGGAAAGCCCCTAAGCTCCTGATCTATTCTGCTTCCCATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATCTTCAGCCTACGACGTTCGGCCCA
GGGACCAAGGTGGAAATCAAACGG

BMS2h-431 (SEQ ID NO: 1231)
GACATCCAGATGACCCAGTCTCCATCCTCCCTGTCTGCATCTGTAGGAGACCGTGTCACT
ATCACTTGCCGGGCAAGTCAGGTTATTGAGGGTAGTTTAAATTGGTACCAGCAGAAACCA

TABLE 4-continued

Human Anti-CD40L VK Domain Encoding Nucleotide Sequences

GGGAAAGCCCCTAAGCTCCTGATCTATCATAGGTCCATTTTGCAAAGTGGGGTCCCATCA
CGTTTCAGTGGCCGTGGATCTGGGACAGATTTCACTCTCACCATCAGCAGTCTGCAACCT
GAAGATTTTGCTACGTACTACTGTCAACAGACTTATCAGCTTCCTTTGACGTTCGGCCAA
GGGACCAAGGTGGAAATCAAACGG

BMS2h-432 (SEQ ID NO: 1232)
GACATCCAGATGACCCAGTCTCCATCCTCCCTGTCTGCATCTGTAGGAGACCGTGTCACC
ATCACTTGCCGGGCAAGTCGTCCTATTAATGGTAAGTTATTTTGGTACCAGCAGAAACCA
GGCAAAGCCCCTAAGCTCCTGATCGCGTTTGCTTCCGCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTGCAGCAGGCTGTGTATCCTATTACGTTCGGCCAA
GGGACCAAGGTGGAAATCAAACGG

BMS2h-433 (SEQ ID NO: 1233)
GACATCCAGATGACCCAGTCTCCATCCTCCCTGTCTGCATCTGTAGGAGACCGTGTCACC
ATCACTTGCCGGGCAAGTCAGGCTATTGAGACGAATTTAGAGTGGTATCAGCAGAAACCA
GGGAAAGCCCCTAAGCTCCTGATCTATGATGGGTCCCTTTTGCAAAGTGGGGTCCCATCA
CGTTTCAGTGGCAGAGGATCTGGGACAGATTTCACTCTCACCATCAGCAGTCTGCAACCT
GAAGATTTTGCTACGTACTACTGTCAACAGTATCATTATCAGCCTGCGACGTTCGGCCAA
GGGACCAAGGTGGAAATCAAACGG

BMS2h-434 (SEQ ID NO: 1234)
GACATCCAGATGACCCAGTCTCCATCCTCCCTGTCTGCATCTGTAGGAGACCGTGTCACC
ATCACTTGCCGGGCAAGTCAGGATATTGAGCATGATTTAGAGTGGTACCAGCAGAAACCA
GGGAAAGCCCCTAAGCTCCTGATCTATTCGGCGTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCAGCAGCAGCCTACTACGTTCGGCCAA
GGGACCAAGGTGGAAATCAAACGG

BMS2h-435 (SEQ ID NO: 1235)
GACATCCAGATGACCCAGTCTCCATCCTCCCTGTCTGCATCTGTAGGAGACCGTGTCACC
ATCACTTGCCGGGCAAGTTCGCAGATTGAGGAGTCTTTATGGTGGTACCAGCAGAAACCA
GGGAAAGCCCCTAAGCTCCTGATCGCGGATGTTTCCCTGTTGCAAAGTGGAGTCCCATCA
CGTTTCAGTGGCAGTGGATCTGGGACAGATTTCACTCTCACCATCAGCAGTCTGCAACCT
GAAGATTTTGCTACGTACTACTGTGCTCAGGGTGTGGTGGAGCCTCGTACGTTCGGCCAA
GGGACCAAGGTGGAAATCAAACGG

BMS2h-436 (SEQ ID NO: 1236)
GACATCCAGATGACCCAGTCTCCATCCTCCCTGTCTGCATCTGTAGGAGACCGTGTCACC
ATCACTTGCCGGGCAAGTCAGTATATTGGTCTGGATTTAGAGTGGTATCAGCAGAAACCA
GGGAAAGCCCCTAAGCTCCTGATCTATGCTGCTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTTTCGGCAGCCTATTACGTTCGGCCAA
GGGACCAAGGTGGAAATCAAACGG

BMS2h-437 (SEQ ID NO: 1237)
GACATCCAGATGACCCAGTCTCCATCCTCCCTGTCTGCATCTGTAGGAGACCGTGTCACC
ATCACTTGCCGGGCAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCATGTGCGTCCTCCTGCGACGTTCGGCCAA
GGGACCAAGGTGGAAATCAAACGG

BMS2h-437-1 (SEQ ID NO: 1238)
GACATCCAGTTGACCCAGTCTCCAACCTCCCTGTCTGCAACTGTAGGAGACCGTGTCACC
ATCACTTGCCGGGCAAGTACGCCGATTGGTACTATGTTAGATTGGTACCAGCAGAAACCT
GGGAAAGCCCCTAAGCTCCTGATCGGGCATTCGTCCTGGTTGCAAAGTGGGGTCCCATCA
CGTTTCAGTGGCAGTGGATCTGGGACTGATTTCACTCTCACCATCAGCAGTCTGCAACCT
GAAGATTTTGCTACGTACTACTGTGGGCAGCATGTGCGTCATCCTGCGACGTTCGGCCAA
GGGACCAAGGTGGAAATCAAGCGG

BMS2h-437-2 (SEQ ID NO: 1239)
GACATCCAGATGACCCAGTCTCCATCCTCCCTGTCTGCATCTGTAGGAGACCGTGTCACC
ATCACTTGCCGGGCAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGACAGCATGTGCGTCCTCCTGCGACGTTCGGCCAA
GGGACCAAGGTGGGAATCAAACGG

BMS2h-437-3 (SEQ ID NO: 1240)
GACATCCAGATGACCCAGTCTCCGTCCTCCCTGTCTGCATCTGTAGGAGACCGTGTCACC
ATCACTTGCCGGGTAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCACCA
CGTTTCAGTGGCAGCGGATCTGGGACAGATTTCACTCTCACCATCAGCAGTCTGCAACCT
GAAGATTTTGCTACGTACTACTGTGGGCAGCATGTGCGTCCTCCTGCGACGTTCGGCCAA
GGGACCAAGGTGGAAATCAAACGG

TABLE 4-continued

Human Anti-CD40L VK Domain Encoding Nucleotide Sequences

BMS2h-437-4 (SEQ ID NO: 1241)
GACATCCAGATGACCCAGTCTCCATCCTCCCTGTCTGCATCTGTAGGAGACCGTGTCACC
ATCACTTGCCGGGCAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCTGTGGATCTGGGACAGATTTCACTCTCACCATCAGCAGTCTGCAACCT
GAAGATTTTGCTACGTACTACTGTGGGCAGCATGTGCGTCCTCCTGCGACGTTCGGCCAA
GGGACCAAGGTGGAAATCAAACGG

BMS2h-437-5 (SEQ ID NO: 1242)
GACATCCAGATGACCCAGTCTCCATCCTCCCTGTCTGCATCTGTAGGAGACCGTGTCACC
ATCACTTGCCGGGCAAGTACGCCGATTGGTACTATGATAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCATGTGCGTCCTCCTGCGACGTTCGGCAAA
GGGACCAAGGTGGAAATCAAACGG

BMS2h-438 (SEQ ID NO: 1243)
GACATCCAGATGACCCAGTCTCCATCCTCCCTGTCTGCATCTGTAGGAGACCGTGTCACC
ATCACATGCCGGGCAAGTCAGTATATTGATACTAATTTAGAGTGGTACCAGCAGAAACCA
GGGAAAGCCCCTAGGCTCCTGATCTATGATGGTTCCCAGTTGCAAAGTGGGGTCCCATCA
CGTTTCAGTGGCAGTGGATCTGGGACAGATTTCACTCTCATCATCAGCAGTCTGCAACCT
GAAGATTTTGCTACGTACTACTGTCAACAGTATCAGGTTGTGCCTGTTACGTTCGGCCAA
GGGACCAAGGTGGAAATCAAACGG

BMS2h-439 (SEQ ID NO: 1244)
GACATCCAGATGACCCAGTCTCCATCCTCCCTGTCTGCATCTGTAGGAGACCGTGTCACC
ATCACTTGCCGGGCAAGTCAGAGCATTAGCAGCTATTTAAATTGGTACCAGCAGAAACCA
GGGAAAGCCCCTAGGCTCCTGATCGTGGATTCTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGGATCGTTGGTCTCCTGCTACGTTCGGCCAA
GGGACCAAGGTGGAAATCAAACGG

BMS2h-440 (SEQ ID NO: 1245)
GACATCCAGATGACCCAGTCTCCATCCTCCCTGTCTGCATCTGTAGGAGACCGTGTCACC
ATCACTTGCCGGGCAAGTTCGCGGATTCAGCATATGTTATCTTGGTACCAGCAGAAACCA
GGGAAAGCCCCTAAGCTCCTGATCGGTGGGCATTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCGCAATCGTGTGCGTGGCCTCTGACGTTCGGCCAA
GGGACCAAGGTGGAAATCAAACGG

BMS2h-441 (SEQ ID NO: 1246)
GACATCCAGATGACCCAGTCTCCATCCTCCCTGTCTGCATCTGTAGGAGACCGTGTCACC
ATCACTTGCCGGGCAAGTAGGGGTATTGATGGTGATTTATGGTACCAGCAGAAACCA
GGGAAAGCCCCTAAGCTCCTGATCGCGGATTCTTCCCTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGGGGCTGTTCGGCCTATGACGTTCGGCCAA
GGGACCAAGGTGGAAATCAAACGG

BMS2h-442 (SEQ ID NO: 1247)
GACATCCAGATGACCCAGTCTCCATCCTCCCTGTCTGCATCTGTAGGAGACCGTGTCACC
ATCACTTGCCGGGCAAGTAGGGGTATTGATACTGATTTATGGTACCAGCAGAAACCA
GGGAAAGCCCCTAAGCTCCTGATCGCGGATTCTTCCCTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGGGGCTGTTCGGCCTATGACGTTCGGCCAA
GGGACCAAGGTGGAAATCAAACGG

BMS2h-443 (SEQ ID NO: 1248)
GACATCCAGATGACCCAGTCTCCATCCTCCCTGTCTGCATCTGTAGGAGACCGTGTCACC
ATCACTTGCCGGGCAAGTTATACTATTCCGGTTGCTTTAGATTGGTACCAGCAGAAACCA
GGGAAAGCCCCTAAGCTCCTGATCGCTGATGCGTCCTTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCGCAGGGTTGGCCGGGGCCTCAGACGTTCGGCCAA
GGGACCAAGGTGGAAATCAAACGG

BMS2h-444 (SEQ ID NO: 1249)
GACATCCAGATGACCCAGTCTCCATCCTCCCTGTCTGCATCTGTAGGAGACCGTGTCACC
ATCACTTGCCGGGCAAGTCAGAGTATTGCGACGGACTTAGAGTGGTATCAGCAGAAACCA
GGGAAAGCCCCTAAGCTCCTGATCTATGATACTTCCATGTTGCAAAGCGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATAGTTATAATCCTTCGACGTTCGGCCAA
GGGACCAAGGTGGAAATCAAACGG

BMS2h-445 (SEQ ID NO: 1250)
GACATCCAGATGACCCAGTCTCCATCCTCCCTGTCTGCATCTGTAGGAGACCGTGTCACC
ATCACTTGCCGGGCAAGTGTGCCTATTACTGAGGGTTTATCGTGGTACCAGCAGAAACCA
GGGAAAGCCCCTAAGCTCCTGATCCAGGCTAATTCCTGGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTGGGCAGTGGGAGCATGTTCCTGCGACGTTCGGCCAA
GGGACCAAGGTGGAAATCAAACGG

BMS2h-446 (SEQ ID NO: 1251)
GACATCCAGATGACCCAGTCTCCATCCTCCCTGTCTGCATCTGTAGGAGACCGTGTCACC
ATCACTTGCCGGGCAAGTAGTATGATTCTTTATGGTTTAGATTGGTACCAGCAGAAACCA
GGGAAAGCCCCTAAGCTCCTGATCGGTGGTACTTCCGCGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGGAGACGGTTCCTGCTACGTTCGGCCAA
GGGACCAAGGTGGAAATCAAACGG

BMS2h-447 (SEQ ID NO: 1252)
GACATCCAGATGACCCAGTCTCCATCCTCCCTGTCTGCATCTGTAGGAGACCGTGTCACC
ATCACTTGCCGGGCAAGTCAGCCTATTAATGGGCTTTTAATTTGGTATCAGCAGAAACCA
GGGAAAGCCCCTAAGCTCCTGATCTATGCGATGTCCAGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTTGGCTCGGATTCCTTTTACGTTCGGCCAA
GGGACCAAGGTGGAATCAAACGG

BMS2h-448 (SEQ ID NO: 1253)
GACATCCAGATGACCCAGTCTCCATCCTCCCTGTCTGCATCTGTAGGAGACCGTGTCACC
ATCACTTGCCGAGCAAGTCAGCTGATTCGGACTTATTTAGCGTGGTACCAGCAGAAACCA
GGGAAAGCCCCTAAGCTCCTGATCTATCAGTCTTCTCAGTTGCAAAGTGGTGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATAATTCTTATCCTGATACGTTCGGCCAA
GGGACCAAGGTGGAAATCAAACGG

BMS2h-47 (SEQ ID NO: 1254)
GACATCCAGATGACCCAGTCTCCATCCTCCCTGTCTGCATCTGTAGGAGACCGTGTCACC
ATCACTTGCCGGGCAAGTCAGTGGATTGGGGATTCGTTAAGTTGGTACCAGCAGAAACCA
GGGAAAGCCCCTAAGCTCCTGATCTATTTTGGTTCCTATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTTGCATACTCCTTCGACGTTCGGCCAA
GGGACCAAGGTGGAAATCAAACGG

BMS2h-484 (SEQ ID NO: 1255)
GACATCCAGATGACCCAGTCTCCATCCTCCCTGTCTGCATCTGTAGGAGACCGTGTCACC
ATCACTTGCCGGGCAAGTCAGGATATTGAGGCGGATTTAGAGTGGTACCAGCAGAAACCA
GGGAAAGCCCCTAAGCTCCTGATCTATCATTCTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGGTTTTAATCCTCCTACGTTCGGCCAA
GGGACCAAGGTGGAAATCAAACGG

BMS2h-485 (SEQ ID NO: 1256)
GACATCCAGATGACCCAGTCTCCATCCTCCCTGTCTGCATCTGTAGGAGACCGTGTCACC
ATCACTTGCCGGGCAAGTTCTCCTATTGAGTATGGTTTAGATTGGTACCAGCAGAAACCA
GGGAAAGCCCCTAAGCTCCTGATCGGGGGGGGGTCCGCGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGGAGGTTCAGCCTGCTACGTTCGGCCAA
GGGACCAAGGTGGAAATCAAACGG

BMS2h-486 (SEQ ID NO: 1257)
GACATCCAGATGACCCAGTCTCCATCCTCCCTGTCTGCATCTGTAGGAGACCGTGTCACC
ATCACTTGCCGGGCAAGTCAGCGGATTGATACTGATTTAGAGTGGTACCAGCAGAAACCA
GGGAAAGCCCCTAAGCTCCTGATCTATGATAGTTCACAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATCATAGTGCGCCTGCGACGTTCGGCCAA
GGGACCAAGGTGGAAATCAAACGG

BMS2h-487 (SEQ ID NO: 1258)
GACATCCAGATGACCCAGTCTCCATCCTCCCTGTCTGCATCTGTAGGAGACCGTGTCACC
ATCACTTGCCGGGCAAGTGGGTGGATTGGTATGTCTTTAGAGTGGCACCAGCAGAAACCA
GGGAAAGCCCCTAAGCTCCTGATCCGTGGGGCTTCCTCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTAGTCAGTCTCGGTGGCCGCCTGTGACGTTCGGCCAA
GGGACCAAGGTGGAAATCAAACGG

BMS2h-488 (SEQ ID NO: 1259)
GACATCCAGATGACCCAGTCTCCATCCTCCCTGTCTGCATCTGTAGGAGACCGTGTCACC
ATCACTTGCCGGGCAAGTCGTAATATTTCGAATGCTTTATCGTGGTACCAGCAGAAACCA
GGGAAAGCCCCTAAGCTCCTGATCCTTGGGGCTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTACTCAGGTGTGGGATAGGCCTTTTACGTTCGGCCAA
GGGACCAAGGTGGAAATCAAACGG

BMS2h-489 (SEQ ID NO: 1260)
GACATCCAGATGACCCAGTCTCCATCCTCCCTGTCTGCATCTGTAGGAGACCGTGTCACC
ATCACTTGCCGGGCAAGTCAGGATATTATGTCGGCTTTATCTTGGTATCAGCAGAAACCA

TABLE 4-continued

Human Anti-CD40L VK Domain Encoding Nucleotide Sequences

```
GGGAAAGCCCCTAAGCTCCTGATCTATTCTACTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTTATTTGCTGCCTGTTACGTTCGGCCAA
GGGACCAAGGTGGAAATCAAACGG

BMS2h-490 (SEQ ID NO: 1261)
GACATCCAGATGACCCAGTCTCCATCCTCCCTGTCTGCATCTGTAGGAGACCGTGTCACC
ATCACTTGCCGGGCAAGTCAGGAGATTGGGATTGATTTAGAGTGGTATCAGCAGAAACCA
GGGAAAGCCCCTAAGCTCCTGATCTATGCTGCTTCTTATTTGCAAAGTGGGGTCCCATCA
CGTTTCAGTAGCAGTGGATCTGGGACAGATTTCACTCTCACCATCAGCAGTCTGCAACCT
GAAGATTTTGCTACGTACTACTGTCAACAGTATGCTTCTAATCCTCCTACGTTCGGCCGA
GGGACCAAGGTGGAAATCAAACGG

BMS2h-491 (SEQ ID NO: 1262)
GACATCCAGATGACCCAGTCTCCATCCTCCCTGTCTGCATCTGTAGGAGACCGTGTCACC
ATCACTTGCCGGGCAAGTCAGATGATTGGGGATTGGTTAAATTGGTACCAGCAGAAACCA
GGGAAAGCCCCTAAACTCCTGATCTATCGTAGTTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTTGTATTTTGGCCTCGTACGTTCGGCCAA
GGGACCAAGGTGGAAATCAAACGG

BMS2h-492 (SEQ ID NO: 1263)
GACATCCAGATGACCCAGTCTCCATCCTCCCTGTCTGCATCTGTAGGAGACCGTGTCACC
ATCACTTGCCGGGCAAGTCAGGCGATTGAGCTTAATTTAGAGTGGTACCAGCAGAAACCA
GGGAAGGCCCCTAAGCTCCTGATCTATGATGCTTCCATGTTGCAAAGCGGGGTCCCATCA
CGTTTCAGTGGCAGTGGATCTGGGACAGATTTCACTCTCACCATTAGCAGTCTGCAACCT
GAAGATTTTGCTACGTACTACTGTCAACAGTATGATGTTTATCCTCCTACGTTCGGCCAA
GGGACCAAGGTGGAAATCAAACGG

BMS2h-492-1 (SEQ ID NO: 1264)
GACATCCAGATGACCCAGTCTCCATCCTCCCTGTCTGCATCTGTAGGAGACCGTGTCACC
ATCACTTGCCGGGCCAGTCAGGCGATTGAGCATAATTTAGAGTGGTACCAGCAGAAGCCA
GGGAAGGCCCCTAAGCTCCTGATCTATGATGCTTCCATGTTGCAAAGCGGGGTCCCATCA
CGTTTCAGTGGCAGTGGATCTGGGACAGATTTCACTCTCACCATTAGCAGTCTCCAACCT
GAAGATTAGCTACGTACTACTGTCAACAGTATGATGCTTATCCTCCTACGTACGGCCAA
GGGACCAAGGTGGAAATCAAACGG

BMS2h-492-2 (SEQ ID NO: 1265)
GACATCCAGATGACACAGTCTCCATCCTCCCTGTCCGCATCTGTAGGAGACCGTGTCACC
ATCACTTGCCGGGCAAGTCGGGCGATAGAGACTAATTTAGAGTGGTACCAGCAGAAACCA
GGGAAGGCCCCTAAGCTCCTGTTCTATGATGCTTCCATGTTGCAAAGCGGGGTCCCATCA
CGTTTCGGTGGCAGTGGATCTGGGACAGATTTCACTCTCACCATTAGCAGTCTGCAACCT
GAAGATTTTGCTACGTACTACTGTCTACAGTATGATGTTTATCCTCCTACGTTCGGCCAA
GGGACCAAGGTGGAAATCAAACGG

BMS2h-492-3 (SEQ ID NO: 1266)
GACATCCAGATGACCCAGTCTCCATCCTCCCTGTCTGCAACTGTAGGAGACCGTGTCACC
ATCACTTGTCGTGCAAGTCAGGCGATTGAGACTAATTTAGAGTGGTACCAGCAGAAACCA
GGGAAGGCCCCTAAGCTCCTGATCTATGATGCTTCCATGTTGCAAAGCGGGGTCCCATCA
CGTTTCAGTGGCAGTGGATCTGGGACAGACTTCACTCTCACCATTAGCAGTCTGCAACCT
GAAGATTTTGCTACGTACTACTGTCAACAGTATGATGCTTATCCTCCTACGTTCGGCCAA
GGGACCAAGGTGGAAATCAAACGG

BMS2h-492-4 (SEQ ID NO: 1267)
GACATCCAGATGACCCAGTCTCCATCCTCCCTGTCTGCATCTGTAGGAGACCGTGTCACC
ATCACTTGCCGGGCAAGTCAGGCGATTGAGCATAACTTAGAGTGGTACCAGCAGAAACCA
GGGAAGGCCCCTAAGCTCCTGATCTATGATGCTTCCATGTTGCAAAGCGGGGTCCCATCA
CGTTTCAGTGGCAGAGGATCTGGGACAGATTTCACTCTCACCATTAGCAGTCTGCAACCT
GAAGATTTTGCTACGTACTACTGTCAACAGTATGATGCTTATCCTCCTACGTTCGGCCAA
GGGACCAAGGTGGAAATCAAACGG

BMS2h-492-5 (SEQ ID NO: 1268)
GACATCCAGATGAACCAGTCTCCATCCTCCCTGTCTGCATCTGTAGGAGACCGTGTCTCC
ATCACTTGCAGGGCAAGTCAGGCTATTGAGCATAATTTAGAGTGGTACCAGCAGAAACCA
GGGAAGGCCCCTAAGCTCCTGATCTATGATGCTTCCATGTTGCAAAGCGGGGTCCCATCA
CGCTTCAGTGGCAGTGGATCTGGGACAGATTTCACTCTCACCATTAGCAGTCTGCAACCT
GAAGATTTTGCTACGTACTACTGTCAACAGTATGATGCTTATCCTCCTACGTTCGGCCAA
GGGACCAAGGTGGAAATCAAACGG

BMS2h-492-6 (SEQ ID NO: 1269)
GACATCCAGATGACCCAGTCTCCATCCTCCCTGTCTGCATCTGTAGGAGACCGTGTCACC
ATCACTTGCCGGGCAAGTCAGGCGATTGAGTCTAATTTAGAGTGGTACCAGCAAAAACCA
GGGAAGGCCCCTAAGCTCCTGATCTATGATGCTTCCATGTTGCAAAGCGGGGTCCCATCA
CGTTTCAGTGGCAGTGGATCTGGGACAGATTTCACTCTCACCATTAGCAGTCTGCAACCT
GAAGATTTTGCTACGTACTACTGTCAACAGTATGATGTTTATCCTCCTACGTTCGGCCAA
GGGACCAAGGTGGAAATCAAACGG
```

TABLE 4-continued

Human Anti-CD40L VK Domain Encoding Nucleotide Sequences

BMS2h-492-7 (SEQ ID NO: 1270)
GACATCCAGATGACCCAGTCTCCATCCTCCCTGTCTGCATCTGTAGGAGACCGTGTCACC
ATCACTTGCCGTGCAAGTCAGGCGATTGAGCATAATTTAGAGTGGTACCAGCAGAAACCA
GGGAAGGCCCCTAAGCTCCTGATCTATGATGCTTCCATGTTGCAAAGCGGGGTCCCATCA
CGTTTCAGTGGCAGTGGATCTGGGACAGATTTCACTCTCACCATTAGCAGTCTGCAACCT
GAAGATTTTGCTACGTACTACTGTCAACAGTATGATGCTTATCCTCCTACGTTCGGCCAA
GGGACCAAGGTGGAAATCAAACGG

BMS2h-493 (SEQ ID NO: 1271)
GACATCCAGATGACCCAGTCTCCATCCTCCCTGTCTGCATCTGTAGGAGACCGTGTCACC
ATCACTTGCCGGGCAAGTCAGGGTATTGATGAGGATTTAGAGTGGTACCAGCAGAAACCA
GGGAAAGCCCCTAGGCTCCTGATCTATTCTAGTTCCTGGTTGCAAAGTGGGGTCCCATCA
CGTTTCAGTGGGAGTGGATCTGGGACAGATTTCACTCTCACCATCAGCAGTCTGCAACCT
GAAGATTTTGCTACGTACTACTGTCAACAGTATTTTCAGTATCCTCCGACGTTCGGCCAA
GGGACCAAGGTGGAAATCAAACGG

BMS2h-494 (SEQ ID NO: 1272)
GACATCCAGATGACCCAGTCTCCATCCTCCCTGTCTGCATCTGTAGGAGACCGTGTCACC
ATCACTTGCCGGGCAAGTCAGAGTATTGATGAGGATTTAGAGTGGTACCAGCAGAAACCA
GGGAAAGCCCCTAGGCTCCTGATCTATTCTAGTTCCTGGTTGCAAAGTGGGGTCCCATCA
CGTTTCAGTGGGAGTGGATCTGGGACAGATTTCACTCTCACCATCAGCAGTCTGCAACCT
GAAGATTTTGCTACGTACTACTGTCAACAGTATTTTCAGTATCCTCCGACGTTCGGCCAA
GGGACCAAGGTGGAAATCAAACGG

BMS2h-494-1 (SEQ ID NO: 1273)
GACATCCAGATGACCCAGTCTCCATCCTCCCTGTCCGCATCTGTAGGAGACCGTGTCACC
ATCACTTGCAGGGCAAGTCAGAGTATTGATGAGGATTTAGAGTGGTACCAGCAGAAACCA
GGGAAAGCCCCTAGGCTCCTGATCTATTCTAGTTCCTGGTTGCAAAGTGGGGTCCCATCA
CGTTTCAGTGGGAGTGGATCTGGGACAGATTTCACTCTCACCATCAGCAGTCTGCAACCT
GAAGATTTTGCTACGTACTACTGTCAACAGTATTCTCAGTATCCTCCGACGTTCGGCCAA
GGGACCAAGGTGGAAATCAAACGG

BMS2h-494-2 (SEQ ID NO: 1274)
GACATCCAGATGACCCAGTCTCCATCCTCCCTGTCTGCATCTGTAGGAGACCGTGTCACC
ATCACTTGCCGGGCAAGTCAGAGTATTGAAGAGGATTTAGAGTGGTACCAGCAGAAACCA
GGGAAAGCCCCTAGGCTCCTGATCTATTCTAGTTCCTGGTTGCAAAGCGGGGTCCCATCA
CGTTTCAGTGGGAGTGGCTCTGGGACAGATTTCACTCTCACCATCAGCAGTCTGCAACCT
GAAGATTTTGCTACGTACTACTGTCAACAGTATTTTCAGTATCCTCCGACGTTCGGCCAT
GGGACCAAGGTGGAAATCAAACGG

BMS2h-494-3 (SEQ ID NO: 1275)
GACATCCAGATGACCCAGTCTCCATCCTCCCTGTCTGCATCTGTAGGAGACCGTGTCACC
ATCACTTGCCGGGCAAGTCAGAGTATTGATGAGGATTTAGAGTGGTACCAGCAGAAACCA
GGGAAAGCCCCTAGGCTCCTGATCTATTCTAGTTCCTGGTTGCAAAGTGGGGTCCCATCA
CGTTTCAGTGGGAGTGGATCTGGGACAGATTTCACTCTCACCATCAGCAGTCTGCAACCT
GAAGATTTTGCTACGTACTTCTGTCAACAGTATTTTCAGTATCCTCCGACGTTCGGCCAA
GGGACCAAGGTGGAAATCAAACGG

BMS2h-494-4 (SEQ ID NO: 1276)
GAGATCCAGATGACCCAGTCTCCATCCTCCCTGTCTGCATCTGTAGGAGACCGTGTCACC
ATGACTTGCCGGGCAAGTCAGAGTATTGATAAGGATTTAGAGTGGTACCAGCAGAAACCA
GGGAAAGCCCCTAGGCTCCTGATCTATTCTAGTTCCTGGTTGCAAAGAGGGGTCCCATCA
CGTTTCAGTGGGAGTGGATCTGGGACAGATTTCACTCTCACCATCAGCAGTCTGCGACCT
GAAGATTTTGCTACGTACTACTGTCAACAGTATTTTCAGTATCCTCCGACGTTGGGCCAA
GGGACCAAGGTGGAAATCAAACGG

BMS2h-494-5 (SEQ ID NO: 1277)
GACATCCAGATGACCCAGTCTCCATCCTCCCTGTCTGCATCTGTAGGAGACCGAGTCACC
ATCACTTGCCGGGCAAGTCAGAGTATTGATGAGGATTTAGAGTGGTACCAGCAGAAACCA
GGGAAAGCCCCTAGGCTCCTGATCTATTCTAGTTCCTGGTTGCAAAGTGGGGTCCCATCA
CGTTTCAGTGGGAGTGGATCTGGGACAGATTTCACTCTCACCATCAGCGGTCTGCAACCT
GAAGATATCGCTACGTACTACTGTAAACAGTATTCTCAGTATCCTCCGACGTTCGGCCAA
GGGACCAAGGTGGAAATCAAACGG

BMS2h-494-6 (SEQ ID NO: 1278)
GACATCCAGATGACCCAGTCCCCACCCTCCCTGTCTGCATCTGTAGGAGACCGTGTCACC
ATCACTTGCCGGGCAAGTCAGAGTATTGATAAGGATTTAGAGTGGTACCAGCAGAAACCA
GGGAAAGCCCCTAGGCTCCTGATCTATTCTAGTTCCTGGTTGCAAAGAGGGGTCCCATCA
CGTTTCAGTGGGAGTGGATCTGGGACAGATTTCACTCTCACCATCAGCAGTCTGCAACCT
GAAGATTTTGCTACGTACCACTGTCAACAGTATTTTCAGTATCCTCCGACGTTCGGCCAA
GGGACCAAGGTGGAAATCAAACGG

BMS2h-495 (SEQ ID NO: 1279)
GACATCCAGATGACCCAGTCTCCATCCTCCCTGTCTGCATCTGTAGGAGACCGTGTCACC
ATCACTTGCCGGGCAAGTGAGTATATTAATGCTGAGTTAGCTTGGTATCAGCAGAAACCA
GGGAAAGCCCCTAAGCTCCTGATCTATGGGAGTTCCGGGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCTGCAGAATGCGATGTGGCCTATTACGTTCGGCCAA
GGGACCAAGGTGGAAATCAAACGG

BMS2h-496 (SEQ ID NO: 1280)
GACATCCAGATGACCCAGTCTCCATCCTCCCTGTCTGCATCTGTAGGAGACCGTGTCACC
ATCACTTGCCGGGCAAGTCTGGATATTAATAATGTTTAATTTGGTACCAGCAGAAACCA
GGGAAAGCCCCTAGGCTCCTGATCTTGGGTGCGTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTTCGCAGGTGCGTTCTCGGCCTTTTACGTTCGGCCAA
GGGACCAAGGTGGAAATCAAACGG

BMS2h-497 (SEQ ID NO: 1281)
GACATCCAGATGACCCAGTCTCCATCCTCCCTGTCTGCATCTGTAGGAGACCGTGTCACC
ATCACTTGCCGGGCAAGTCAGGATATTCTGAGTGCGTTAGCTTGGTATCAGCAGAAACCA
GGGAAAGCCCCTAAGCTCCTGATCTATGGGAGTTCCGTTTTGCAAAGTGGGGTCCCATCA
CGTTTCAGTGGCAGTGGATCAGGGACAGATTTCACTCTCACCATCAGCAGTCTGCAACCT
GAAGATTTTGCTACGTACTACTGTCAACAGAATTATAGTCTTCCTATTACGTTCGGCCAA
GGGACCAAGGTGGAAATCAAACGG

BMS2h-498 (SEQ ID NO: 1282)
GACATCCAGATGACCCAGTCTCCATCCTCCCTGTCTGCATCTGTAGGAGACCGTGTCACC
ATCACTTGCCGGGCAAGTTCTCCTATTGAGTCGTATTTAAGGTGGTACCAGCAGAAACCA
GGGAAAGCCCCTAAGCTCCTGATCAGGTATGTGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGTTTCGGGCGCCTGTTACGTTCGGCCAA
GGGACCAAGGTGGAAATCAAACGG

BMS2h-499 (SEQ ID NO: 1283)
GACATCCAGATGACCCAGTCTCCATCCTCCCTGTCTGCATCTGTAGGAGACCGTGTCACC
ATCACTTGCCGGGTAAGTGAGTCTATTAATGCTGAGTTACATTGGTACCAGCAGAAACCA
GGGAAAGCCCCTAAGCTCCTGATCTCTGGGTTTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTGCAGTTTGCGATGTGGCCTTTTACGTTCGGCCAA
GGGACCAAGGTGGAAATCAAACGG

BMS2h-500 (SEQ ID NO: 1284)
GACATCCAGATGACCCAGTCTCCATCCTCCCTGTCTGCATCTGTAGGAGACCGTGTCACC
ATCACTTGCCGGGCAAGTATGATGATTAGGTTTGGGTTAGATTGGTACCAGCAGAAACCA
GGGAAAGCCCCTAAGCTCCTGATCGGTGGTGGGTCCTCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCATGAGCGGTGGCCTGCTACGTTCGGCCAA
GGGACCAAGGTGGAAATCAAACGG

BMS2h-501 (SEQ ID NO: 1285)
GACATCCAGATGACCCAGTCTCCATCCTCCCTGTCTGCATCTGTAGGAGACCGTGTCACC
ATCACTTGCCGGGCAAGTCAGAGTATTGGTACTCTTTTACGTTGGTATCAGCAGAAACCA
GGGAAAGCCCCTAAGCTCCTGATCTATCTTACTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATGGTTTATCGTCCTTATACGTTCGGCCAA
GGGACCAAGGTGGAAATCAAACGG

BMS2h-502 (SEQ ID NO: 1286)
GACATCCAGATGACCCAGTCTCCATCCTCCCTGTCTGCATCTGTAGGAGACCGTGTCACC
ATCACTTGCCGGGCAAGTCAGACTATTGAGACTAATTTAGAGTGGTACCAGCAGAAACCA
GGGAAAGCCCCTAAGCTCCTGATCTATGATTCTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGATAAGGTTCCTGCGACGTTCGGCCAA
GGGACCAAGGTGGAAATCAAACGG

BMS2h-503 (SEQ ID NO: 1287)
GACATCCAGATGACCCAGTCTCCATCCTCCCTGTCTGCATCTGTAGGAGACCGTGTCACC
ATCACTTGCCGGGCAAGTCATCATATTCAGAGGTATTTATCGTGGTACCAGCAGAAACCA
GGGAAAGCCCCTAAGCTCCTGATCCTTTGGGGTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGTGGGCTCCTCCTCCGACGTTCGGCCAA
GGGACCAAGGTGGAAATCAAACGG

BMS2h-503-1 (SEQ ID NO: 1288)
GACATCCAGATGACCCAGTCTCCATCCTCCCTGTCTGCATCTGTAGGAGACCGTGTCACC
ATCACTTGCCGGGCAAGTCATCATATTCAGAGGTATTTATCGTGGTACCAGCAGAAACCA
GGGAAAGCCCCTAAGCTCCTGATCCTTTGGGGTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGTGGGCTCCTCCTCAGACGTTCGGCCAA
GGGACCAAGGTGGAAATCAAACGG

BMS2h-503-2 (SEQ ID NO: 1289)
GACATCCAGATGACCCAGTCTCCATCCTCCCTGTCTGCATCTGTAGGAGACCGTGTCACC
ATCACTTGCCGGGCAAGTCATGATATTCAGAGGTATTTATCGTGGTACCAGCAGAAACCA

TABLE 4-continued

Human Anti-CD40L VK Domain Encoding Nucleotide Sequences

GGGAAAGCCCCTAAGCTCCTGATCCTTTGGGGTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGTGGGCTCCTCCTCAGACGTTCGGCCAA
GGGACCAAGGTGGAAATCAAACGG

BMS2h-504 (SEQ ID NO: 1290)
GACATCCAGATGACCCAGTCTCCATCCTCCCTGTCTGCATCTGTAGGAGACCGTGTCACC
ATCACATGCCGGGCAAGTCAGTATATTGATACTAATTTAGAGTGGTACCAGCAGAAACCA
GGGAAAGCCCCTAAGCTCCTGATCTATGATGGTTCCCTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGGGGGCTGTTGTGCCTGTTACGTTCGGCCAA
GGGACCAAGGTGGAAATCAAACGG

BMS2h-508 (SEQ ID NO: 1291)
GACATCCAGATGACCCAGTCTCCATCCTCCCTGTCTGCATCTGTAGGAGACCGTGTCACC
ATCACTTGCCGGGCAAGTCAGGATATTGCTTTTGATTTAGAGTGGTATCAGCAGAAACCA
GGGAAAGCCCCTAAGCTCCTGATCTATTCGGCGTCCATGTTGCAAAGTGGGGTCCCATCA
CGTTTCAGTGGCAGTGGATCTGGGTCAGATTTCACTCTCACCATCAGCAGTCTGCAACCT
GAAGATTTTGCTACGTACTACTGTCAACAGTATAATCTTCAGCCTCCTACGTTCGGCCAA
GGGACCAAGGTGGAAATCAAACGG

BMS2h-509 (SEQ ID NO: 1292)
GACATCCAGATGACCCAGTCTCCATCCTCCCTGTCTGCATCTGTAGGAGACCGTGTCACC
ATCACTTGCCGGGCAAGTCAGAATATTGCTACGCTGTTACGTTGGTACCAGCAGAAACCA
GGGAAAGCCCCTAAGCTCCTGATCTATGCTGGTTCCATGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATGTGGCAGCGTCCTTATACGTTCGGCCAA
GGGACCAAGGTGGAAATCAAACGG

BMS2h-51 (SEQ ID NO: 1293)
GACATCCAGATGACCCAGTCTCCATCCTCCCTGTCTGCATCTGTAGGAGACCGTGTCACC
ATCACTTGCCGGGCAAGTCAGCCTATTGTTGATGAGTTAGATTGGTACCAGCAGAAACCA
GGGAAAGCCCCTAAGCTCCTGATCTATGCTGCGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCATCAGTGGTCTACTTATCCTACGACGTTCGGCCAA
GGGACCAAGGTGGAAATTAAACGG

BMS2h-510 (SEQ ID NO: 1294)
GACATCCAGATGACCCAATCTCCATCCTCCCTGTCTGCATCTGTAGGAGACCGTGTCACC
ATCACTTGCCGGGCAAGTCAGAGCATTAGCAGCTATTTAAATTGGTACCAGCAGAAACCA
GGGAAAGCCCCTAAGCTCCTAATCGATGGTGTTTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGGATTGGGATTGGCCTCGTACGTTCGGCCAA
GGGACCAAGGTGGAAATCAAACGG

BMS2h-511 (SEQ ID NO: 1295)
GACATCCAGATGACCCAGTCTCCATCCTCCCTGTCTGCATCTGTAGGAGACCGTGTCACC
ATCACTTGCCGGGCAAGTAGGAATATTCGTGATTGGTTACGGTGGTACCAGCAGAAACCA
GGGAAAGCCCCTAAGCTCCTGATCGATTGGGGGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGACGTGGGATGATCCTCTGACGTTCGGCCAA
GGGACCAAGGTGGAAATCAAACGG

BMS2h-511-1 (SEQ ID NO: 1296)
GACATCCAGATGACCCAGTCTCCATCCTCCCTGTCTGCATTTGTAGGAGACCGTGTCACC
ATCACTTGCCGGGCAAGTAGGAATATTCGTGATTGGTTACGGTGGTACCAACAGAAACCA
GGGAAAGCCCCTAAGCTCCTGATCGATTGGGGGTCCGAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGACGTGGTATGATCCTCTGACGTTCGGCCAC
GGGACCAAGGTGGAAATCAAACGG

BMS2h-512 (SEQ ID NO: 1297)
GACATCCAGATGACCCAGTCTCCATCCTCCCTGTCTGCATCTGTAGGAGACCGTGTCACC
ATCACTTGCCGGGCAAGTATTGATATTCATGGTGGTTTAACTTGGTACCAGCAGAAACCA
GGGAAAGCCCCTAAGCTCCTGATCGTGGGGGTTTCCGGTTTGCAAAGTGGGGTCCCATCA
CGTTTCAGTGGCAGTGGATCTGGGACAGATTTCACTCTCACCATCAGCAATCTGCAACCT
GAAGATTTTGCTACGTACTACTGTGCGCAGGTGTGGCGTAGGCCTTTTACGTTCGGCCAA
GGGACCAAGGTGGAAATCAAACGG

BMS2h-513 (SEQ ID NO: 1298)
GACATCCAGATGACCCAGTCTCCATCCTCCCTGTCTGCATCTGTAGGAGACCGTGTCACC
ATCACTTGCCGGGCAAGTCAGGATATTGGGAGTTCGTTATCTTGGTATCAGCAGAAACCA
GGGAAAGCCCCTAAGCTCCTGATCTATGCTTCTTCCCTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTTATGCTCTTCCTGTTACGTTCGGCCAA
GGGACCAAGGTGGAAATCAAACGG

TABLE 4-continued

Human Anti-CD40L VK Domain Encoding Nucleotide Sequences

BMS2h-514 (SEQ ID NO: 1299)
GACATCCAGATGACCCAGTCTCCATCCTCCCTGTCTGCATCTGTAGGAGACCGTGTCACC
ATCACTTGCCGGGCAAGTCAGCAGATTGAGACGAATTTAGAGTGGTATCAGCAGAAACCA
GGGAAAGCCCCTAAGCTCCTGATCTATGATGGTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATAAGTATCTGCCTGTGACGTTCGGCCAA
GGGACCAAGGTGGAAATCAAACGG

BMS2h-52 (SEQ ID NO: 1300)
GACATCCAGATGACCCAGTCTCCATCCTCCCTGTCTGCATCTGTAGGTGACCGTGTCACC
ATCACTTGCCGGGCAAGTCAGGATATTGGGTCTGCGTTAAGGTGGTATCAGCAGAAACCA
GGGAAAGCCCCTAAGCTCCTGATCTATTTGGGTTCCGATTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGCAGTATTTTCCTACGACGTTCGGCCAA
GGGACCAAGGTGGAAATCAAACGG

BMS2h-53 (SEQ ID NO: 1301)
GACATCCAGATGACCCAGTCTCCATCCTCCCTGTCTGCATCTGTAGGAGACCGTGTCACC
ATCACTTGCCGGGCAAGTCAGGCGATTTATGGGGGGTTACGGTGGTACCAGCAGAAACCA
GGGAAAGCCCCTAAGCTCCTGATCTATGGGGAGTCCATGTTGCAAAGTGGGGTCCCATCA
CGTTTCAGTGGCAGTGGATCTGGGACAGATTTCACTCTCACCATCAGCAGTCTGCATCCT
GAAGATTTTGCTACGTACTACTGTCAACAGGTTTATCATAAGCCTTTTACGTTCGGCCAA
GGGACCAAGGTGGAAATCAAACGG

BMS2h-536 (SEQ ID NO: 1302)
GACATCCAGATGACCCAGTCTCCATCCTCCCTGTCTGCATCTGTAGGAGACCGTGTCACC
ATCACGTGCCGGGCAAGTCAGCGTATTGGGGTGTGGTTAGATTGGTATCAGCAGAAACCA
GGGAAAGCCCCTAAGCTCCTGATCTATGATGGTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACTTTTTCGAGTCCTTCTACGTTCGGCCAA
GGGACCAAGGTGGAAATCAAACGG

BMS2h-537 (SEQ ID NO: 1303)
GACATCCAGATGACCCAGTCTCCATCCTCCCTGTCTGCATCTGTAGGAGACCGTGTCCCC
ATCACTTGCCGGGCAAGTCAGTGGATTGGGGATGAGTTATATTGGTATCAGCAGAAACCA
GGGAAAGCCCCTAAGCTCCTGATCTATAGTTCTTCCACTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCGTTTCAGTTTCCTTATACGTTCGGCCAA
GGGACCAAGGTGGAAATCAAACGG

BMS2h-538 (SEQ ID NO: 1304)
GACATCCAGATGACCCAGTCTCCATCCTCCCTGTCTGCATCTGTAGGAGACCGTGTCACC
ATCACTTGCCGGGCAAGTAGTAATATTACGGGCCGTTAGAGTGGTACCAGCAGAAACCA
GGGAAAGCCCCTAAGCTCCTGATCCCTGGTTGGTCCACTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGGTGTGGGGGGAGCCTGTTACGTTCGGCCAA
GGGACCAAGGTGGAAATCAAACGG

BMS2h-539 (SEQ ID NO: 1305)
GACATCCAGATGACCCAGTCTCCATCCTCCCTGTCTGCGTCTATAGGAGACCGTGTCACC
ATCACTTGCCGGGCAAGTCAGCGTATTGCTTATGTTTACATTGGTTACCAGCAGAAACCA
GGGAAAGCCCCTAGGCTCCTGATCGGGGGCGGTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTGCAGCCTGGGATGCCGCCTGATACGTTCGGCCAA
GGGACCAAGGTGGAAATCAAACGG

BMS2h-540 (SEQ ID NO: 1306)
GACATCCAGATGACCCAGTCTCCATCCTCCCTGTCTGCATCTGTAGGAGACCGTGTCACC
ATCACTTGCCGGGCAAGTAAGCAGATTGTTGGTGGTTTATCTTGGTACCAGCAGAAACCA
GGGAAAGCCCCTAAGCTCCTGATCGGGCGTCATTCTGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCAGGGGGTTTGGGCTCCTGGGACGTTCGGCCAA
GGGACCAAGGTGGAAATCAAACGG

BMS2h-541 (SEQ ID NO: 1307)
GACATCCAGATGACCCAGTCTCCATCCTCCCTGTCTGCATCTGTAGGAGACCGTGTCACC
ATCACTTGCCGGGCAAGTCCTGCTATTGCTGCTAAGTTAGATTGGTACCAGCAGAAACCA
GGGAAAGCCCCTAAGCTCCTGATCGGTGCGGATTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGCTGTGGGCGGGGCCTCCGACGTTCGGCCAA
GGGACCAAGGTGGAAATCAAACGG

BMS2h-542 (SEQ ID NO: 1308)
GACATCCAGATGACCCAGTCTCCATCCTCCCTGTCTGCATCTGTAGGAGACCGTGTCACC
ATCACTTGCCGGGCAAGTCGTACTATTGCTGATGGGTTAGATTGGTACCAGCAGAAACCA
GGGAAAGCCCCTAAGCTCCTGATCGGGGCGTATTCCGGTTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

```
GAAGATTTTGCTACGTACTACTGTGGTCAGCTTTGGGAGGGTCCTCCGACGTTCGGCCAA
GGGACCAAGGTGGAAATCAAACGG

BMS2h-543 (SEQ ID NO: 1309)
GACATCCAGATGACCCAGTCTCCATCCTCCCTGTCTGCATCTGTAGGAGACCGTGTCACC
ATCACTTGCCGGGCAAGTCAGAGGATTTATGGGTTTTTAGATTGGTCAGCAGCAGAAACCA
GGGAAAGCCCCTAAGCTCCTGATCTATGGGGTGTCCTCGTTGCAAAGTGGGGTCCCATCA
CGTTTTAGTGGCAGCGGATCTGGGACAGATTTCACTCTCACCATCAGCAGTCTGCAACCT
GAAGATTTTGCTACGTACTACTGTCAACAGACTTTGGCGTGGCCTTTTACGTTCGGCCAA
GGGACCAAGGTGGAAATCAAACGG

BMS2h-544 (SEQ ID NO: 1310)
GACATCCAGATGACCCAGTCTCCATCCTCCCTGTCTGCATCTGTAGGAGACCGTGTCACC
ATCACTTGCCGGGCAAGTCAGGATATTCGGGATTGGTTAATGTGGTACCAGCAGAAACCA
GGGAAAGCCCCTAAGCTCCTGATCTATTGGGGTTCCTTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCTGTATGATACTCCTTATACGTTCGGCCAA
GGGACCAAGGTGGAAATCAAACGG

BMS2h-545 (SEQ ID NO: 1311)
GACATCCAGATGACCCAGTCTCCATCCTCCCTGTCTGCATCTGTAGGAGACCGTGTCACC
ATCACTTGCCGGGCAAGTCAGAATATTAATACGGGTTTAGATTGGTATCAGCAGAAACCA
GGGAAAGCCCCTAAGCTCCTGATCTATGATAGTTCCGCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGTCGTATTATCCTTATACGTTCGGCCAA
GGGACCAAGGTGGAAATCAAACGG

BMS2h-546 (SEQ ID NO: 1312)
GACATCCAGATGACCCAGTCTCCATCCTCCCTGTCTGCATCTGTAGGAGACCGTGTCACC
ATCACTTGCCGGGCAAGTCAGAAGATTTTTGGTTGGTTAGATTGGTACCAGCAGAAACCA
GGGAAAGCCCCTAAGCTCCTGATCTATGGGACTTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTTATTCGCTTCCTTATACGTTCGGCCAA
GGGACCAAGGTGGAAATCAAACGG

BMS2h-547 (SEQ ID NO: 1313)
GACATCCAGATGACCCAGTCTCCATCCTCCCTGTCTGCATCTGTAGGAGACCGTGTCACC
ATCACTTGCCGGGCAAGTTCGAATATTGGGGCGGATTTAGATTGGTACCAGCAGAAACCA
GGGAAAGCCCCTAAGCTCCTGATCGGGGGGGCGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCTGTGGAATGGGCCTCCTACGTTCGGCCAA
GGGACCAAGGTGGAAATCAAACGG

BMS2h-548 (SEQ ID NO: 1314)
GACATCCAGATGACCCAGTCTCCATCCTCCCTGTCTGCATCTGTAGGAGACCGTGTCACC
ATCACTTGCCGGGCAAGTAGTCCGATTTATGATGGTTTAGATTGGTACCAGCAGAAACCA
GGGAAAGCCCCTAAGCTCCTGATCTCTGGTGCTTCCTGGTTGCAAAGTGGGGTCCCATCA
CGCTTCAGTGGCAGTGGATCTGGGACAGATTTCACTCTCACCATCAGCAGTCTGCAACCT
GAAGATTTTGCTACGTACTACTGTGGTCAGTTGTGGTTGGGTCCTCCGACGTTCGGCCAA
GGGACCAAGGTGGAAATCAAACAG

BMS2h-549 (SEQ ID NO: 1315)
GACATCCAGATGACCCAGTCTCCATCCTCCCTGTCTGCATCTGTAGGAGACCGTGTCACC
ATCACTTGCCGGGCAAGTTCGCGTATTTATAATGGTTTACATTGGTACCAGCAGAAACCA
GGGAAAGCCCCTAAGCTCCTGATCGGTGGTCGGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGGTGGGGGAGGCTCCTTCTACGTTCGGCCAA
GGGACCAAGGTGGAAATCAAACGG

BMS2h-550 (SEQ ID NO: 1316)
GACATCCAGATGACCCAGTCTCCATCCTCCCTGTCTGCATCTGTAGGAGACCGTGTCACC
ATCACTTGCCGGGCAAGTAGGTTTATTAATGAGGAGTTAGATTGGTACCAGCAGAAACCA
GGGAAAGCCCCTAAGCTCCTGATCTCGTGGTCTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGTGCAGCCGGGGGTGGTCCTGGGACGTTCGGCCAA
GGGACCAAGGTGGAAATCAAACGG

BMS2h-551 (SEQ ID NO: 1317)
GACATCCAGATGACCCAGTCTCCATCCTCCCTGTCTGCATCTGTAGGAGACCGTGTCACC
ATCACTTGCCGGGCAAGTAGGGATATTCTGGATGAGTTAGATTGGTACCAGCAGAAACCA
GGGAAAGCCCCTAGGCTCCTGATCGGTGGGGGGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGCTGTGGCATGGGCCTCCGACGTTCGGCCAA
GGGACCAAGGTGGAAATCAAACGG

BMS2h-552 (SEQ ID NO: 1318)
GACATCCAGATGACCCAGTCTCCATCCTCCCTGTCTGCATCTGTAGGAGACCGTGTCACC
ATCACTTGCCGGGCAAGTAGTCCTATTTATACGGGTTTACATTGGTACCAGCAGAAACCA
```

TABLE 4-continued

Human Anti-CD40L VK Domain Encoding Nucleotide Sequences

GGGAAAGCCCCTAAGCTCCTGATCGGTGGGCGGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTATGCAGGTTGGGACGGCTCCTGCTACGTTCGGCCAA
GGGACCAAGGTGGAAATCAAACGG

BMS2h-585 (SEQ ID NO: 1319)
GACATCCGGATGACCCAGTCTCCATCCTCCCTGTCTGCATCTGTAGGAGACCGTGTCACC
ATCACTTGCCGGGCAAGTCAGAATATTTCTAGGCGGTTACTGTGGTACCAGCAGAAACCA
GGGAAAGCCCCTAAGCTCCTGATCTATTCTTCTTCCCGGTTGCAAAGTGGGGTCCCATCA
CGTTTCGGTGGCAGTGGATCTGGGACGGATTTCACTCTCACCATCAGCAGTCTGCAACCT
GAAGATTTTGCTACGTACTACTGTCAACAGACGTATAGCTATCCTCATACGTTCGGCCAA
GGGACCAAGGTGGAAATCAAACGG

BMS2h-604 (SEQ ID NO: 1320)
GACATCCAGATGACCCAGTCTCCATCCTCCCTGTCTGCATCTGTAGGAGACCGTGTCACC
ATCACTTGCCGGGCAAGTAGTCCGATTCCGCAGGATTTATATTGGTACCAGCAGAAACCA
GGGAAAGCCCCTAAGCTCCTGATCGTTGGGATTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTTGTGGAGTGCGCCTGCTACGTTCGGCCAA
GGGACCAAGGTGGAAATCAAACGG

BMS2h-605 (SEQ ID NO: 1321)
GACATCCAGATGACCCAGTCTCCATCCTCCCTGTCTGCATCTGTAGGAGACCGTGTCACC
ATCACTTGCCGGGCAAGTAAGTCTATTGATGGGATGTTAGATTGGTACCAGCAGAAACCA
GGGAAAGCCCCTAAGCTCCTGATCCCTGGTTTTTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTCGGTTGAGGCGCCTTGGACGTTCGGCCAA
GGGACCAAGGTGGAAATCAAACGG

BMS2h-606 (SEQ ID NO: 1322)
GACATCCAGATGACCCAGTCTCCATCCTCCCTGTCTGCATCTGTAGGAGACCGTGTCACC
ATCACTTGCCGGGCAAGTCGGTATATTGCTCATCCTTTAGATTGGTACCAGCAGAAACCA
GGGAAAGCCCCTAAGCTCCTGATCCCGGGTTCGTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGTCAGTCGGTTGTGGTGCCTTGGACGTTCGGCCAA
GGGACCAAGGTGGAAATCAAACGG

BMS2h-607 (SEQ ID NO: 1323)
GACATCCAGATGACCCAGTCTCCATCCTCCCTGTCTGCATCTGTAGGAGACCGTGTCACC
ATCACTTGCCGGGCAAGTCGGACGATTGAGGGTGGTTTAGATTGGTACCAGCAGAAACCA
GGGAAAGCCCCTAAGCTCCTGATCATGGGGGGTTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTTGTGGGTGGGTCCTCCTACGTTCGGCCAA
GGGACCAAGGTGGAAATCAAACGG

BMS2h-608 (SEQ ID NO: 1324)
GACATCCAGATGACCCAGTCTCCATCCTCCCTGTCTGCATCTGTAGGAGACCGTGTCACC
ATCACTTGCCGGGCAAGTAAGTTTATTAGGGATGAGTTATATTGGTACCAGCAGAAACCA
GGGAAAGCCCCTAGGCTCCTGATCGGTGGTTCGTCCTTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCTGTGGCGGGCGCCTGCGACGTTCGGCCAA
GGGACCAAGGTGGAAATCAAACGG

BMS2h-609 (SEQ ID NO: 1325)
GACATCCAGATGACCCAGTCTCCATCCTCCCTGTCTGCATCTGTAGGAGACCGTGTCACC
ATCACTTGCCGGGCAAGTAAGCCGATTTATGGTGGTTTAGAGTGGTACCAGCAGAAACCA
GGGAAAGCCCCTAGGCTCCTGATCGGGGGGGGTTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGGTGTGGGGGGTCCTGTTACGTTCGGCCAA
GGGACCAAGGTGGAAATCAAACGG

BMS2h-610 (SEQ ID NO: 1326)
GACATCCGGATGACCCAGTCTCCATCCTCCCTGTCTGCATCTGTAGGAGACCGTGTCACC
ATCACTTGCCGGGCAAGTCGGCCGATTAGTGGTTGTTTAGATTGGTACCAGCAGAAACCA
GGGAAAGCCCCTAAGCTCCTGATCGATGGGGCTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTGGTGGGAGTATCCTCCTACGTTCGGCCAA
GGGACCAAGGTGGAAATCAAACGG

BMS2h-611 (SEQ ID NO: 1327)
GACATCCAGATGACCCAGTCTCCATCCTCCCTGTCTGCATCTGTAGGAGACCGTGTCACC
ATCACTTGCCGGGCAAGTAAGCCTATTGTGAGGGATTTAGAGTGGTACCAGCAGAAACCA
GGGAAAGCCCCTAAGCTCCTGATCCATGGTGTGTCCACGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCTTGAGGCGGCGCCTGCGACGTTCGGCCAA
GGGACCAAGGTGGAAATCAAACGG

TABLE 4-continued

Human Anti-CD40L VK Domain Encoding Nucleotide Sequences

BMS2h-612 (SEQ ID NO: 1328)
GACATCCAGATGACCCAGTCTCCATCCTCCCTGTCTGCATCTGTAGGAGACCGTGTCACC
ATCACTTGCCGGGCAAGTCGGGATATTGGTGATTGGTTATATTGGTACCAGCAGAAACCA
GGGAAAGCCCCTAGGCTCCTGATCGTTTGGGCGTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCGCAGTGGGGGACTCCTCCTACGACGTTCGGCCAA
GGGACCAAGGTGGAAATCAAACGG

BMS2h-613 (SEQ ID NO: 1329)
GACATCCAGATGACCCAGTCTCCATCCTCCCTGTCTGCATCTGTAGGAGACCGTGTCACC
ATCACTTGCCGGGCAAGTAATCGTATTGAGTATGGTTTAGATTGGTACCAGCAGAAACCA
GGGAAAGCCCCTAAGCTCCTGATCTCGGGGTCTTCCCGTTTGCAAAGTGGGGTCCCATCA
CGTTTCAGTAGCAGTGGATCTGGGACAGATTTCACTCTCACCATCAGCAGTCTGCAACCT
GAAGATTTTGCTACGTACTACTGTGGGCAGCTTGAGGCGGCGCCTGCGACGTTCGGCCAA
GGGACCAAGGTGGAAATCAAACGG

BMS2h-614 (SEQ ID NO: 1330)
GACATCCAGATGACCCAGTCTCCATCCTCCCTGTCTGCATCTGTAGGAGACCGTGTCACC
ATCACTTGCCGGGCAAGTCGGAATATTGGGCATTTTTTAGATTGGTACCAGCAGAAACCA
GGGAAAGCCCCTAAGCTCCTGATCTTGGGGGGGTCCTCGTTGCAAAGTGGGGTCCCATCA
CGTTTCAGTGGCAGCGGGTCTGGGACAGATTTCACTCTCACCATCAGCAGTCTGCAACCT
GAAGATTTTGCTACGTACTACTGTGGGCAGTTGGTGGAGCCTCCTGCGACGTTCGGCCAA
GGGACCAAGGTGGAAATCAAACGG

BMS2h-615 (SEQ ID NO: 1331)
GACATCCAGATGACCCAGTCTCCATCCTCCCTGTCTGCATCTGTAGGAGACCGTGTCACC
ATCACTTGCCGGGCAAGTTCGAGTATTTATAGTGATTTATATTGGTACCAGCAGAAACCA
GGGAAAGCCCCTAAGCTCCTGATCGATGGGTGGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCTGCATCGTGCTCCTGCGACGTTCGGCCAA
GGGACCAAGGTGGAAATCAAACGG

BMS2h-616 (SEQ ID NO: 1332)
GACATCCAGATGACCCAGTCTCCATCCTCCCTGTCTGCATCTGTAGGAGACCGTGTCACC
ATCACTTGCCGGGCAAGTAGGTTTATTACTGATCGTTTAGATTGGTACCAGCAGAAACCA
GGGAAAGCCCCTAAGCTCCTGATCGGTGGTGTTTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGAGTTCGGAGTTGCCTTGGACGTTCGGCCAA
GGGACCAAGGTGGAAATCAAACGG

BMS2h-617 (SEQ ID NO: 1333)
GACATCCAGATGACCCAGTCTCCATCCTCCCTGTCTGCATCTGTAGGAGACCGTGTCACC
ATCACTTGCCGGGCAAGTCGTAAGATTGGTAGTGAGTTATATTGGTACCAGCAGAAACCA
GGGAAAGCCCCTAAGCTCCTGATCGGTGGTAGGTCCCGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGTTGTGGGAGCCTCCTGCGACGTTCGGCCAA
GGGACCAAGGTGGAAATCAAACGG

BMS2h-618 (SEQ ID NO: 1334)
GACATCCAGATGACCCAGTCTCCATCCTCCCTGTCTGCATCTGTAGGAGACCGTGTCACC
ATCACTTGCCGGGCAAGTAGGAATATTGGTAATGGTTTAGATTGGTACCAGCAGAAACCA
GGGAAAGCCCCTAAGCTCCTGATCGGGGAGGGTCCCGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCTTTGGCATACTCCTCCTACGTTCGGCCAA
GGGACCAAGGTGGAAATCAAACGG

BMS2h-619 (SEQ ID NO: 1335)
GACATCCAGATGACCCAGTCTCCATCCTCCCTGTCTGCATCTGTAGGAGACCGTGTCACC
ATCACTTGCCGGGCAAGTCGGAATATTTATGGTTGGTTATCGTGGTACCAGCAGAAACCA
GGGAAAGCCCCTAGGCTCCTGATCGGTGGGTGGTCCGGTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCGCAGGATTATACGTTGCCTGGTACGTTCGGCCAA
GGGACCAAGGTGGAAATCAAACGG

BMS2h-730 (SEQ ID NO: 1336)
GACATCCAGATGACCCAGTCTCCATCCTCCCTGTCTGCATCTGTAGGAGACCGTGTCACC
ATCACTTGCCGGGCAAGTCAGGATATTAAGGATTGGTTACATTGGTACCAGCAGAAACCA
GGGAAAGCCCCTAAGCTCCTGATCTATTTTGCGTCCGGTTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGCATTATAGTACGCCTTATACGTCCGGCCAA
GGGACCAAGGTGGAAATCAAACGG

BMS2h-731 (SEQ ID NO: 1337)
GACATCCAGATGACCCAGTCTCCACCCTCCCTGTCTGCATCTGTAGGAGACCGTGTCACC
ATCACTTGCCGGGCAAGTCAGTTGATTCTTCTCATTTAGATTGGTACCAGCAGAAACCA
GGGAAAGCCCCTAAGCTCCTGGTCTATGATGCTTCCGAGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGCATCGCAGTCTGCCTTTTACGTTCGGCCAA
GGGACCAAGGTAGAAATCAAACGG

BMS2h-732 (SEQ ID NO: 1338)
GACATCCAGATGACCCAGTCTCCATCCTCCCTGTCTGCATCTGTAGGAGACCGTGTCACC
ATCACTTGCCGGGCAAGTCAGTGGATTGGTGGGGCGTTAGCGTGGTACCAGCAGAAACCA
GGGAAAGCCCCTAGGCTCCTTATCTATCAGATTTCCGTTTTGCAAAGTGGGATCCCATCA
CGTTTCAGTGGCAGTGGATCTGGGACAGATTTCACTCTCACCATCAGCAGTCTGCAACCT
GAAGATTTTGCTACGTACTACTGTCAACAGTATATTCGGTCTCCTTTTACGTTCGGCCAA
GGGACCAAGGTGGAAATCAAACGG

BMS2h-733 (SEQ ID NO: 1339)
GACATCCAGATGACCCAGTCTCCATCCTCCCTGTCTGCATCTGTAGGAGACCGTGTCACC
ATCACTTGCCGGGCAAGTCAGAGTATTGGGGCGGCGTTAAATTGGTATCAGCAGAAACCA
GGGAAAGCCCCTAAGCTCCTGATCTATGGTCTGTCCTCTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCTGTTTAGGCTTCCTTTGACGTTCGGCCAA
GGGACCAAGGTGGAAATCAAACGG

BMS2h-734 (SEQ ID NO: 1340)
GACATCCAGATGACCCAGTCTCCATCCTCCCTGTCTGCATCTGTAGGAGACCGTGTCACC
ATCACTTGCCGGGCAAGTCAGCCTATTGGGGGTCGTTTAGTGTGGTACCAGCAGAAACCA
GGGAAAGCCCCTAAGCTCCTGATCTATGGGTCTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATGCTGAGGCTCCTATTACGTTCGGCCAA
GGGACCAAGGTGGAAATCAAACGG

BMS2h-735 (SEQ ID NO: 1341)
GACATCCAGATGACCCAGTCTCCATCCTCCCTGTCTGCATCTGTAGGAGACCGTGTCACC
ATCACTTGCCGGGCAAGTCAGAATATTGGGTCTAGTTTAATTTGGTACCAGCAGAAACCA
GGGAAAGCCCCTACGCTCCTGATCTATTATTCGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTCTTTGTCGAGTCCTTATACGGTCGGCCAA
GGGACCAAGGTGGAAATCAAACGG

BMS2h-736 (SEQ ID NO: 1342)
GACATCCAGATGACCCAGTCTCCATCCTCCCTGTCTGCATCTGTAGGAGACCGTGTCACC
ATCACTTGCCGGGCAAGTCAGTGGATTGGGAGTGAGTTAGCGTGGTATCAGCAGAAACCA
GGGAAAGCCCCTAAGCTCCTGATCTATTGGACGTCCAATTTGCAAAGTGGGGTCCCATCA
CGTTTCAGTGGCAGTGGATCTGGGACAGATTTCACTCTCACCATCAGCAATCTGCAACCT
GAAGATTTTGCTACGTACTACTGTCAACAGATTCTGGAGACTCCTTTGACGTTTGGCCAA
GGGACCAAGGTGGAAATCAAACGG

BMS2h-737 (SEQ ID NO: 1343)
GACATCCAGATGACCCAGTCTCCATCCTCCCTGTCTGCATCTGTAGGAGACCGTGTCACC
ATCACTTGCCGGGCAAGTCAGAAGATTTGGGATGCTTTATATTGGTATCAGCAGAAACCA
GGGAAAGCCCCTAAGCTCCTGATCTATCGTGGGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTTTTATCGGTGGCCTCATACGTTCGGCCAA
GGGACCAAGGTGGAAATCAAACGG

BMS2h-738 (SEQ ID NO: 1344)
GACATCCAGATGACCCAGTCTCCATCCTCCCTGTCTGCATCTGTAGGAGACCGTGTCACC
ATCACTTGCCGGGCAAGTCAGCATATTGAGGATTCTTTACGGTGGTACCAGCAGAAACCA
GGGAAAGCCCCTAAGCTCCTGATCTATTATGGTTCCGTGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATGTATAAGTTTCCTATTACGTTCGGCCAA
GGGACCAAGGTGGAAATCAAACGG

BMS2h-739 (SEQ ID NO: 1345)
GACATCCAGACGACCCAGTCTCCATCCTCCCTGTCTGCATCTGTAGGAGACCGTGTCACC
ATCACTTGCCGGGCAAGTCAGCGGATTAATTCTTCTTTACTGTGGTACCAGCAGAAACCA
GGGAAAGCCCCTAAGCTCCTGATCTATGATACTTCCACTTTGCAAAGTGGGGTCCCATCA
CGTTTCAGTGGCAGTAGATCTGGGACAGATTTCACTCTCACCATCAGCAGTCTGCAACCT
GAAGATTTCGCTACGTACTACTGTCAACAGATTTGGGGTTCGCCTCCTACGTTCGGCCAG
GGGACCAAGGTGGAAATCAAACGG

BMS2h-740 (SEQ ID NO: 1346)
GACATCCAGATGACCCAGTCTCCATCCTCCCTGTCTGCATCTGTAGGAGACCGTGTCACC
ATCACTTGCCGGGCAAGTCAGTCGATTCCTGTTGGTTTAAATTGGTACCAGCAGAAACCA
GGGAAAGCCCCTAGGCTCCTGATCTATTCTGGGTCCACTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGATTGGTATTATCCTAATACGTTCGGCCAA
GGGACCAAGGTGGAAATCAAACGG

BMS2h-785 (SEQ ID NO: 1347)
GACATCCAGATGACCCAGTCTCCATCCTCCCTGTCTGCATCTGTAGGAGACCGTGTCACC
ATCACTTGCCGGGCAAGTCAGCCTATTTATGGTTGGTTAAATTGGTATCAGCAGAAACCA

TABLE 4-continued

Human Anti-CD40L VK Domain Encoding Nucleotide Sequences

```
GGGAAAGCCCCTAAGCTCCTGATCTATTTGACGTCCGGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGATTCATAGTTCTCCTTTTACGTTCGGCCAA
GGGACCAAGGTGGAAATCAAACGG

BMS2h-8 (SEQ ID NO: 1348)
GACATCCAGATGACCCAGTCTCCATCCTCCCTGTCTGCATCTGTAGGAGACCGTGTCACC
ATCACTTGCCGGGCAAGTCAGTTTATTGATACGTCGTTAGAGTGGTATCAGCAGAAACCA
GGGAAAGCCCCTAAGCTCCTGATCTATGATGGGTCCCATTTGCAAAGTGGGGTCCCATCA
CGTTTCAGTGGCAGTGGATCTGGGACAGATTTCACTCTCACCATCAGCAGTCTGCAACCT
GAAGATTTAGCTACGTACTACTGTCAACAGTATTGGGTTCTTCCTCTGACGTTCGGCCAA
GGGACCAAGGTGGAAATCAAACGG

BMS2h-86 (SEQ ID NO: 1349)
GACATCCAGATGACCCAGTCTCCATCCTCCCTGTCTGCATCTGTAGGAGACCGTGTCACC
ATCACTTGCCGGGCAAGTCAGGATATTGGGGATGCTTTATTTTGGTACCAGCAGAAACCA
GGGAAAGCCCCTAAGCTCCTGATCTATTATTCTTCCATGTTGCAAAGTGGGGTCCCATCA
CGTTTCAGTGGCGGTGGATCTGGGACAGATTTCACTCTCACCATCAGCAGTCTGCAACCT
GAAGATTTTGCTACGTACTACTGTCAACAGCGGCATAGTACTCCTGCTACGTTCGGCCAA
GGGACCAAGGTGGAAATCAAACGG

BMS2h-87 (SEQ ID NO: 1350)
GACATCCAGATGACCCAGTCTCCATCCTCCCTGTCTGCATCTGTAGGAGACCGTGTCACC
ATCACTTGCCGGGCAAGTCAGGATATTGATGAGTCTTTAATGTGGTACCAGCAGAAACCA
GGGAAAGCCCCTAGGCTCCTGATCTATGGGGTGTCCTATTTGCAAAGTGGGGTCCCATCA
CGTTTCAGTGGCAGTGGATCTGGGACAGATTTCACTCTCACCATCAGCAGTCTGCAACCT
GAAGATTTCGCTACGTACTACTGTCAACAGCGGTGGAAGGCTCCTTTTACGTTCGGCCAA
GGGACCAAGGTGGAAATCAAACGG

BMS2h-88 (SEQ ID NO: 1351)
GACATCCAGATGACCCAGTCTCCATCCTCCCTGTCTGCATCTGTAGGAGACCGTGTTACC
ATCACTTGCCGGGCAAGTCAGGAGATTGTGGAGGATTTATATTGGTATCAGCAGAAACCA
GGGAAAGCCGCTAAGCTCCTGATCTATGGTGCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGCGTAGGCGTCCTTATACGTTCGGCCAA
GGGACCAAGGTGGAAATCAAACGG

BMS2h-89 (SEQ ID NO: 1352)
GACATCCAGATGACCCAGTCTCCAGCCTCCCTGTCTGCATCTGTAGGAGACCGTGTCACC
ATCACTTGCCGGGCAAGTCAGGATATTGATCCTATGTTAAGGTGGTACCAGCAGAAACCA
GGGAAAGCCCCTAAGCTCCTGATCTATGCGGGTTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGACGCTGGTGACTCCTTATACGTTCGGCCAA
GGGACCAAGGTGGAAATCAAACGG

BMS2h-90 (SEQ ID NO: 1353)
GACATCCAGATGACCCAGTCTCCATCCTCCCTGTCTGCATCTGTAGGAGACCGTGTCACC
ATCACTTGCCGGGCAAGTCAGTCGATTTCGGATGCGTTATTTTGGTACCAGCAGAAACCA
GGGAAAGCCCCTAGGCTCCTGATCTATTATGGTTCCGTTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGCGTTTTCAGGAGCCTGTGACGTTCGGCCAA
GGGACCAAGGTGGAAATCAAACGG

BMS2h-91 (SEQ ID NO: 1354)
GACATCCAGATGACCCAGTCTCCATCCTCCCTGTCCGCATCTGTAGGAGACCGTGTCACC
ATCACTTGCCGGGCAAGTCAGCAGATTAGTGATGAGTTAAATTGGTATCAGCAGAAACCA
GGGAAAGCCCCTAAGCTCCTGATCTATGCTGTGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTGGTTGAGTTTTCCTTCGACGTTTGGCCAA
GGGACCAAGGTGGAAATCAAACGG
```

Example 1

Generation of Human Anti-CD40L Variable Domains BMS2h-2 Through BMS2h-785

The following example describes the generation of the 2h lineage of anti-human CD40L variable domains, designated BMS2h-2 through BMS2h-785. Following recombinant expression of a repertoire of single immunoglobulin variable domains on the surface of phage, selection is performed by contacting the phage repertoire with immobilized target antigen, washing to remove unbound phage, and propagating the bound phage. This process is frequently referred to as "panning." It is applicable to the screening of single immunoglobulin variable domains, as well as other antibody fragments that can be expressed on a display library, e.g., scFv, Fab, and Fab'. Alternatively, phage may be pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749, for example.

The screening of phage antibody libraries is generally described, for example, by Harrison et al., *Meth. Enzymol.* 267: 83-109 (1996).

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., *BioTechnology* 11: 1145 (1993); de Kruif et al., *Proc. Natl. Acad. Sci. USA* 92: 3938 (1995)). Another alternative involves selection by binding biotinylated antigen in solution, followed by capture on streptavidin-coated beads.

dAb Selection for Clone BMS2h-719 and BMS2h-7xx Series:

Three rounds of selection using decreasing concentrations of antigen (500 nM at round 1; 50 nM at round 2; 50 nM or 5 nM at round 3 depending on the library output used) were performed in parallel against biotinylated (1.2 moles biotin/mole CD40L) human CD40L monomer triple mutant (T211E, S222Y, H224K, [108-261] Construct #7) provided by Bristol-Myers Squibb. Phage from the naïve 4G and 6G Domantis dAb libraries were combined into the pools a) to g) indicated below before initiating selections:

a) 4G VH CDR3 lengths between 7-10 amino acids.
b) 4G VH CDR3 lengths between 11-15 amino acids.
c) 4G VH CDR3 lengths between 7-15 amino acids.
d) 4G VK
e) 6G VH CDR3 lengths between 7-9
f) 6G VH CDR3 lengths between 10-15
g) 6G VK Each round of selection involved adding the desired concentration of biotinylated CD40L to a mixture of 200 µl of phage (from one of the naïve library pools indicated above, or subsequent selection output phage) and 1000 µl of 2% MPBS (Phosphate Buffered Saline) containing 2% (w/v) Marvel [Premier Foods, UK]) and incubating at room temperature for 1 hour by mixing end-over-end. The biotinylated antigen phage complex was then captured by adding 100 µl of resuspended Dynabeads M-280 Streptavidin [Invitrogen, UK] and incubated for 5 minutes with mixing end-over-end at room temperature. The Dynabeads were then recovered using a KingFisher magnetic separator [Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 µl of trypsin-PBS (50 µl of 10 mg/ml trypsin [Sigma-Aldrich, UK] dissolved in 50 mM Tris-HCl pH 7.4, 1 mM $CaCl_2$ added to 450 µl PBS). The phage-containing solution was recovered and 250 µl used to infect 1.75 ml of logarithmic growth phase *E. coli* TG1 (at an $OD_{600}$ of 0.4) for 30 minutes at 37° C. The *E. coli* TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 litre, autoclaved for 15 minutes at 121° C.) and plated onto a 9 cm Petri dish containing TYE media supplemented with 15 µg/ml tetracycline. The plates were incubated overnight at 37° C. then 2 ml of 2×TY supplemented with 15% glycerol was added to each plate and cells loosened with a glass spreader and mixed thoroughly. Fifty microlitres of the scraped bacteria was used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated CD40L monomer triple mutant antigen.

Phage ELISA

Monoclonal phage ELISAs were carried out following selection rounds 2 and 3. All washes were performed using 3 washes of 250 µl PBST followed by 3 washes of 250 µl PBS. The plates were coated overnight at 4° C. with 50 µl/well of 1 µg/ml NeutrAvidin [Thermo Scientific, UK] in 0.2M carbonate-bicarbonate buffer, pH 9.4. The plates were washed and then blocked with 2% MPBS for 1 hour at room temperature. The plates were then washed and incubated with 50 µl/well of ~1.0 µg/ml biotinylated human CD40L monomer triple mutant in 2% MPBS. The plates were washed and 25 µl/well phage supernatants added to an equal volume of 2% MPBS and incubated for 1 hour at room temperature. The plates were washed and bound phage detected with 50 µl/well anti-M13-HRP conjugate [GE Healthcare, UK] diluted 1:5000 in 2% MPBS and incubated for 1 hour at room temperature. The plates were washed and the ELISA developed using 50 µl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells coated with NeutrAvidin but without biotinylated CD40L monomer triple mutant.

Recovery of dAb Genes from MidiPrep pDOM4 Plasmid

The dAb V-genes from the following round 3 outputs were recovered by DNA restriction enzyme digestion of the phage vector pDOM4:

a) 4G VH CDR3 lengths between 7-10 amino acids (50 nM antigen concentration).
b) 4G VH CDR3 lengths between 11-15 amino acids (50 nM antigen concentration).
c) 4G VH CDR3 lengths between 11-15 amino acids (5 nM antigen concentration).
d) 4G VH CDR3 lengths between 7-15 amino acids (50 nM antigen concentration).
e) 4G VK (50 nM antigen concentration).
f) 4G VK (5 nM antigen concentration).
g) 6G VH CDR3 lengths between 7-9 (50 nM antigen concentration).
h) 6G VH CDR3 lengths between 10-15 (5 nM antigen concentration).

Approximately 20 µg of MidiPrep [Qiagen, UK] DNA was digested with SalI and NoI as follows: 20 µl DNA (~1 µg/µl) was mixed with 1.5 µl SalI (20 U/µl) [NEB, UK] and 3 µl NoI (10 U/µl) [NEB, UK], 4 µl Buffer 3 [NEB, UK], 0.4 µl BSA (10 mg/ml) [NEB, UK] and tissue culture grade water [Sigma, UK] added to 40 µl. Samples were incubated for 5 hours at 37° C. in an air incubator following which the digested dAb genes were isolated by running the digestion mix on a 2% agarose gel [E-gel, Invitrogen, UK], the appropriate DNA bands excised and cleaned using a PCR purification kit [Qiagen, UK]. The purified V-genes were ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 µl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to CD40L monomer triple mutant and IZ-CD40L mutant (CD40L containing an isoleucine zipper trimerization domain, supplied by Bristol-Myers Squibb). MaxiSorp 96 well immunoplates [Nunc, USA] were coated overnight at 4° C. with 50 µl/well of 1 µg/ml NeutrAvidin in 0.2 M carbonate-bicarbonate buffer, pH 9.4. All washes were as described for the phage ELISA. The plates were blocked for 1 hour at room temperature with 200 µl of PBS containing 1% Tween 20. The plate was then washed and incubated for 1 hour at room temperature with 50 µl/well of 1 µg/ml biotinylated human CD40L monomer triple mutant in PBST or 1 µg/ml biotinylated human IZ-CD40L mutant in PBST (both antigens supplied by Bristol-Myers Squibb). The ELISA plate was washed and dAb-containing culture supernatant clarified by centrifugation at 1,800 g for 10 min at 4° C., then added to the ELISA plate (30 µl/well) to which was added an equal volume of PBST. The plates were incubated for 1 hour at room temperature and then washed. Bound dAb was detected by adding 50 µl/well 9E10 [anti-myc IgG, Sigma-Aldrich, UK] diluted 1:2000 in PBST and incubating for 1 hour at room temperature; the ELISA plate was then washed and 50 µl/well anti-mouse Fc-HRP [Sigma-Aldrich, UK] diluted 1:2000 in PBST added and incubated for 1 hour at room temperature. The plates were washed and the ELISA developed by adding 50 µl/well SureBlue 1-Component TMB MicroWell Peroxidase solution [KPL Inc, USA] and the colour allowed to develop. The colourimetric reaction was stopped by the addition of an equal volume of 1 M HCl and the ELISA plate read at 450 nm. Antigen binding dAbs were identified by comparison of the signal intensity from human CD40L monomer triple mutant and human IZ-CD40L mutant wells with control wells not containing antigen.

Expression & Purification of dAb at 50 ml Scale

Unique dAbs were identified by DNA sequencing ELISA positive clones. The unique dAbs identified were expressed as follows in 250 ml baffled flasks, to which was added:
 a) 50 ml of Terrific Broth [Sigma-Aldrich, UK].
 b) 100m/ml carbenicillin [Sigma-Aldrich, UK].
 c) 1 drop of antifoam A204 [Sigma-Aldrich, UK].
 d) Novagen Overnight Express Autoinduction Kit [Novagen, UK].

A bacterial scrape from a fresh confluent 9 cm diameter agar plate or from a glycerol stock of the desired dAb clone was used to inoculate the Terrific Broth, then the flask was sealed with Milliwrap PTFE membrane [Millipore, UK], and incubated for 48 hrs, 250 rpm shaking at 30° C. The bacterial overnight culture was clarified by centrifugation and the VH or VK dAb purified using Streamline Protein A [GE Healthcare, UK] or Protein L agarose [generated in-house] respectively. The resulting purified proteins were assayed by RBA to determine which clones could inhibit the binding of CD40L for CD40.

CD40L Bead Receptor Binding Assay

Inhibitory dAbs were initially identified by screening purified dAb in a CD40L bead receptor binding assay (RBA). Sphero streptavidin polystyrene beads (0.5% w/v, 6.7 µm diameter) [Saxon, Europe] were prepared and washed according to the manufacturer's instructions. The beads were then pelleted at 11,600 g for 1 minute, the supernatant discarded and the beads resuspended in 1 ml PBS by vortexing. The washing step was repeated twice more, the supernatant discarded and the beads resuspended in 1 ml (0.5 mg/ml) of biotinylated human IZ-CD40L in PBS and incubated overnight at room temperature with end-over-end rotation. Following incubation, the beads were pelleted and washed three times with 1 ml PBS as before and then resuspended in 0.5 ml PBS containing 0.1% bovine serum albumin (BSA). The antigen coated beads were then diluted 1:10 in PBS containing 0.1% BSA prior to use. The reagents for the RBA assay were added as follows to duplicate wells in a 384-well black sided clear bottomed FMAT plate [Applied Biosystems, UK]:
 a) 12.5 µl dAb protein or buffer control. The dAb titration starting concentration was typically 10 µM (final concentration) which was diluted 1:3.3 (i.e., 30 µl sample added to 70 µl PBS containing 0.1% BSA) to produce an 8-point titration effect curve.
 b) 12.5 µl CD40-Fc [supplied by Bristol-Myers Squibb, USA; lot CY24Feb06-1] at 0.2 µg/ml (for a final concentration of 0.05 µg/ml) diluted in PBS containing 0.1% BSA.
 c) 12.5 µl Mixture of mouse anti-human Fc [Sigma-Aldrich, UK] at 2 µg/ml (for a final concentration of 0.5 µg/ml) and goat anti-mouse Alexa Fluor 647 [Invitrogen, UK] at 1 µg/ml (for a final concentration of 0.25 µg/ml) diluted in PBS containing 0.1% BSA.
 d) 12.5 µl IZ-CD40L coated beads described above were added to the centre of the well so they did not disperse to the edge of the well.

Following addition of the reagents to the 384 well plate, it was incubated at room temperature for 6 hours in the dark and then read in an AB8200 FMAT system [Applied Biosystems, UK].

Example 2 dAb Selection for Clone BMS2h-572

Three rounds of selection using decreasing concentrations of antigen (300 nM at round 1; 30 nM at round 2; 3 nM at round 3) were performed in parallel against biotinylated (1.42 moles biotin/mole trimer) human isoleucine zipper-CD40L (IZ-hCD40L) provided by Bristol-Myers Squibb. Phage from the naïve 4G and 6G Domantis dAb libraries were combined into the pools a) to h) indicated below before initiating selections:
 a) 4G VH CDR3 lengths between 7-9 amino acids.
 b) 4G VH CDR3 lengths between 10-12 amino acids.
 c) 4G VH CDR3 lengths between 13-15 amino acids.
 d) 4G VK
 e) 6G VH CDR3 lengths between 7-9
 f) 6G VH CDR3 lengths between 10-12
 g) 6G VH CDR3 lengths between 13-15
 h) 6G VK Each round of selection involved adding the desired concentration of biotinylated CD40L to a mixture of phage (from one of the naïve library pools indicated above, or subsequent selection output phage) in 1000 μl of 2% MPBS (Phosphate Buffered Saline containing 2% (w/v) Marvel [Premier Foods, UK]) and incubating at room temperature for 1 hour by mixing end-over-end. The biotinylated antigen phage complex was then captured by adding 100 μl of resuspended Dynabeads M-280 Streptavidin [Invitrogen, UK] (rounds 1 and 3) or 50 μl of M-280 tosylactivated Dynabeads (Invitrogen) that had been coupled with NeutrAvidin [Thermo Fisher Scientific, UK] (round 2) and incubated for 5 minutes with mixing end-over-end at room temperature. The Dynabeads were then recovered using a KingFisher magnetic separator [Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 μl of trypsin-PBS (50 μl of 10 mg/ml trypsin [Sigma-Aldrich, UK] dissolved in 50 mM Tris-HCl pH 7.4, 1 mM $CaCl_2$ added to 450 μl PBS). The phage-containing solution was recovered and 250 μl used to infect 1.75 ml of logarithmic growth phase E. coli TG1 (at an $OD_{600}$ of 0.4) for 30 minutes at 37° C. The E. coli TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 litre, autoclaved for 15 minutes at 121° C.) and plated onto a 9 cm Petri dish containing TYE media supplemented with 15 μg/ml tetracycline. The plates were incubated overnight at 37° C. then 2 ml of 2×TY supplemented with 15% glycerol was added to each plate and cells loosened with a glass spreader and mixed thoroughly. Fifty microlitres of the scraped bacteria was used to inoculate 50 ml of 2×TY supplemented with 15 μg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated IZ-hCD40L.

Phage ELISA

Monoclonal phage ELISAs were carried out following selection rounds 2 and 3. All washes were performed using 3 washes of 250 μl PBST followed by 3 washes of 250 μl PBS. The plates were coated overnight at 4° C. with 50 μl/well of 1 μg/ml IZ-hCD40L in PBS. The plates were washed and then blocked with 2% MPBS for 1 hour at room temperature. The plates were washed and 25 μl/well phage supernatants added to an equal volume of 2% MPBS and incubated for 1 hour at room temperature. The plates were washed and bound phage detected with 50 μl/well anti-M13-HRP conjugate [GE Healthcare, UK] diluted 1:5000 in 2% MPBS and incubated for 1 hour at room temperature. The plates were washed and the ELISA developed using 50 μl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells that were not coated with antigen but otherwise identically treated.

Recovery of dAb Genes from pDOM4 Plasmid

The dAb V-genes from round 2 and 3 outputs were recovered by SalI and NotI restriction enzyme digestion of the phage vector pDOM4 and ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 μl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to IZ-hCD40L. MaxiSorp 96 well immunoplates [Nunc, USA] were coated overnight at 4° C. with 50 μl/well of 1 μg/ml IZ-hCD40L in PBS. All washes were as described for the phage ELISA. The plates were blocked for 1 hour at room temperature with 200 μl of PBS containing 1% Tween 20. The ELISA plate was washed and dAb-containing culture supernatant clarified by centrifugation at 1,800 g for 10 min at 4° C., then added to the ELISA plate (30 μl/well) to which was added an equal volume of PBST. The plates were incubated for 1 hour at room temperature and then washed. Bound dAb was detected by adding 50 μl/well 9E10 [anti-myc IgG, Sigma-Aldrich, UK] diluted 1:2000 in PBST and incubating for 1 hour at room temperature; the ELISA plate was then washed and 50 μl/well anti-mouse Fc-HRP [Sigma-Aldrich, UK] diluted 1:2000 in PBST added and incubated for 1 hour at room temperature. The plates were washed and the ELISA developed by adding 50 μl/well SureBlue 1-Component TMB MicroWell Peroxidase solution [KPL Inc, USA] and the colour allowed to develop. The colorimetric reaction was stopped by the addition of an equal volume of 1 M HCl and the ELISA plate read at 450 nm. Antigen binding dAbs were identified by comparison of the signal intensity from IZ-hCD40L wells with control wells not containing antigen.

Example 3

Identification of Clones BMS2h-503-1, BMS2h-719-2, and BMS2h-572-6

BMS2h-503, BMS2h-719 and BMS2h-572 dAbs were subjected to error-prone affinity maturation to generate BMS2h-503, BMS2h-719 and BMS2h-572 lineages, respectively. This was performed using random mutagenesis where on average 3.6 amino acid changes were introduced per dAb. Phage libraries (average size $6 \times 10^8$) were selected using biotinylated monomeric and trimeric human CD40L with alternating streptavidin/neutravidin bead capture of the antigen (as described). Three rounds of selections using decreasing concentrations of antigen (100 nM at round 1; 10 nM at round 2; 1 nM at round 3) were performed. Sequencing was used to monitor diversity following each selection round. Selection outputs (round 2 selected on CD40L trimer for BMS2h-572; round 3 selected on CD40L trimer for BMS2h-503 and round 3 selected on CD40L monomer for BMS2h-719) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-503-1 (sequence listed in TABLE 3), BMS2h-719-2 and BMS2h-572-6 dAbs (sequences listed in TABLE 1) were identified. Activities of these dAbs are listed in TABLE 5 below.

Formatting BMS2h-503-1, BMS2h-719-2 and BMS2h-572-6 as Fc Fusions

BMS2h-572-6, BMS2h-503-1 and BMS2h-719-2 dAbs were cloned into pDOM38 vector containing Fc tail derived from human IgG1 to create DMS0502, DMS0500 and DMS0501, respectively. BMS2h-572-6, BMS2h-503-1 and BMS2h-719-2 dAbs were also cloned into pDOM38 vector containing Fc tail derived from human IgG4 to create DMS0505, DMS0506 and DMS0504, respectively. The constructs were transiently expressed in HEK293 cells and the proteins were purified using Protein A. Purified Fc fusions were analysed by Biacore for binding to monomeric and trimeric CD40L as well as in various cell assays (as described).

Identification of Clones BMS2h-572-608, BMS2h-572-614 and BMS2h-572-619

BMS2h-572-6 dAb was subjected to affinity maturation using doped oligo approach. Four doped libraries were constructed for this dAb:
Library 1-5 residues in CDR1 diversified
Library 2-6 residues in CDR2 diversified
Library 3-13 residues in CDR2 diversified
Library 4-7 residues in CDR3 diversified In each library, diversification was performed using nnS codons where n retained a large fraction of the parent base (85%) and split the rest between the equimolar amounts of the remaining three bases (5% each) and S stood for G or C. Phage libraries (average size 8×10$^8$) were selected using biotinylated monomeric and trimeric human CD40L with alternating streptavidin/neutravidin bead capture of the antigen (as described). Libraries 2 and 3 were pulled together during the selection process. Three rounds of selections using decreasing concentrations of antigen (50 nM at round 1; 5 nM at round 2; 1 nM at round 3 with 200 fold excess of competitor—non biotinylated CD40L trimer) were performed. Sequencing was used to monitor diversity following each selection round. Selection outputs (rounds 2 and 3) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-572-608, BMS2h-572-614 and BMS2h-572-619 dAbs were identified.

Construction of Clone BMS2h-572-633

Sequence analysis revealed that all of the amino acid differences between BMS2h-572-608 and the parental dAb BMS2h-572-6 were located in CDR1 and the differences between BMS2h-572-614 and parental dAb BMS2h-572-6 were located in CDR3. Both matured dAbs shared CDR2 with the parental dAb BMS2h-572-6. This created an opportunity to construct a combination mutant which had CDR1 of BMS2h-572-608 and CDR3 of BMS2h-572-614. Firstly, CDR1 region of BMS2h-572-608 was PCR amplified. Secondly, CDR2+CDR3 fragment of BMS2h-572-614 was PCR amplified. This was followed by SOE PCR assembly of the two fragments to create a combination mutant BMS2h-572-633. The assembled dAb PCR product was cloned into soluble expression vector pDOM13 (no C terminal tag), sequence verified, expressed, purified and then assayed using the BMS2h bead RBA as well as cellular CD40L driven assays (as described).

Formatting BMS2h-572-633 as Fc Fusion

BMS2h-572-633 dAb was cloned into pDOM38 vector containing Fc tail derived from human IgG1 to create DMS0507. The construct was transiently expressed in HEK293 cells and the protein was purified using Protein A. Purified Fc fusion was analysed by Biacore for binding to monomeric and trimeric CD40L as well as in various cell assays (as described).

Example 4

CD40L Activity Cell Assays

Anti-human CD40L dAbs were assayed functionally for their ability to antagonize CD40L activities. The CD40L activities tested were B cell proliferation and cytokine production by hCD40L-driven activation of primary monocytes-derived dendritic cells (DCs). Unless otherwise noted, all assays were performed in RPMI media supplemented with 10% fetal calf serum (FCS). The results of various assays, described in detail below, are shown in TABLE 5 and TABLE 6.

Soluble 1Z-hCD40L-Driven Primary Human B Cell Proliferation:

1×10$^5$ tonsillar human B cells were incubated with 0.6 µg/ml of IZ-hCD40L along with varying titration of dAb or mAb in a final volume of 200 µl/well in a 96-well round bottom plate. The plates were incubated at 37° C. for 72 hours following which thymidine ($^3$H; 0.5 µci/well) was added for 6 hours. B cell proliferation was quantified based on thymidine incorporation. All assays, unless otherwise noted, were performed in RPMI media supplemented with 10% fetal calf serum (FCS).

CHO-hCD40L-Driven Primary Human B Cell Proliferation:

CHO cells were transfected with human CD40L to generate a stable cell line expressing high levels of CD40L on the cell surface. CHO-CD40L cells were irradiated at 10,000 Rads before incubation with human B cells. 1×10$^5$ tonsillar human B cells were incubated with 1×10$^3$ CHO-CD40L cells (1:100 ratio of CHO-CD40L:human B cells) along with varying titration of dAb or mAb in a final volume of 200 µl/well in a 96-well round bottom plate. The plates were incubated at 37° C. for 72 hours following which thymidine ($^3$H; 0.5 µci/well) was added for 6 hours. B cell proliferation was quantified based on thymidine incorporation. All assays, unless otherwise noted, were performed in RPMI media supplemented with 10% fetal calf serum (FCS).

Primary T Cell-Driven Human B Cell Proliferation:

T cells were isolated from human peripheral blood mononuclear cells (PBMCs) and enriched using via sheep red blood cell (SRBC) affinity. Enriched human T cells were cultured with PM-LCLs (EBV-transformed B cell line; irradiated at 10,000 Rads) at a 5:1 ratio (T:LCL) for 6 days at 37° C. to generate a population of allogeneic T cells. At day 6, the expanded T cells were isolated and irradiated at 3000 Rads, and then cultured ($5 \times 10^4$ T cells/well) with primary human tonsillar B cells ($1 \times 10^5$ B cells/well) at a 1:2 ratio in 96-well flat bottom plated coated with anti-CD3 mAb (OKT3). Varying titrations of dAbs/mAbs were added to each well; the final volume in each well was 200 µl. Test plates were incubated at 37° C. for 3 days. Human B cell proliferation was determined via the addition of thymidine ($^3$H; 0.5 µci/well) to the cultures for the last 18 hours. All assays, unless otherwise noted, were performed in RPMI media supplemented with 10% fetal calf serum (FCS). In some instances, the supernatant was harvested and measured for the presence of IL-6.

CHO-hCD40L-Driven Activation of Primary Human Monocytes-Derived Dendritic Cells (DCs):

Human PBMCs were enriched for monocytes by depleting T cells via SRBC resetting. The monocyte-enriched PBMCs were cultured with 10 ng/ml GM-CSF and 5 ng/ml IL-4 in 6-well plates for six days at 37° C. The cultured plates were replenished with fresh media (with GM-CSF and IL-4) on days 2 and 5. The immature DCs were used in cell assays on day 6. $8 \times 10^4$ immature DCs were cultured with $4 \times 10^3$ CHO-hCD40L cells (irradiated at 10,000 Rads) along with varying titrations of dAbs/mAbs in a 96-well flat bottom plate. After 24 hours, supernatants were harvested and tested for the presence of various cytokines (IL-12, TNF, IL-23). DC activation was determined by the levels of cytokine production. All assays, unless otherwise noted, were performed in RPMI media supplemented with 10% fetal calf serum (FCS).

TABLE 5

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h116-13 | 130.0 ± 40.0 | 1300.0, 700.0 | | 888.0, >2000.0, 1000.0 |
| 2h116-1312 | 23.0 ± 3.0 | 530.0 ± 300.0 | 234 ± 46 | 112.0 ± 47.0 |
| 2h116-1313 | 29.0 ± 4.0 | 211.0, 334.0 | 258 ± 79 | 136.0 ± 51.0 |
| 2h116-1314 | 41.0 ± 10.0 | 1300.0, 4400.0 | 1687 ± 1150 | 664.0 ± 353.0 |
| 2h116-1319 | 180.0 ± 57.0 | >7000.0 | | |
| 2h116-1320 | 20.0 ± 7.0 | 138.0 ± 60.0 | 191 ± 72 | 32.0 ± 10.0 |
| 2h437 | 5700.0 ± 1800 | | | |
| 2h437-4 | 203.0 ± 90.0 | >7000.0 | | 1329.0 ± 412.0 |
| 2h492 | >7000.0 | | | |
| 2h492-3 | 1100.0 ± 400.0 | >7000.0 | | |
| 2h492-4 | 1700.0 ± 900.0 | >7000.0 | | |
| 2h492-5 | 2300.0 ± 700.0 | | | |
| 2h492-6 | 6300.0 ± 1400.0 | | | |
| 2h492-7 | 1900.0 ± 600.0 | | | |
| 2h494 | 6100.0 ± 1200.0 | | | |
| 2h494-2 | 4800.0 ± 2300.0 | | | |
| 2h494-3 | >7000.0 | | | |
| 2h494-4 | 590.0 ± 250.0 | >7000.0 | | |
| 2h494-6 | 2000.0 ± 2100.0 | >7000.0 | | |
| 2h503 | 4200.0 ± 316.0 | >7000.0 | | |
| 2h503-1 | 24.0 ± 2.0 | 2300.0 ± 700.0 | | 756.0 ± 333.0 |
| 2h503-104 | 16.0, 19.0 | | | |
| 2h503-2 | 44.0 ± 6.0 | 3000.0 ± 1000.0 | | 1562.0 ± 96.0 |
| 2h572 | >7000.0 | | | |
| 2h572-6 | 208.0 ± 73.0 | >7000.0 | >7000.0 | >2000.0, 608.0 ± 260.0 |
| 2h572-604 | 254.0, 354.0 | >700.0 | | 387.0 |
| 2h572-608 | 96.0 ± 19.0 | | >7000.0 | 152.0 ± 61.0 |
| 2h572-610 | 109.0 ± 34.0 | | >7000.0 | 207.0 ± 87.0 |
| 2h572-614 | 93.0 ± 53.0 | | >7000.0 | 135.0 ± 54.0 |
| 2h572-616 | 204.0, 340.0 | | >7000.0 | 608.0 ± 136.0 |
| 2h572-617 | 157.0, 189.0 | | >7000.0 | 338.0 ± 101.0 |
| 2h572-619 | 90.0 ± 62.0 | 421.0, 1496.0 | >7000.0 | 188.0 ± 41.0 |
| 2h572-622 | 301.0, 293.0 | | >7000.0 | 281.0 ± 127.0 |
| 2h572-623 | 181.0, 261.0 | | >7000.0 | 280.0 ± 73.0 |
| 2h572-630 | 103.0 ± 71.0 | | | 246.0 ± 240.0 |
| 2h572-631 | 108.0 ± 77.0 | | | 230.0 ± 200.0 |
| 2h572-632 | 117.0 ± 91.0 | | | 241.0 ± 190.0 |
| 2h572-633 | 20.0 ± 15.0 | | | 53.0 ± 60.0 |
| 2h572-634 | 31.0 ± 18.0 | | | 77.0 ± 67.0 |
| 2h572-635 | 29.0 ± 19.0 | | | 52.0 ± 26.0 |
| 2h572-9 | 324.0, 243.0 | | | >2000.0 |
| 2h572-11 | 140.0 ± 33.0 | >7000.0 | | 671.0 ± 165.0 |
| 2h572-12 | 79.0, 76.0 | | | 225.0, >2000.0 |
| 2h572-14 | 134.0 ± 12.0 | >7000.0 | | 882.0 ± 310.0 |
| 2h572-15 | 168.0 ± 67.0 | >7000.0 | | 876.0 ± 391.0 |
| 2h572-22 | 357.0, 305.05 | | | |
| 2h702 | >7000.0 | | | |
| 2h703 | >7000.0 | | | |

TABLE 5-continued

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h706 | >7000.0 | | | |
| 2h707 | >7000.0 | | | |
| 2h710 | >7000.0 | | | |
| 2h712 | >7000.0 | | | |
| 2h717 | >7000.0 | | | |
| 2h719 | 600.0 ± 640.0 | | | 134.0, 646.0 |
| 2h719-2 | 82.0 ± 39.0 | >7000.0 | | 196.0 ± 150.0 |
| 2h719-202 | 29.0 ± 12.0 | | | 79.0 ± 29.0 |
| 2h719-203 | 81.0, 96.0 | | | |
| 2h719-213 | 62.0, 98.0 | | | |
| 2h719-214 | 66.0, 89.0 | | | |
| 2h719-215 | 92.0, 91.0 | | | |
| 2h719-218 | 57.0, 60.0 | | | |
| 2h719-225 | 253.0, 198.0 | | | 176.0 ± 84.0 |
| 2h719-226 | 164.0, 247.0 | | | 812.0 ± 53.0 |
| 2h719-12 | 358.0 ± 159.0 | | | 266.0 ± 66.0 |
| 2h719-13 | 50.0 ± 8.0 | 659.0, 683.0, 4450.0, 1750.0 | | 219.0 ± 88.0 |
| 2h719-17 | 132.0 ± 50.0 | 236.0, 268.0 | | 113.0 ± 49.0 |
| 2h719-19 | 138.0 ± 31.0 | 202.0, >7000.0, >7000.0, 3800.0, 5400.0 | | 184.0 ± 99.0 |
| 2h722 | >7000.0 | | | |
| 2h723 | >7000.0 | | | |
| 2h725 | 6400.0 ± 1200.0 | | | |
| 2h725-2 | >7000.0 | | | |
| 2h725-9 | >7000.0 | | | |
| 2h725-19 | >7000.0 | | | |
| 2h726 | >7000.0 | | | |
| 2h730 | >7000.0 | | | |
| 2h731 | 5800.0 ± 2500.0 | | | |
| 2h744 | >7000.0 | | | |
| 2h745 | 6400.0, 3500.0, >7000.0 | | | |
| 2h745-1 | >7000.0 | | | |
| 2h745-2 | >7000.0 | | | |
| 2h745-9 | >7000.0 | | | |
| 2h745-13 | >7000.0 | | | |
| 2h745-14 | >7000.0 | | | |
| 2h746 | >7000.0 | | | |
| 2h747 | >7000.0 | | | |
| 2h752 | >7000.0 | | | |
| 2h754 | 6600.0 ± 900.0 | | | |
| 2h757 | 6400.0 ± 800.0 | | | |
| 2h758 | 5900.0 ± 1500.0 | | | |
| 2h758-1 | >7000.0 | | | |
| 2h758-2 | >7000.0 | | | |
| 2h758-3 | >7000.0 | | | |
| 2h758-4 | >7000.0 | | | |
| 2h758-5 | >7000.0 | | | |
| 2h765 | >7000.0 | | | |
| 2h766 | >7000.0 | | | |
| 2h774 | >7000.0 | | | |
| 2h775 | >7000.0 | | | |
| 2h780 | >7000.0 | | | |
| 2h781 | >7000.0 | | | |
| 2h782 | >7000.0 | | | |
| 2h783 | >2000.0 | | | |
| 2h784 | >4700.0 | | | |
| 2h785 | 3700.0, >7000.0 | | | |

TABLE 6

Potency of Fc*-formatted Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | T-B cell MLR IL-6 EC50 (nM) | CHO-hCD40L-driven DC Activation IL-12 EC50 (nM) | CHO-hCD40L-driven DC Activation IL-6 EC50 (nM) | CHO-hCD40L-driven DC Activation IL-23 EC50 (nM) | CHO-hCD40L-driven DC Activation TNF EC50 (nM) |
|---|---|---|---|---|---|---|---|---|
| 2h116-1320-Fc | 13.0 ± 2.0 | >130.0 | 244.0 ± 112.0 | | 14.0 ± 11.0 | | | |
| 2h503-1 Fc | 4.0 ± 0.5 | 60.0 ± 20.0 | 45 ± 6 | | 2.8 ± 2.0 | | | |
| 2h503-1 IgG1 | 4.5 ± 1.0 | 67.0 ± 40.0 | 39.5 ± 12.04 | | 1.4 ± 0.7 | | | |
| 2h503-1 IgG4 | 2.5 ± 1.0 | 69.0 ± 50.0 | 48.3 ± 8.8 | | 18.1 ± 6.4 | | | |
| 2h572-6 Fc | 0.6 ± 0.4 | 3.0 ± 1.0 | 1.9 ± 0.7 | | 0.22 ± 0.18 | | | |
| 2h572-6 IgG1 | 1.0 ± 0.4 | 10.0 ± 5.0 | 3.1 ± 1.4 | 2.9 ± 1.7 | 0.58 ± 0.36 | | | |
| 2h572-6 IgG4 | 0.9 ± 0.2 | 11.0 ± 5.0 | 3.2 ± 1.5 | 1.3 ± 0.5 | 1.1 ± 0.5 | | | |
| 2h572-6-CT Long Fc | 1.0 ± 0.5 | 6.0 ± 6.0 | 13.6 ± 9.2 | 8.1 ± 3.1 | 3.0 ± 1.9 | | | |
| 2h572-633 Fc | 3.5 ± 0.6 | 3.0 ± 3.0 | 0.15 ± 0.02 | 0.11 ± 0.02 | 0.34 ± 0.17 | | | |
| 2h572-634 Fc | 3.0 ± 0.0 | 3.5 ± 3.0 | 0.23 ± 0.08 | 0.19 ± 0.03 | 0.42 ± 0.05 | | | |
| 2h572-635 Fc | 2.0 ± 0.8 | 2.5 ± 1.0 | 0.16 ± 0.09 | 0.11 ± 0.02 | 0.445 ± 0.14 | | | |
| 2h572-619-Ctshort Fc | 1.5 ± 0.6 | 2.0 | 0.40 ± 0.1 | 0.3 ± 0.07 | 1.8 ± 1.3 | | | |
| 2h572-619-Ctlong Fc | 1.6 ± 0.5 | 2.0 ± 1.0 | 0.72 ± 0.45 | 0.43 ± 0.12 | 1.4 ± 0.6 | 1.5 ± 0.36 | 1.5 ± 0.46 | 2.0 ± 0.7 |
| 2h572-619-N297Qshort Fc | 0.9 ± 0 | 1.0 ± 0.6 | 0.226, 0.216 | 0.1, 0.1 | 1.2 ± 0.6 | | | |
| 2h572-619-N297Qlong Fc | 0.98 ± 0.05 | 2.0 ± 0.0 | 0.480, 0.474 | 0.22, 0.11 | 1.1 ± 0.23 | | | |
| 2h572-608-N297Qshort Fc | 1.0 ± 0.05 | 2.0 ± 0.0 | | | 0.93 ± 0.4 | | | |
| 2h572-608-CT Long Fc | 2.0 ± 1.0 | 2.0 ± 1.0 | 0.468 ± 0.156 | 0.38 ± 0.06 | 1.6 ± 0.74 | | | |
| 2h572-614-CT Long Fc | 2.0 ± 1.0 | 2.0 ± 0.5 | 0.283 ± 0.038 | 0.25 ± 0.02 | 1.4 ± 0.68 | | | |
| 2h572-633-CT Long Fc | 3.0 ± 0.7 | 1.0 ± 1.0 | 0.174 ± 0.077 | 0.13 ± 0.07 | 1.9 ± 1.3 | 1.3 ± 0.3 | 1.2 ± 0.3 | 1.7 ± 0.43 |
| 2h572-633-CT-Fc SP5 | 5.0 ± 0.5 | 1.0 ± 0.5 | 0.161 ± 0.053 | 0.13 ± 0.04 | 2.3 ± 1.5 | 1.5 ± 0.7 | | 2.9 ± 1.3 |
| 2h572-634-CT Long Fc | 2.0 ± 1.0 | 1.0 ± 0.6 | 0.162 ± 0.029 | 0.13 ± 0.02 | 1.5 ± 0.91 | | | |
| 2h572-635-CT Long Fc | 3.0 ± 1.0 | 2.0 ± 0.6 | 0.149 ± 0.014 | 0.13 ± 0.01 | 1.6 ± 0.93 | | | |
| 2h719-2 Fc | 1.0 ± 0 | 0.7 ± 0.4 | 6 ± 1.4 | | 0.13 ± 0.08 | | | |
| 2h719-2 IgG1 | 1.0 ± 0.5 | 6.0 ± 0.3 | 13.8 ± 10.6 | 2.2 ± 1.3 | 0.35 ± 0.23 | | | |
| 2h719-2 IgG4 | 1.5 ± 0.6 | 16.0 ± 13.0 | 15.9 ± 10.9 | 2.1 ± 0.7 | 1.1 ± 0.48 | | | |
| 2h719-202-N297Qshort Fc | 1.8 ± 0.5 | 1.7 ± 0.7 | | | 0.66 ± 0.26 | | | |
| 2h719-202-CT Long Fc | 3.0 ± 1.0 | 2.5 ± 0.6 | 1.7 ± 0.7 | 1.3 ± 0.3 | 3.1 ± 2.0 | | | |

*FIG. 3 provides sequences of various Fc domains. FIG. 4 shows examples of various Fc-formatted dAbs.

Example 5

Binding Kinetics and CD40L Affinity of Various Antibodies

BMS-986004 is a dimeric fusion protein, composed of a modified Fc fragment of IgG1 linked to the C-terminus of the dAb BMS2h-572-633. Surface plasmon resonance (SPR) was used to characterize the kinetics and affinity of BMS-986004 or the monovalent component domain antibody BMS2h-572-633 binding to CD40L. The BMS-986004 values were compared to those for the benchmark antibodies 5c8-IgG1 and 5c8-CT and the monovalent component 5c8 FAB fragment. The SPR experiments utilized a hCD40L construct containing an N-terminal isoleucine zipper motif (IZ-hCD40L) which facilitates the specific assembly of the CD40L molecule into the native trimeric form. A biotinylated version of IZ-hCD40L (biot-IZ-hCD40L) with equivalent binding activity was also utilized for some SPR experiments.

The monovalent BMS2h-572-633 domain antibody binds biot-IZ-hCD40L with a Kd of 7.8 nM, compared to an affinity of 5.4 nM for the monovalent 5c8 FAB fragment, TABLE 7. Because BMS-986004 is bivalent, and the IZ-hCD40L target is trivalent, the SPR binding data are influenced by avidity regardless of whether CD40L target is on the chip surface or in solution. To estimate the avidity-influenced binding affinity, the SPR data for BMS-986004 binding to a biot-IZ-hCD40L surface was fitted to a 1:1 Langmuir model, suggesting a dissociation constant of less than 1 nM, TABLE 7. Similar results were obtained for 5c8-IgG1 and 5c8-CT.

TABLE 7

IZ-hCD40L kinetic and affinity values as determined using SPR (Biacore)

| Anti-CD40L Ab | Temperature (° C.) | Model | ka (M−1s−1) | kd (s−1) | Kd (nM) |
|---|---|---|---|---|---|
| BMS-986004 | 25 | 1:1 Langmuir | 2.3E+06* | 2.6E−04* | 0.11* |
| 2h572-633 | 25 | 1:1 Langmuir | 1.0E+06 | 8.1E−03 | 7.8 |
| 5c8-IgG1 | 25 | 1:1 Langmuir | 5.4E+05* | 2.3E−04* | 0.42* |
| 5c8-CT | 25 | 1:1 Langmuir | 5.8E+05* | 1.3E−04* | 0.22* |
| 5c8 FAB fragment | 25 | 1:1 Langmuir | 1.4E+05 | 7.6E−04 | 5.4 |

*Value is influenced by avidity due to analyte bivalency.

Figure 5:
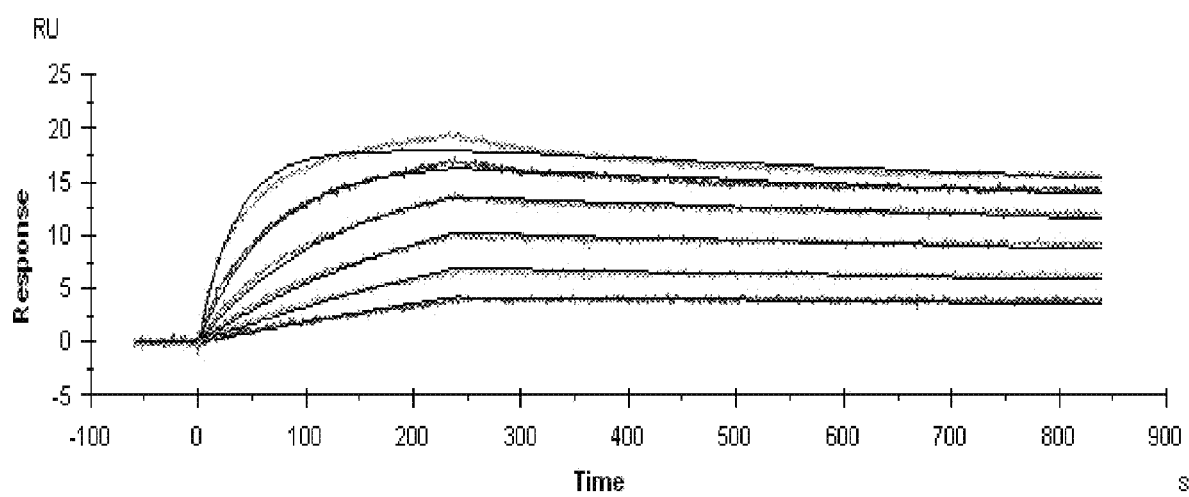
FIG. 5 depicts SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

FIG. 5 shows SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

Figure 6:
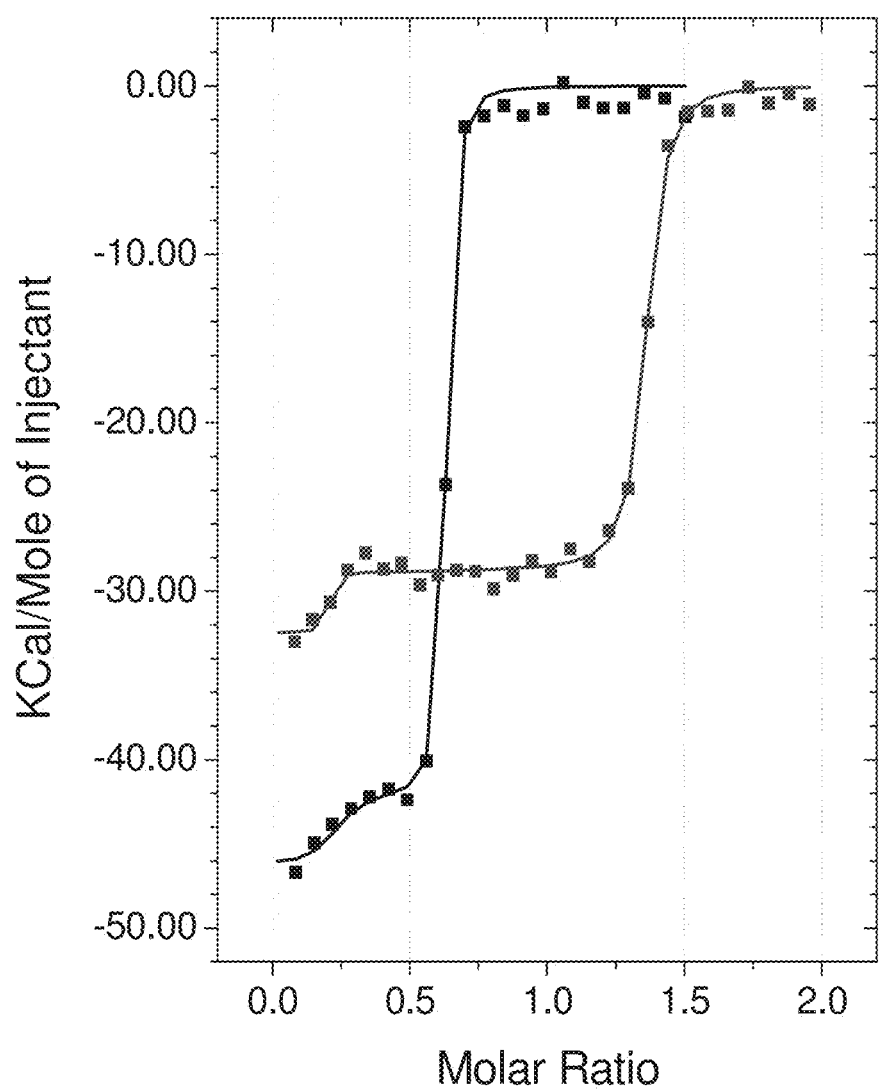
FIG. 6 shows ITC data for titrations of 19 μM IZ-hCD40L into 2 μM BMS-986004 (black) or 18 μM BMS-986004 into 2 μM IZ-hCD40L (blue). The molar ratio (apparent stoichiometry) is defined per mole of IZ-hCD40L trimer and per mole of bivalent BMS-986004 Fc-dimer. Molar ratio values obtained as the equivalence points on the abscissa suggest more than one mole of BMS-986004 can bind per mole of IZ-hCD40L trimer; however, an exact structural model for the complex cannot be determined from the ITC data alone. Squares represent the integrated heat of binding data and solid lines represent the best fit to a "2 sets of sites model."

The affinity and thermodynamics of BMS-986004 binding to CD40L were also characterized in solution using isothermal titration calorimetry (ITC) at temperatures ranging from 15-37° C. These data suggested the presence of multiple thermodynamically distinct binding modes (FIG. 6) with Kd values for the different modes beyond the high-affinity limit of detection (Kd<2 nM) (TABLE 8), consistent with the SPR data. The affinity of the monovalent 5c8 FAB fragment for IZ-hCD40L as determined by ITC (3.5 nM) was also consistent with the value determined by SPR.

TABLE 8

IZ-hCD40L affinity as determined using ITC

| Molecule in the ITC syringe | Molecule in the ITC cell | Kd (nM) |
|---|---|---|
| BMS-986004 | IZ-hCD40L | <2 |
| 5c8-CT | IZ-hCD40L | <2 |
| IZ-hCD40L | BMS-986004 | <2 |
| IZ-hCD40L | 5c8-CT | <2 |
| IZ-hCD40L | 5c8 FAB fragment | 3.5 |

Example 6

Fc Receptor Affinity of Various Antibodies

The Fc-domain of BMS-986004 (termed "CT") was engineered from a wild type IgG1 Fc domain to retain the ability to bind FcRn, but to disrupt the binding to Fcγ receptors. To confirm that the engineered molecule has the desired Fc receptor binding profile, the binding affinities of BMS-986004 for human FcRn, and the human Fcγ receptors CD64 (FcγRI), CD32a (FcγRIIa), CD32b/c (FcγRIIb/c), CD16a (FcγRIIIa), CD16b (FcγRIIIb) were measured using SPR, in comparison to 5c8-IgG1 and 5c8-CT. For these experiments, BMS-986004 was captured via the domain antibody domains on a biot-IZ-hCD40L sensor surface, and the soluble Fc receptor proteins were tested for binding to the exposed Fc domain. Likewise, 5c8-IgG1 and 5c8-CT were captured on a biot-IZ-hCD40L surface via the FAB domains, with soluble FcR binding.

BMS-986004 bound FcRn with Kd of 670 nM at pH 6.0 which is the relevant pH for binding within the endosome, TABLE 9. However, binding was significantly reduced (Kd>5000 nM) at neutral pH suggesting efficient release of from FcRn under these conditions. BMS-986004 bound CD64 with a Kd of 0.6 nM, and had a statistically weak affinity for CD32a, CD32b/c, CD16a and CD16b (Kd>3000 nM). Both 5c8-IgG1 and 5c8-CT had a similar FcRn affinity as BMS-986004. 5c8-CT, which has the identical "CT" Fc region as BMS-986004, also had a similar FcγR binding properties as BMS-986004, whereas 5c8-IgG1, which has a wild type IgG1 Fc domain, bound more strongly to FcγRs, TABLE 9.

TABLE 9

Fc receptor affinity as determined using SPR (Biacore).

| Sample | pH | BMS-986004 Kd (nM) | 5c8-IgG1 Kd (nM) | 5c8-CT Kd (nM) |
|---|---|---|---|---|
| hFcRn | 6 | 670 | 590 | 720 |
| hFcRn | 7.1 | >5000 | >5000 | >5000 |
| CD64 | 7.1 | 0.6 | <0.05 | 0.9 ± 0.4 |
| CD32a | 7.1 | >3000 | ~$10^{-7}$ M* | >3000 |
| CD32b/c | 7.1 | >3000 | >3000 | >3000 |
| CD16a | 7.1 | >3000 | 240 ± 40 | >3000 |
| CD16b | 7.1 | >3000 | >3000 | >3000 |

*CD32a binding to 5c8-IgG1 was biphasic. Kd was estimated as ~$10^{-7}$ M based on steady state fit to dominant binding even. This Kd is in range of literature reported KD for CD32a binding to IgG1.

Example 7

In-Vitro Cell-Based Assays

The potency of BMS-986004 was evaluated in various primary immune cell assays to ensure robust potency across different cell types. The primary human B cell proliferation assays were conducted two ways, as described in detail above in Example 4: (1) recombinant CD40L trimer was used to drive B cell proliferation; and (2) CHO cells expressing CD40L on the membrane (CHO-CD40L) were utilized to induce B cell proliferation. The utility of CHO-CD40L cells was particularly important to ensure that signals from membrane-bound CD40L were inhibited equally well when compared to the soluble CD40L trimer. The CHO-CD40L cells were also used to drive the activation of primary human DCs differentiated from culturing PBMC-derived monocytes in presence of GM-CSF and IL-4. Similarly, the T-B MLR assay measured B cell activation driven by CD40L present on activated T cells. In all of the above described primary assays, BMS-986004 was equipotent to the benchmark 5c8 mAb: potencies ranged from was single-digit nM to sub-nM, depending on the assay (TABLE 10).

TABLE 10

Potency of BMS-986004 in Various Primary Cell Assays

| mAb/dAb-Fc | Trimer B cell Assay EC50 (nm) | CHO-CD40L B cell Assay EC50 (nM) | T-B MLR EC50 (nM) | T-B MLR IL-6 EC50 (nM) | CHO-CD40L DC Assay IL-12 EC50 (nM) | CHO-CD40L DC Assay IL-6 EC50 (nM) | CHO-CD40L DC Assay TNF-a EC50 (nM) |
|---|---|---|---|---|---|---|---|
| 5c8 | 8.0 ± 3.0 | 2.0 ± 2.0 | 0.54 ± 0.37 | 0.23 ± 0.09 | 2.0 ± 1.5 | | |
| 5c8-IgG1 | 5.0 ± 1.0 | 2.0 ± 2.0 | 0.34 ± 0.13 | 0.21 ± 0.06 | 0.92 ± 0.94 | 0.73 ± 0.5 | 2.3 ± 1.3 |
| BMS-986004 | 5.0 ± 0.5 | 1.0 ± 0.5 | 0.16 ± 0.05 | 0.13 ± 0.04 | 3.1 ± 1.6 | 1.9 ± 0.6 | 3.6 ± 1.1 |

Example 8

Assessment of Whole Blood Receptor Occupancy (RO)

A receptor occupancy method was developed to measure CD40L target engagement by BMS-986003 in cynomolgus whole blood samples and, subsequently, in BMS-986004 in human whole blood samples. BMS-986003 is a dAb which shares the same amino acid sequence as BMS-986004, except for a non-native glycine residue at its amino-terminus.

Occupancy is measured on CD4+ T cells by flow cytometry using an anti-CD40L mAb that competes for binding to CD40L with BMS-986003/BMS-986004, and is cross-reactive with human and cynomolgus CD40L. In the presence of bound dAb, the anti-CD40L detection mAb is blocked from binding to CD40L in a concentration-dependent manner, providing a measure of target occupancy. Given that basal CD40L is expressed at low levels on resting T cells in peripheral blood, RO was assessed in both unstimulated blood samples and in samples where phytohemagglutinin (PHA) was used to induce up-regulation of CD40L on the T cell surface. Binding potency curves were generated following ex vivo whole blood treatment with BMS-986003 and BMS-986004. The average $EC_{50}$ and $EC_{90}$ values obtained are shown in TABLE 11.

TABLE 11

Binding Potency of BMS-986003 and BMS-986004 on CD4+ T-cells in ex vivo Whole Blood Receptor Occupancy Assay

| | n | Average $EC_{50}$, nM | Average $EC_{90}$, nM |
|---|---|---|---|
| BMS-986003 | | | |
| Human (basal) | 1 | 0.9 | 3 |
| Human (PHA-induced) | 6 | 0.8 | 9 |
| Cyno (basal) | 3 | 0.6 | 3 |
| Cyno (PHA-induced) | 3 | 0.4 | 2 |
| BMS-986004 | | | |
| Human (basal) | 3 | 0.4 | 3 |
| Human (PHA-induced) | 3 | 0.7 | 5 |

The target binding potency in whole blood for BMS-986003 and BMS-986004 closely correlates between human and cynomolgus monkey. The $EC_{50}$ values for BMS-986003 and BMS-986004 are also similar when bound to basal and PHA-induced CD40L. Additionally, these values are comparable to those obtained in human in vitro cell based assays (see TABLE 10). Based on the measured $EC_{90}$ values, full target saturation in peripheral blood should be achieved at concentrations ≤10 nM.

To support the preclinical PK/PD profile of BMS-986003 and BMS-986004, RO was assessed in both the cynomolgus KLH study (immunization with keyhole limpet hemocyanin) with BMS-986003 and the IV bridging study with BMS-986004. Further details of these findings can be found in Examples below.

Example 9

In Vivo Pharmacology

To show efficacy of a CD40L dAb in mouse disease models, a mouse CD40L dAb 2m126-24 was formatted with mouse IgG1 Fc with D265A point mutation to further lower the Fc effector function. This mouse surrogate dAb 2m126-24-Fc shows potency comparable to BMS-986004 and MR-1, a hamster anti-mouse CD40L antibody (TABLE 12).

TABLE 12

In vitro Potency Comparison

| | mAb/dAb-Fc | Trimer B cell Assay EC50 (nm) | CHO-CD40L B cell Assay EC50 (nM) | CHO-CD40L DC Assay IL-6 EC50 (nM) |
|---|---|---|---|---|
| Human | 5c8 | 8.0 ± 3.0 | 2.0 ± 2.0 | |
| | BMS-986004 | 5.0 ± 0.5 | 1.0 ± 0.5 | 1.9 ± 0.6 |
| Mouse | 2m126-24-Fc | 4.7 ± 0.9 | 0.4 ± 0.06 | 0.5 ± 0.2 |
| | MT-1 9mAb) | 1.7 ± 0.4 | 0.6 ± 0.2 | 0.6 ± 0.3 |

Inhibition of KLH Induced Antibody Response by the Mouse CD40L dAb

Figure 7:
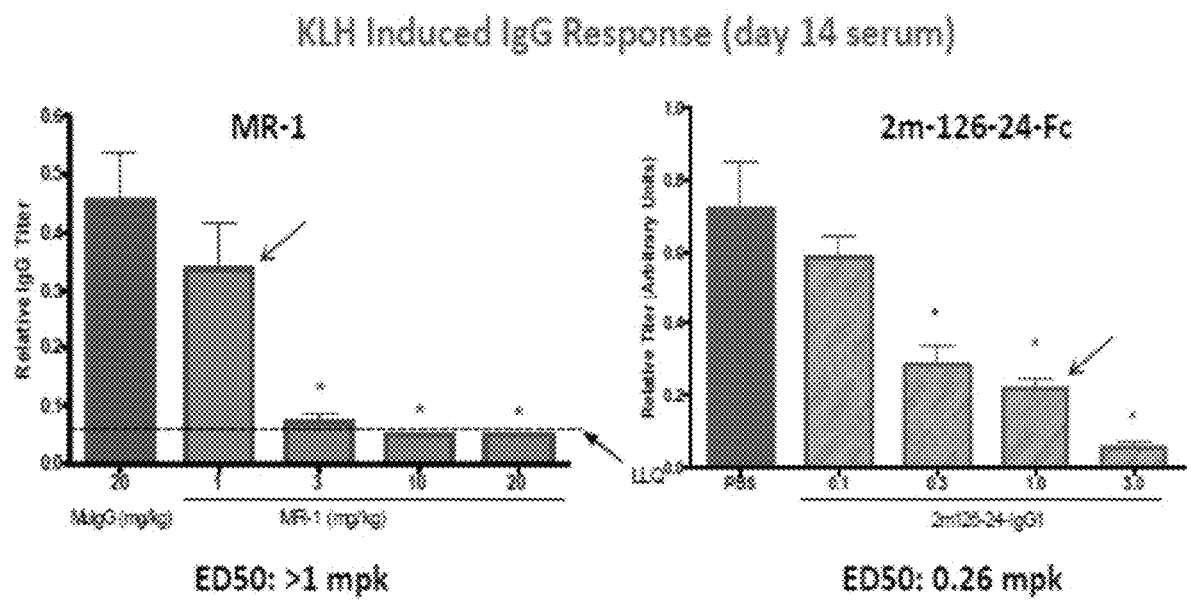
FIG. 7 shows in vivo efficacy of mouse CD40L surrogate dAb-Fc (KLH-induced antibody response.

Female BALB/c mice were injected intraperitoneally (i.p.) with 250 µg KLH on day 0. Mice were dosed subcutaneously (s.c.) with MR-1 or BMS-2m-126-24-Fc at indicated doses on day −1 and day 6. Blood was collected and the serum was analyzed for anti-KLH IgM on day 7 and IgG on day 14 by ELISA. Serum from BALB/c mice collected on day 14 after immunization with KLH was pooled and used as a positive comparator, and the data is expressed as a ratio of the titre of the test serum to the titre of the pooled BALB/c serum. As shown in FIG. 7, BMS-2m-126-24-Fc demonstrated a dose dependent suppression of IgG titers with maximal effect shown at 3 mg/kg, with ED50 calculated to be 0.26 mg/kg. Both the CD40L dAb and the antibody were tested at 1 mg/kg, showing 70% vs. 30% reduction in IgG response, respectively. Similar exposure of the dAb and the antibody were observed at 1 mg/kg, suggesting that the dAb is slightly more potent than the antibody at suppressing KLH-induced IgG response. In conclusion, the CD40L dAb has demonstrated at least the same level of efficacy as the anti-CD40L antibody at inhibiting a T cell dependent antibody response.

Inhibition of TNBS-Induced Colitis by the Mouse CD40L dAb

Figure 8:
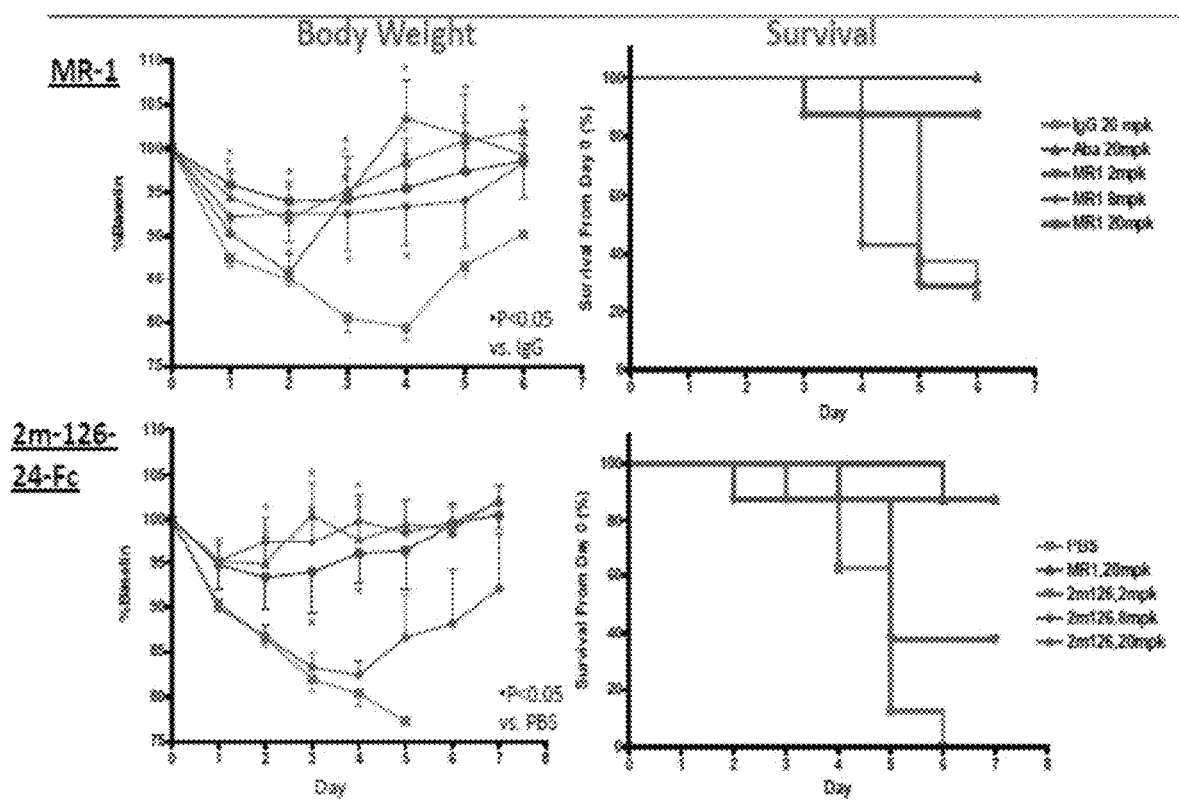
FIG. 8 demonstrates that mouse dAb BMS-2m-126-24-Fc and antibody MR-1 inhibit TNBS-induced colitis in mice.

Male SJL/J mice were intrarectally administered with 2.5 mg Trinitrobenzene sulfonic acid (TNBS) in 50% EtOH via a catheter inserted 4 cm distal to the anus. Mice were dosed once s.c. with MR-1 or BMS-2m-126-24-Fc at indicated doses 4 hours prior to TNBS injection. FIG. 8 presents the changes in the mean body weight and the percent survival of groups of mice treated with PBS/IgG or varying dose levels of MR-1 or the dAb. Abatacept was used as a positive control (20 mg/kg, i.p. every other day). A typical profile of TNBS-induced colitis was shown in the IgG control group: loss of body weight, peaking at day 3-4; colitis-related death occurring at day 3 and beyond; and the survived mice showing signs of recovery after day 4. Treatment with the CD40L dAb or the antibody (both tested at 2, 8 and 20 mg/kg) caused a dose-dependent inhibition of the body-weight loss and the increase in survival rate; both compounds at 8 mg/kg yielded a degree of efficacy that is comparable to that of Abatacept at 20 mg/kg. In conclusion, the mouse CD40L dAb BMS-2m-126-24-Fc has demonstrated comparable efficacy to the anti-CD40L antibody MR-1 in an acute TNBS-induced colitis model.

Figure 9:
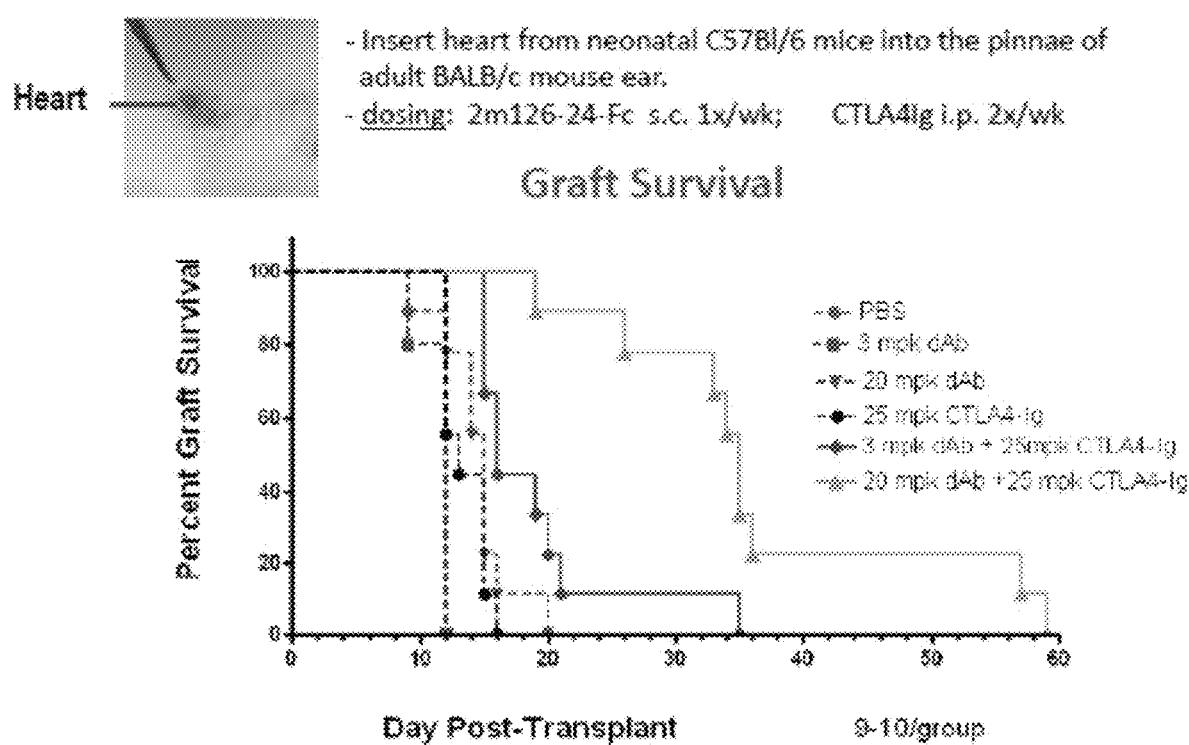
FIG. 9 shows that BMS-2m-126-24-Fc and CTLA4-Ig work synergistically to prolong the survival of cardiac allografts.

Synergistic Effect Between CTLA4 Ig and the Mouse CD40L dAb in a Mouse "Heart-to-Ear" Transplant Model Heart grafts from neonatal (48-72 hrs) C57Bl/6 mice were implanted into a subcutaneous pocket created in the ear pinnae of BALB/c mice. Mice were treated with CTLA4-Ig (i.p. 2x/wk), BMS-2m126-24-Fc (s.c. 1x/wk), or combination of both at indicated doses, with first dosing initiated the day prior to transplantation. Time to rejection was defined by the absence of cardiac contractility for three consecutive days as assessed daily by the electrocardiogram (ECG) device of allograft. As expected, without any treatment, C5713116 mice that received the neonatal BALE/c heart rejected the graft shortly thereafter, with median survival time (MST) of 12 days. The monotherapy with 3, 20 mg/kg of the dAb or 25 mg/kg of CTLA4-Ig had no or little impact on prolonging the survival of the allograft (MST: 12, 15 and 13 days respectively). However, in the groups treated with combination of 20 mg/kg of the dAb and 25 mg/kg of CTLA4-Ig, the graft survival was significantly prolonged showing MST of 35 days (FIG. 9). This data has provided rationale for combining CD40L dAb with belatacept in human renal transplant patients. Future transplant studies in non-human primates will further define the dose level and assess the potential effect on tolerance induction with CD40L dAb BMS-986004.

Example 10

In Vivo Nonclinical Pharmacokinetics (PK) and Pharmcodynamics (PD)

Various in vivo studies were conducted to characterize the PK and PD of BMS-986004, BMS-986003, and a mouse CD40L dAb-Fc surrogate BMS-2m-126-24-CT, in the nonclinical setting. The key findings are summarized below.

ELISA to Measure BMS-986004 dAb

Enzyme-linked immunosorbency assay (ELISA)-based bioanalytical methods were developed to support the PK studies, acute and chronic efficacy studies in mice, and exploratory PK/PD studies employing cynomolgus monkeys. In all cases, whole blood was obtained and plasma prepared in the presence of EDTA, the samples were then subjected to ELISA analysis.

Plasma concentrations of BMS-986004 were measured with an ELISA assay that utilized human CD40L antigen to capture the analyte from test samples. Test samples were thawed at 4° C., mixed well and diluted 1:100 in assay diluent composed of 1×PBS, 0.05% Tween-20, and 1% BSA (PTB). Subsequent dilutions of the sample were made using 1% normal monkey plasma/PTB as diluent. This allowed the test analyte to be assayed at several dilutions ($10^2$-$10^5$) while keeping the sample matrix at 1%.

Recombinant trimeric human CD40L was obtained from Protein Structure and Science (PSS), LVL and was bound to 96 well plates at a final concentration of 2 µg/mL. Test samples, quality control (QC) samples and the standards were detected with affinity-purified rabbit anti-heavy chain (Vh) domain framework polyclonal antibody (Covance Research Products, Denver, Pa.) diluted to a concentration of 0.25 µg/ml in PTB, followed by horseradish peroxidase-labeled donkey anti-rabbit polyclonal secondary antibody (Jackson Immunoresearch, West Grove, Pa.) with substrate (TMB—tetramethylbenzidine) added, and the enzymatic reaction stopped with 1 M phosphoric acid. Absorbance was measured at a wavelength of 450 nm. The analysis of BMS-986004 in test samples was conducted using a standard curve. Standard curve calibrators prepared on the day of each run in 1% monkey plasma were used to define the dynamic range of the bioanalytical method. The range of resulting standard curve in 100% plasma was 10-1200 ng/mL. The reference standard for BMS-986004 was obtained from Biologics Process and Product Development (BPPD), HPW. The reference standard material was representative of the manufacturing batch and was used in the study protocol. Standard curves and QCs were evaluated using criteria for accuracy and precision of ≤20% which was considered to be acceptable for assay performance. Test samples were quantified using a 4-parameter logistic fit regression model weighted by reciprocal concentration (1/x) derived from the calibrators.

Performance of the QC samples, measured by the deviation of the calculated concentration from its nominal value indicated the reference material was stable in neat monkey plasma at concentrations of 30-1000 ng/ml when stored at −70° C. for over 2 months.

ELISA to Measure a Mouse Surrogate dAb

Mouse CD40L-specific dAb BMS-2m-126-24-CT was measured in mouse plasma samples to provide exposure data in support of several acute and chronic efficacy studies as well as PK assessment.

While the assay format for mouse dAbs was quite similar to that for human dAbs in monkey samples, there were a few differences. The mouse plasma matrix was diluted to 1:10 (10%) in assay diluent, and all subsequent dilutions of test samples were made using 10% mouse matrix. Likewise, all standards and QCs were also incubated on ELISA plates in 10% mouse plasma. The concentration of BMS-2m-126-24-CT in test samples from mice was measured using mouse CD40L to capture the analyte. As the mouse dAb has Vk framework, all test samples, QCs, and the standards were detected with affinity purified rabbit anti-kappa (Vk) domain polyclonal antibody (Covance Research Products, Denver, Pa.) diluted to a concentration of 0.5 μg/mL in PTB. The rest of the assay and analysis procedure was similar to the procedure for the analysis of human CD40L dAbs. Acceptance criteria for back-calculated concentrations of standards and QCs were also similar to those for human CD40L dAbs. The quantitative range of BMS-2m-126-24-CT as determined from the standard curve was 12.5 to 600 ng/mL in neat sample matrix.

Nonclinical Pharmacokinetics

TABLE 13 summarizes the PK parameters for BMS-986004, BMS-986003, and BMS-2m-126-24-CT in nonclinical animal species.

studies. Immunogenicity testing of the plasma samples collected at 38 d after BMS-986004 treatment suggested that all monkeys developed anti-drug antibody (ADA); and that the monkeys with higher ADA levels showed faster clearance. Although no immunogenicity test was conducted for the IV PK study with BMS-986003, a similar level of immunogenicity was observed in monkeys after subcutaneous dosing with BMS-986003 in the PK/PD study, suggesting both proteins were immunogenic in monkeys. The terminal half-life (T1/2) of 124 and 106 h for BMS-986004 and BMS-986003 was, therefore, determined using the exposures collected up to two weeks (336 h) only. The steady-state volume of distribution (Vss) of BMS-986004 and BMS-986003 was 0.098 and 0.074 L/kg, respectively. The values are greater than the plasma volume (0.06 L/kg) but less than the volume of extracellular fluid (0.2 L/kg), suggesting that the proteins largely reside in the extracellular space. The total body plasma clearance (CLTp) of BMS-986004 and BMS-986003 was 0.59 and 0.65 mL/h/kg, respectively.

The PK parameters of BMS-986004 in monkeys were compared to those of abatacept, a similar size protein (78.5 vs 78-kDa BMS-986004, based on amino acid sequence), with the same modified human IgG1 Fc format. As expected, the parameters of BMS-986004 were nearly identical with those of abatacept (CLTp of 0.6 mL/h/kg, Vss of 0.087 L/kg, T1/2 of 5 d), suggesting the humans PK of BMS-986004 and abatacept is likely to be similar.

Figure 12:
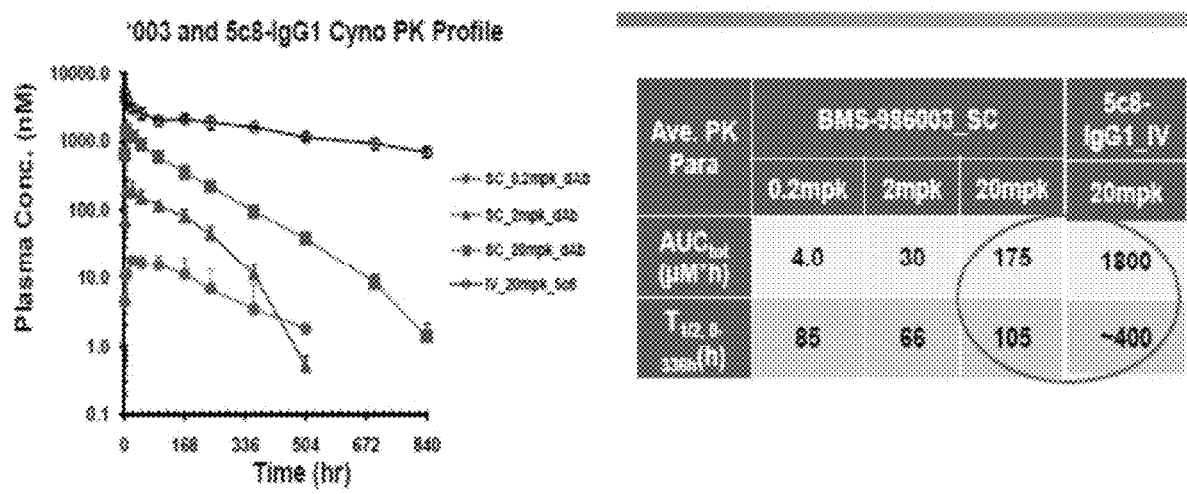
FIG. 12 presents plasma concentrations vs. time profiles of BMS-986003 (after SC dosing at 0.2, 2 and 20 mg/kg in monkeys) and of 5c8 IgG1 (after IV dosing at 20 mg/kg in monkeys).

The absorption of BMS-986003 after subcutaneous (SC) administration was evaluated in the monkey PK/PD study. The monkeys were administered with BMS-986003 as single subcutaneous doses of 0 (vehicle control), 0.2, 2 and 20 mg/kg, at 24 h prior to the immunization with keyhole limpet hemocyanin (KLH), a T cell-dependent antigen. After dosing, BMS-986003 was slowly absorbed, with a Tmax ranging from 6-96 h (FIG. 12). The exposure of BMS-986003 appeared to be less than dose-proportional across all

TABLE 13

Single-dose PK Parameters (mean ± SD) from Two Nonclinical Animal Species

| Species | dAb | Route | Dose (mg/kg) | Cmax (μM) | Tmax (h) | AUC0-inf (μM · h) | T½ (h) | CLTp (mL/h/kg) | Vss (L/kg) | F (%) |
|---|---|---|---|---|---|---|---|---|---|---|
| Mouse | BMS-2m-126-24-CT | IV | 1 (N = 3) | — | — | 6.9 | 101 | 1.85 | 0.26 | — |
| | | SC | 1 (N = 3) | 0.063 | 24 | 10 | 100 | — | — | 100 |
| | | | 10 (N = 3) | 0.68 | 24 | 114 | 120 | — | — | 100 |
| Monkey | BMS-986003 | IV | 2 (N = 2) | — | — | 40 | 106 | 0.67 | 0.067 | — |
| | | SC | 0.2 (N = 4) | 0.019 ± 0.004 | 60 ± 72 | 4.0 ± 2.7 | 85 ± 29 | — | — | 88 |
| | | | 2 (N = 4) | 0.22 ± 0.075 | 33 ± 43 | 29.7 ± 4.9 | 68 ± 11 | — | — | 74 |
| | | | 20 (N = 4) | 1.48 ± 0.34 | 11 ± 9 | 175 ± 27 | 105 ± 18 | — | — | 44 |
| | BMS-986004 | IV | 11 (N = 4) | — | — | 241 ± 18 | 124 ± 12 | 0.59 ± 0.04 | 0.098 ± 0.01 | — |
| | 5c8-IgG1 | IV | 20 (N = 4) | — | — | 1800 ± 74 | 400 | 0.074 | 0.042 | — |

Figure 11A:
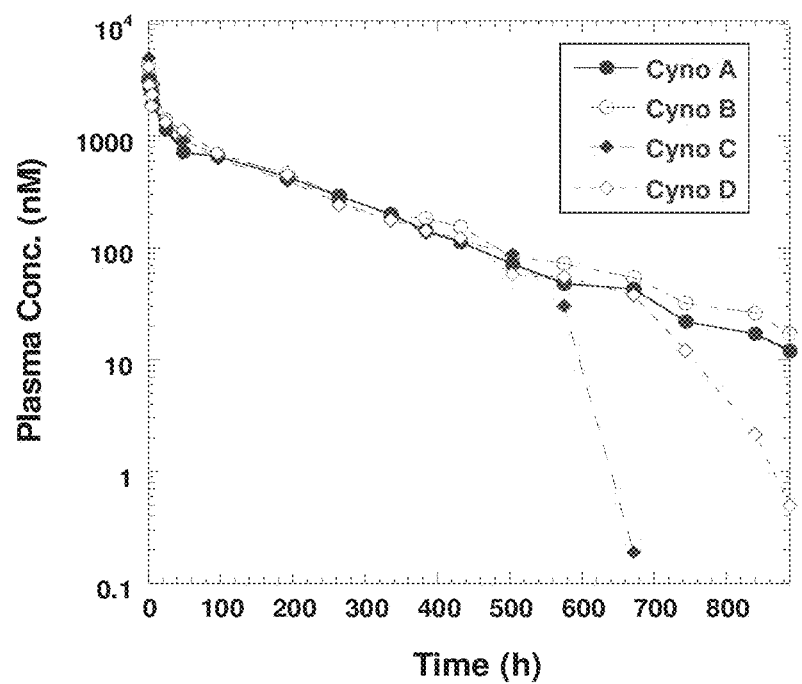
FIG. 11A shows plasma concentration vs. time profile of BMS-986004 after IV dosing of 11 mg/kg in monkeys.
Figure 11B:
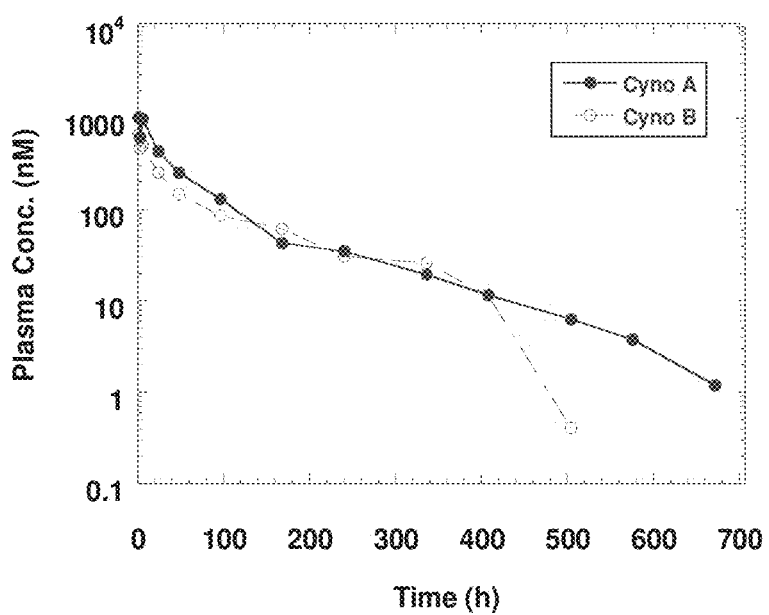
FIG. 11B demonstrates plasma concentration vs. time profiles of BMS-986003 after IV dosing of 2 mg/kg in monkeys.

BMS-986004 and BMS-986003 exhibited comparable PK profiles in monkeys (FIG. 11A and FIG. 11B). After IV administration, the plasma concentrations of BMS-986004 and BMS-986003 exhibited a bi-exponential decline up to 504 and 408 h, respectively. Accelerated clearance was observed afterward in 50% of monkeys enrolled in both studies.

dose levels. With a dose ratio of 1:10:100, the average Cmax and AUC0-inf ratios were 1:12:80 and 1:7:44, respectively. With the exposure following the IV dose (2 mg/kg) as reference, and assuming linear PK after IV dosing, the SC bioavailability of BMS-986003 was 88%, 74%, and 44% at 0.2, 2, and 20 mg/kg, respectively. The terminal T1/2 was confounded by the immunogenicity observed with most of the monkeys at 2 to 5 weeks after dosing. Therefore, the T1/2 was estimated to be 85, 66, and 105 h at 0.2, 2 and 20 mg/kg, respectively.

The PK of 5c8-IgG1, an anti-human CD40L monoclonal antibody used as a positive control in the PK/PD study, was evaluated after IV administration at 20 mg/kg (FIG. 12). 5c8-IgG1 exhibited 10-fold higher plasma exposures and 4-fold longer T1/2 when compared to BMS-986003 given SC at the same dose (TABLE 13).

Figure 13:
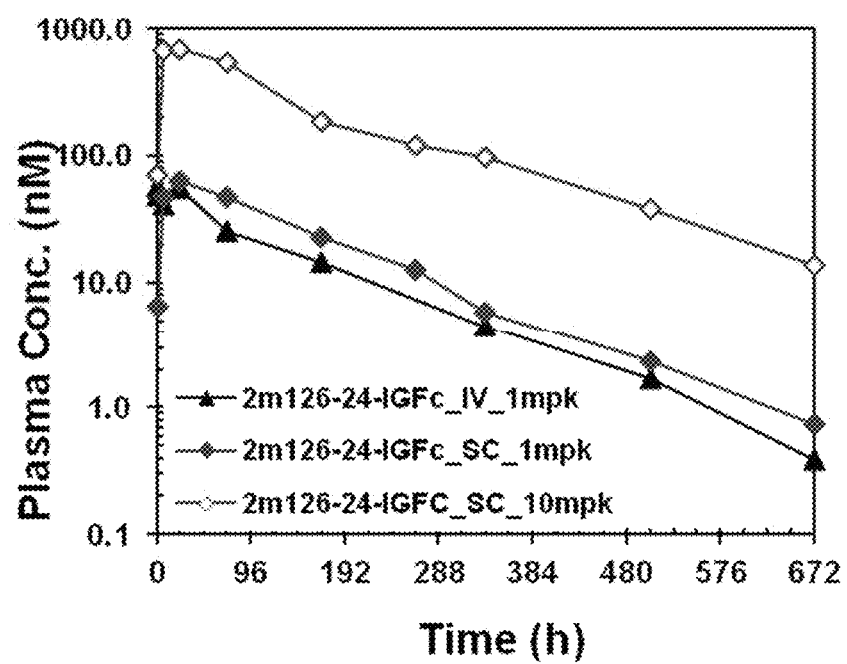
FIG. 13 shows plasma concentrations vs. time profiles of BMS-2m-126-24-CT after 1 mg/kg IV and SC dosing, and 10 mg/kg SC dosing to mice.

The PK of the mouse surrogate dAb-Fc fusion protein, BMS-2m-126-24-CT, was evaluated in mice following single IV and SC administration (TABLE 13). After a single IV (1 mg/kg), the plasma concentrations followed a mono-exponential decline with a terminal T1/2 of 101 h (FIG. 13). The CLTp was 1.85 mL/h/kg; and the Vss was at 0.26 L/kg, indicating extracellular distribution. After single SC doses of 1 and 10 mg/kg, BMS-2m-126-24-CT was slowly absorbed with a Tmax of 24 h. The systemic exposures increased in a dose-proportional manner. With a dose ratio of 1:10, the Cmax and AUC0-inf increased in the proportion of 1:11. The terminal T1/2 was 100 and 120 h at 1 and 10 mg/kg, respectively. The ratio of the dose-adjusted exposure (AUC0-inf) after SC and IV administration was greater than 1, suggesting complete absorption after SC administration.

Pharmacokinetic/Pharmacodynamic Modeling

The PD of BMS-986003 was measured as the suppression of anti-KLH antibody response in the PK/PD study. BMS-986003 suppressed 70% the antibody response to KLH $$\left( \% \text{ response suppressed} = \left(1 - \frac{AUEC_{0-1008h \; IgG \; titers} \text{treatedgroup}}{AUEC_{0-1008h \; IgG \; titers} \text{vehicle group}}\right) * 100 \right)$$

at the highest dose of 20 mg/kg. Marginal (15%) and no suppression of the antibody response occurred at 2 and 0.2 mg/kg. In comparison, 5c8-IgG1 exhibited 10-fold higher plasma exposures and 4-fold longer T1/2 than BMS-986003 at the same dose level (20 mg/kg). As a result, 5c8-IgG1 suppressed 97% anti-KLH antibody response. In order to compare the in vivo potency between BMS-986003 and 5c8-IgG1, PK/PD modeling was performed using SAAM II (version 1.2.1, Seattle, Wash.). The plasma concentrations of BMS-986003 following SC administration were described using a first-order absorption kinetics coupled with a 2-compartment model, where the elimination occurred in both central and peripheral compartments. Because of complications from immunogenicity and possible nonlinear absorption, the PK data were fitted individually at each dose.

For 5c8-IgG1, a two-compartment model with central elimination was used. The anti-KLH antibody response, expressed as the average value of IgG titers, was modeled using a 6-compartment signal transduction model. The kinetics of KLH in the body was assumed to be a 1-compartment model. The inhibition of the IgG production by BMS-986003 and 5c8-IgG1 was described using an Imax model, with a maximum inhibition equal to 100%. As shown in FIG. 14, the model-fitted curves were able to describe both the PK and PD profile. The plasma IC50 of BMS-986003 and 5c8-IgG1 for the suppression of KLH-induced IgG production was estimated to be 74±14 and 60±18 nM, respectively. These results demonstrated that the potency of these two molecules was comparable in vivo.

The CD40L receptor occupancy (RO) of BMS-986004 was measured in the IV PK study. Following IV administration of 11 mg/kg, the RO of BMS-986004 on the peripheral-blood mononuclear cells (PBMC) was time- and concentration-dependent. PK/PD modeling was performed to estimated an RO EC50. The plasma concentrations were modeled using a modified two-compartment model with an additional ADA-mediated first order elimination constant introduced at 504 h after dosing; and the RO was modeled using an Emax model $$\left( RO \; \% = \frac{Emax^* \; Cp^\gamma}{EC50^\gamma + Cp^\gamma} \right).$$

Figure 15:
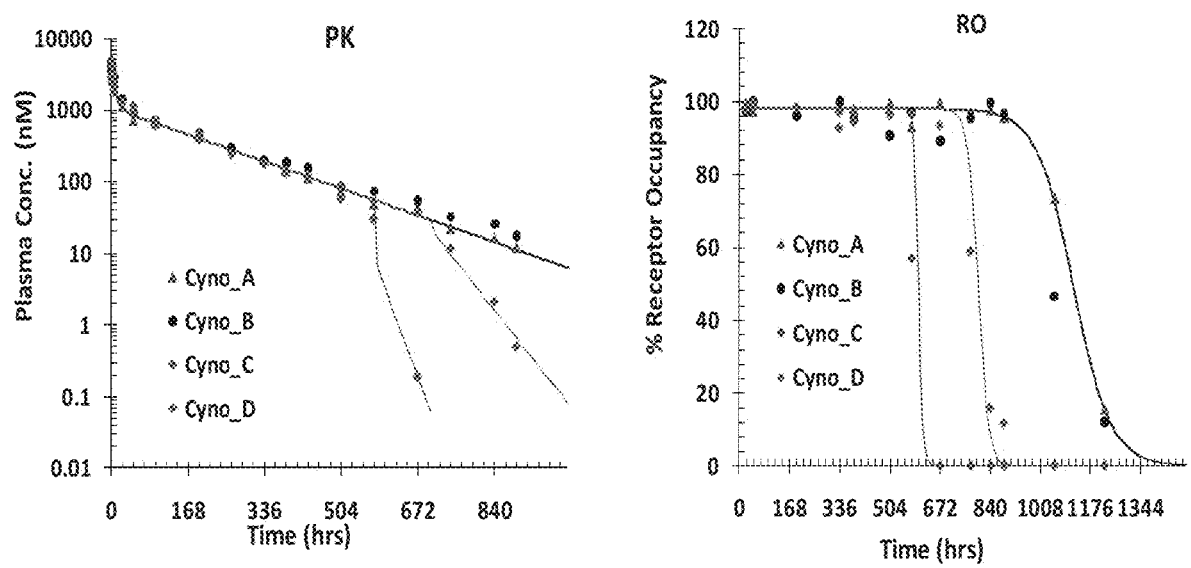
FIG. 15 shows PK/PD modeling of BMS-986004 plasma exposures and ex vivo RO on peripheral blood mononuclear cells (PBMC).

As shown in FIG. 15, the fitted curves were able to describe both exposure and RO, with an estimated RO EC50 of 3.4±0.3 nM and the γ (hill factor) of 3.1±0.1. In comparison, the RO EC50 was ~22-fold lower than the anti-KLH antibody response IC50 of 74±14 nM, suggesting that >95% RO is required in order to achieve appreciable (>50%) anti-KLH antibody suppression.

Example 11

Nonclinical Toxicology Single-Dose PK/PD Study

The objectives of this study were to 1) determine the tolerability of BMS-986003, including its potential immunogenicity, when given subcutaneously as a single dose to monkeys; 2) evaluate its PD (e.g., inhibition of the antibody response to T-cell-dependent antigen) and PK profiles; 3) evaluate the receptor occupancy of BMS-986003 and peripheral T-cell counts following subcutaneous dosing; and 4) aid dose selection for renal transplant studies and first-in-human dosing.

BMS-986003 was administered s.c. in the posterior thorax as single doses of 0 (vehicle control), 0.2, 2, or 20 mg/kg to groups of 2 cynomolgus monkeys per sex. An additional two monkeys/sex received a single intravenous dose of 20 mg/kg 5c8-IgG1, a monoclonal antibody to human CD40L that was used as a positive control in this study. All doses were administered at 2 mL/kg in the vehicle (PBS; pH 7.2). To assess the effects on the T-cell dependent antibody response, animals were immunized at approximately 24 hours after dosing with test article or immediately after dosing the positive control with 10 mg of KLH by intramuscular injection (posterior quadriceps or caudal thigh). Criteria for evaluation included survival, PK, immunogenicity, PD (inhibition of the antibody response to the T-cell-dependent antigen, KLH), clinical signs, body weights, food consumption, peripheral-blood immunophenotyping, receptor occupancy, and clinical-pathology evaluations (hematology, serum chemistry, and coagulation). Animals were returned to stock following a 6-week post-dose observation period.

At doses ≤20 mg/kg, BMS-986003 was slowly absorbed (Tmax=6-96 h) and Cmax and AUCtot values increased in a less than dose-proportional manner across all dose groups and there were no apparent gender differences. The T1/2 values estimated ranged from 69-104 h across all doses. BMS-986003 was substantially immunogenic; all monkeys developed a positive anti-drug antibody (ADA) response during the 6-week post-dose period. At 0.2 and 2 mg/kg, the mean group total ADA response peaked at Day 22 at mean group end point titers (EPT) of 4203 and 6469, respectively. At 20 mg/kg, the ADA response, while positive, was somewhat delayed and partially suppressed, consistent with target pharmacology, peaking at Day 36 at a mean group EPT of 1828. Further characterization of the antibodies demonstrated the majority of binding to the dAb (non-Fc) portion of the molecule and these antibodies were shown to block the binding of BMS-986003 to CD40L in 2 different immunoassay formats suggesting that the ADA were neutralizing. In addition, the formation of ADA appeared to accelerate the elimination of BMS-986003 in several monkeys.

Mean PK parameters for BMS-986003 are presented in TABLE 14.

TABLE 14

Pharmacokinetic Summary

| Mean Parameter | BMS-986003 SC | | | 5C8-IgG1 IV |
| --- | --- | --- | --- | --- |
| | 0.2 mg/kg (N = 4) | 2 mg/kg (N = 4) | 20 mg/kg (N = 4) | 20 mg/kg (N = 4) |
| Gender | Male/Female | Male/Female | Male/Female | Male/Female |
| AUC(0-inf) µg · h/mL | 219/407 | 2165/2477 | 14195/13114 | 267750/272250 |
| CLTp mL/h/kg | Not applicable | Not applicable | Not applicable | ND/0.074 |
| T½ h | 69/101 | 68/69 | 107/104 | ND/400 |
| Cmax µg/mL | 69/101 | 45/49 | 88/91 | Not applicable |
| Tmax h | 24/96 | 51/15 | 6/15 | Not applicable |

Molecular weight used for conversion was 78104 Da for BMS-986003, 150000 Da for 5c8-IgG1 mAb.
ND = not determined,; AUCextra for males was above 20%, therefore the T½ was not reported.

There were no BMS-986003- or 5c8-IgG1-related clinical observations or effects on body weights or clinical pathology parameters except 1 male treated with 5c8-IgG1 had decreased red blood cells (0.74× control), hemoglobin (0.73× predose), and hematocrit (0.75× predose) on Day 8, and 3 of 4 monkeys receiving 5c8-IgG1 had decreased lymphocytes (0.53× to 0.65× predose) on Day 8, suggestive of lymphocyte depletion.

CD40L receptor occupancy was generally time- and dose-dependent and more sustained following administration of 20 mg/kg BMS-986003, consistent with higher and more sustained exposures at this dose and PD activity. For BMS-986003, mean peak receptor occupancy on peripheral-blood mononuclear cells (PBMC) was achieved at 24 hrs (97%), 6 hrs (99%) or 48 hrs (99%) post-dose, decreasing to <90% occupancy at 240, 360, or 696 hrs and to <50% occupancy at 360, 696, or 1032 hrs, at 0.2, 2, or 20 mg/kg, respectively. In comparison, for 5c8-IgG1 at 20 mg/kg, mean peak receptor occupancy on PBMC was achieved at 48 hours 100%), and was sustained at ≥97% for the entire study (1032 hr or through Day 44).

BMS-986003 suppressed the antibody response to KLH only at the high dose of 20 mg/kg. On Days 8-30 at 20 mg/kg, there was a 69 to 83% suppression of the geometric group mean antibody response to KLH, relative to the control group, with a peak suppression of 83% occurring on Day 16. No suppression of the antibody response occurred at 0.2 or 2 mg/kg BMS-986003. These data demonstrate that BMS-986003 at a sustained receptor occupancy of >90% for at least 1 month and at sustained plasma concentrations above ~10 µg/mL through Day 11 is able to inhibit a T-cell dependent antibody response in cynomolgus monkeys. For the positive control antibody, 5c8-IgG1, suppression of 74-97% of the geometric group mean antibody response to KLH occurred on Days 8-30, with peak suppression of 97% by Day 16 which was generally sustained through Day 30.

No biologically relevant BMS-986003 related changes in absolute numbers of B cells (CD45+, CD20+, CD3−), total T (CD45+, CD3+) cells, helper T (CD45+, CD3+, CD4+, CD8−) cells, cytotoxic T (CD45+, CD3+, CD4−, CD8+) cells, or natural killer (CD45+, CD3−, CD16+) cells occurred during the study, which confirmed lack of any Fc effector function. However, on Day 8, 3 of 4 monkeys treated with 20 mg/kg 5c8-IgG1 had decreased T-lymphocytes (0.53×-0.66× predose), both helper T-cell (0.64× to 0.77× predose) and cytotoxic (0.40× to 0.61× predose) T-cell populations, suggestive of depletion.

In conclusion, BMS-986003 administered as single SC doses of 0.2, 2, or 20 mg/kg (AUC≤14195 µg*hr/mL) was well tolerated in cynomolgus monkeys with no adverse drug-related effects. The positive control, 5c8-IgG1, at a dose of 20 mg/kg, resulted in complete, sustained inhibition of the antibody response to KLH and sustained receptor occupancy of nearly 100% through 30 days post-dose. Mild depletion of T-cells was also noted by Day 8 in monkeys receiving 5c8-IgG1 (0.40× to 0.77× predose), which was not observed with BMS-986003. BMS-986003 was able to suppress an antibody response to KLH at 20 mg/kg (peak suppression of 83%) following KLH immunization on Day 1 and had sustained receptor occupancy of ≥90% through Day 22 and ≥50% through Day 29. Similar dampening of the immunogenicity to BMS-986003 occurred at 20 mg/kg. However, lower BMS-986003 doses of 0.2 and 2 mg/kg did not suppress the antibody response to KLH or the anti-drug antibody response. The lack of pharmacology at the lower doses also correlated with decreasing receptor occupancy (i.e., <90% by Day 11 [0.2 mg/kg] or 16 [2 mg/kg]; <50% by Day 16 [0.2 mg/kg] or 30 [2 mg/kg]) and accelerated clearance, presumably due to the formation of ADA. The inhibition of TDAR is consistent with the mechanism of action of this compound and was not considered adverse.

Example 12

Evaluation of the Risk for TE/Thrombosis

It has been hypothesized that the TE associated with administration of the anti-CD40L monoclonal antibodies is mediated by anti-CD40L mAb-CD40L immune complex (IC)-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. The following methods and approaches were designed to evaluate the risk of TE and/or thrombosis.

In Vitro Platelet Activation Assays

Several in vitro assays were conducted to test the hypothesis that platelets are activated by CD40L mab/sCD40L IC in a FcgRIIa-dependent manner. The positive control 5c8-IgG1 was used to validate the assays prior to testing BMS-986003 and BMS-986004. Blood from human donors or mice expressing hFcgRIIa receptor on platelets were used for these studies. Platelet activation was detected by flow cytometry using antibodies against the well-validated platelet activation markers P-selectin (CD62P) and PAC-1 (activated GPIIb/IIIa). Briefly, blood was diluted 1:25 in modified Tyrodes-HEPES containing 1 mM CaCl2 to which detection antibodies and test reagents was added, incubated, and analyzed for platelet activation. Initial experiments determined that sCD40L or 5c8IgG1 alone did not activate platelets, but different immune complex ratios of 1:1 to 1:8 of 5c8:sCD40L significantly activated platelets. Subsequent experiments used 5c8-IgG1 or 5c8-mIgG2a IC, mostly at a 1:3 molar ratio of 5c8:sCD40L.

Platelet Activation by 5c8/sCD40L IC can be Blocked by Anti-FcgRIIa Antibody

Figure 16:
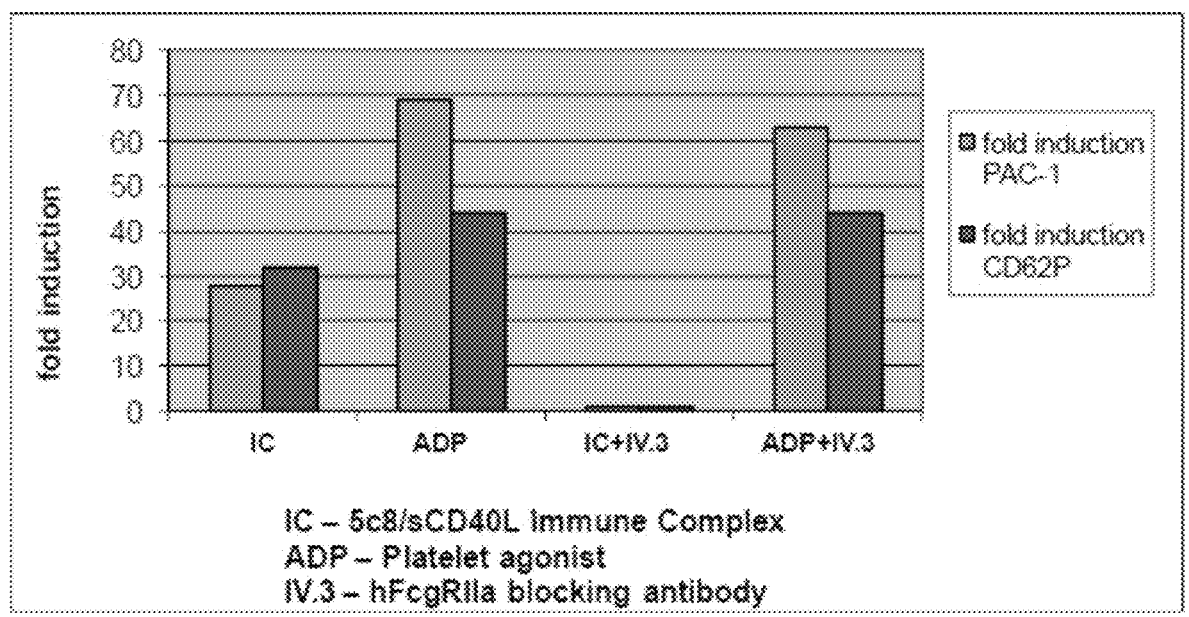
FIG. 16 demonstrates that IV.3 blocks 5c8/sCD40L IC-mediated activation of platelets in human blood.

Studies were conducted with the FcgRIIa blocking antibody IV.3 to test whether activation of platelets by 5c8/sCD40L IC was indeed FcgRIIA-mediated. Blood from human donors was pre-incubated with 0.5 µg/µl of the FcgRIIa blocking antibody IV.3 prior to dilution and incubation with detection antibodies as described above. Adenosine diphosphate (ADP), a platelet activator via a different mechanism, was used as a positive control. As illustrated in FIG. 16, platelet activation by 5c8/sCD40 IC was completely blocked by IV.3, while activation by ADP was not inhibited by the blocking antibody, indicating that activation by the IC is FcgRIIa-mediated.

Selection of Inert Fc Tails

Figure 17:
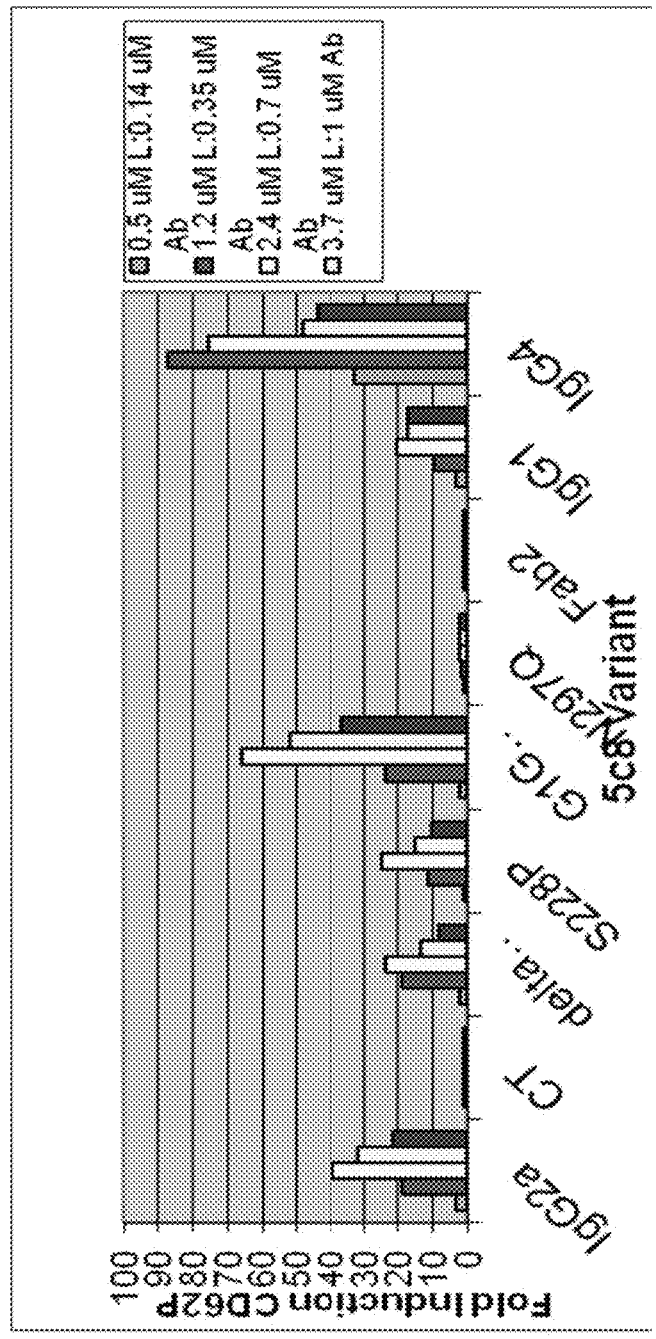
FIG. 17 shows the effect of Fc variants on platelet activation in human blood.

A requirement for potential candidate molecules was absence of binding to FcgRIIa to prevent potential platelet activation. Several 5c8 constructs containing different mutations derived from IgG1 (e.g 5c8-CT and N297Q) or IgG4 (e.g., 5c8-S228P) were expressed and screened for Fc tails that did not activate platelets using different molar ratios of sCD40L to mAbs. Wild-type and most mutated constructs activated platelets except for 5c8-CT and 5c8-N297Q (FIG. 17). Absence of Fc (5c8-Fab2) also did not activate platelets further confirming that IC-platelet activation is Fc-mediated. The CT tail was chosen to format the dAb candidates BMS-986003 and BMS-986004.

Effect of FcgRIIa Polymorphism on Platelet Activation

Figure 18:
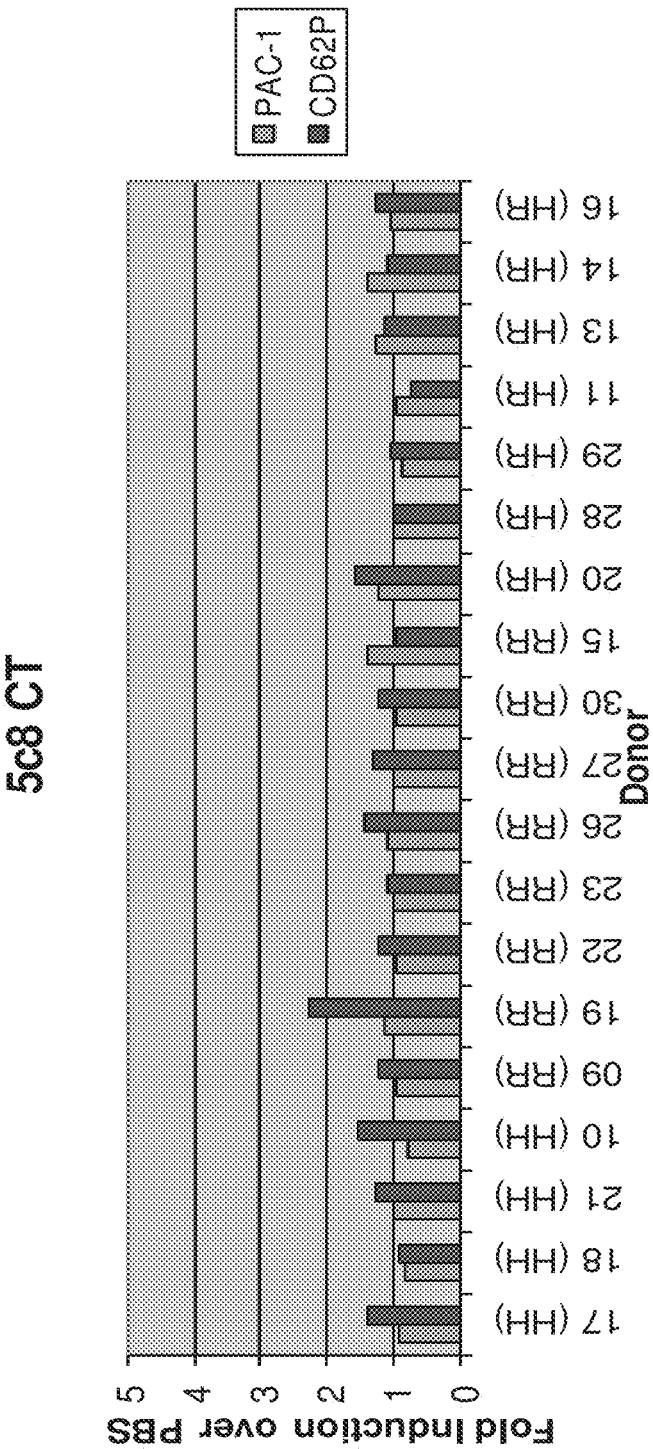
FIG. 18 demonstrates activation of platelets with 5c8-CT/sCD40L IC in blood from human donors genotyped for FcgRIIa polymorphism.

The gene for FcgRIIa is variable at codon 131, resulting in His-Arg (CAT/CGT) polymorphism. The genotype distribution in approximately 100 individuals with about equal distribution of Caucasians and African Americans was A/A (His homozygous; 14%), A/G (His/Arg heterozygous; 60%), and G/G (Arginine homozygous; 26%) for Caucasian Americans and A/A (30%), A/G (51%), and G/G (19%) for African-Americans. Reilly et al., Clin. Diagn. Lab. Immunol. 1: 640-644 (1994). Fc-dependent platelet aggregation was noted in samples from R131 individuals when treated with anti-CD9 in mIgG2 or mIgG1 Fc format, while platelets from H131 individuals aggregated only with anti-CD9 as mIgG2 format; this suggests that Fc-dependent aggregation with an IgG1 mAb could potentially segregate a patient population into low and high responders, which has previously been reported with this polymorphism. Tomiyama et al., Blood 80: 2261-2268 (1992). To address any potential differences in platelet activation with the IgG1 and CT Fc tail, 19 donors were genotyped for hFcgRIIa polymorphism and samples tested for platelet activation. The donor pool polymorphism (RR; 42%, HH; 21%, HR; 37%) was sufficient to evaluate any potential differences in platelet activation to the IgG1 format. Representative of literature reports, platelet activation with 5c8-IgG1/sCD40L IC was similar across all genotyped individuals. No activation was found with 5c8-CT/sCD40L IC (FIG. 18), suggesting no or minimal risk of increased TE in a patient population with an antibody formatted with the CT tail.

BMS-986004: Platelet Activation in Human Blood Donors

Figure 19:
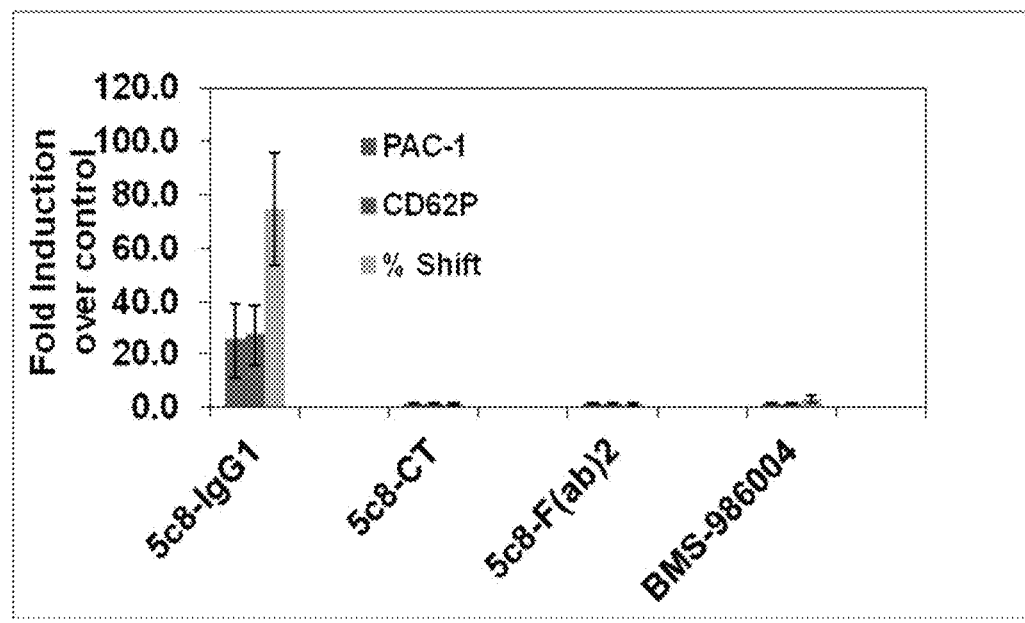
FIG. 19 diagrams platelet activation by various antibodies in blood from human donors.

The experiments described above using 5c8, supported selection of the CT-tail as the best format for BMS-986004 (also called BMS2h-572-633-CT-L2). Blood obtained from 6 donors was treated with 5c8-IgG1, 5c8-CT, F(ab)$_2$, and BMS-986004. Platelets were activated by 5c8-IgG1 but not by any of the other constructs, including BMS-986004 (FIG. 19), suggesting that this dAb has no or low risk for causing platelet activation and TE in clinical studies.

BMS-986003: Platelet Activation in Blood from Mice Expressing hFcgRIIa

Figure 20:
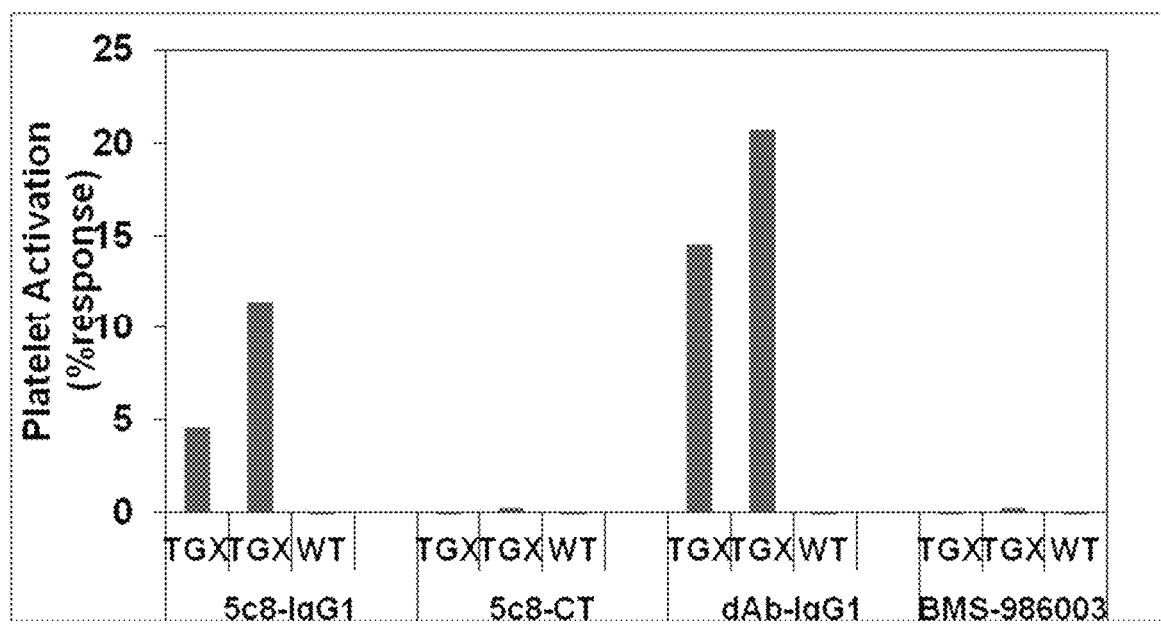
FIG. 20 shows levels of platelet activation by various antibodies, including BMS-986003, in hFcgRIIa-expressing transgenic mice.

To further confirm that activation of platelets by anti-CD40L antibodies was mediated by FcgRIIa receptor, blood from transgenic mice expressing the human receptor (R131 genotype) was treated with 5c8-IgG1, 5c8-IgG2a, dAb-IgG1, 5c8-CT, and BMS-986003 (also called BMS-2h572-633-CT). Platelets were specifically activated by 5c8-IgG1, 5c8-IgG2a, and dAb-IgG1/sCD40L IC in blood from mice expressing hFcgRIIa, but not wild-type littermates. 5c8-CT and BMS-986003 did not activate platelets, further confirming a low risk for TE with the presently disclosed antibodies (FIG. 20).

Example 13

Epitope Binding Experiments

Figure 25:
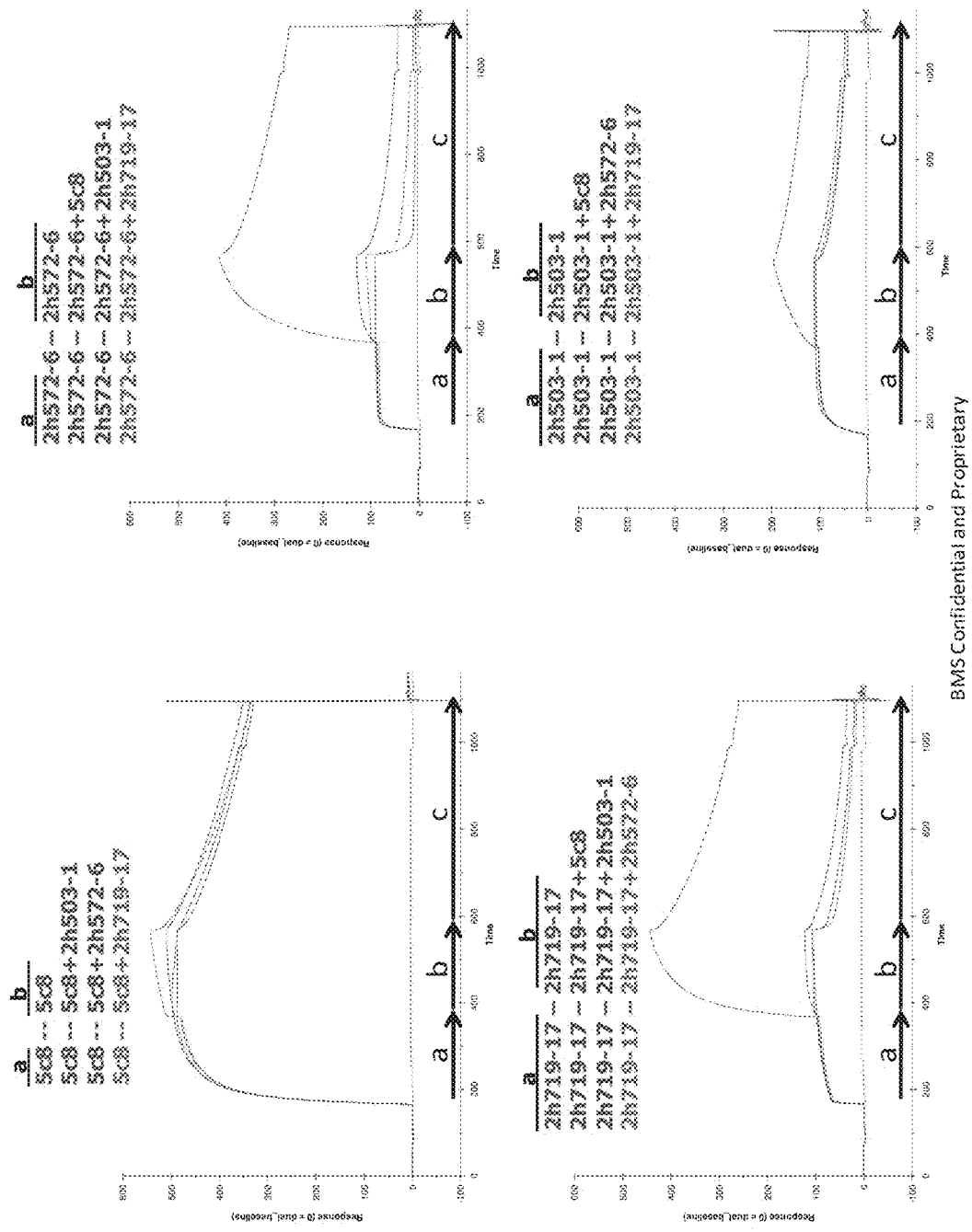
FIG. 25 shows SPR sensorgram data for binding experiments using monovalent dAbs BMS2h-503-1, BMS2h-572-6, BMS2h-719-17, and monovalent Fab fragment of 5c8, where the indicated molecules compete with each other for binding to CD40L (biotinylated IZ-hCD40L).

FIG. 25 shows SPR sensorgram data for experiments designed to test whether or not monovalent dAb molecules BMS2h-503-1, BMS2h-572-6, BMS2h-719-17, and the monovalent anti-CD40L 5c8 Fab fragment compete with each other for binding to CD40L. Experiments were performed using biotinylated CD40L (biot-IZ-hCD40L) that was captured on a streptavidin sensor chip surface. The tests involved the sequential injection of a specified molecule (phase "a"), immediately followed by injection of the same molecule in the presence of a second specified molecule (phase "b"), followed by dissociation (phase "c"). Competition for binding is identified as a reduction (blocking) of the binding signal for the second molecule in the presence of the first, with the level of blocking being governed by the association and dissociation kinetics of each molecule. For each pair of molecules tested, the binding of the second molecule was shown to be reduced when the first molecule was present. These result suggest that BMS2h-503-1, BMS2h-572-6, BMS2h-719-17, and 5c8 Fab compete with each other for binding to biot-IZ-hCD40L.

Figure 26:
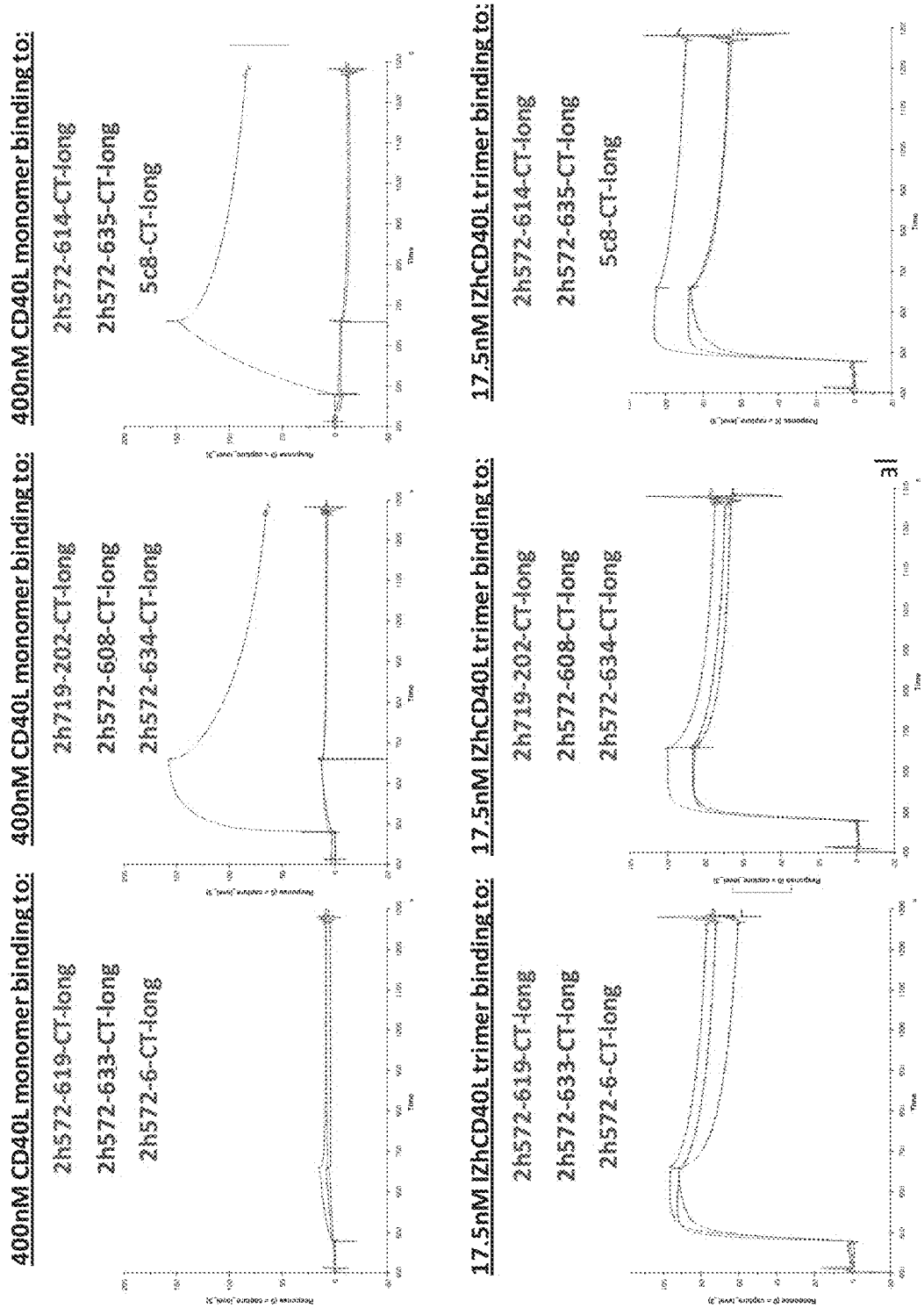
FIG. 26 shows SPR sensorgram data for experiments testing the binding of BMS2h-572-619-CT-long, BMS2h-572-633-CT-long, BMS2h-572-6-CT-long, BMS2h-719-202-CT-long, BMS2h-572-608-CT-long, BMS2h-572-634-CT-long, BMS2h-572-614-CT-long, BMS2h-572-635-CT-long, and 5c8-CT-long molecules to either CD40L monomer (upper 3 panels) or CD40L trimer (lower 3 panels).

FIG. 26 shows SPR sensorgram data for binding of the indicated dAb-CT-long and the 5c8-CT-long molecules to either human CD40L monomer (triple CD40L mutant (T211E, S222Y, H224K, [108-261])) or to CD40L trimer (IZ-hCD40L). The dAb-CT-long and the 5c8-CT-long molecules were captured via their "CT-long" Fc-domain on an immobilized anti-human IgG Fc (Biacore, GE Healthcare) antibody sensor chip surface. The data in the top 3 panels show that human CD40L monomer binds specifically to BMS2h-719-202-CT-long and 5c8-CT-long, but does not bind to any of the indicated dAb-CT-long molecules that contain dAbs from the BMS2h-572-6 lineage. In contrast, the bottom 3 panels show that CD40L trimer (IZ-hCD40L) binds strongly to all the tested dAb-CT-long molecules from the BMS2h-572-6 lineage, as well as to BMS2h-719-202-CT-long and 5c8-CT-long. These results suggest that the molecules from the BMS2h-572-6xx-CT-long lineage are specific for an epitope that is only present on the CD40L trimer and not present on monomeric human CD40L, whereas BMS2h-719-202-CT-long and 5c8-CT-long bind to an epitope that is present on both the CD40L monomer and trimer.

Although the present embodiments have been described in detail with reference to examples above, it is understood that various modifications can be made without departing from the spirit of these embodiments, and would be readily known to the skilled artisan.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11180567B2). An electronic copy of the "Sequence Listing" will also be available from the USPTO upon request and payment of the fee set forth in 37 CFR 1.19(b)(3).

What is claimed is:

1. An isolated antibody polypeptide comprising a fusion of
   (i) a single variable domain comprising three complementarity determining regions (CDR) and that specifically binds human CD40L, and
   (ii) an Fc domain,
   wherein
   a) CDR1 of the single variable domain has the same amino acid sequence as amino acids 31 to 35 of BMS2h-572-633 (SEQ ID NO: 274);
   b) CDR2 of the single variable domain has the same amino acid sequence as amino acids 50 to 66 of BMS2h-572-633 (SEQ ID NO: 274); and
   c) CDR3 of the single variable domain has the same amino acid sequence as amino acids 101 to 107 of BMS2h-572-633 (SEQ ID NO: 274).

2. The antibody polypeptide of claim 1, wherein the Fc domain comprises an IgG4 Fc domain.

3. The antibody polypeptide of claim 1, wherein the Fc domain comprises an IgG1 Fc domain.

4. The antibody polypeptide of claim 1, wherein the Fc domain comprises the amino acid sequence of amino acids 139 to 370 of SEQ ID NO: 1362.

5. The antibody polypeptide of claim 1, wherein the single variable domain and the Fc domain are linked by an amino acid sequence selected from the group consisting of: AS, AST, TVAAPS (SEQ ID NO: 13), TVA, ASTSGPS (SEQ ID NO: 14) and (GGGGS)n (SEQ ID NO: 12) wherein n is 1, 2, 3, 4, or 5.

6. The antibody polypeptide of claim 5, wherein the single variable domain comprises the amino acid sequence of SEQ ID NO: 274.

7. The antibody polypeptide of claim 5, wherein the single variable domain consists of the amino acid sequence of SEQ ID NO: 274.

8. The antibody polypeptide of claim 1, wherein the Fc domain consists of the amino acid sequence of amino acids 139 to 370 of SEQ ID NO: 1362.

9. The antibody polypeptide of claim 8, wherein the single variable domain and the Fc domain are linked by an amino acid sequence selected from the group consisting of: AS, AST, TVAAPS (SEQ ID NO: 13), TVA, ASTSGPS (SEQ ID NO: 14) and (GGGGS)n (SEQ ID NO): 12) wherein n is 1, 2.3, 4, or 5.

10. The antibody polypeptide of claim 9, wherein the single variable domain comprises the amino acid sequence of SEQ ID NO: 274.

11. The antibody polypeptide of claim 1, wherein the antibody polypeptide further comprises a second single variable domain that specifically binds a second antigen, wherein the second antigen is an antigen other than human CD40L.

12. The antibody polypeptide of claim 11, wherein the second antigen is a cluster of differentiation (CD) molecule, a Major Histocompatibility Complex (MHC) Class II molecule, or serum albumin (SA).

13. A pharmaceutical composition comprising a therapeutically-effective amount of the antibody polypeptide of claim 1 and a pharmaceutically acceptable carrier.

14. The pharmaceutical composition of claim 13, further comprising an immunosuppressive/immunomodulatory and/or anti-inflammatory agent.

15. The pharmaceutical composition of claim 13, wherein the antibody polypeptide is the antibody polypeptide of claim 6.

16. The pharmaceutical composition of claim 13, wherein the antibody polypeptide is the antibody of claim 10.

17. A method of treating an immune disease in a patient in need of such treatment comprising administering to a patient a therapeutically effective amount of an antibody polypeptide according to claim 1,
   wherein the immune disease is selected from the group consisting of immune thrombocytopenic purpura (ITP), systemic lupus erythematosus (SLE), proliferative lupus glomerulonephritis, inflammatory bowel disease (IBD), Crohn's disease, atherosclerosis, graft-vs-host disease (GVHD), and myasthenia gravis.

18. The method of claim 17, wherein the antibody polypeptide is the antibody polypeptide of claim 6.

19. The method of claim 17, wherein the antibody polypeptide is the antibody polypeptide of claim 10.

20. The method of claim 17, wherein the antibody polypeptide is administered in combination with an immunosuppressive/immunomodulatory and/or anti-inflammatory agent.

* * * * *

UNITED STATES PATENT AND TRADEMARK OFFICE
CERTIFICATE OF CORRECTION

PATENT NO. : 11,180,567 B2
APPLICATION NO. : 16/218077
DATED : November 23, 2021
INVENTOR(S) : Steven G. Nadler et al.

It is certified that error appears in the above-identified patent and that said Letters Patent is hereby corrected as shown below:

In the Claims

At Column 264, Claim 9, Line 18, "(SEQ ID NO): 12)" should read -- (SEQ ID NO: 12) --

At Column 264, Claim 9, Line 29, "2.3, 4, or 5." should read -- 2, 3, 4, or 5. --

At Column 264, Claim 16, Line 53, "the antibody of claim 10" should read -- the antibody polypeptide of claim 10 --

At Column 264, Claim 17, Line 59, "consisting ofimmune thrombocytopenic" should read -- consisting of: immune thrombocytopenic --

Signed and Sealed this
Nineteenth Day of April, 2022

Katherine Kelly Vidal
*Director of the United States Patent and Trademark Office*